United States Patent
Duan et al.

(10) Patent No.: US 9,708,253 B2
(45) Date of Patent: Jul. 18, 2017

(54) CYCLOHEXYL SULFONE RORγ MODULATORS

(71) Applicant: BRISTOL-MYERS SQUIBB COMPANY, Princeton, NJ (US)

(72) Inventors: Jingwu Duan, Yardley, PA (US); T. G. Murali Dhar, Newtown, PA (US); Bin Jiang, Bryn Mawr, PA (US); Ananta Karmakar, Bangalore (IN); Arun Kumar Gupta, Bangalore (IN); Zhonghui Lu, King of Prussia, PA (US); Carolyn A. Weigelt, Langhorne, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/109,733

(22) PCT Filed: Jan. 5, 2015

(86) PCT No.: PCT/US2015/010084
§ 371 (c)(1),
(2) Date: Jul. 5, 2016

(87) PCT Pub. No.: WO2015/103507
PCT Pub. Date: Jul. 9, 2015

(65) Prior Publication Data
US 2016/0326104 A1    Nov. 10, 2016

Related U.S. Application Data

(60) Provisional application No. 61/923,906, filed on Jan. 6, 2014.

(51) Int. Cl.
| | |
|---|---|
| C07C 317/20 | (2006.01) |
| C07C 317/24 | (2006.01) |
| C07C 317/30 | (2006.01) |
| C07D 205/04 | (2006.01) |
| C07D 207/27 | (2006.01) |

(Continued)

(52) U.S. Cl.
CPC .......... *C07C 317/20* (2013.01); *C07C 317/24* (2013.01); *C07C 317/30* (2013.01); *C07C 317/46* (2013.01); *C07D 205/04* (2013.01); *C07D 207/27* (2013.01); *C07D 207/277* (2013.01); *C07D 211/46* (2013.01); *C07D 211/48* (2013.01); *C07D 211/62* (2013.01); *C07D 211/78* (2013.01); *C07D 213/30* (2013.01); *C07D 213/40* (2013.01); *C07D 213/56* (2013.01); *C07D 213/71* (2013.01); *C07D 213/75* (2013.01); *C07D 213/81* (2013.01); *C07D 213/82* (2013.01); *C07D 231/12* (2013.01); *C07D 231/14* (2013.01); *C07D 231/54* (2013.01); *C07D 231/56* (2013.01); *C07D 237/08* (2013.01); *C07D 237/20* (2013.01); *C07D 237/22* (2013.01); *C07D 237/24* (2013.01); *C07D 239/28* (2013.01); *C07D 241/24* (2013.01); *C07D 249/04* (2013.01); *C07D 249/06* (2013.01); *C07D 277/60* (2013.01); *C07D 277/82* (2013.01); *C07D 295/096* (2013.01); *C07D 295/16* (2013.01); *C07D 295/185* (2013.01); *C07D 295/195* (2013.01); *C07D 295/205* (2013.01); *C07D 309/04* (2013.01); *C07D 309/08* (2013.01); *C07D 335/02* (2013.01); *C07D 401/04* (2013.01); *C07D 401/06* (2013.01); *C07D 401/12* (2013.01); *C07D 403/04* (2013.01); *C07D 405/04* (2013.01);
(Continued)

(58) Field of Classification Search
None
See application file for complete search history.

(56) References Cited

U.S. PATENT DOCUMENTS

| | | | |
|---|---|---|---|
| 9,458,171 B2 | 10/2016 | Duan et al. | |
| 2004/0122050 A1* | 6/2004 | Churcher | C07C 317/14 514/317 |

(Continued)

FOREIGN PATENT DOCUMENTS

| | | |
|---|---|---|
| WO | WO 2013/169588 | 11/2013 |
| WO | WO 2014/028669 | 2/2014 |

(Continued)

*Primary Examiner* — Nyeemah A Grazier
(74) *Attorney, Agent, or Firm* — Elliott Korsen

(57) ABSTRACT

Described are RORγ modulators of the formula (I), or stereoisomers, tautomers, pharmaceutically acceptable salts, solvates, or prodrugs thereof, wherein all substituents are defined herein. Also provided are pharmaceutical compositions comprising the same. Such compounds and compositions are useful in methods for modulating RORγ activity in a cell and methods for treating a subject suffering from a disease or disorder in which the subject would therapeutically benefit from modulation of RORγ activity, for example, autoimmune and/or inflammatory disorders.

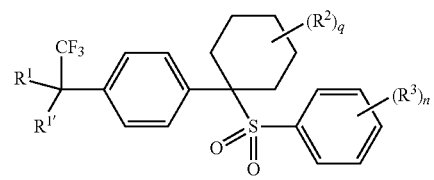

13 Claims, No Drawings

(51) Int. Cl.
| | |
|---|---|
| *C07D 211/46* | (2006.01) |
| *C07D 211/78* | (2006.01) |
| *C07D 213/30* | (2006.01) |
| *C07D 231/12* | (2006.01) |
| *C07D 213/81* | (2006.01) |
| *C07D 213/82* | (2006.01) |
| *C07D 309/08* | (2006.01) |
| *C07D 231/14* | (2006.01) |
| *C07D 231/56* | (2006.01) |
| *C07D 401/04* | (2006.01) |
| *C07D 403/04* | (2006.01) |
| *C07D 237/08* | (2006.01) |
| *C07D 237/20* | (2006.01) |
| *C07D 237/24* | (2006.01) |
| *C07D 405/04* | (2006.01) |
| *C07D 239/28* | (2006.01) |
| *C07C 317/46* | (2006.01) |
| *C07D 241/24* | (2006.01) |
| *C07D 249/04* | (2006.01) |
| *C07D 471/04* | (2006.01) |
| *C07D 207/277* | (2006.01) |
| *C07D 277/60* | (2006.01) |
| *C07D 295/096* | (2006.01) |
| *C07D 211/48* | (2006.01) |
| *C07D 211/62* | (2006.01) |
| *C07D 295/185* | (2006.01) |
| *C07D 213/56* | (2006.01) |
| *C07D 213/71* | (2006.01) |
| *C07D 213/75* | (2006.01) |
| *C07D 309/04* | (2006.01) |
| *C07D 335/02* | (2006.01) |
| *C07D 401/06* | (2006.01) |
| *C07D 401/12* | (2006.01) |
| *C07D 295/205* | (2006.01) |
| *C07D 213/40* | (2006.01) |
| *C07D 231/54* | (2006.01) |
| *C07D 237/22* | (2006.01) |
| *C07D 249/06* | (2006.01) |
| *C07D 277/82* | (2006.01) |
| *C07D 295/16* | (2006.01) |
| *C07D 295/195* | (2006.01) |

(52) U.S. Cl.
CPC ........ *C07D 471/04* (2013.01); *C07C 2101/02* (2013.01); *C07C 2101/14* (2013.01)

(56) References Cited

U.S. PATENT DOCUMENTS

2016/0326103 A1* 11/2016 Duan .................... C07D 213/81
2016/0326115 A1* 11/2016 Duan .................... C07D 309/08

FOREIGN PATENT DOCUMENTS

| WO | WO2014/062938 | 4/2014 |
| WO | WO2015/035278 | 3/2015 |
| WO | WO2015/042212 | 3/2015 |
| WO | WO2015/103507 | 7/2015 |
| WO | WO2015/103508 | 7/2015 |
| WO | WO2015/103509 | 7/2015 |
| WO | WO2015/103510 | 7/2015 |

* cited by examiner

CYCLOHEXYL SULFONE RORγ MODULATORS

CROSS-REFERENCE TO RELATED APPLICATIONS

This application claims the benefit of U.S. Provisional Application No. 61/923,906, filed Jan. 6, 2014, the disclosure of which is incorporated herein by reference in its entirety.

FIELD OF THE INVENTION

This invention relates to modulators of the retinoid-related orphan receptor RORγ and methods for using such modulators. The compounds described herein can be particularly useful for diagnosing, preventing, or treating a variety of diseases and disorders in humans and animals. Exemplary disorders include, but are not limited to, psoriasis, rheumatoid arthritis, inflammatory bowel disease, Crohn's disease, ulcerative colitis, acute graft-versus-host disease, psoriatic arthritis, ankylosing spondylitis and multiple sclerosis.

BACKGROUND OF THE INVENTION

The retinoid-related orphan receptors RORα, RORβ, and RORγ play an important role in numerous biological processes including organ development, immunity, metabolism, and circadian rhythms. See, for example, Dussault et al. in Mech. Dev. (1998) vol. 70, 147-153; Andre et al. in EMBO J. (1998) vol. 17, 3867-3877; Sun et al. in Science (2000) vol. 288, 2369-2373; and Jetten in Nucl. Recept. Signal. (2009) vol. 7, 1-32.

RORγ is expressed in several tissues including the thymus, kidney, liver, and muscle. Two isoforms of RORγ have been identified: RORγ1 and RORγ2 (also known, respectively, as RORγ and RORγt). See, for example, Hirose et al. in Biochem. Biophys. Res. Commun. (1994) vol. 205, 1976-1983; Oritz et al. in Mol. Endocrinol. (1995) vol. 9, 1679-1691; and He et al. in Immunity (1998) vol. 9, 797-806. Expression of RORγt is restricted to lymphoid cell types including CD4+CD8+ thymocytes, IL-17 producing T helper (Th17) cells, lymphoid tissue inducer (LTi) cells, and γδ cells. RORγt is essential for the development of lymph nodes and Peyer's patches and for the normal differentiation of Th17, γδ, and LTi cells. See, for example, Sun et al. in Science (2000) vol. 288, 2369-2373; Ivanov et al. in Cell (2006) vol. 126, 1121-1133; Eberl et al. in Nat. Immunol. (2004) vol. 5, 64-73; Ivanov et al. in Semin. Immunol. (2007) vol. 19, 409-417; and Cua and Tato in Nat. Rev. Immunol. (2010) vol. 10, 479-489.

Proinflammatory cytokines such as IL-17A (also referred to as IL-17), IL-17F, and IL-22 produced by Th17 cells and other RORγ+ lymphocytes activate and direct the immune response to extracellular pathogens. See, for example, Ivanov et al. in Semin. Immunol. (2007) vol. 19: 409-417; and Marks and Craft in Semin. Immunol. (2009) vol. 21, 164-171. RORγ directly regulates IL-17 transcription and disruption of RORγ in mice attenuates IL-17 production. See, for example, Ivanov et al. in Cell (2006) vol. 126, 1121-1133.

Dysregulated production of IL-17 has been implicated in several human autoimmune and inflammatory diseases including multiple sclerosis, rheumatoid arthritis, psoriasis, inflammatory bowel disease (IBD), and asthma. See, for example, Lock et al. in Nat. Med. (2002) vol. 8, 500-508; Tzartos et al. in Am. J. Pathol. (2008) vol. 172, 146-155; Kotake et al. in J. Clin. Invest. (1999) vol. 103, 1345-1352; Kirkham et al. in Arthritis Rheum. (2006) vol. 54, 1122-1131; Lowes et al. in J. Invest. Dermatol. (2008) vol. 128, 1207-1211; Leonardi et al. in N. Engl. J. Med. (2012) vol. 366, 1190-1199; Fujino et al. in Gut (2003) vol. 52, 65-70; Seiderer et al. in Inflamm. Bowel Dis. (2008) vol. 14, 437-445; Wong et al. in Clin. Exp. Immunol. (2001) vol. 125, 177-183; and Agache et al. in Respir. Med. (2010) 104: 1131-1137. In murine models of these diseases, inhibition of IL-17 function by neutralizing antibodies or genetic disruption of IL-17 or IL-17 receptor ameliorates the disease course or clinical symptoms. See, for example, Hu et al. in Ann. N.Y. Acad. Sci. (2011) vol. 1217, 60-76.

Disruption of RORγ in mice also attenuates disease progression or severity in animal models of autoimmunity and inflammation including experimental autoimmune encephalomyelitis (EAE), imiquimod induced psoriasis, colitis, and allergic airway disease. See, for example, Ivanov et al. in Cell (2006) vol. 126, 1121-1133; Yang et al. in Immunity (2008) vol. 28, 29-39; Pantelyushin et al. in J. Clin. Invest. (2012) vol. 122, 2252-2256; Leppkes et al. in Gastroenterology (2009) vol. 136, 257-267; and Tilley et al. in J. Immunol. (2007) vol. 178, 3208-3218.

Each of the references in this Background section is hereby incorporated herein by reference in its entirety for all purposes.

Therapeutic agents exist to treat a variety of inflammatory and autoimmune diseases, but there still remains a significant unmet medical need in these therapeutic areas. Given the role of IL-17 in human disease and the validation of IL-17 and RORγ as targets in murine disease models, compounds capable of modulating RORγt activity are contemplated to provide a therapeutic benefit in the treatment of multiple immune and inflammatory disorders.

SUMMARY OF THE INVENTION

In one aspect, the invention comprises compounds of the formula (I),

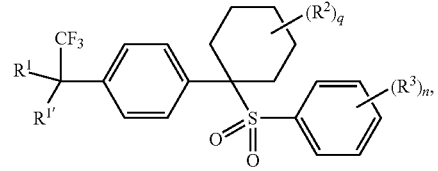

or pharmaceutically acceptable salts thereof, wherein all substituents are defined herein. The invention includes stereoisomers, tautomers, pharmaceutically acceptable salts, solvates, or prodrugs thereof.

In another aspect, the invention comprises pharmaceutical compositions comprising a compound according to formula (I), stereoisomeric form or pharmaceutically acceptable salt, as described herein, and a pharmaceutically acceptable carrier, excipient, or diluent.

In another aspect, the invention comprises methods for antagonizing RORγ in a cell comprising contacting the cell with an effective amount of a compound according to formula (I), stereoisomeric form or pharmaceutically acceptable salt, as described herein. This aspect may be conducted in vitro or in vivo.

In another aspect, the invention comprises methods for treating a subject suffering from a disease or disorder modulated by RORγ, the method comprising administering to a subject a therapeutically effective amount of compound according to formula (I), stereoisomeric form, pharmaceutically acceptable salt or pharmaceutical composition as described herein.

In another aspect, the invention comprises a method for treating a disease or disorder selected from an inflammatory disease or disorder, an autoimmune disease or disorder, an allergic disease or disorder, a metabolic disease or disorder, and/or cancer in a subject, the method comprising administering to the subject a therapeutically effective amount of compound according to formula (I), or a stereoisomeric form, pharmaceutically acceptable salt or pharmaceutical composition as described herein.

DETAILED DESCRIPTION OF THE INVENTION

In one aspect, the invention comprises compounds of formula (I),

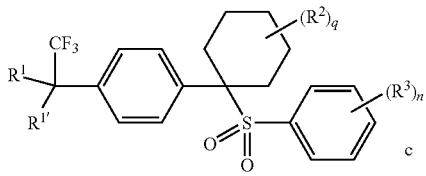

I or stereoisomers, tautomers, pharmaceutically acceptable salts, solvates, or prodrugs thereof, wherein $R^1$ and $R^{1'}$ are, independently at each occurrence, hydrogen, halo, $CF_3$, $OCF_3$, CN, $NO_2$, —$(CH_2)_rOR^b$, —$(CH_2)_rS(O)_pR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle substituted with 0-3 $R^a$, or —$(CH_2)_r$-5-7 membered heterocycle comprising carbon atoms and 1-4 heteroatoms selected from N, O, and $S(O)_p$ substituted with 0-3 $R^a$;

$R^2$ is independently at each occurrence, hydrogen, =O, —$(CH_2)_rOR^{2b}$, —$(CH_2)_rC(O)R^{2b}$, —$(CH_2)_rOC(O)OR^{2b}$, —$(CH_2)_rOC(O)NR^{11}R^{11}$, —$(CH_2)_rNR^{2b}C(O)R^{2c}$, —$(CH_2)_rNR^{2b}C(O)OR^{2c}$, —$(CH_2)_rNR^{2b}C(O)NR^{11}R^{11}$, —$(CH_2)_rNR^{11}R^{11}$, —$NR^{2b}S(O)R^c$, —$(CH_2)_rNR^{2b}S(O)_pNR^{11}R^{11}$, $C_{1-6}$ alkyl, —(CH2)r-3-10 membered carbocycle substituted with 0-3 R2a or —$(CH_2)_r$-4-10 membered heterocycle comprising carbon atoms, and 1-4 heteroatoms selected from N, O, and $S(O)_p$ substituted with 0-3 $R^{2a}$; or one $R^2$ together with an $R^2$ on an adjacent carbon combine to form a fused ring substituted with 0-3 $R^{2a}$, wherein the fused ring is selected from 3-10 membered carbocycle substituted with 0-3 $R^{2a}$, or 4-7 membered heterocycle comprising carbon atoms and 1-4 heteroatoms selected from N, O, and $S(O)_p$ substituted with 0-3 $R^{2a}$;

$R^{2a}$ is, independently at each occurrence, hydrogen, =O, halo, $OCF_3$, CN, $NO_2$, —$(CH_2)_rOR^b$, —$(CH_2)_rS(O)_pR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle substituted with 0-3 $R^a$, or —$(CH_2)_r$-5-7 membered heterocycle comprising carbon atoms and 1-4 heteroatoms selected from N, O, and $S(O)_p$ substituted with 0-3 $R^a$;

$R^{2b}$ is, independently at each occurrence, hydrogen, $CF_3$, —$(CH_2)rOR^b$, —$(CH_2)_rS(O)_pR^b$, —$(CH_2)_rC(O)R^{1d}$, —$(CH_2)_rC(O)OR^b$, —$(CH_2)rOC(O)R^b$, —$(CH_2)rNR^{11}R^{11}$, —$(CH_2)_rC(O)NR^{11}R^{11}$, —$(CH_2)rNR^bC(O)R^{1c}$, —$(CH_2)rNR^bC(O)OR^c$, —$(CH_2)rNR^bC(O)NR^{11}R^{11}$, —$(CH_2)rS(O)_2NR^{11}R^{11}$, —$(CH_2)rNR^bS(O)_2R^c$, $C_{1-6}$ alkyl substituted with 0-2 $R^a$, $C_{1-6}$ haloalkyl, —$(CH_2)_r$-3-14 membered carbocycle substituted with 0-3 $R^a$, or —$(CH_2)_r$-5-7 membered heterocycle comprising carbon atoms and 1-4 heteroatoms selected from N, O, and $S(O)_p$ substituted with 0-2 $R^a$;

$R^{2c}$ is, independently at each occurrence, hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or —$(CH_2)_r$-5-10 membered heterocycle comprising carbon atoms and 1-4 heteroatoms selected from N, O, and $S(O)_p$, substituted with 0-3 $R^a$;

$R^{2d}$ is, independently at each occurrence, hydrogen, $C_{1-6}$ alkyl substituted with 0-2 $R^d$, $C_{1-6}$ haloalkyl, $C(O)NR^{11}R^{11}$, $C_{3-6}$ cycloalkyl substituted with 0-2 $R^d$, or $(CH_2)_r$-phenyl substituted with 0-2 $R^a$, a 5-10 membered heterocycle comprising carbon atoms and 1-4 heteroatoms selected from N, O, and S, substituted with 0-3 $R^a$;

$R^3$ is selected from hydrogen, halo, $N_3$, CN, —$(CH_2)_rOR^{3b}$, —$(CH_2)_rNR^{11}R^{11}$, $C_{1-6}$ alkyl substituted with 0-3 $R^{3a}$, and $C_{3-10}$ cycloalkyl substituted with 0-3 $R^{3a}$; 4-10 membered heterocycle comprising carbon atoms and 1-4 heteroatoms selected from N, O, and $S(O)_p$, substituted with 0-3 $R^a$, or together with the carbon atoms to which they are attached, one $R^3$ combines with a second $R^3$ located on an adjacent atom to form a 5-7 membered carbocycle or a 5-7 membered heterocycle comprising carbon atoms and 1-4 heteroatom selected from N, O and $S(O)_p$, each optionally substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CH_2)_rOR^b$, —$(CH_2)_rS(O)_pR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CH_2)_r$-3-14 membered carbocycle substituted with 0-3 $R^a$, or a —$(CH_2)_r$-5-10 membered heterocycle comprising carbon atoms and 1-4 heteroatoms selected from N, O, and $S(O)_p$ substituted with 0-3 $R^a$;

$R^{3b}$ is, independently at each occurrence, hydrogen, $CF_3$, —$(CH_2)rOR^b$, —$(CH_2)_rS(O)_pR^b$, —$(CH_2)_rC(O)R^{1d}$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^{1c}$, —$(CH_2)_rNR^bC(O)OR^c$, —$(CH_2)_rNR^bC(O)NR^{11}R^{11}$, —$(CH_2)_rS(O)_2NR^{11}R^{11}$, —$(CH_2)_rNR^bS(O)_2R^c$, $C_{1-6}$ alkyl substituted with 0-3 $R^a$, $C_{1-6}$ haloalkyl, —$(CH_2)_r$-3-14 membered carbocycle substituted with 0-3 $R^a$, or —$(CH_2)_r$-5-7 membered heterocycle comprising carbon atoms and 1-4 heteroatoms selected from N, O, and $S(O)_p$ substituted with 0-3 $R^a$;

$R^{11}$ is, independently at each occurrence, hydrogen, $C_{1-6}$ alkyl substituted with 0-3 $R^f$, $CF_3$, $C_{3-10}$ cycloalkyl substituted with 0-3 $R^f$, —$(CH)_r$-phenyl substituted with 0-3 $R^d$, or —$(CH_2)_r$-5-7 membered heterocycle comprising carbon atoms and 1-4 heteroatoms selected from N, O, and $S(O)_p$ substituted with 0-3 $R^d$;

or one R¹¹ and a second R¹¹, both attached to the same nitrogen atom, combine to form a heterocycle comprising carbon atoms and 1-4 heteroatoms selected from N, O, and S(O)$_p$ substituted with 0-3 R$^d$;

R$^a$ is, independently at each occurrence, hydrogen, =O, halo, OCF$_3$, CF$_3$, CHF$_2$, CN, NO$_2$, —(CH$_2$)$_r$OR$^b$, —(CH$_2$)$_r$S(O)$_p$R$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR¹¹R¹¹, —(CH$_2$)$_r$C(O)NR¹¹R¹¹, —(CH$_2$)$_r$NR$^b$C(O)R, —(CH$_2$)$_r$NR$^b$C(O)OR$^c$, —NR$^b$C(O)NR¹¹R¹¹, —S(O)$_p$NR¹¹R¹¹, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle, or —(CH$_2$)$_r$-5-7 membered heterocycle comprising carbon atoms and 1-4 heteroatoms selected from N, O, and S(O)$_p$ substituted with 0-3 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, —(CH$_2$)$_r$-5-7 membered heterocycle comprising carbon atoms and 1-4 heteroatoms selected from N, O, and S(O)$_p$ substituted with 0-3 R$^f$, or —(CH$_2$)$_r$-6-10 carbocycle substituted with 0-3 R$^d$;

R$^c$ is, independently at each occurrence, C$_{1-6}$ alkyl substituted with 0-3 R$^f$, —(CH$_2$)$_r$—C$_{3-6}$ cycloalkyl substituted with 0-3 R$^f$, or —(CH$_2$)$_r$-phenyl substituted with 0-3 R$^f$;

R$^d$ is, independently at each occurrence, hydrogen, =O, halo, OCF$_3$, CF$_3$, CN, NO$_2$, —OR$^e$, —(CH$_2$)$_r$C(O)R$^c$, —NR$^e$R$^e$, —NR$^e$C(O)OR$^c$, C(O)NR$^e$R$^e$, —NR$^e$C(O)R$^c$, CO$_2$R$^c$, —NR$^e$SO$_2$R$^c$, SO$_2$R$^c$, C$_{1-6}$ alkyl substituted with 0-3 R$^f$, C$_{3-6}$ cycloalkyl substituted with 0-3 R$^f$, —(CH$_2$)$_r$-phenyl substituted with 0-3 R$^f$ or —(CH$_2$)$_r$-5-7 membered heterocycle comprising carbon atoms and 1-4 heteroatoms selected from N, O, and S(O)$_p$ substituted with 0-3 R$^f$;

R$^e$ is, independently at each occurrence, selected from hydrogen, C(O)NR$^f$R$^f$, C$_{1-6}$ alkyl, C$_{3-6}$ cycloalkyl, or —(CH$_2$)$_r$-phenyl substituted with 0-3 R$^f$;

R$^f$ is, independently at each occurrence, =O, halo, CN, NH$_2$, NH(C$_{1-6}$ alkyl), N(C$_{1-6}$ alkyl)$_2$, SO$_2$(C$_{1-6}$ alkyl), CO$_2$H, CO$_2$(C$_{1-6}$ alkyl), OH, C$_{3-6}$ cycloalkyl, CF$_3$ or O(C$_{1-6}$ alkyl);

or R$^f$ is, independently at each occurrence, an optionally substituted —(CH$_2$)$_r$-5-10 membered heterocycle comprising carbon atoms and 1-4 heteroatoms selected from N, O, and S(O), phenyl or C$_{3-6}$ cycloalkyl, each group optionally substituted with halo, CN, CF$_3$, C$_{1-6}$ alkyl or O(C$_{1-6}$ alkyl);

q and n are independently selected from 0, 1, 2 and 3;

p is 0, 1, or 2; and r is 0, 1, 2, 3, or 4.

In another aspect, there is provided a compound of Formula (I), or stereoisomers, tautomers, pharmaceutically acceptable salts, solvates, or prodrugs thereof, wherein R¹' is CF$_3$.

In another aspect, there is provided a compound of Formula (I), or stereoisomers, tautomers, pharmaceutically acceptable salts, solvates, or prodrugs thereof, wherein:

R¹ is halo, phenyl substituted with 0-3 R$^{1a}$, or C$_{1-6}$ alkyl substituted with 0-3 R$^{1a}$; and R$^{1a}$ is, independently at each occurrence, hydrogen, CF$_3$, halo, C$_{1-6}$ alkyl substituted with 0-3 R$^a$, —(CH$_2$)$_r$OR$^b$, and —(CH$_2$)$_r$-phenyl substituted with 0-3 R$^f$.

In another aspect, there is provided a compound of Formula (I), or stereoisomers, tautomers, pharmaceutically acceptable salts, solvates, or prodrugs thereof, wherein:
(CH$_2$)$_r$OR$^{2b}$, —(CH$_2$)$_r$C(O)R$^{2b}$, —(CH$_2$)$_r$OC(O)OR$^{2b}$, —(CH$_2$)$_r$OC(O)NR¹¹R¹¹, —(CH$_2$)$_r$NR$^{2b}$C(O)R$^{2c}$, —(CH$_2$)$_r$NR$^{2b}$C(O)OR$^{2c}$, —(CH$_2$)$_r$NR¹¹R¹¹, —(CH$_2$)$_r$NR$^{2b}$C(O)NR¹¹R¹¹, —NR$^{2b}$S(O)$_p$R$^c$, C$_{1-6}$ alkyl, —(CH$_2$)$_r$-4-10 membered heterocycle comprising carbon atoms, and 1-4 heteroatoms selected from N, O, and S(O)$_p$ substituted with 0-3 R$^{2a}$; or one R$^2$ together with an R$^2$ on an adjacent carbon combine to form a fused ring substituted with 0-3 R$^{2a}$, wherein the fused ring is selected from a 4-7 membered heterocycle comprising carbon atoms and 1-4 heteroatoms selected from N, O, and S(O)$_p$ substituted with 0-3 R$^{2a}$;

R$^{2a}$ is hydrogen, NR¹¹R¹¹, or C$_{1-6}$ alkyl substituted with 0-3 R$^a$;

R$^{2b}$ is hydrogen, (CH$_2$)$_r$NR¹¹R¹¹, C$_{1-6}$ alkyl substituted with 0-3 R$^a$, C$_{3-6}$ cycloalkyl substituted with 0-3 R$^a$, or 5-7 membered heterocycle comprising carbon atoms and 1-4 heteroatoms selected from N, O, and S(O)$_p$ substituted with 0-3 R$^a$, or —(CH$_2$)$_r$-phenyl substituted with 0-3 R$^a$;

R$^{2c}$ is independently at each occurrence hydrogen, C$_{1-6}$ alkyl substituted with 0-3 R$^a$, C$_{2-6}$ alkenyl substituted with 0-3 R$^a$, C$_{3-6}$ cycloalkyl substituted with 0-3 R$^a$, C$_{6-10}$ aryl substituted with 0-3 R$^a$, or a 5-10 membered heterocycle comprising carbon atoms and 1-4 heteroatoms selected from N, O, and S, substituted with 0-3 R$^a$;

R$^{2d}$ is, independently at each occurrence, hydrogen, C$_{1-6}$ alkyl substituted with 0-3 R$^d$, C$_{1-6}$ haloalkyl, C(O)NR¹¹R¹¹, C$_{3-6}$ cycloalkyl substituted with 0-2 R$^d$ (Preferably, cycloalkyl is cyclobutyl, cyclohexyl, or cyclopentyl substituted with 0-2 R$^d$), —(CH$_2$)$_r$-phenyl substituted with 0-2 R$^a$, or a 5-10 membered heterocycle containing 1-4 heteroatoms selected from N, O, and S(O)$_p$, substituted with 0-3 R$^a$ (Preferably, the heterocycle is furyl, morpholinyl, piperidinyl, piperazinyl, tetrahydropyranyl, aziridinyl, pyrolidinyl, pyridyl, or benzoisothiazolyl, each substituted with 0-3 R$^a$).

In another aspect, there is provided a compound of Formula (I), or stereoisomers, tautomers, pharmaceutically acceptable salts, solvates, or prodrugs thereof, wherein:

R$^3$ is hydrogen, halo, N$_3$, CN, OR$^{3b}$, —NH$_2$, NH(C$_{1-6}$ alkyl), N(C$_{1-6}$ alkyl)$_2$, C$_{1-6}$ alkyl substituted with 0-3 R$^{3a}$ or C$_{3-10}$ cycloalkyl substituted with 0-3 R$^{3a}$;

R$^{3a}$ is, independently at each occurrence, hydrogen, =O, halo, OCF$_3$, OCHF$_2$, CF$_3$, CHF$_2$, CN, NO$_2$, —(CH$_2$)$_r$OR$^b$, —(CH$_2$)rS(O)pRb, —(CH$_2$)$_r$C(O)R$^b$, —(CH$_2$)$_r$C(O)OR$^b$, —(CH$_2$)$_r$OC(O)R$^b$, —(CH$_2$)$_r$NR¹¹R¹¹, —(CH$_2$)$_r$C(O)NR¹¹R¹¹, —(CH$_2$)$_r$NR$^b$C(O)R$^c$, —(CH$_2$)$_r$NR$^b$C(O)OR$^c$, —NR$^b$C(O)NR¹¹R¹¹, —S(O)$_p$NR¹¹R¹¹, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CH$_2$)$_r$-3-14 membered carbocycle substituted with 0-3 R$^a$, a —(CH$_2$)$_r$-5-7 membered heteroaryl comprising carbon atoms and 1-4 heteroatoms selected from N, S or O substituted with 0-3 R$^a$, or a —(CH$_2$)$_r$-5-10 membered heterocycle comprising carbon atoms and 1-4 heteroatoms selected from N, O, and S(O)$_p$ substituted with 0-3 R$^a$; and R$^{3b}$ is, independently at each occurrence, hydrogen, C$_{1-6}$ alkyl substituted with 0-3 R$^a$ or phenyl substituted with 0-3 R$^a$.

In another aspect, there is provided a compound having the following formula:

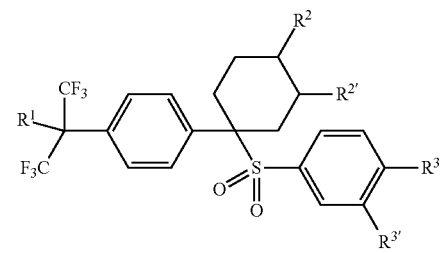

or stereoisomers, tautomers, pharmaceutically acceptable salts, solvates, or prodrugs thereof, wherein:

$R^1$ is hydrogen, $CF_3$, halo, $C_{1-6}$ alkyl substituted with 0-3 $R^a$, —$(CH_2)_rOR^b$, and —$(CH_2)_r$-phenyl substituted with 0-3 $R^a$;

$R^2$ and $R^{2'}$ are, independently at each occurrence, selected from hydrogen, =O, —$(CH_2)_rOR^{2b}$, —$(CH_2)_rC(O)R^{2b}$, —$(CH_2)_rOC(O)OR^{2b}$, —$(CH_2)_rOC(O) NR^{11}R^{11}$, —$(CH_2)_r NR^{2b}C(O)R^{2c}$, —$(CH_2)_r NR^{2b}C(O)OR^{2c}$, —$(CH_2)_r NR^{11}R^{11}$, —$NR^{2b}S(O)_pR^c$, —$(CH_2)_r$-5-7 membered heterocycle comprising carbon atoms, and 1-4 heteroatoms selected from N, O, and $S(O)_p$ substituted with 0-3 $R^{2a}$; or one $R^2$ together with an $R^2$ on an adjacent carbon combine to form a fused ring substituted with 0-3 $R^{2a}$, wherein the fused ring is selected from a 4-7 membered heterocycle comprising carbon atoms and 1-4 heteroatoms selected from N, O, and $S(O)_p$ substituted with 0-3 $R^{2a}$;

$R^{2a}$ is hydrogen, $NR^{11}R^{11}$, or $C_{1-6}$ alkyl substituted with 0-3 $R^a$;

$R^{2b}$ is hydrogen, $C_{1-6}$ alkyl substituted with 0-3 $R^a$, $C_{3-6}$ cycloalkyl substituted with 0-3 $R^a$, or 5-7 membered heterocycle comprising carbon atoms and 1-4 heteroatoms selected from N, O, and $S(O)_p$ substituted with 0-3 $R^a$, or —$(CH_2)_r$-phenyl substituted with 0-3 $R^a$;

$R^{2c}$ is independently at each occurrence hydrogen, $C_{1-6}$ alkyl substituted with 0-3 $R^a$, $C_{2-6}$ alkenyl substituted with 0-3 $R^a$, $C_{3-6}$ cycloalkyl substituted with 0-3 $R^a$, $C_{6-10}$ aryl substituted with 0-3 $R^a$, or a 5-10 membered heterocycle comprising carbon atoms and 1-4 heteroatoms selected from N, O, and S, substituted with 0-3 $R^a$;

$R^{2d}$ is, independently at each occurrence, hydrogen, $C_{1-6}$ alkyl substituted with 0-3 $R^d$ (Me) $C_{1-6}$ haloalkyl, $C(O) NR^{11}R^{11}$, $C_{3-6}$ cycloalkyl substituted with 0-2 $R^d$, or —$(CH_2)_r$-phenyl substituted with 0-2 $R^a$, a 5-10 membered heterocycle comprising carbon atoms and 1-4 heteroatoms selected from N, O, and S, substituted with 0-3 $R^a$;

$R^3$ and $R^{3'}$ are, independently, hydrogen, halo, $N_3$, CN, $OR^{3b}$, —$NH_2$, $NH(C_{1-6}$ alkyl), $N(C_{1-6}$ alkyl)$_2$, $C_{1-6}$ alkyl substituted with 0-3 $R^{3a}$ or $C_{3-10}$ cycloalkyl substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CH_2)_rOR^b$, —(CH2)rS(O)pRb, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CH_2)_r$-3-14 membered carbocycle substituted with 0-3 $R^a$, or a —$(CH_2)_r$-5-10 membered heterocycle comprising carbon atoms and 1-4 heteroatoms selected from N, O, and $S(O)_p$ substituted with 0-3 $R^a$;

$R^{3b}$ is, independently at each occurrence, hydrogen, $C_{1-6}$ alkyl substituted with 0-3 $R^a$ or phenyl substituted with 0-3 $R^a$;

$R^{11}$ is, independently at each occurrence, hydrogen, $C_{1-6}$ alkyl substituted with 0-3 $R^f$, $CF_3$, $C_{3-10}$ cycloalkyl substituted with 0-3 $R^f$, —$(CH)_r$-phenyl substituted with 0-3 $R^d$, or —$(CH_2)_r$-5-7 membered heterocycle comprising carbon atoms and 1-4 heteroatoms selected from N, O, and $S(O)_p$ substituted with 0-3 $R^d$;

$R^a$ is, independently at each occurrence, hydrogen, =O, halo, $OCF_3$, $CF_3$, $CHF_2$, CN, $NO_2$, —$(CH_2)_rOR^b$, —(CH2)rS(O)pRb, —$(CH_2)_rC(O)R^b$, —$(CH_2)_rC(O)OR^b$, —$(CH_2)_rOC(O)OR^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O) NR^{11}R^{11}$, —$S(O)_pNR^{11}R^{11}$, —$NR^bS(O)_pR^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle, or —$(CH_2)_r$-5-7 membered heterocycle comprising carbon atoms and 1-4 heteroatoms selected from N, O, and $S(O)_p$ substituted with 0-3 $R^f$;

$R^b$ is, independently at each occurrence, hydrogen, $C_{1-6}$ alkyl substituted with 0-3 $R^d$, $C_{1-6}$ haloalkyl, $C_{3-6}$ cycloalkyl substituted with 0-3 $R^d$, or —$(CH_2)_r$-5-7 membered heterocycle comprising carbon atoms and 1-4 heteroatoms selected from N, O, and $S(O)_p$ substituted with 0-3 $R^f$, or $(CH_2)_r$-6-10 carbocycle substituted with 0-3 $R^d$;

$R^c$ is, independently at each occurrence, $C_{1-6}$ alkyl substituted with 0-3 $R^f$, —$(CH_2)_r$—$C_{3-6}$ cycloalkyl substituted with 0-3 $R^f$, —$(CH_2)_r$-phenyl substituted with 0-3 $R^f$, or $R^d$ is, independently at each occurrence, hydrogen, =O, halo, $OCF_3$, $CF_3$, CN, $NO_2$, —$OR^e$, —$(CH_2)_rC(O)R^c$, —$NR^eR^e$, —$NR^eC(O)OR^c$, —$C(O)NR^eR^e$, —$NR^eC(O)R^c$, $CO_2R^c$, —$NR^eSO_2R^c$, $SO_2R^c$, $C_{1-6}$ alkyl substituted with 0-3 $R^f$, $C_{3-6}$ cycloalkyl substituted with 0-3 $R^f$, —$(CH_2)_r$-phenyl substituted with 0-3 $R^f$ or —$(CH_2)_r$-5-7 membered heterocycle comprising carbon atoms and 1-4 heteroatoms selected from N, O, and $S(O)_p$ substituted with 0-3 $R^f$;

$R^e$ is, independently at each occurrence, selected from hydrogen, $C(O)NR^fR^f$, $C_{1-6}$ alkyl, $C_{3-6}$ cycloalkyl, and —$(CH_2)_r$-phenyl substituted with 0-3 $R^f$;

$R^f$ is, independently at each occurrence, hydrogen, =O, halo, CN, $NH_2$, $NH(C_{1-6}$ alkyl), $N(C_{1-6}$ alkyl)$_2$, $SO_2(C_{1-6}$ alkyl), $CO_2H$, $CO_2(C_{1-6}$ alkyl), OH, $C_{3-6}$ cycloalkyl, $CF_3$ or $O(C_{1-6}$ alkyl);

or $R^f$ is, independently at each occurrence, an optionally substituted —$(CH_2)_r$-5-10 membered heteroaryl comprising carbon atoms and 1-4 heteroatoms selected from N, O, and S(O), phenyl or $C_{3-6}$ cycloalkyl, each group optionally substituted with halo, CN, $CF_3$, $C_{1-6}$ alkyl or $O(C_{1-6}$ alkyl);

p is 0, 1, or 2; and r is 0, 1, 2, 3, or 4.

In another aspect, there is provided a compound of Formula (I), or stereoisomers, tautomers, pharmaceutically acceptable salts, solvates, or prodrugs thereof, wherein $R^1$ is

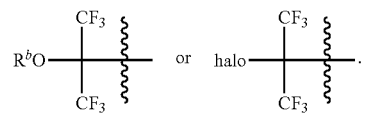

In another aspect, there is provided a compound of Formula (I), or stereoisomers, tautomers, pharmaceutically acceptable salts, solvates, or prodrugs thereof, wherein $R^{2'}$ is hydrogen.

In another aspect, there is provided a compound of Formula (I), or stereoisomers, tautomers, pharmaceutically acceptable salts, solvates, or prodrugs thereof, wherein

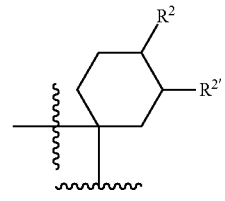

is selected from:
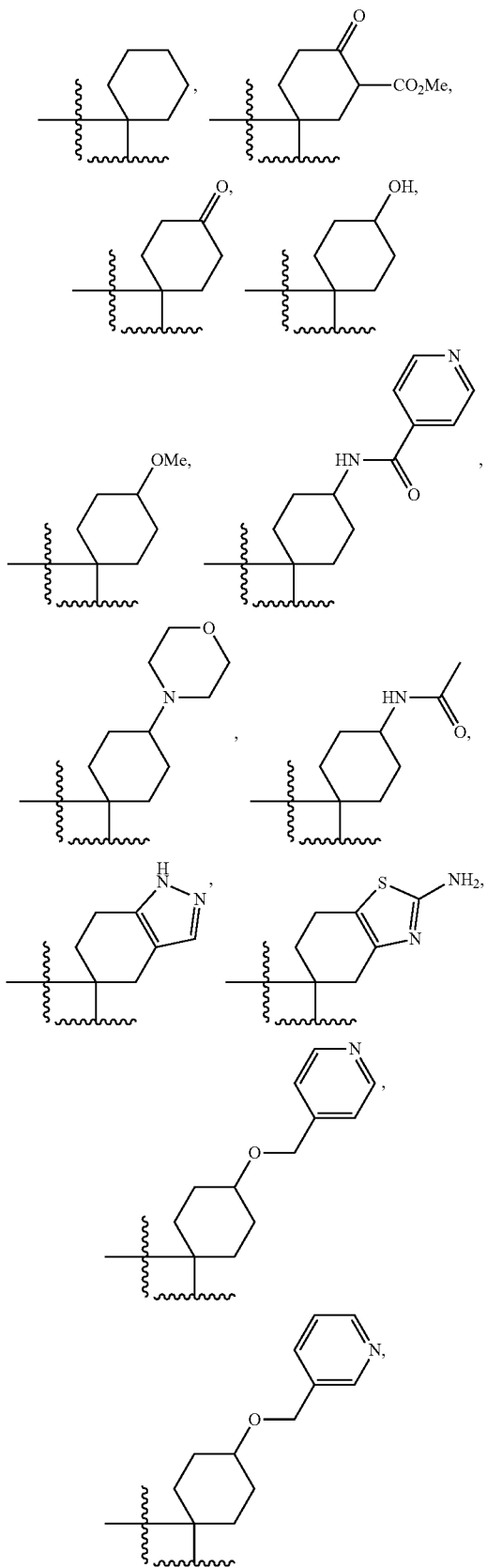
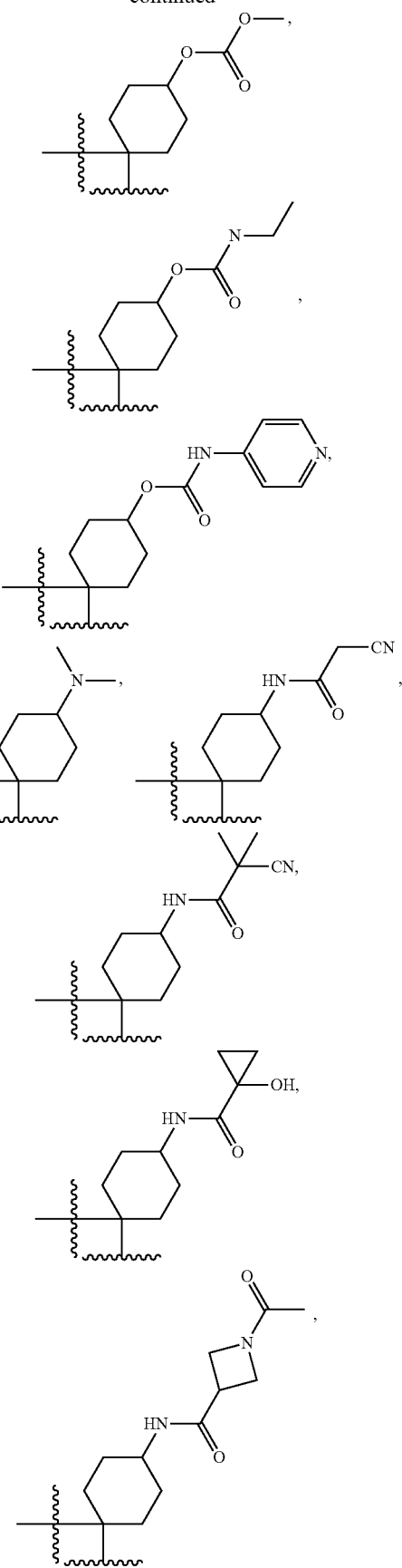

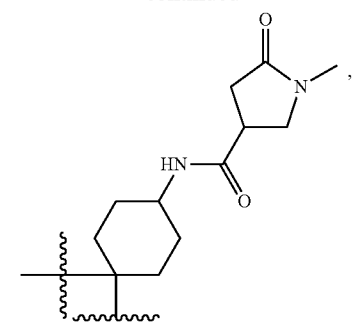
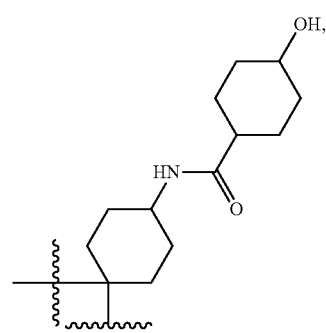
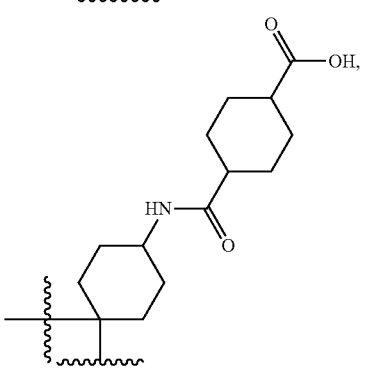
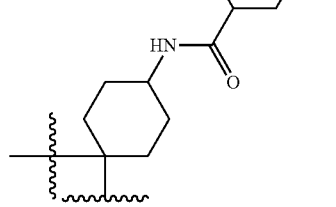
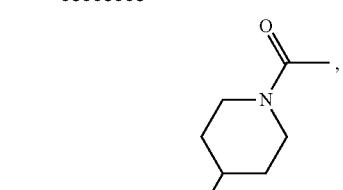
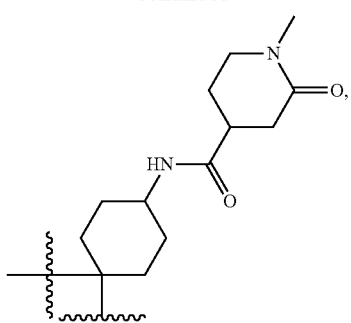
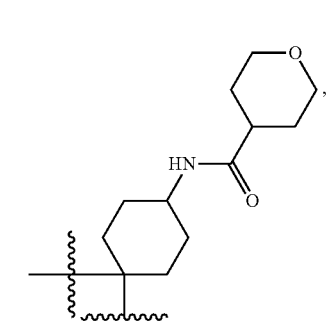
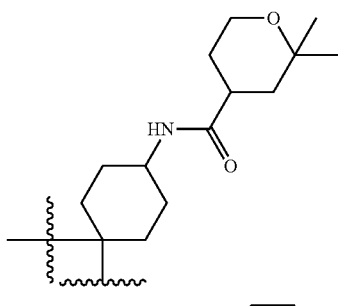
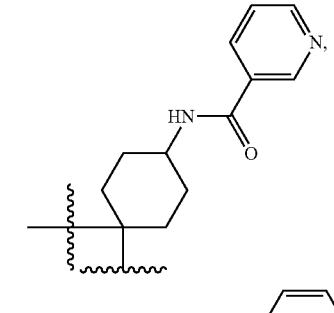
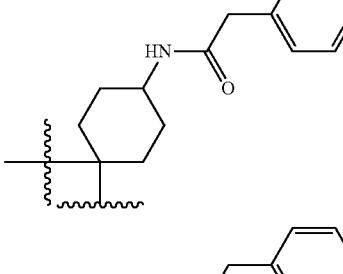

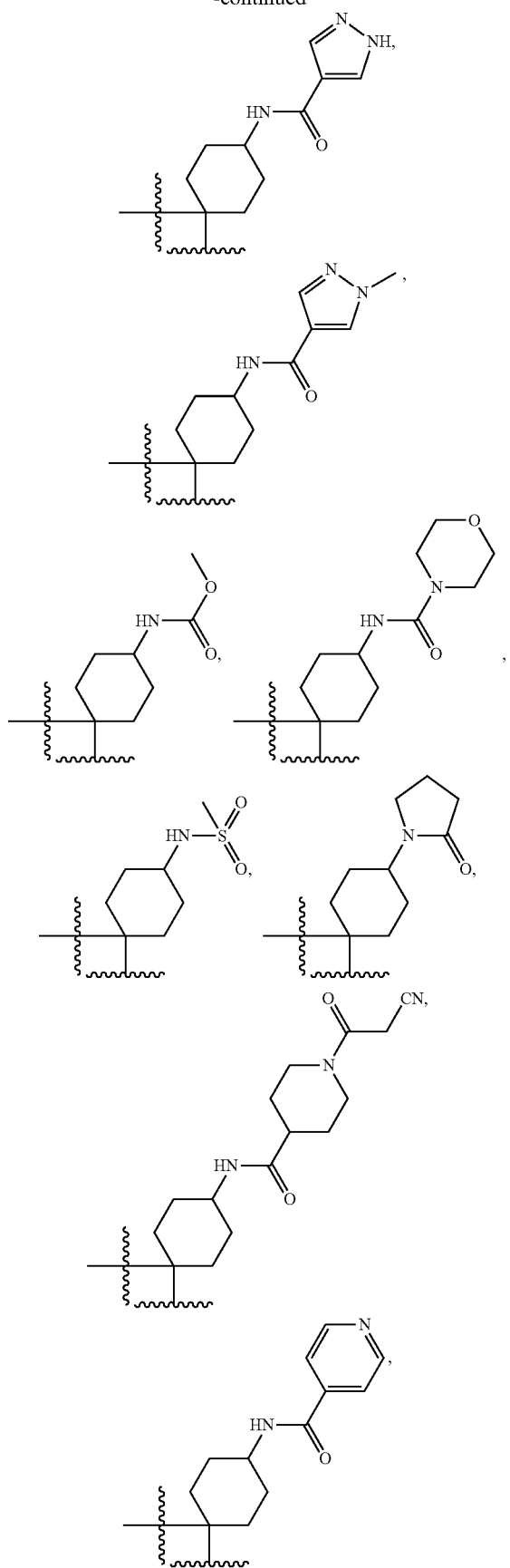
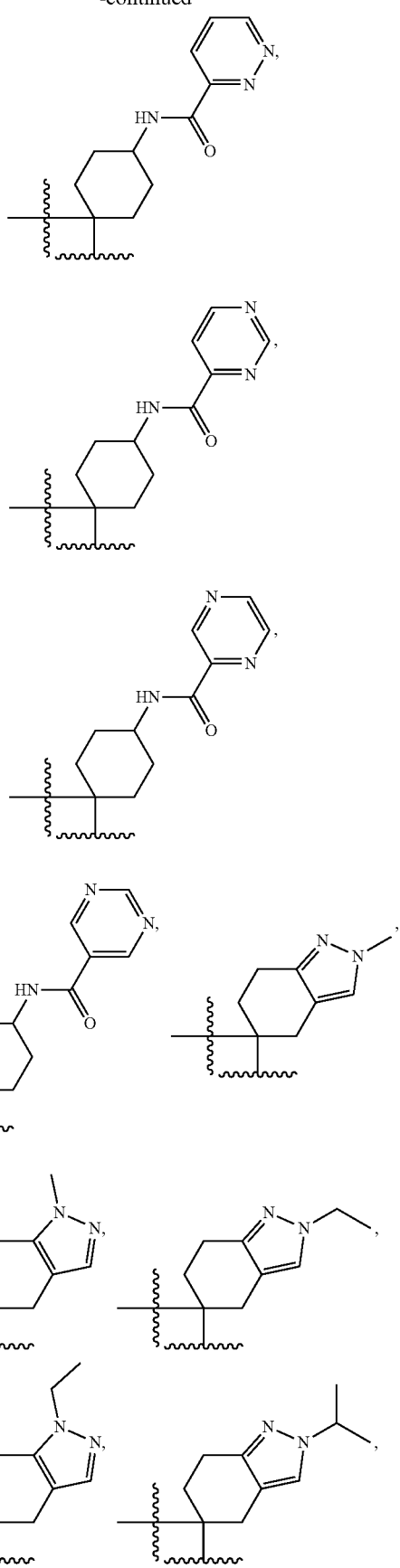

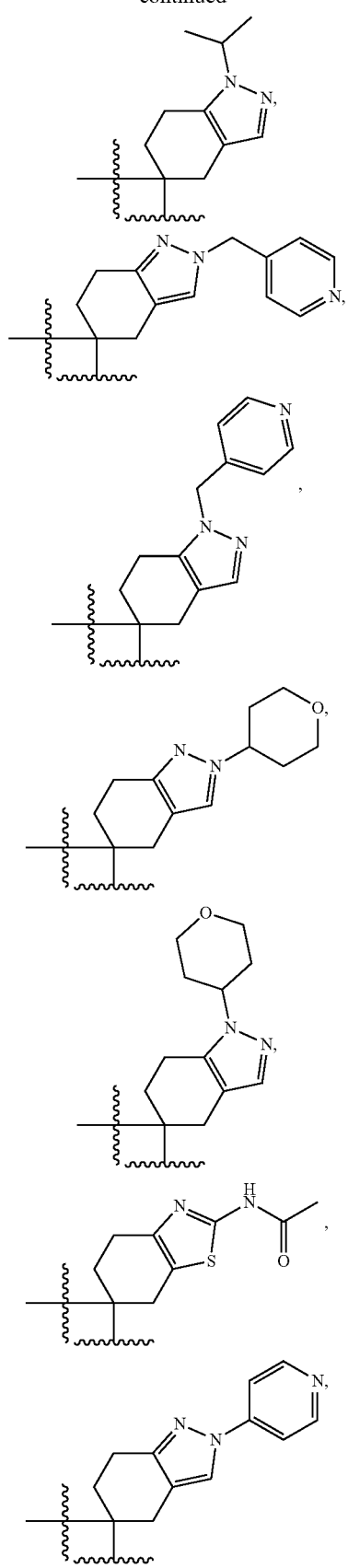
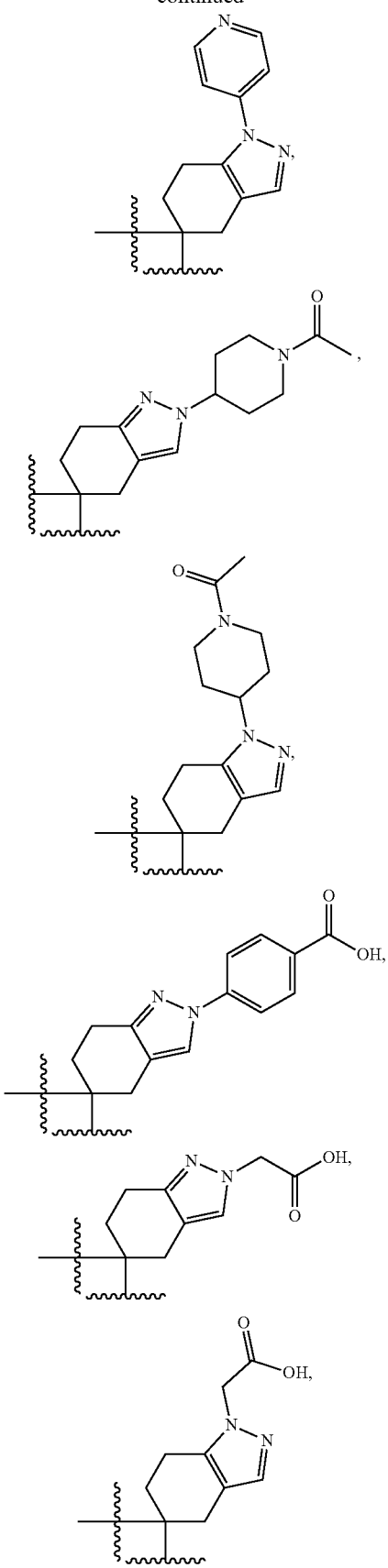

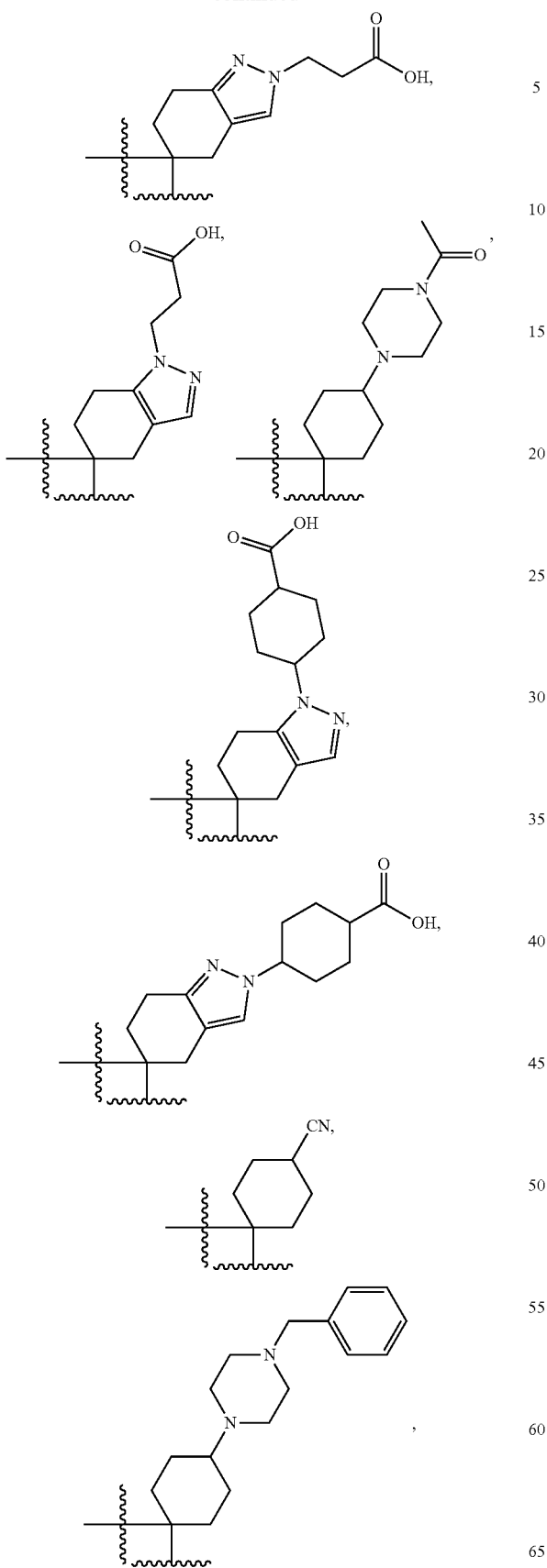
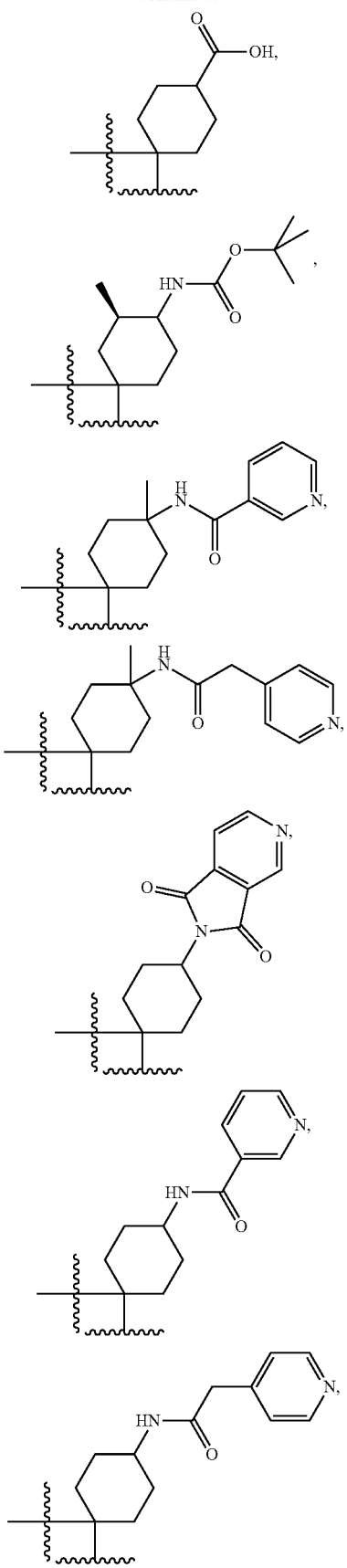

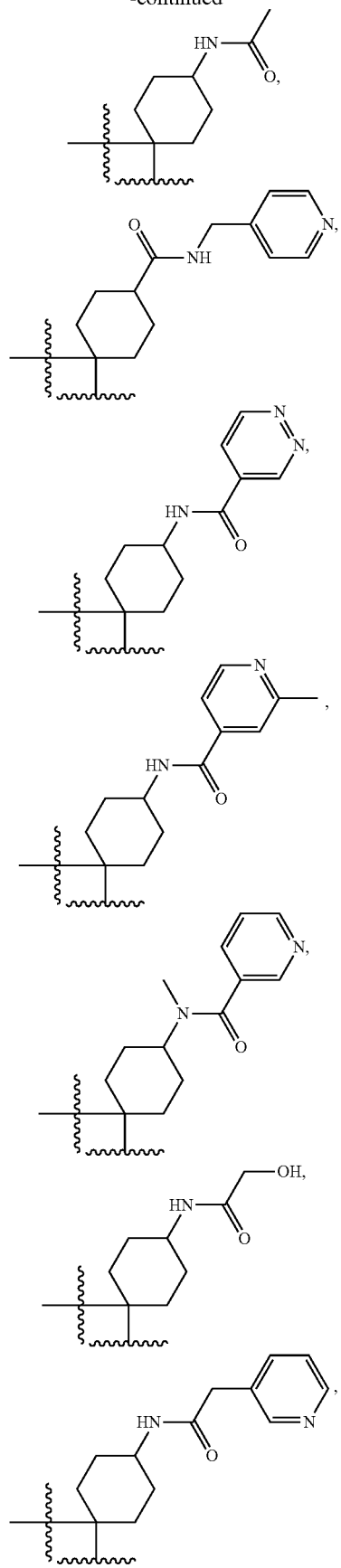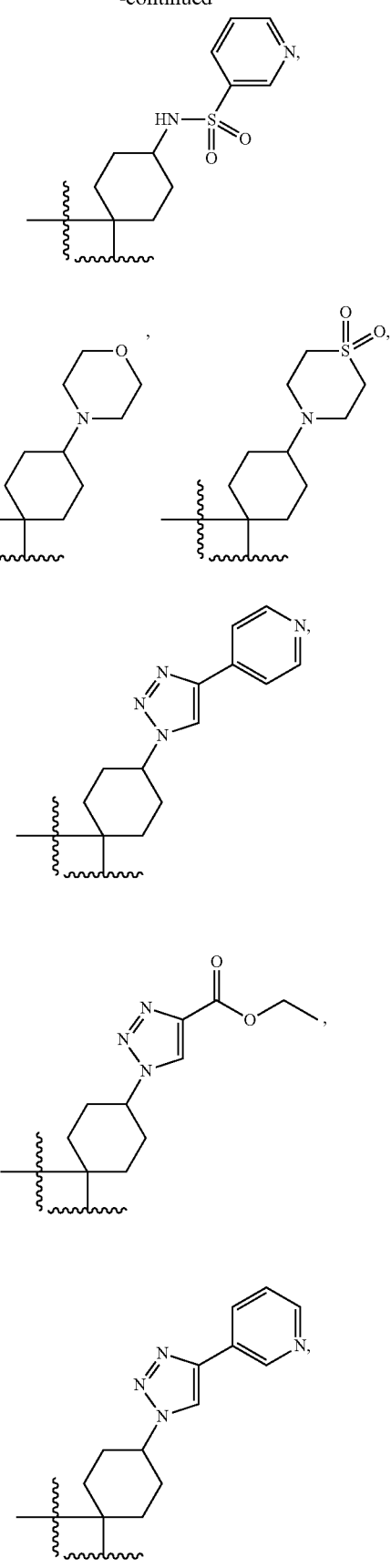

21
-continued
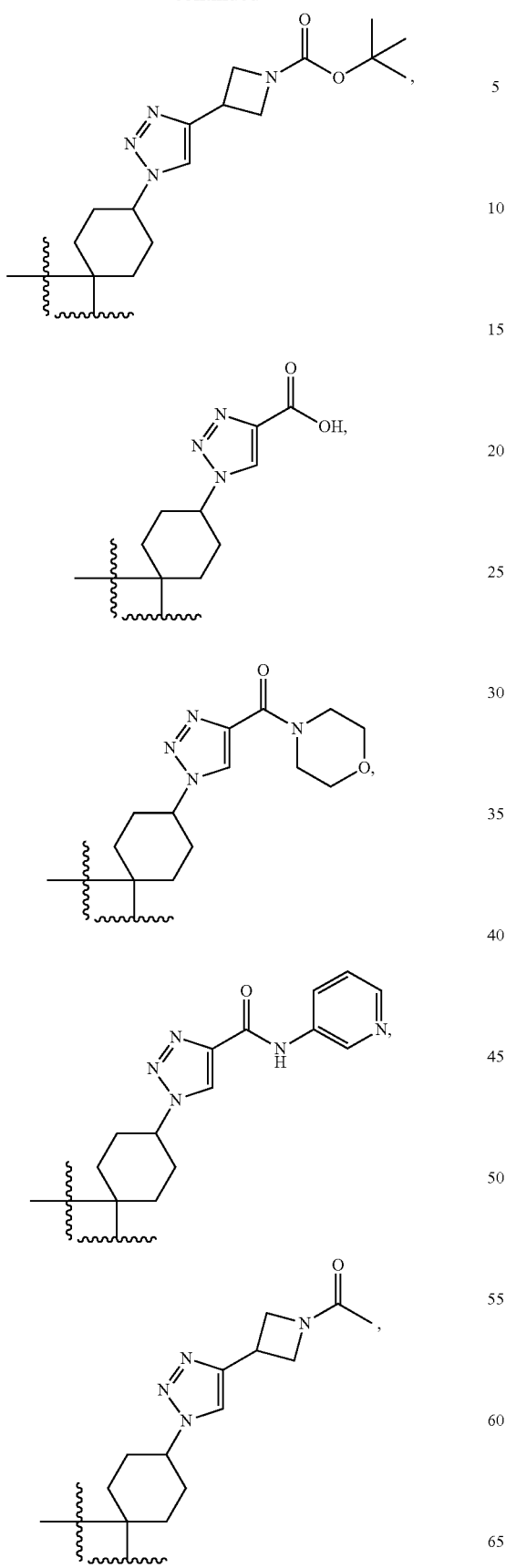
22
-continued
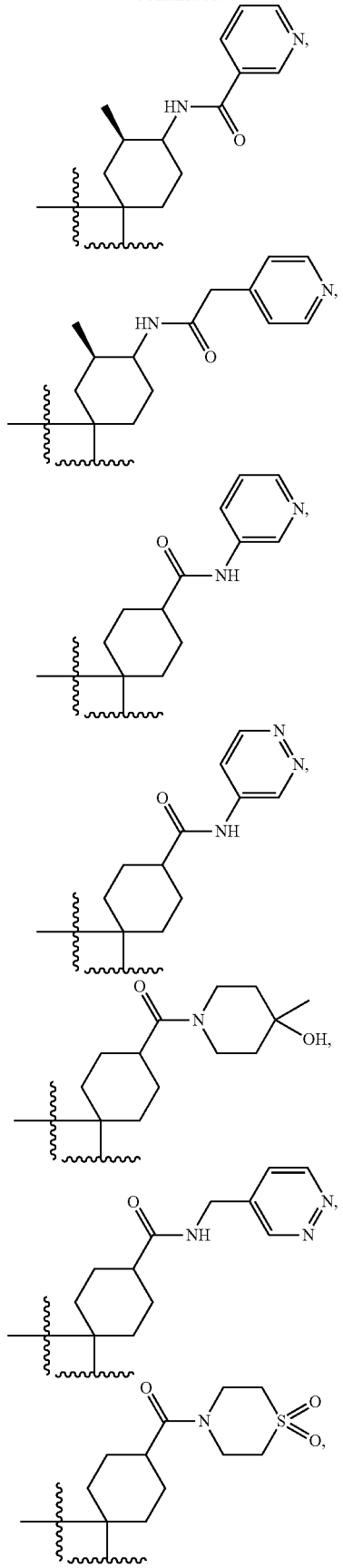

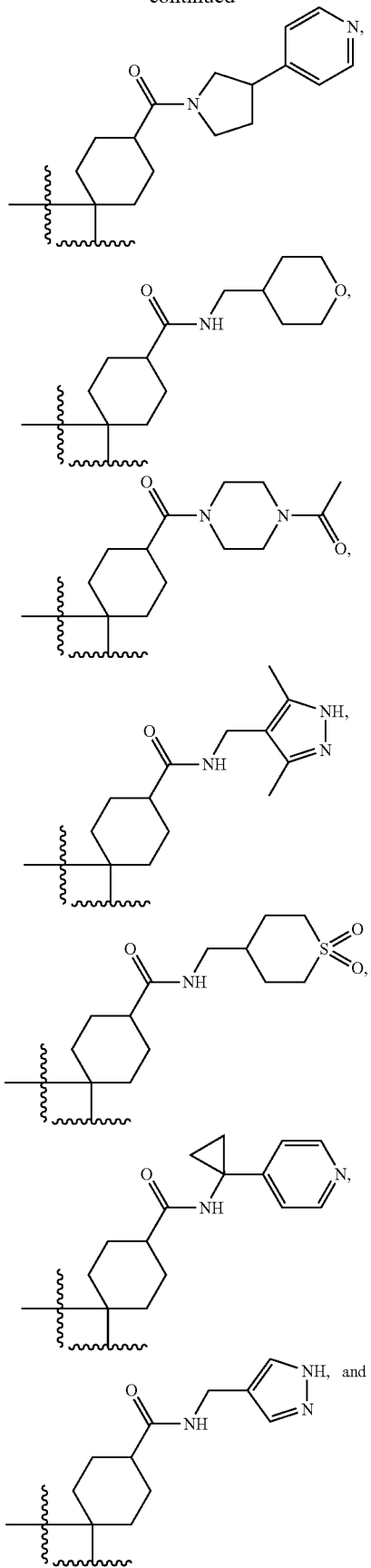

In another aspect, there is provided a compound of Formula (I), or stereoisomers, tautomers, pharmaceutically acceptable salts, solvates, or prodrugs thereof, wherein $R^3$ is halo and $R^{3'}$ is hydrogen.

In another aspect, there is provided a compound of Formula (I), or stereoisomers, tautomers, pharmaceutically acceptable salts, solvates, or prodrugs thereof, wherein $R^3$ and $R^{3'}$ are, independently, hydrogen, halo, $N_3$, CN, —O(phenyl), —$NH_2$, NH($C_{1-6}$ alkyl), N($C_{1-6}$ alkyl)$_2$, $C_{1-6}$ alkyl or $C_{3-6}$ cycloalkyl. Preferably, $R^3$ is F, H, OMe, $NH_2$, $N_3$, CN, OPh, cyclopropyl, or $CH_3$, and $R^{3'}$ is hydrogen. More preferably $R^3$ is F and $R^{3'}$ is hydrogen.

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

In another embodiment, the invention provides a compound of the present invention for use in treating diseases (or a method of treating diseases) in which inflammation is a component including, without limitation, diseases such as psoriasis, rheumatoid arthritis, inflammatory bowel disease, Crohn's disease, ulcerative colitis, acute graft-versus-host disease, psoriatic arthritis, ankylosing spondylitis and multiple sclerosis.

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —CONH$_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound."

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

One skilled in the field will understand that, when the designation "CO$_2$" is used herein, this is intended to refer to the group

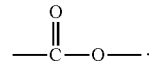

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl. The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, S(O)$_2$H, or S(O)H group.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3, 4, 5, 6, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Accordingly, in compounds of formula I, the term "cycloalkyl" includes cyclopropyl, cyclobutyl, cyclopentyl, cyclohexyl, cycloheptyl, bicyclooctyl, etc., as well as the following ring systems:

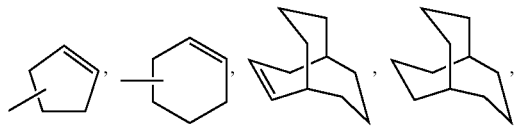

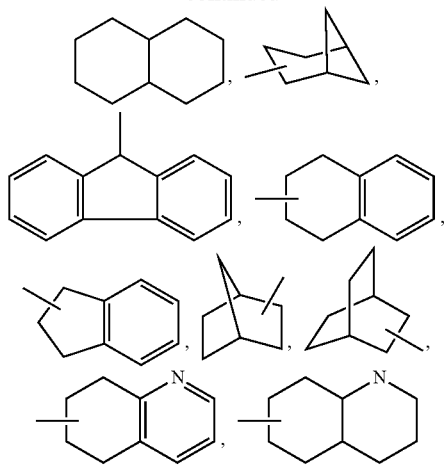

and the like, which optionally may be substituted at any available atoms of the ring(s). Preferred cycloalkyl groups include cyclopropyl, cyclopentyl, cyclohexyl, and

The term "halo" or "halogen" refers to chloro, bromo, fluoro and iodo.

The term "haloalkyl" means a substituted alkyl having one or more halo substituents. For example, "haloalkyl" includes mono, di, and trifluoromethyl.

The term "haloalkoxy" means an alkoxy group having one or more halo substituents. For example, "haloalkoxy" includes OCF$_3$.

Thus, examples of aryl groups include:

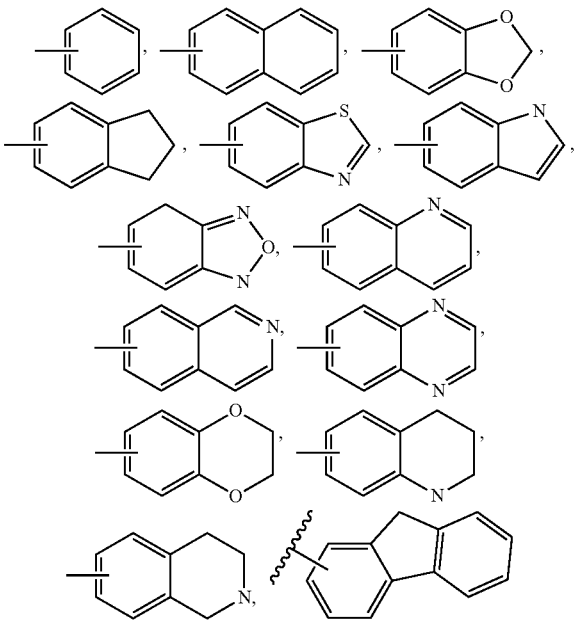

(fluorenyl) and the like, which optionally may be substituted at any available carbon or nitrogen atom. A preferred aryl group is optionally-substituted phenyl.

The terms "heterocycle", "heterocycloalkyl", "heterocyclo", "heterocyclic", or "heterocyclyl" may be used interchangeably and refer to substituted and unsubstituted 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or fully unsaturated. The heterocyclo group may be attached at any available nitrogen or carbon atom. As used herein the terms "heterocycle", "heterocycloalkyl", "heterocyclo", "heterocyclic", and "heterocyclyl" include "heteroaryl" groups, as defined below.

In addition to the heteroaryl groups described below, exemplary monocyclic heterocycle groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include

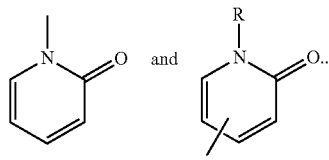

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

In compounds of formula I, preferred heteroaryl groups include

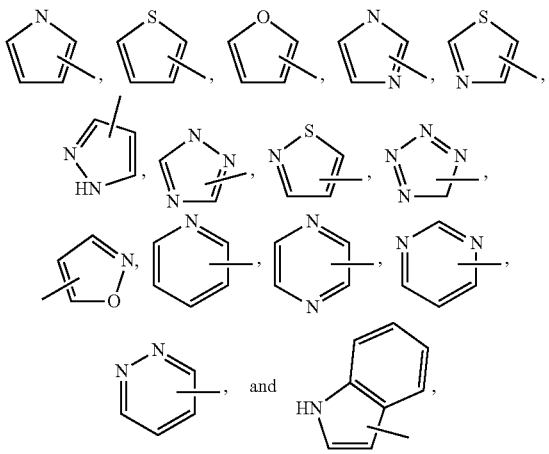

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0 to 2, substituents selected from those recited above for the aryl, cycloalkyl, heterocyclo and/or heteroaryl groups, as appropriate.

The terms "carbocycle", "carbocyclyl" or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula I may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s)" may include zwitterions (inner salts), e.g., when a compound of formula I, contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Any compound that will be converted in vivo to provide the bioactive agent (i.e., the compound for formula I) is a prodrug within the scope and spirit of the invention. For example, compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$ alkanoyloxy-$C_{1-6}$alkyl, e.g., acetoxymethyl, pivaloyloxymethyl or propionyloxymethyl, $C_{1-6}$alkoxycarbonyloxy-$C_{1-6}$ alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:
a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and
c) Bundgaard, H., *Adv. Drug Deliv. Rev.*, 8:1-38 (1992), each of which is incorporated herein by reference.

Compounds of the formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers.

It should further be understood that solvates (e.g., hydrates) of the compounds of Formula I are also with the scope of the present invention. Methods of solvation are generally known in the art.

Another aspect of the invention is a pharmaceutical composition including a compound, stereoisomeric form, pharmaceutical salt, solvate or hydrate as described herein. The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by U.S. regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the subject by employing procedures known in the art.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a subject will vary depending upon what is being administered, the purpose of the administration, such as prophylaxis or therapy, the state of the subject, the manner of administration, and the like. In therapeutic applications, compositions can be administered to a subject already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the subject, and the like.

The compositions administered to a subject can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the subject, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular subject, the relative biological efficacy of the compound selected, formulation of the excipient, and its route of administration. Effective doses can be extrapolated from dose-response curves derived from in vitro or animal model test systems.

The compounds of the present invention are useful to prevent, diagnose, and treat various medical disorders in humans or animals. The compounds are used to inhibit or reduce one or more activities associated with RORγ receptors, relative to RORγ receptors in the absence of the same compounds. Thus, in one aspect of the invention, a method for treating a disease or disorder selected from an autoimmune disease or disorder, asthma, an allergic disease or disorder, a metabolic disease or disorder, and cancer in a subject comprises administering to the subject a therapeutically effective amount of compound according to formula (I), stereoisomeric form, N-oxide, pharmaceutically acceptable salt, solvate, hydrate or pharmaceutical composition as described herein. See, e.g., L. A. Solt et al., "Action of RORs and their ligands in (patho)physiology," *Trends Endocrinol Metab.*, preprint available online Jul. 11, 2012 at http://www.sciencedirect.com/science/article/pii/S1043276012000926; M. S. Maddur et al., "Th17 cells: biology, pathogenesis of autoimmune and inflammatory diseases, and therapeutic strategies," *Am. J. Pathol.* 2012 July; 181(1):8-18; and A. M. Jetten, "Retinoid-related orphan receptors (RORs): critical roles in development, immunity, circadian rhythm, and cellular metabolism," *Nucl. Recept. Signal.* 2009; 7:e003, each of which is hereby incorporated herein by reference in its entirety, as well as the references discussed in the Background section. In certain embodiments, the autoimmune disease or disorder is selected from rheumatoid arthritis, ankylosing spondylitis, psoriasis and psoriatic arthritis, multiple sclerosis, inflammatory bowel diseases and lupus. In certain embodiments, the allergic disease or disorder is selected from allergic rhinitis and dermatitis. In certain embodiments, the metabolic disease or disorder is selected from obesity, obesity-induced insulin resistance and type II diabetes.

In certain embodiments, the disease or disorder is rheumatoid arthritis. See, e.g., L. A. Solt et al., referenced above, as well as the references discussed in the Background section.

In other embodiments, the disease or disorder is multiple sclerosis. See, e.g., L. Codarri et al., "RORγt drives production of the cytokine GM-CSF in helper T cells, which is essential for the effector phase of autoimmune neuroinflammation," Nat. Immunol., 2011 June; 12(6):560-7, which is hereby incorporated herein by reference in its entirety, as well as the references discussed in the Background section.

In other embodiments, the disease or disorder is ankylosing spondylitis. See, e.g., E. Toussirot, "The IL23/Th17 pathway as a therapeutic target in chronic inflammatory diseases," Inflamm. Allergy Drug Targets, 2012 April; 11(2): 159-68, which is hereby incorporated herein by reference in its entirety, as well as the references discussed in the Background section.

In other embodiments, the disease or disorder is inflammatory bowel disease. See, e.g., M. Leppkes et al., "ROR-gamma-expressing Th17 cells induce murine chronic intestinal inflammation via redundant effects of IL-17A and IL-17F," Gastroenterology, 2009 January; 136(1):257-67, which is hereby incorporated herein by reference in its entirety, as well as the references discussed in the Background section.

In other embodiments, the disease or disorder is lupus. See, e.g., K. Yoh et al., "Overexpression of RORγt under control of the CD2 promoter induces polyclonal plasmacytosis and autoantibody production in transgenic mice," Eur. J. Immunol., 2012 August; 42(8): 1999-2009, which is hereby incorporated herein by reference in its entirety, as well as the references discussed in the Background section.

In other embodiments, the disease or disorder is psoriasis. See, e.g., S. Pantelyushin et al., "RORγt+ innate lymphocytes and γδ T cells initiate psoriasiform plaque formation in mice," J. Clin. Invest., 2012 Jun. 1; 122(6):2252-6; and S. P. Raychaudhuri, "Role of IL-17 in Psoriasis and Psoriatic Arthritis," Clin. Rev. Allergy Immunol., preprint available online Feb. 24, 2012 at http://rd.springer.com/article/10.1007/s12016-012-8307-1 (PubMed PMID: 22362575), each of which is hereby incorporated herein by reference in its entirety, as well as the references discussed in the Background section.

In other embodiments, the disease or disorder is psoriatic arthritis. See, e.g., S. P. Raychaudhuri, referenced above, as well as the references discussed in the Background section.

In other embodiments, the disease or disorder is graft-vs.-host disease (GVHD). Y. Yu et al., "Prevention of GVHD while sparing GVL effect by targeting Th1 and Th17 transcription factorT-bet and RORγt in mice," Blood, 2011 Nov. 3; 118(18):5011-20, which is hereby incorporated herein by reference in its entirety, as well as the references discussed in the Background section.

In other embodiments, the disease or disorder is autoimmune uveitis. See, e.g., R. Horai et al., "Cytokines in autoimmune uveitis," J. Interferon Cytokine Res., 2011 October; 31(10):733-44, which is hereby incorporated herein by reference in its entirety, as well as the references discussed in the Background section.

In other embodiments, the disease or disorder is obesity and/or insulin resistance. See, e.g., B. Meissburger et al., "Adipogenesis and insulin sensitivity in obesity are regulated by retinoid-related orphan receptor gamma," EMBO Mol. Med., 2011 Nov.; 3(11):637-51, which is hereby incorporated herein by reference in its entirety, as well as the references discussed in the Background section.

In other embodiments, the disease or disorder is melanoma. See, e.g., Purwar R, et al. Robust tumor immunity to melanoma mediated by interleukin-9-producing T cells. Nat. Med., 2012 July:18:1248-53, which is hereby incorporated herein by reference in its entirety, as well as the references discussed in the Background section.

In certain aspects, the medical disorder being diagnosed, treated, or prevented by use of the presently disclosed compounds can be, for example, an autoimmune disorder. In other embodiments, the disorder being diagnosed, treated or prevented by use of the presently disclosed compounds can be an inflammatory disorder. For example, in certain embodiments, the disorder is selected from arthritis, diabetes, multiple sclerosis, uveitis, rheumatoid arthritis, psoriasis, asthma, bronchitis, allergic rhinitis, chronic obstructive pulmonary disease, atherosclerosis, H. pylori infection and inflammatory bowel disease. In other embodiments, the disorder is selected from Crohn's disease, ulcerative colitis, sprue and food allergies. In other embodiments, the disorder is experimental autoimmune encephalomyelitis, imiquimod-induced psoriasis, colitis or allergic airway disease.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; or (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; (ii) eliciting the biological or medicinal response that is being sought in a tissue, system, animal, individual or human by a researcher, veterinarian, medical doctor or other clinician; or (iii) inhibiting the referenced disease state; for example, inhibiting a disease, condition or disorder in an individual who is experiencing or displaying the pathology or symptomatology of the disease, condition or disorder.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products.

Scheme 1 illustrates a general synthesis of cyclohexane derivatives 7 and 12. Appropriately functionalized benzyl halide 1 can be reacted with functionalized thiophenol 2 using a base such as potassium carbonate or sodium hydroxide in a solvent such as tetrahydrofuran, ethanol or N,N-dimethylformamide to provide sulfide intermediate 3. Oxidation of 3 to sulfone 4 can be accomplished with mCPBA or other oxidant such as oxone and sodium tungstate. Sulfone 4 can also be synthesized in one step by treating 1 with sodium benzenesulfinate 5 in a solvent such as N,N-dimethylformamide. Treatment of 4 with appropriately functionalized 1,5-di-halo-pentane 6 (di-chloro, di-bromo, or di-iodo) with a base such as sodium hydride can lead to cyclohexane product 7. Alternatively, using a base such as potassium tert-butoxide, sulfone 4 can react with two equivalents of tert-butyl acrylate via double Michael additions followed by Dieckmann condensation to produce β-keto ester 8. Upon treatment with an acid (such as trifluoroacetic acid) at elevated temperature, β-keto ester 8 can undergo t-butyl ester hydrolysis and subsequent de-carboxylation to yield cyclohexanone 9. Reaction of 9 with hydroxylamine hydrochloride in the presence of pyridine can produce oxime 10, which can be converted to amine 11 using hydrogen and Raney nickel as a catalyst.

The amine group of compound 11 can be functionalized using various well known transformations to give 12. Examples of these transformations include, but are not limited to, alkylation reaction with alkyl halide and a base such as Hunig's base, reductive alkylation with aldehyde/ketone and a reducing reagent such as sodium triacetoxyborohydride, coupling reaction with carboxylic acid using an activating agent such as BOP or HOBt/EDC, and other acylation reactions using acid chloride, anhydride, chloroformate, isocyanate, and sulfonyl chloride. The cis and trans isomers of 11 can be separated and carried on individually to 12, or separated at the final product 12.

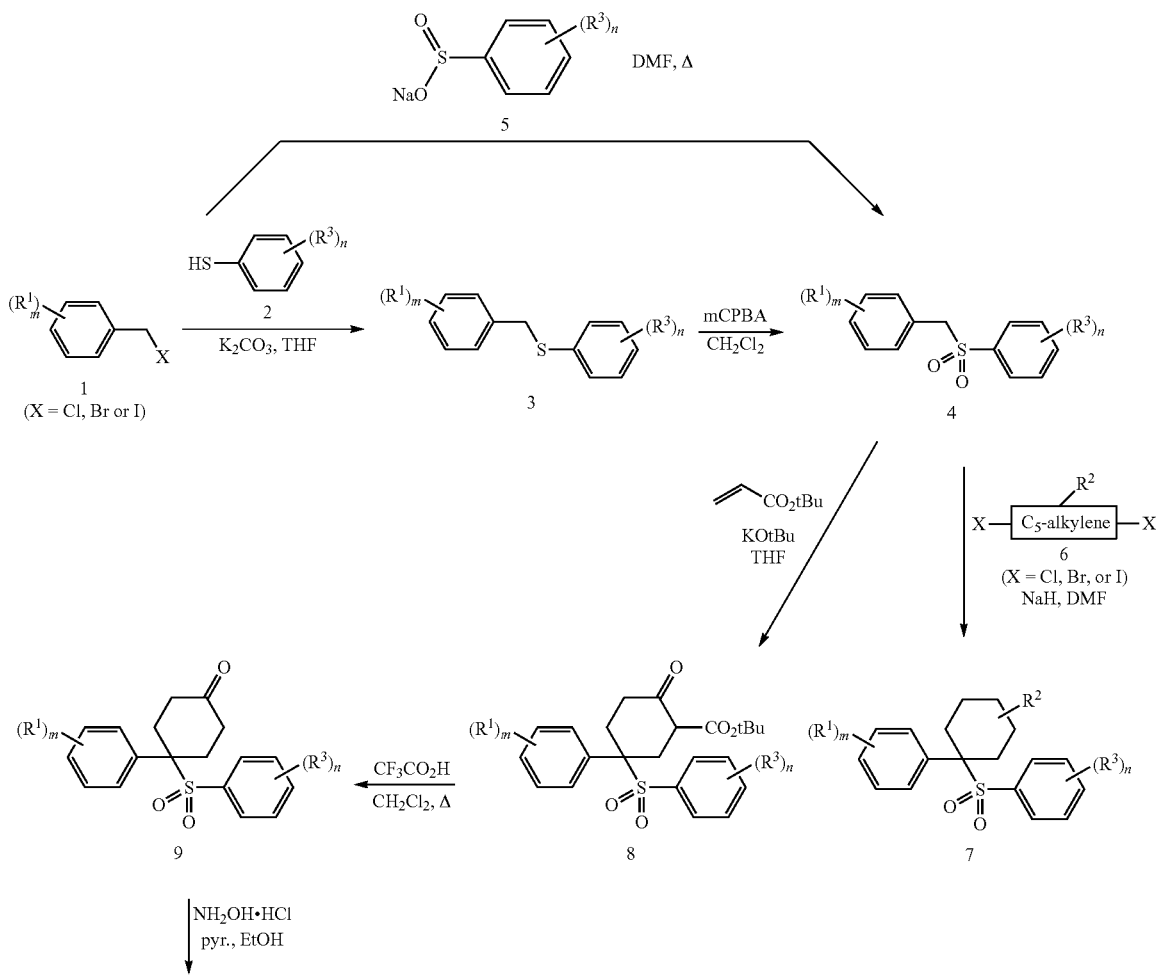

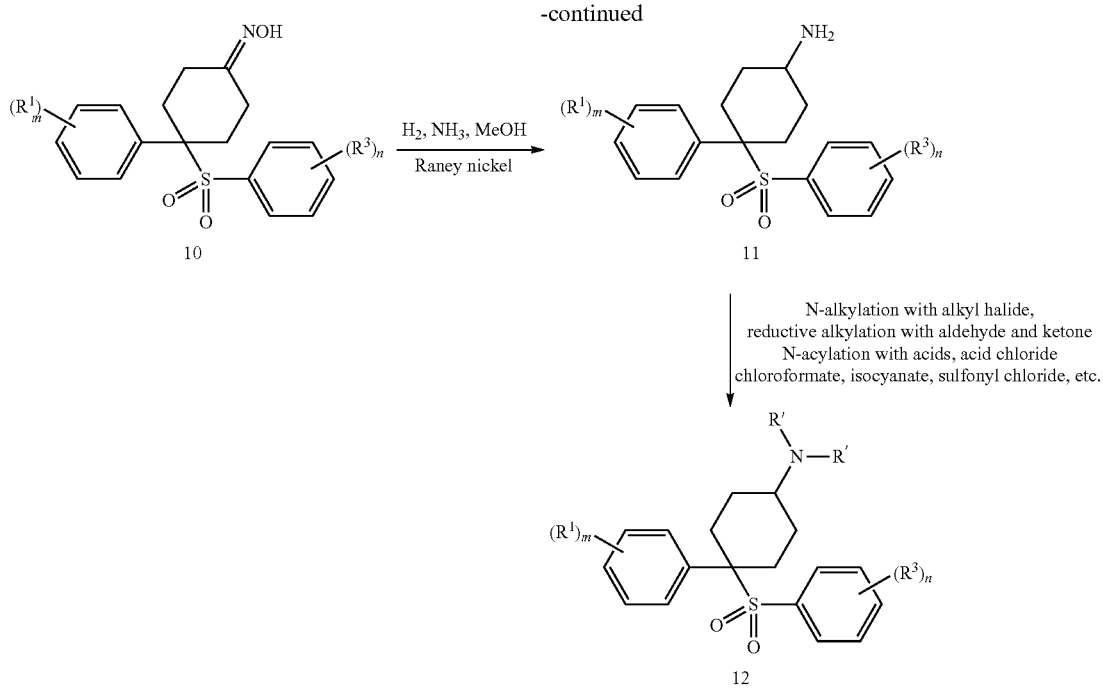

Scheme 2 illustrates a synthesis of a series of cyclohexanes where $R^1$ is 1,1,1,3,3,3-hexafluoro-2-hydroxypropan-2-yl group. Commercially available 1,1,1,3,3,3-hexafluoro-2-(p-tolyl)propan-2-ol (13) can be selectively brominated with N-bromosuccinimide in refluxing carbon tetrachloride using AIBN as a radical initiator to yield bromide 14. Reaction of 14 with sodium benzenesulfinate 5 in a solvent such as N,N-dimethylformamide can lead to sulfone product 15. The hydroxyl group in 15 can be protected as a benzyl ether using conditions such as benzyl bromide and potassium carbonate in N,N-dimethylformamide to give 16. Following conditions described for Scheme 1, sulfone 15 can be converted to cyclohexanone 18 and, subsequently, to final products analogous to compounds 7 and 12.

In addition, cyclohexanone 18 can be a versatile intermediate for further diversification. For example, reduction with sodium borohydride in ethanol can provide alcohol 19, which can be alkylated with $R^{3a}$—X (X=Cl, Br, or I) with a base such as sodium hydride to give product 20. In another instance, treatment of 18 with trimethylphenylammonium tribromide can lead to α-bromo ketone 21. Subsequent reaction with thiourea at elevated temperature can provide aminothiazole 22. Cyclohexanone 18 can also be reacted with ethyl formate using a base such as potassium t-butoxide to yield β-keto aldehyde 23. Treatment of 23 with appropriate hydrazine ($R^{3a}$—NHNH$_2$) in acetic acid at elevated temperature can provide regioisomeric pyrazoles 24 and 25. The benzyl ether group in compound 20, 22, 24 and 25 can be cleaved by palladium(II) hydroxide-catalyzed hydrogenolysis to provide the corresponding alcohols.

Scheme 2

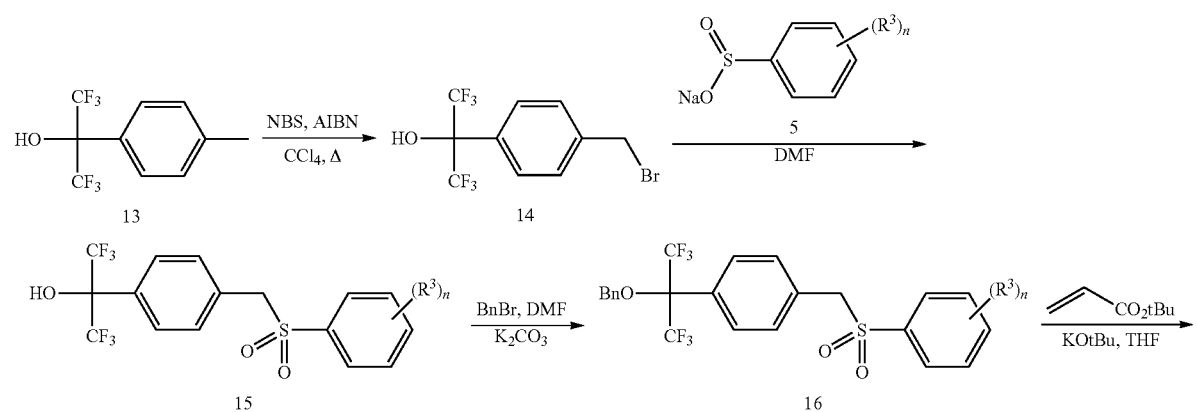

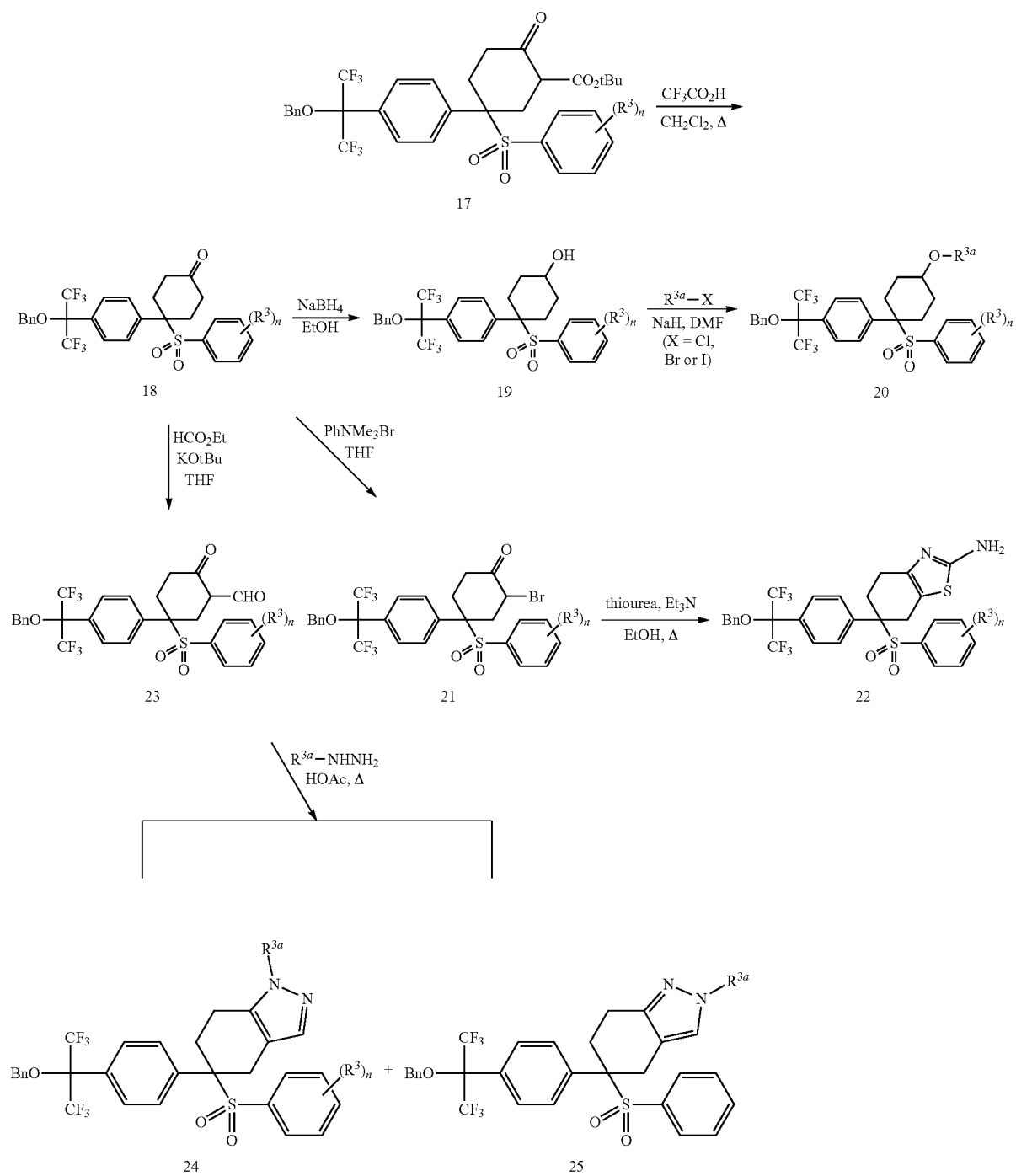

Compound 26, prepared following synthetic description for Schemes 1 and 2, can also be useful intermediate for further derivatization (Scheme 3). For example, it can be alkylated with $R^{1a}$-halide (chloride, bromide or iodide) under basic conditions such as potassium carbonate or sodium hydride to give 27. Alternatively, compound 27 can be synthesized from 26 and alcohol $R^{1a}$—OH using Mitsunobu conditions involving an azodicarboxylate such as diethyl azodicarboxylate (DEAD) and a phosphine ligand such as triphenylphosphine or tributylphosphine. The hydroxyl group in 26 can also be displaced with a fluoro group using (diethylamino)sulfur trifluoride (DAST) to give perfluoroisopropyl analogue 28. In addition, the OH group in 26 can be arylated with diphenyliodonium iodide 29 using a base such as potassium methoxide or sodium hydride to give phenyl ether 30.

Scheme 3

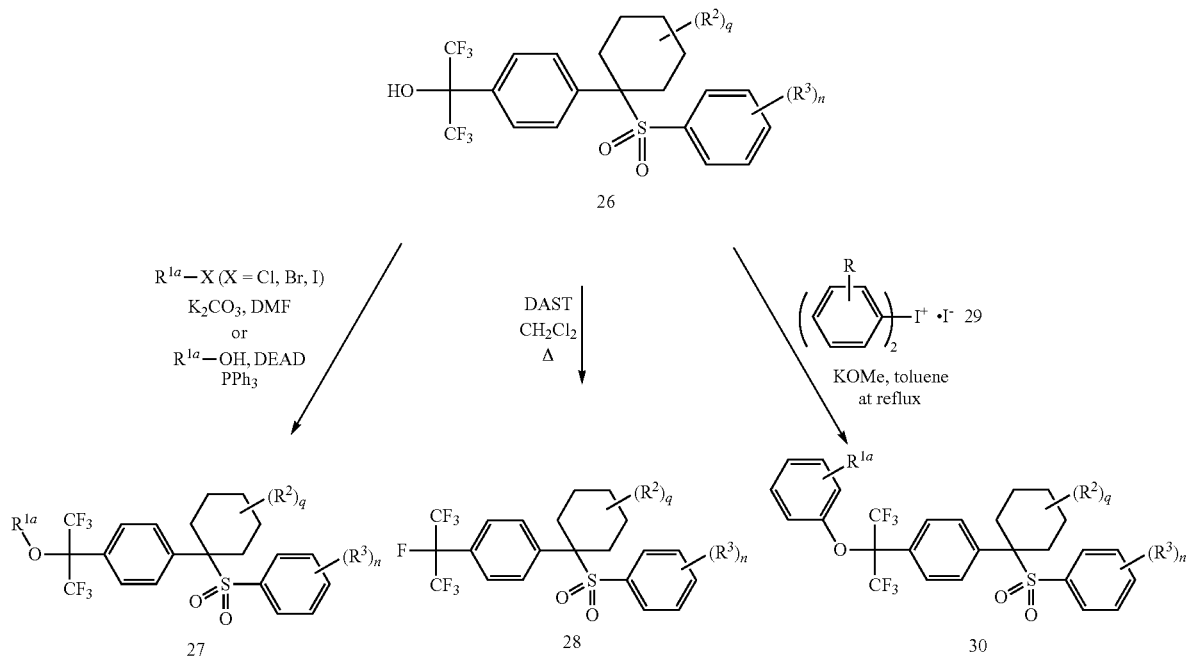

Iodide 31, prepared from the sequence outlined in Scheme 1, can be a useful intermediate for further diversification to prepare 33, 35 and 36 (Scheme 4). It can be reacted with aryl/heteroaryl boronic acid (or ester) 32 under well-known Suzuki coupling conditions using a catalyst such as palladium tetrakis(triphenylphosphine) or Pd(dppf)Cl$_2$ to give compound 33. Compound 33 can also be obtained under Stille coupling conditions using aryl/heteroaryltin in place of the boronic acid 32. Iodide 31 can also be treated with tert-butyllithium or ethylmagensium bromide to produce the corresponding aryllithium or arylmagnesium species, which can react with ketone 34 to produce alcohol 35. Compound 35 can in turn be converted to ether 36 using previously described conditions.

Scheme 4

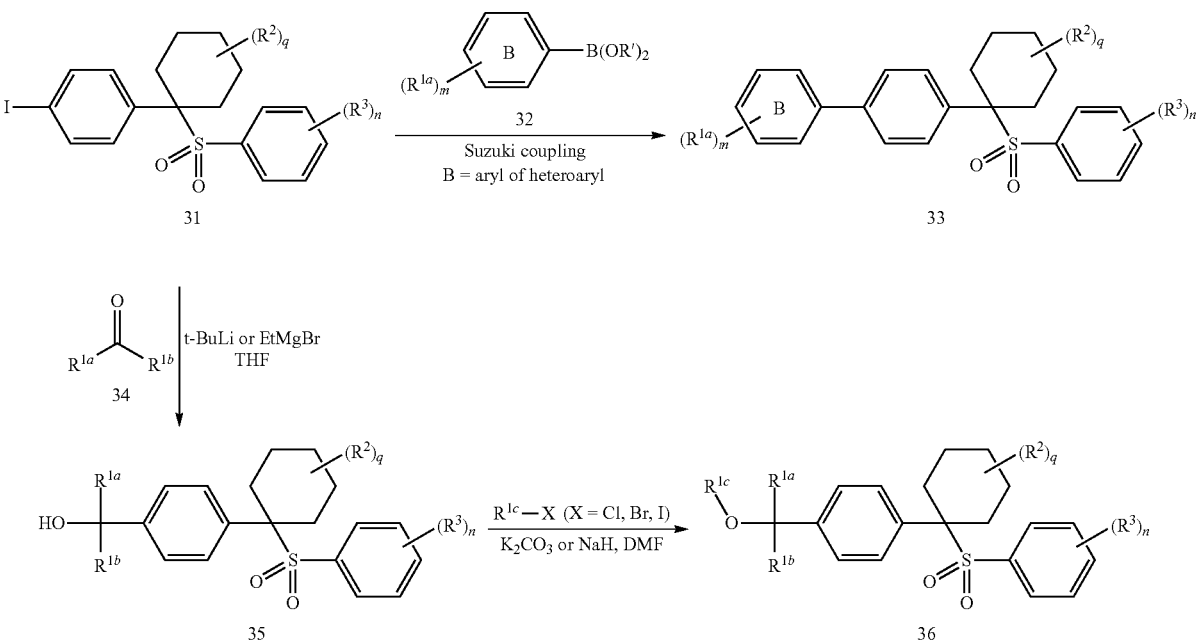

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example and are identified sequentially (e.g., Intermediate 1, Intermediate 2, etc.) and are abbreviated as Int. 1, Int. 2, etc. Compounds of the Examples are identified by the example and step in which they were prepared (e.g., "1-A" denotes the Example 1, step A), or by the example only where the compound is the title compound of the example (for example, "1" denotes the title compound of Example 1). In some instances alternate preparations of intermediates or examples are described. Frequently chemists skilled in the art of synthesis may devise alternative preparations which may be desirable based on one or more considerations such as shorter reaction time, less expensive starting materials, ease of operation, amenable to catalysis, avoidance of toxic reagents, accessibility of specialized instrumentation, and decreased number of linear steps, etc. The intent of describing alternative preparations is to further enable the preparation of the examples of this invention. In some instances some functional groups in the outlined examples and claims may be replaced by well known bioisosteric replacements known in the art, for example, replacement of a carboxylic acid group with a tetrazole or a phosphate moiety.

HPLC Conditions

Condition A:
Column: YMC Combiscreen ODS-A 4.6×50 mm (4 min.); Linear gradient of 0 to 100% solvent B over 4 min with 1 min hold at 100% B; UV visualization at 220 nm; Solvent A=10% MeOH, 90% $H_2O$, 0.2% $H_3PO_4$; Solvent B=90% MeOH, 10% $H_2O$, 0.2% $H_3PO_4$; Flow: 4 mL/min.

Condition B:
Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Condition C:
Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

Condition D:
Column: XBridge Phenyl, 4.6×150 mm, 3.5 micron; Mobile Phase A: 5:95 acetonitrile:water with 0.05% TFA; Mobile Phase B: 95:5 acetonitrile:water with 0.05% TFA; Gradient: 10-100% B over 25 minutes, then a 5-minute hold at 100% B; Flow: 1 mL/min.

Condition E:
Column: ZORBAX CN, 4.6×150 mm, 5 micron; Mobile Phase A: 5:95 acetonitrile:water with 10 mM ammonium acetate; Mobile Phase B: 95:5 acetonitrile:water with 10 mM ammonium acetate; Gradient: 10-100% B over 25 minutes, then a 5-minute hold at 100% B; Flow: 1 mL/min.

Condition F:
Column: SUNFIRE C18, 4.6×150 mm, 3 0.5 micron; Mobile Phase A: 5:95 acetonitrile:water with 0.05% TFA; Mobile Phase B: 95:5 acetonitrile:water with 0.05% TFA; Gradient: 10-100% B over 25 minutes, then a 5-minute hold at 100% B; Flow: 1 mL/min.

Condition G:
Column: Ascentis Express C18 (4.6×50) mm, 2.7 m; Mobile Phase A: 5:95 acetonitrile:water with 10 mM ammonium acetate; Mobile Phase B: 95:5 acetonitrile:water with 10 mM ammonium acetate; Temperature: 45° C.; Gradient: 0-100% B over 4 minutes; Flow: 4.00 mL/min.

Condition H:
Column: Ascentis Express C18 (2.1×50) mm, 2.7 m; Mobile Phase A: 5:95 acetonitrile:water with 10 mM ammonium acetate; Mobile Phase B: 95:5 acetonitrile:water with 10 mM ammonium acetate; Gradient: 0-100% B over 3.4 minutes; Flow: 1.11 mL/min.

Condition I:
Waters Acquity UPLC BEH C18 (2.1×50) mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 2-98% B over 1 minutes, then a 0.5-minute hold at 98% B; Flow: 0.80 mL/min.

Intermediate 1

2-(4-((1r,4r)-4-amino-1-((4-fluorophenyl)sulfonyl)cyclohexyl)phenyl)-1,1,1,3,3,3-hexafluoropropan-2-ol Step A: 4-(4-(2-(benzyloxy)-1,1,1,3,3,3-hexafluoropropan-2-yl)phenyl)-4-((4-fluorophenyl)sulfonyl)cyclohexanone oxime

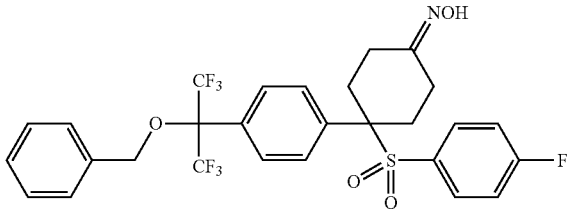

To a solution of 4-(4-(2-(benzyloxy)-1,1,1,3,3,3-hexafluoropropan-2-yl)phenyl)-4-((4-fluorophenyl)sulfonyl)cyclohexanone (1.2 g, 2.039 mmol, prepared form Step F of Example 89) in ethanol (50 mL) was added pyridine (0.379 mL, 4.69 mmol), hydroxylamine hydrochloride (0.213 g, 3.06 mmol) at room temperature. The resulting reaction mixture was heated to 80° C. for 1.5 h. The mixture was concentrated under reduced pressure to remove ethanol. The residue was taken in chloroform (25 mL), water (20 mL) and 1.5 N HCl solution (2 mL). The organic layer was separated, dried over anhydrous sodium sulphate, filtered and concentrated under reduced pressure to yield crude 4-(4-(2-(benzyloxy)-1,1,1,3,3,3-hexafluoropropan-2-yl)phenyl)-4-((4-fluorophenyl)sulfonyl)cyclohexanone oxime (1.0 g).

Step B: (1r,4r)-4-(4-(2-(benzyloxy)-1,1,1,3,3,3-hexafluoropropan-2-yl)phenyl)-4-((4-fluorophenyl)sulfonyl)cyclohexanamine, and (1s,4s)-4-(4-(2-(benzyloxy)-1,1,1,3,3,3-hexafluoropropan-2-yl)phenyl)-4-((4-fluorophenyl)sulfonyl)cyclohexanamine

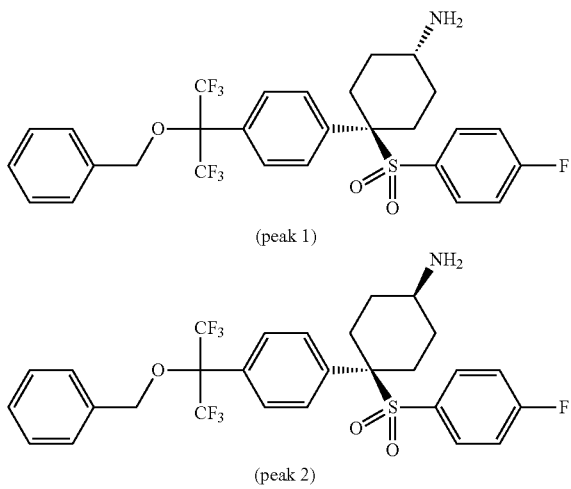

To the crude oxime (1 g, 1.657 mmol) in dry MeOH (75 mL) was added ammonia (2 M solution in methanol, 0.828 mL, 1.657 mmol) and Raney nickel (1.065 g, 12.43 mmol) at room temperature. The reaction mixture was stirred under hydrogen atmosphere (bladder) for 48 h, and filtered through 1.5 inch celite pad. The pad was washed with 3×100 mL methanol. The combined methanol solution was evaporated under reduced pressure to produce gummy liquid of crude product (1.1 g). Diastereomers were then separated by chiral SFC purification to achieve (1r,4r)-4-(4-(2-(benzyloxy)-1,1,1,3,3,3-hexafluoropropan-2-yl)phenyl)-4-((4-fluorophenyl)sulfonyl)cyclohexanamine (peak 1, 250 mg, 0.422 mmol, 21%) and (1s,4s)-4-(4-(2-(benzyloxy)-1,1,1,3,3,3-hexafluoropropan-2-yl)phenyl)-4-((4-fluorophenyl)sulfonyl)cyclohexanamine (peak 2, 200 mg, 0.337 mmol, 16%).

Analytical data of (1r,4r)-4-(4-(2-(benzyloxy)-1,1,1,3,3,3-hexafluoropropan-2-yl)phenyl)-4-((4-fluorophenyl)sulfonyl)cyclohexanamine: 1H NMR (400 MHz, DMSO-d6): δ ppm 7.60-7.32 (m, 10H), 7.21 (d, J=4.0 Hz, 4H), 4.64 (s, 2H), 2.72-2.55 (m, 4H), 2.19-2.05 (m, 2H), 1.78 (d, J=13.2 Hz, 2H), 0.92-0.78 (m, 2H).

Analytical data of (1s,4s)-4-(4-(2-(benzyloxy)-1,1,1,3,3,3-hexafluoropropan-2-yl)phenyl)-4-((4-fluorophenyl)sulfonyl)cyclohexanamine: 1H NMR (400 MHz, DMSO-d6): δ ppm 7.60-7.30 (m, 10H), 7.27-7.21 (m, 4H), 4.61 (s, 2H), 2.73-2.59 (m, 2H), 2.45-2.27 (m 2H), 2.00-1.88 (m, 2H), 2.68-2.50 (m, 2H), 0.92-0.78 (m, 2H).

Step C: 2-(4-((1r,4r)-4-amino-1-((4-fluorophenyl)sulfonyl)cyclohexyl)phenyl)-1,1,1,3,3,3-hexafluoropropan-2-ol

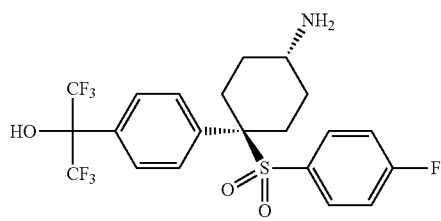 [SMILES: N[C@H]1CC[C@](c2ccc(C(O)(C(F)(F)F)C(F)(F)F)cc2)(S(=O)(=O)c2ccc(F)cc2)CC1]

In a 250 ml round-bottomed flask (1r,4r)-4-(4-(2-(benzyloxy)-1,1,1,3,3,3-hexafluoropropan-2-yl)phenyl)-4-((4-fluorophenyl)sulfonyl)cyclohexanamine (1.0 g, 1.696 mmol) was dissolved in methanol (100 mL). Pd/C (0.217 g, 2.035 mmol) was added and stirred at room temperature under hydrogen atmosphere through bladder for 2 h. Reaction monitored by TLC. Reaction mass was filtered through celite bed. Celite bed was washed with methanol (3×50 ml). Combined organic layer was concentrated to get crude product as off white solid (800 mg Crude). The crude was purified by combi-flash chromatogram to produce desired 2-(4-((1r,4r)-4-amino-1-((4-fluorophenyl)sulfonyl)cyclohexyl)phenyl)-1,1,1,3,3,3-hexafluoropropan-2-ol (370 mg, 0.741 mmol, 43% yield). LC/MS (M+1): 498.0; LC retention time: 7.67 min (analytical HPLC Method D); 1H NMR (400 MHz, DMSO-d6): δ ppm 7.61 (d, J=8.4 Hz, 2H), 7.41 (d, J=8.8 Hz, 2H), 7.22-7.18 (m, 4H), 2.76 (d, J=11.2 Hz, 1H), 2.61 (d J=12.8 Hz, 2H), 2.07 (t, J=6.8 Hz, 2H), 1.84 (s, 2H), 0.96-0.87 (m, 2H).

Intermediate 2

2-(4-((1s,4s)-4-amino-1-((4-fluorophenyl)sulfonyl)cyclohexyl)phenyl)-1,1,1,3,3,3-hexafluoropropan-2-ol

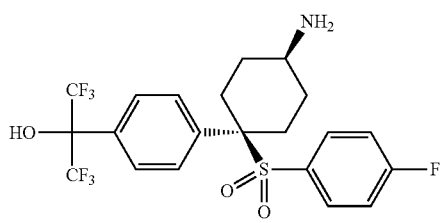 [SMILES: N[C@H]1CC[C@@](c2ccc(C(O)(C(F)(F)F)C(F)(F)F)cc2)(S(=O)(=O)c2ccc(F)cc2)CC1]

Following conditions similar to Step C of Intermediate 1, (1s,4s)-4-(4-(2-(benzyloxy)-1,1,1,3,3,3-hexafluoropropan-2-yl)phenyl)-4-((4-fluorophenyl)sulfonyl)cyclohexanamine was converted to 2-(4-((1s,4s)-4-amino-1-((4-fluorophenyl)sulfonyl)cyclohexyl)phenyl)-1,1,1,3,3,3-hexafluoropropan-2-ol. LC/MS (M+1): 498.0; LC retention time: 7.61 min (analytical HPLC Method D); 1H NMR (400 MHz, DMSO-d6): δ ppm 7.60 (d, J=8.4 Hz, 2H), 7.40 (d, J=8.8 Hz, 2H), 7.24-7.19 (m, 4H), 3.00 (s, 1H), 2.56-2.50 (m, 2H), 2.24 (t, J=13.2 Hz, 2H), 1.61 (d, J=12.0 Hz, 2H), 1.30-1.28 (m, 2H).

Example 1

1,3-difluoro-2-(((1,1,1,3,3,3-hexafluoro-2-(4-(1-((4-fluorophenyl)sulfonyl)cyclohexyl)phenyl)propan-2-yl)oxy)methyl)benzene Step A: 2-(4-(bromomethyl)phenyl)-1,1,1,3,3,3-hexafluoropropan-2-ol

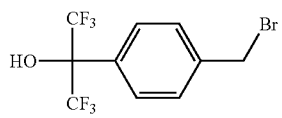

N-Bromosuccinimide (13.79 g, 77 mmol) and 2,2'-azobis(2-methylpropionitrile) (0.025 g, 0.155 mmol) were added to a solution of 1,1,1,3,3,3-hexafluoro-2-(p-tolyl)propan-2-ol (20.00 g, 77 mmol) in carbon tetrachloride (80 mL). The resulting suspension was heated to reflux under nitrogen for 4 h, cooled to room temperature and filtered through a celite pad. The filter cake was rinsed with ether and the filtrate was concentrated under reduced pressure. The residue was treated with ether (100 mL) and hexanes (50 mL), stirred for 15 min and filtered. The filtrate was concentrated under reduced pressure and dried under vacuum to give crude product as tan liquid (27.07 g). 1H NMR analysis showed a 69:15:16 molar ratio of the desired 2-(4-(bromomethyl) phenyl)-1,1,1,3,3,3-hexafluoropropan-2-ol, unreacted 1,1,1, 3,3,3-hexafluoro-2-(p-tolyl)propan-2-ol and 2-(4-(dibromomethyl)phenyl)-1,1,1,3,3,3-hexafluoropropan-2-ol. The mixture was used without further purification, assuming ~70% purity of the desired 2-(4-(bromomethyl)phenyl)-1,1,1,3,3,3-hexafluoropropan-2-ol.

Step B: 1,1,1,3,3,3-hexafluoro-2-(4-((phenylsulfonyl)methyl)phenyl)propan-2-ol

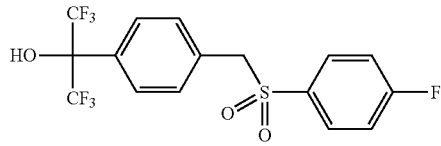 [SMILES: O=S(=O)(Cc1ccc(C(O)(C(F)(F)F)C(F)(F)F)cc1)c1ccc(F)cc1]

Sodium 4-fluorobenzenesulfinate (12.62 g, 69.3 mmol) was added in small portions to a stirred solution of 2-(4-(bromomethyl)phenyl)-1,1,1,3,3,3-hexafluoropropan-2-ol (20.00 g, ~70% pure from Step A) in N,N-dimethylformamide (80 mL). The mixture warmed up slightly during the addition. After 6 h at ambient temperature, the mixture was diluted with ethyl acetate (1 L), washed with water (3×200 mL), brine (100 mL), dried (magnesium sulfate), filtered and concentrated under reduced pressure. The residue was dissolved in dichloromethane (40 mL), triturated with hexanes (400 mL), stirred for 30 min and filtered. The filter cake was washed with hexanes (100 mL) and dried under vacuum to give 1,1,1,3,3,3-hexafluoro-2-(4-((phenylsulfonyl)methyl) phenyl)propan-2-ol as white solid (14.84 g, 82% yield). LC/MS (M+23): 439.2; 1H NMR (400 MHz, CDCl$_3$) δ ppm 7.64 (d, J=8.1 Hz, 2H), 7.62-7.54 (m, 2H), 7.20 (d, J=8.6 Hz, 2H), 7.15-7.06 (m, 2H), 4.34 (s, 2H), 3.59 (s, 1H).

Step C: 1,3-difluoro-2-(((1,1,1,3,3,3-hexafluoro-2-(4-(((4-fluorophenyl)sulfonyl)methyl)phenyl)propan-2-yl)oxy)methyl)benzene

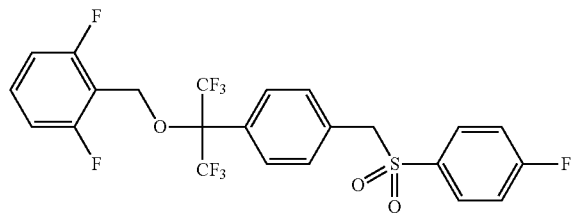 [SMILES: O=S(=O)(Cc1ccc(C(OCc2c(F)cccc2F)(C(F)(F)F)C(F)(F)F)cc1)c1ccc(F)cc1]

A mixture of 1,1,1,3,3,3-hexafluoro-2-(4-(((4-fluorophenyl)sulfonyl)methyl)phenyl)propan-2-ol (12.625 g, 30.3 mmol), 2-(bromomethyl)-1,3-difluorobenzene (6.59 g, 31.8 mmol) and potassium carbonate (12.57 g, 91 mmol) in N,N-dimethylformamide (120 mL) was stirred under nitrogen at room temperature for 22 h. The mixture was quenched with saturated ammonium chloride (100 mL), diluted with ethyl acetate (800 mL), washed with water (3×100 mL), brine (50 mL), dried (magnesium sulfate), filtered and concentrated under reduced pressure. The residue was treated with dichloromethane (20 mL) and toluene (40 mL), sonicated, triturated with hexanes (500 mL), stirred for 15 min and filtered. The filter cake was washed with hexanes (100 mL) and dried under vacuum to give first batch of 1,3-difluoro-2-(((1,1,1,3,3,3-hexafluoro-2-(4-(((4-fluorophenyl)sulfonyl)methyl)phenyl)propan-2-yl)oxy)methyl) benzene as white solid (14.881 g). The filtrate was concentrated. Silica gel chromatography, eluting with 5-30% ethyl acetate in hexanes, gave second batch of the desired product as white solid (0.735 g). The combined amount of the product is 15.616 g (95% yield). LC/MS (M+18): 560.2; LC retention time: 4.460 min (analytical HPLC Method A); 1H NMR (400 MHz, CDCl$_3$) δ ppm 7.68-7.57 (m, 4H), 7.37 (tt, J=8.4, 6.4 Hz, 1H), 7.28-7.21 (m, 2H), 7.15-7.07 (m, 2H), 7.01-6.91 (m, 2H), 4.68 (s, 2H), 4.36 (s, 2H).

Step D: 1,3-difluoro-2-(((1,1,1,3,3,3-hexafluoro-2-(4-(1-(((4-fluorophenyl)sulfonyl)cyclohexyl)phenyl) propan-2-yl)oxy)methyl)benzene

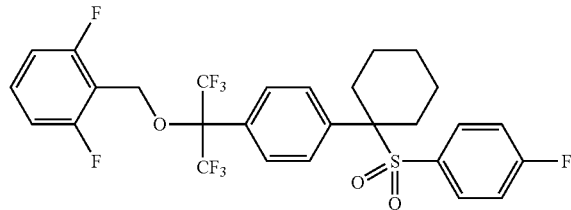 [SMILES: O=S(=O)(c1ccc(F)cc1)C1(c2ccc(C(OCc3c(F)cccc3F)(C(F)(F)F)C(F)(F)F)cc2)CCCCC1]

Sodium hydride (9.73 mg, 0.243 mmol, 60% suspension in mineral oil) was added to a solution of 1,3-difluoro-2-(((1,1,1,3,3,3-hexafluoro-2-(4-(((4-fluorophenyl)sulfonyl) methyl)phenyl)propan-2-yl)oxy)methyl)benzene (13.2 mg, 0.024 mmol) and 1,5-diiodopentane (31.5 mg, 0.097 mmol) in N,N-dimethylformamide (1 mL). After 1 h at room temperature, LCMS analysis showed that the reaction was complete. The mixture was quenched with water (1 mL), diluted with ether (10 mL), washed with water (2×10 mL), brine (5 mL), dried (magnesium sulfate), filtered and concentrated under reduced pressure. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 60-100% B over 15 minutes, then a 5-minute hold at 100% B; Flow: 20 mL/min. Fractions containing the desired product were combined and dried via centrifugal evaporation to give Example 1 (9.0 mg, 57% yield). LC/MS (M+18): 628.1; LC retention time: 3.130 min (analytical HPLC Method C); 1H NMR (500 MHz, 1:1 mixture of CDCl$_3$-CD$_3$OD) δ ppm 7.66-7.58 (m, 2H), 7.49-7.38 (m, 3H), 7.30-7.21 (m, 2H), 7.08-6.95 (m, 4H), 4.73 (s, 2H), 2.66 (d, J=12.9 Hz, 2H), 2.26 (td, J=13.3, 3.2 Hz, 2H), 1.83 (d, J=13.4 Hz, 2H), 1.67 (d, J=12.4 Hz, 1H), 1.47-1.34 (m, 1H), 1.28 (q, J=13.0 Hz, 2H).

Example 2 methyl 5-(4-(2-((2,6-difluorobenzyl)oxy)-1,1,1,3,3,3-hexafluoropropan-2-yl)phenyl)-5-((4-fluorophenyl)sulfonyl)-2-oxocyclohexanecarboxylate

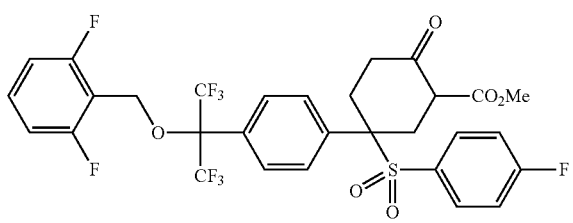

To a solution of 1,3-difluoro-2-(((1,1,1,3,3,3-hexafluoro-2-(4-(((4-fluorophenyl)sulfonyl)methyl)phenyl)propan-2-yl)oxy)methyl)benzene (250 mg, 0.461 mmol, from Step C of Example 1) in tetrahydrofuran (5 mL) under nitrogen atmosphere was added methyl acrylate (79 mg, 0.922 mmol) followed by addition of potassium tert-butoxide (103 mg, 0.922 mmol). The reaction mixture was stirred at room temperature for 2.5 h, quenched with saturated ammonium chloride (30 mL) and extracted with ethyl acetate (2×30 mL). The combined organic layer was dried (sodium sulfate), filtered and concentrated under reduced pressure to yield crude product (390 mg). The compound was purified by prep HPLC to yield methyl 5-(4-(2-((2,6-difluorobenzyl)oxy)-1,1,1,3,3,3-hexafluoropropan-2-yl)phenyl)-5-((4-fluorophenyl)sulfonyl)-2-oxocyclohexanecarboxylate as mixture of diastereomers (50 mg, 16% yield) as off white solid. LC/MS (M+18): 700.0; LC retention time: 12.86 min (analytical HPLC Method D); 1H NMR (DMSO-d6, 400 MHz, mixture of diastereomers): δ ppm 7.65-7.45 (m), 7.37-7.14 (m), 4.66 (s), 3.79 (s), 3.66 (s), 3.28-3.23 (m), 3.00 (d, J=15.6 Hz), 2.83-2.75 (m), 2.42-2.35 (m), 2.10-1.99 (m).

Example 3

4-(4-(2-((2,6-difluorobenzyl)oxy)-1,1,1,3,3,3-hexafluoropropan-2-yl)phenyl)-4-((4-fluorophenyl)sulfonyl)cyclohexanone Step A: tert-butyl 5-(4-(2-((2,6-difluorobenzyl)oxy)-1,1,1,3,3,3-hexafluoropropan-2-yl)phenyl)-5-((4-fluorophenyl)sulfonyl)-2-oxocyclohexanecarboxylate

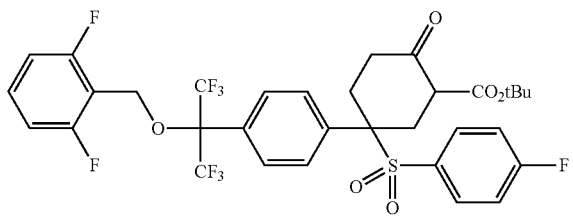 [SMILES: CC(C)(C)OC(=O)C1CC(c2ccc(C(OCc3c(F)cccc3F)(C(F)(F)F)C(F)(F)F)cc2)(S(=O)(=O)c2ccc(F)cc2)CCC1=O]

In a 50 mL dry round bottomed flask, to a solution of 1,3-difluoro-2-(((1,1,1,3,3,3-hexafluoro-2-(4-(((4-fluorophenyl)sulfonyl)methyl)phenyl)propan-2-yl)oxy)methyl)benzene (200 mg, 0.369 mmol, from Step C of Example 1) in tetrahydrofuran (10 mL) under nitrogen atmosphere was added tert-butyl acrylate (95 mg, 0.737 mmol) followed by addition of potassium tert-butoxide (83 mg, 0.737 mmol). The reaction mixture was stirred at room temperature for 2 h, quenched with water (20 mL) and extracted with ethyl acetate (2×20 mL). The combined organic layer was dried (sodium sulfate), filtered and concentrated under reduced pressure. Silica gel chromatography, eluting with 20% ethyl acetate in hexanes, gave the desired tert-butyl 5-(4-(2-((2,6-difluorobenzyl)oxy)-1,1,1,3,3,3-hexafluoropropan-2-yl)phenyl)-5-((4-fluoro phenyl)sulfonyl)-2-oxocyclohexanecarboxylate (190 mg) as off white gummy solid, which was about 41% pure based on LCMS analysis. This material was taken to the next reaction without purification.

Step B: 4-(4-(2-((2,6-difluorobenzyl)oxy)-1,1,1,3,3,3-hexafluoropropan-2-yl)phenyl)-4-((4-fluorophenyl)sulfonyl)cyclohexanone

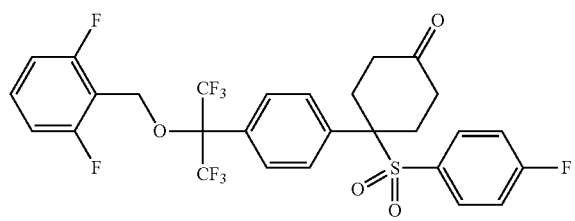 [SMILES: O=C1CCC(c2ccc(C(OCc3c(F)cccc3F)(C(F)(F)F)C(F)(F)F)cc2)(S(=O)(=O)c2ccc(F)cc2)CC1]

To a solution of the impure tert-butyl 5-(4-(2-((2,6-difluoro benzyl)oxy)-1,1,1,3,3,3-hexafluoropropan-2-yl)phenyl)-5-((4-fluorophenyl)sulfonyl)-2-oxocyclohexanecarboxylate (190 mg, from Step A) in dichloromethane (5 mL) was added trifluoroacetic acid (0.16 mL, 2.076 mmol). After stirring at 60° C. overnight, the mixture was concentrated under reduced pressure. The residue was purified by preparative HPLC to yield 4-(4-(2-((2,6-difluorobenzyl)oxy)-1,1,1,3,3,3-hexafluoropropan-2-yl)phenyl)-4-((4-fluorophenyl) sulfonyl)cyclohexanone (39.3 mg, 17% yield over two steps) as white solid. LC/MS (M+18): 642.2; LC retention time: 16.76 min (analytical HPLC Method D); 1H NMR (DMSO-d6, 400 MHz): δ ppm 7.68-7.57 (m, 5H), 7.35-7.20 (m, 6H), 4.67 (s, 2H), 2.91 (d, J=13.2 Hz, 2H), 2.63-2.43 (m, 2H), 2.36 (d, J=15.6 Hz, 2H), 2.20-2.13 (m, 2H); 19F NMR (376 MHz): δ −69.98, −104.03, −115.00.

Examples 4 and 5

(1s,4s)-4-(4-(2-((2,6-difluorobenzyl)oxy)-1,1,1,3,3,3-hexafluoropropan-2-yl)phenyl)-4-((4-fluorophenyl)sulfonyl)cyclohexanol, and (1r,4r)-4-(4-(2-((2,6-difluorobenzyl)oxy)-1,1,1,3,3,3-hexafluoropropan-2-yl)phenyl)-4-((4-fluorophenyl)sulfonyl)cyclohexanol

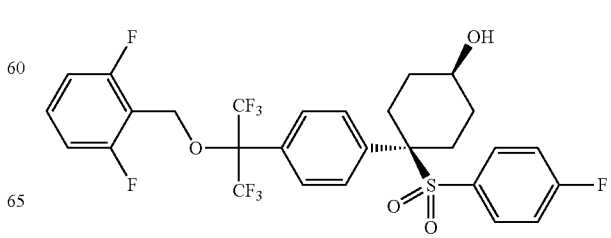

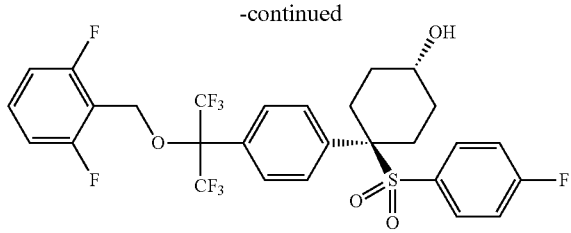

A mixture of 4-(4-(2-((2,6-difluorobenzyl)oxy)-1,1,1,3,3,3-hexafluoropropan-2-yl)phenyl)-4-((4-fluorophenyl)sulfonyl)cyclohexanone (20 mg, 0.032 mmol, from Example 3), acetic acid (2.8 μl, 0.048 mmol) and dimethylamine (0.048 mL, 0.096 mmol, 2 M solution in tetrahydrofuran) in 1,2-dichloroethane (0.5 mL) was stirred at room temperature for 10 min. Sodium cyanoborohydride (6.0 mg, 0.096 mmol) was added. After stirring at room temperature overnight, LCMS analysis showed that the anticipated reductive amination product was not observed. Instead, the alcohol product was formed. The crude material was purified via preparative LC/MS with the following conditions: Column: Waters XBridge C18, 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 35-100% B over 25 minutes, then a 5-minute hold at 100% B; Flow: 20 mL/min. Two isomers were isolated corresponding to Examples 4 and 5. The stereochemistry of each isomer was not determined. Analytical data for Example 4: 14.4 mg (72% yield); LC/MS (M+18): 644.3; LC retention time: 2.18 min (analytical HPLC Method B); 1H NMR (400 MHz, 1:1 mixture of CDCl₃-CD₃OD) δ ppm 7.61 (d, J=8.5 Hz, 2H), 7.48-7.37 (m, 3H), 7.30-7.20 (m, 2H), 7.07-6.95 (m, 4H), 4.70 (s, 2H), 3.75-3.63 (m, 1H), 2.67 (d, J=12.0 Hz, 2H), 2.32 (td, J=13.7, 3.0 Hz, 2H), 2.01 (dd, J=13.1, 3.5 Hz, 2H), 1.27-1.12 (m, 2H). Analytical data for Example 5: 2.6 mg (13% yield); LC/MS (M+18): 644.4; LC retention time: 2.25 min (analytical HPLC Method B); 1H NMR (400 MHz, 1:1 mixture of CDCl₃-CD₃OD) δ ppm 7.60 (d, J=8.3 Hz, 2H), 7.46-7.39 (m, 3H), 7.31-7.22 (m, 2H), 7.06-6.95 (m, 4H), 4.71 (br. s., 2H), 3.86 (br. s., 1H), 2.72 (td, J=13.7, 3.3 Hz, 2H), 2.39 (d, J=12.8 Hz, 2H), 1.85 (d, J=12.8 Hz, 2H), 1.42 (t, J=13.8 Hz, 2H).

Example 6

1,3-difluoro-2-(((1,1,1,3,3,3-hexafluoro-2-(4-(1-((4-fluorophenyl)sulfonyl)-4-methoxycyclohexyl)phenyl)propan-2-yl)oxy)methyl)benzene Step A: 4-(4-(2-((2,6-difluorobenzyl)oxy)-1,1,1,3,3,3-hexafluoropropan-2-yl)phenyl)-4-((4-fluorophenyl)sulfonyl)cyclohexanol

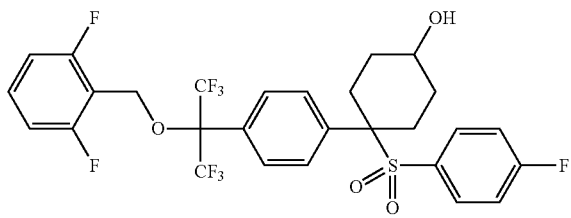 [SMILES: O=S(=O)(c1ccc(F)cc1)C1(c2ccc(C(OCc3c(F)cccc3F)(C(F)(F)F)C(F)(F)F)cc2)CCC(O)CC1]

Under inert atmosphere, to a solution of 4-(4-(2-((2,6-difluorobenzyl)oxy)-1,1,1,3,3,3-hexafluoropropan-2-yl) phenyl)-4-((4-fluorophenyl)sulfonyl)cyclohexanone (100 mg, 0.160 mmol, from Example 3) in ethanol (2.5 mL) and tetrahydrofuran (1.3 mL) was added sodium borohydride (6.06 mg, 0.160 mmol) at 0° C. After stirring for 1.5 h at room temperature, the reaction mixture was quenched with water (30 mL) and extracted with dichloromethane (2×30 mL). The combined organic layer was washed with water (20 mL) and saturated brine (25 mL), dried (sodium sulfate), filtered and concentrated under reduced pressure to yield 4-(4-(2-((2,6-difluorobenzyl)oxy)-1,1,1,3,3,3-hexafluoropropan-2-yl)phenyl)-4-((4-fluorophenyl) sulfonyl)cyclohexanol as a mixture of two diastereomers (90 mg, 90% yield) as white solid. LC/MS (M+18): 644.2.

Step B: 1,3-difluoro-2-(((1,1,1,3,3,3-hexafluoro-2-(4-(1-((4-fluorophenyl)sulfonyl)-4-methoxycyclohexyl)phenyl)propan-2-yl)oxy)methyl)benzene

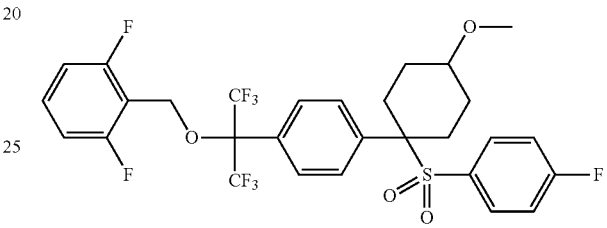

Sodium hydride (1.6 mg, 0.040 mmol, 60% suspension in mineral oil) was added to a solution of 4-(4-(2-((2,6-difluorobenzyl)oxy)-1,1,1,3,3,3-hexafluoropropan-2-yl)phenyl)-4-((4-fluorophenyl)sulfonyl)cyclohexanol (25 mg, 0.040 mmol) in N,N-dimethylformamide (1 mL) at 0° C. After stirring at 0° C. for 30 minutes, methyl iodide (5.7 mg, 0.040 mmol) was added. The resulting mixture was stirred at room temperature for 6 h and quenched with water (0.2 mL). The crude product was purified by reverse phase Agilent prep HPLC system: Column X-bridge prep OBD C18 (19×150) mm, 5 μm; solvent A: 10 mm ammonium acetate in water; solvent B: Methanol. The fractions containing desired product was concentrated to give Example 6 as a mixture of two diastereomers. LC/MS (M+18): 658.0; LC retention time: 2.523 min (analytical HPLC Method G).

Example 7

N-((1s,4s)-4-(4-(2-((2,6-difluorobenzyl)oxy)-1,1,1,3,3,3-hexafluoropropan-2-yl)phenyl)-4-((4-fluorophenyl)sulfonyl)cyclohexyl)isonicotinamide Step A: 4-(4-(2-((2,6-difluorobenzyl)oxy)-1,1,1,3,3,3-hexafluoropropan-2-yl)phenyl)-4-((4-fluorophenyl)sulfonyl)cyclohexanone oxime

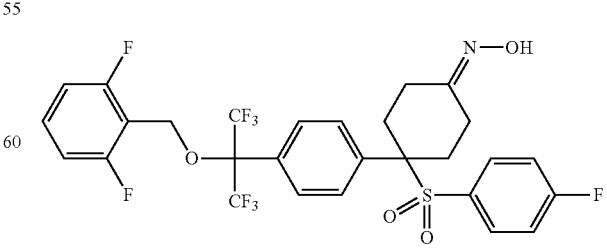

To a solution of 4-(4-(2-((2,6-difluorobenzyl)oxy)-1,1,1,3,3,3-hexafluoropropan-2-yl)phenyl)-4-((4-fluorophenyl)

sulfonyl)cyclohexanone (1.20 g, 1.92 mmol, from Example 3) in ethanol (40 mL) was added pyridine (0.36 mL, 4.420 mmol) and hydroxylamine hydrochloride (200 mg, 2.88 mmol) at 25° C. After stirring at 80° C. for 1.5 h, the reaction mixture was cooled to room temperature and concentrated under reduced pressure to remove ethanol. The residue was diluted with chloroform (40 mL), water (30 mL) and 1.5 N hydrochloric acid (3 mL). The organic layer was separated. The aqueous layer was extracted with chloroform (2×30 mL). The combined organic layer was dried (sodium sulfate), filtered and concentrated under reduced pressure to yield 4-(4-(2-((2,6-difluorobenzyl)oxy)-1,1,1,3,3,3-hexafluoropropan-2-yl)phenyl)-4-((4-fluorophenyl)sulfonyl)cyclohexanone oxime (1.0 g, 81% yield) as off white solid. LC/MS (M+1): 640.2.

Step B: (1r,4r)-4-(4-(2-((2,6-difluorobenzyl)oxy)-1,1,1,3,3,3-hexafluoropropan-2-yl)phenyl)-4-((4-fluorophenyl)sulfonyl)cyclohexanamine and (1s,4s)-4-(4-(2-((2,6-difluorobenzyl)oxy)-1,1,1,3,3,3-hexafluoropropan-2-yl)phenyl)-4-((4-fluorophenyl)sulfonyl)cyclohexanamine

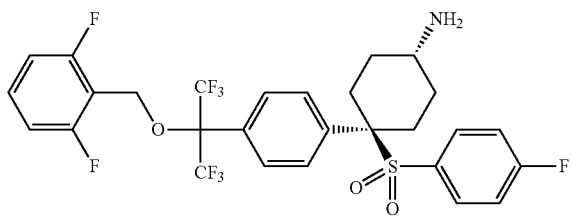

trans-isomer

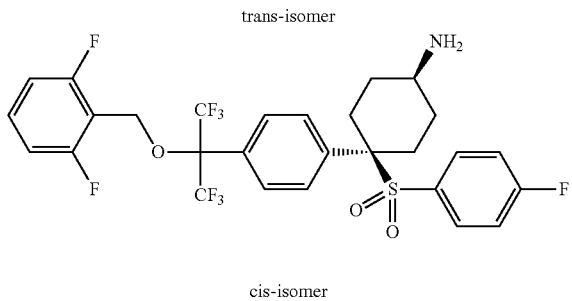

cis-isomer

To a solution of 4-(4-(2-((2,6-difluorobenzyl)oxy)-1,1,1,3,3,3-hexafluoropropan-2-yl)phenyl)-4-((4-fluorophenyl)sulfonyl)cyclohexanone oxime (1.0 g, 1.564 mmol) in methanol (30 mL) was added ammonia (30 mL, 2 M solution in methanol) and Raney nickel (1.005 g, 11.73 mmol) at room temperature. The reaction mixture was stirred for 24 h under hydrogen atmosphere (bladder). The reaction mixture was filtered through 1-inch bed of celite and washed with methanol (2×50 mL). The filtrate was concentrated under reduced pressure to give crude product mixture. Two diastereomers of the mixture was separated by SFC purification to yield (1r,4r)-4-(4-(2-((2,6-difluorobenzyl)oxy)-1,1,1,3,3,3-hexafluoropropan-2-yl)phenyl)-4-((4-fluorophenyl)sulfonyl)cyclohexanamine (trans-isomer, peak 1, 675 mg) as off white solid and (1s,4s)-4-(4-(2-((2,6-difluorobenzyl)oxy)-1,1,1,3,3,3-hexafluoropropan-2-yl)phenyl)-4-((4-fluorophenyl)sulfonyl)cyclohexanamine (cis-isomer, peak 2, 295 mg) as white solid. Analytical data for the trans-isomer: LC/MS (M+1): 626.2; LC retention time: 14.04 min (analytical HPLC Method D); 1H NMR (400 MHz, DMSO-d6): δ ppm 7.60-7.49 (m, 5H), 7.27-7.20 (m, 6H), 4.66 (s, 2H), 2.68-2.60 (m, 3H), 2.14 (t, J=13.2 Hz, 2H), 1.78 (d, J=10.4 Hz, 2H), 0.85 (q, J=12 Hz, 2H); 19F NMR (376 MHz): δ -70.0, -104.56, -115.01. Analytical data for the cis-isomer: LC/MS (M+1): 626.2; LC retention time: 14.24 min (analytical HPLC Method D); 1H NMR (400 MHz, DMSO-d6): δ ppm 7.59-7.49 (m, 5H), 7.26-7.20 (m, 6H), 4.65 (s, 2H), 3.04 (s, 1H), 2.68-2.54 (m, 2H), 2.33-2.27 (m, 2H), 1.65 (d, J=12.8 Hz, 2H), 1.34-1.30 (m, 2H); 19F NMR (376 MHz): δ -70.03, -104.67, -115.02.

Step C: N-((1s,4s)-4-(4-(2-((2,6-difluorobenzyl)oxy)-1,1,1,3,3,3-hexafluoropropan-2-yl)phenyl)-4-((4-fluorophenyl)sulfonyl)cyclohexyl)isonicotinamide

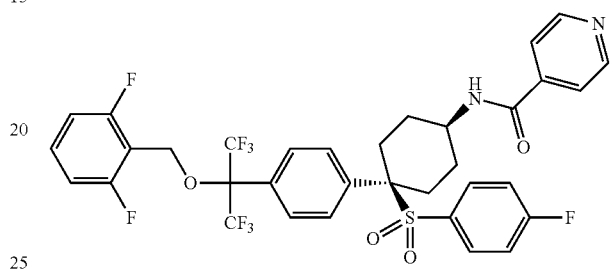

A mixture of (1s,4s)-4-(4-(2-((2,6-difluorobenzyl)oxy)-1,1,1,3,3,3-hexafluoropropan-2-yl)phenyl)-4-((4-fluorophenyl)sulfonyl)cyclohexanamine (10 mg, 0.016 mmol), isonicotinic acid (1.97 mg, 0.016 mmol), (benzotriazol-1-yloxy)tris(dimethylamino)phosphonium hexafluorophosphate (7.07 mg, 0.016 mmol) and Hunig's Base (8.38 µl, 0.048 mmol) was stirred at room temperature for 30 min. LCMS analysis showed that the reaction was complete. The crude material was purified via preparative LC/MS with the following conditions: Column: Waters XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-100% B over 20 minutes, then a 5-minute hold at 100% B; Flow: 20 mL/min. Fractions containing the desired product were combined and dried via centrifugal evaporation to give Example 7 (7.1 mg, 60% yield). LC/MS (M+1): 731.3; LC retention time: 2.17 min (analytical HPLC Method B); 1H NMR (500 MHz, DMSO-d6) δ ppm 8.73 (d, J=5.0 Hz, 2H), 8.66 (d, J=5.4 Hz, 1H), 7.71 (d, J=5.4 Hz, 2H), 7.62-7.50 (m, 5H), 7.29-7.18 (m, 6H), 4.66 (s, 2H), 3.89 (d, J=6.4 Hz, 1H), 2.65-2.54 (m, 2H), 2.43 (d, J=13.8 Hz, 2H), 2.07 (d, J=11.1 Hz, 2H), 1.49-1.38 (m, 2H).

Example 8

4-((1s,4s)-4-(4-(2-((2,6-difluorobenzyl)oxy)-1,1,1,3,3-hexafluoropropan-2-yl)phenyl)-4-((4-fluorophenyl)sulfonyl)cyclohexyl)morpholine

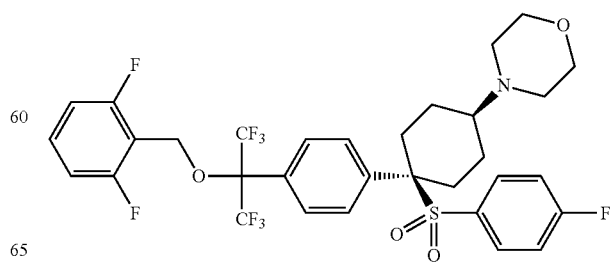

A N,N-dimethylformamide (0.5 mL) solution of (1s,4s)-4-(4-(2-((2,6-difluorobenzyl)oxy)-1,1,1,3,3,3-hexafluoropropan-2-yl)phenyl)-4-((4-fluorophenyl)sulfonyl)cyclohexanamine (10 mg, 0.016 mmol), 1-iodo-2-(2-iodoethoxy)ethane (15.63 mg, 0.048 mmol) and potassium carbonate (26 mg, 0.188 mmol) was stirred at room temperature for 3 days. LCMS analysis showed that the reaction was near completion. The mixture was diluted with ethanol (1 mL) and filtered. The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-100% B over 25 minutes, then a 5-minute hold at 100% B; Flow: 20 mL/min. Fractions containing the desired product were combined and dried via centrifugal evaporation to give Example 8 (4.5 mg, 36% yield). LC/MS (M+1): 696.3; LC retention time: 2.46 min (analytical HPLC Method B); 1H NMR (400 MHz, 1:1 mixture of CDCl$_3$-CD$_3$OD) δ ppm 7.60 (d, J=8.4 Hz, 2H), 7.43-7.34 (m, 3H), 7.24 (dd, J=8.9, 5.1 Hz, 2H), 7.02-6.90 (m, 4H), 4.73 (s, 2H), 3.79 (br. s., 3H), 2.81 (d, J=8.1 Hz, 2H), 2.51 (br. s., 3H), 2.28-2.06 (m, 5H), 1.46-1.20 (m, 4H).

Example 9

N-((1s,4s)-4-((4-fluorophenyl)sulfonyl)-4-(4-(perfluoropropan-2-yl)phenyl)cyclohexyl)acetamide Step A: 4-(4-(2-(benzyloxy)-1,1,1,3,3,3-hexafluoropropan-2-yl)phenyl)-4-((4-fluorophenyl)sulfonyl)cyclohexanamine

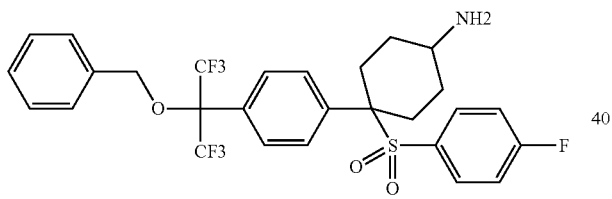

To a solution of 4-(4-(2-(benzyloxy)-1,1,1,3,3,3-hexafluoropropan-2-yl)phenyl)-4-((4-fluorophenyl)sulfonyl)cyclohexanone (1.2 g, 2.039 mmol, prepared using conditions similar to the synthesis of Example 3) in ethanol (50 mL) was added pyridine (0.379 mL, 4.69 mmol) and hydroxylamine hydrochloride (0.213 g, 3.06 mmol) at room temperature. The resulting mixture was heated to 80° C., stirred for 1.5 h, and concentrated under reduced pressure. The residue was taken in chloroform (25 mL), water (20 mL) and 1.5 N hydrochloric acid (2 mL). The organic layer was separated, dried (sodium sulphate), filtered and concentrated under reduced pressure to yield crude 4-(4-(2-(benzyloxy)-1,1,1,3,3,3-hexafluoropropan-2-yl)phenyl)-4-((4-fluorophenyl)sulfonyl)cyclohexanone oxime (1.0 g).

To the crude oxime (1 g, 1.657 mmol) in dry methanol (75 mL) was added a 2 M methanol solution of ammonia (0.828 mL, 1.657 mmol) and Raney nickel (1.065 g, 12.43 mmol) at room temperature. The reaction mixture was stirred under hydrogen atmosphere (bladder) for 48 h and filtered through 1.5-inch celite pad. The pad was rinsed with methanol (3×100 mL). The combined methanol solution was evaporated under reduced pressure to produce crude 4-(4-(2-(benzyloxy)-1,1,1,3,3,3-hexafluoropropan-2-yl)phenyl)-4-((4-fluorophenyl)sulfonyl)cyclohexanamine (1.1 g). LCMS analysis showed that the material was approximately 70% pure. The crude product was taken directly for next step without purification. LC/MS (M+1): 590.2.

Step B: tert-butyl (4-(4-(2-(benzyloxy)-1,1,1,3,3,3-hexafluoropropan-2-yl)phenyl)-4-((4-fluorophenyl)sulfonyl)cyclohexyl)carbamate

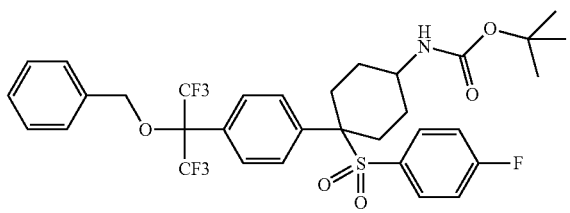 [SMILES: CC(C)(C)OC(=O)NC1CCC(c2ccc(C(OCc3ccccc3)(C(F)(F)F)C(F)(F)F)cc2)(S(=O)(=O)c2ccc(F)cc2)CC1]

To a solution of crude 4-(4-(2-(benzyloxy)-1,1,1,3,3,3-hexafluoropropan-2-yl)phenyl)-4-((4-fluorophenyl)sulfonyl)cyclohexanamine from Step A (1 g) in dichloromethane (50 mL) was added di-tert-butyl dicarbonate (0.473 mL, 2.035 mmol) and triethylamine (0.355 mL, 2.54 mmol) at room temperature. The reaction mixture was stirred for 6 h, quenched with saturated ammonium chloride (50 mL) and extracted with ethyl acetate (3×50 mL). The combined organic layer was washed with saturated brine (50 mL), dried (sodium sulphate), filtered and concentrated under reduced pressure to give crude tert-butyl(4-(4-(2-(benzyloxy)-1,1,1,3,3,3-hexafluoropropan-2-yl)phenyl)-4-((4-fluorophenyl)sulfonyl)cyclohexyl)carbamate (1.2 g). LC/MS (M+18): 634.4.

Step C: tert-butyl ((1s,4s)-4-((4-fluorophenyl)sulfonyl)-4-(4-(1,1,1,3,3,3-hexafluoro-2-hydroxypropan-2-yl)phenyl)cyclohexyl)carbamate, and tert-butyl ((1r,4r)-4-((4-fluorophenyl)sulfonyl)-4-(4-(1,1,1,3,3,3-hexafluoro-2-hydroxypropan-2-yl)phenyl)cyclohexyl)carbamate

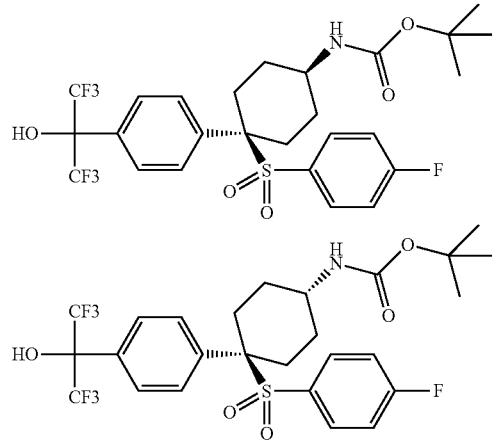

To a solution of crude tert-butyl (4-(4-(2-(benzyloxy)-1,1,1,3,3,3-hexafluoropropan-2-yl)phenyl)-4-((4-fluorophenyl)sulfonyl)cyclohexyl)carbamate from Step B (1 g) in methanol (50 mL) was added palladium on carbon (0.154 g, 0.145 mmol) at room temperature. The resulting mixture was stirred under hydrogen bladder for 12 h and filtered through celite pad. The pad was rinsed with methanol (3×100 mL). The combined methanol solution was evaporated under reduced pressure to give the crude product (980 mg). Two diastereomers of tert-butyl (4-((4-fluorophenyl)sulfonyl)-4-(1,1,1,3,3,3-hexafluoro-2-hydroxypropan-2-yl)phenyl)cyclohexyl)carbamate were separated by Prep-HPLC to give tert-butyl ((1s,4s)-4-((4-fluorophenyl)sulfonyl)-4-(4-(1,1,1,3,3,3-hexafluoro-2-hydroxypropan-2-yl)phenyl)cyclohexyl)carbamate (Peak 1, 318 mg, 37% yield) as white solids and tert-butyl ((1r,4r)-4-((4-fluorophenyl)sulfonyl)-4-(4-(1,1,1,3,3,3-hexafluoro-2-hydroxypropan-2-yl)phenyl)cyclohexyl)carbamate (Peak 2, 440 mg, 51% yield) as off white solids. Analytical data of Peak 1: LC/MS (M+18): 617.2; LC retention time: 18.39 min (analytical HPLC Method D); 1H NMR (DMSO-d6, 400 MHz): δ ppm 8.74 (s, 1H), 7.57 (d, J=8.4 Hz, 2H), 7.37 (d, J=8.4 Hz, 2H), 7.25-7.00 (m, 5H), 3.40 (br-s, 1H), 2.43 (d, J=13.4 Hz, 2H), 2.29 (d, J=13.4 Hz, 2H), 1.83 (d, J=14.4 Hz, 2H), 1.40 (s, 9H), 1.23 (t, J=13.2 Hz, 2H); 19F NMR (DMSO, 376 MHz): δ −73.92, −104.71. Analytical data of Peak 2: LC/MS (M+18): 617.2; LC retention time: 18.42 min (analytical HPLC Method D); 1H NMR (DMSO-d6, 400 MHz): δ ppm 8.78 (s, 1H), 7.60 (d, J=8.4 Hz, 2H), 7.42 (d, J=8.4 Hz, 2H), 7.22 (d, J=7.2 Hz, 4H), 6.66 (d, J=7.2 Hz, 1H), 3.27-3.24 (m, 1H), 2.62 (d, J=12.8 Hz, 2H), 2.06 (t, J=13.2 Hz, 2H), 1.81 (d, J=10.8 Hz, 2H), 1.31 (s, 9H), 1.06-0.98 (m, 2H); 19F NMR (DMSO, 376 MHz): δ −73.89, −104.46.

Step D: tert-butyl ((1s,4s)-4-((4-fluorophenyl)sulfonyl)-4-(4-(perfluoropropan-2-yl)phenyl)cyclohexyl)carbamate

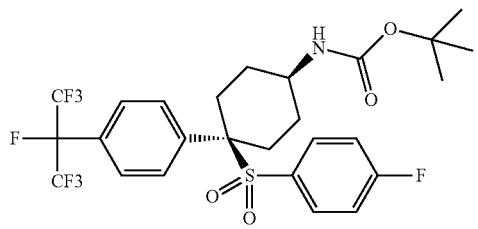 [SMILES: CC(C)(C)OC(=O)N[C@H]1CC[C@@](c2ccc(C(F)(C(F)(F)F)C(F)(F)F)cc2)(S(=O)(=O)c2ccc(F)cc2)CC1]

A stirred dichloromethane (1 mL) suspension of tert-butyl ((1s,4s)-4-((4-fluorophenyl)sulfonyl)-4-(4-(1,1,1,3,3,3-hexafluoro-2-hydroxypropan-2-yl)phenyl)cyclohexyl)carbamate (155 mg, 0.259 mmol) and diethylaminosulfur trifluoride (0.102 mL, 0.776 mmol) was heated at 50° C. in a sealed vial for 22 h. The crude mixture was cooled to room temperature, slowly added to ethanol (5 mL) while stirring and concentrated under reduced pressure. Silica gel chromatography, eluting with 0-100% ethyl acetate in hexanes, gave the desired product as yellow solid (141 mg, 91% yield). LC/MS (M−56+1): 546.3; LC retention time: 4.635 min (analytical HPLC Method A); 1H NMR (400 MHz, CDCl₃) δ ppm 7.53 (d, J=8.4 Hz, 2H), 7.35 (d, J=8.7 Hz, 2H), 7.15 (dd, J=8.8, 5.0 Hz, 2H), 6.94 (t, J=8.5 Hz, 2H), 4.89 (br. s., 1H), 3.76 (br. s., 1H), 2.59-2.47 (m, 2H), 2.44-2.35 (m, 2H), 1.96 (d, J=11.9 Hz, 2H), 1.52-1.45 (m, 11H); 19F NMR (400 MHz, CDCl₃) δ ppm −75.62, −102.78, −182.89.

Step E: (1s,4s)-4-((4-fluorophenyl)sulfonyl)-4-(4-(perfluoropropan-2-yl)phenyl)cyclohexanamine

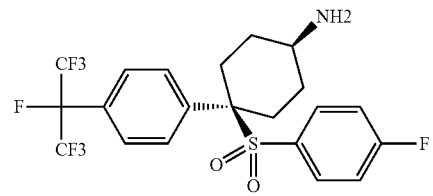

A 4 M dioxane solution of hydrogen chloride (0.5 mL, 2.000 mmol) was added to a stirred solution of tert-butyl ((1s,4s)-4-((4-fluorophenyl)sulfonyl)-4-(4-(perfluoropropan-2-yl)phenyl)cyclohexyl)carbamate (141 mg, 0.235 mmol) in dichloromethane (0.5 mL) at room temperature. After 1 h at room temperature, the mixture was concentrated under reduced pressure and dried under vacuum to give (1s,4s)-4-((4-fluorophenyl)sulfonyl)-4-(4-(perfluoropropan-2-yl)phenyl)cyclohexanamine hydrochloride as off-white solid (104.9 mg, 83% yield). LC/MS (M+1): 502.3; 1H NMR (400 MHz, 1:1 mixture of CDCl₃-CD₃OD) δ ppm 7.51 (d, J=8.6 Hz, 2H), 7.35 (d, J=8.6 Hz, 2H), 7.20-7.13 (m, 2H), 6.97 (t, J=8.6 Hz, 2H), 3.26 (d, J=3.9 Hz, 1H), 2.85-2.75 (m, 2H), 2.38-2.28 (m, 2H), 2.27-2.14 (m, 2H), 1.87 (td, J=9.3, 4.5 Hz, 2H); 19F NMR (400 MHz, 1:1 mixture of CDCl₃-CD₃OD) d −76.31, −103.07, −183.39.

Step F: N-((1s,4s)-4-((4-fluorophenyl)sulfonyl)-4-(4-(perfluoropropan-2-yl)phenyl)cyclohexyl)acetamide

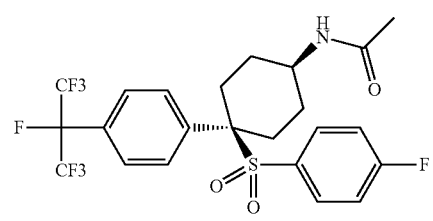 [SMILES: CC(=O)N[C@H]1CC[C@@](c2ccc(C(F)(C(F)(F)F)C(F)(F)F)cc2)(S(=O)(=O)c2ccc(F)cc2)CC1]

Hunig's Base (0.013 mL, 0.074 mmol) was added to a stirred solution of (1s,4s)-4-((4-fluorophenyl)sulfonyl)-4-(4-(perfluoropropan-2-yl)phenyl)cyclohexanamine hydrochloride (8 mg, 0.015 mmol) and acetic anhydride (3 mg, 0.029 mmol) in acetonitrile (0.5 mL) at room temperature. After 45 min at room temperature, LCMS analysis showed that the reaction was complete. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 15 minutes, then a 7-minute hold at 100% B; Flow: 20 mL/min. Fractions containing the desired product were combined and dried via centrifugal evaporation to give Example 9 (7.6 mg, 90% yield). LC/MS (M+1): 544.2; LC retention time: 1.94 min (analytical HPLC Method B); 1H NMR (400 MHz, 1:1 mixture of CDCl₃-CD₃OD) δ ppm 7.54 (d, J=8.5 Hz, 2H), 7.41 (d, J=8.8 Hz, 2H), 7.22-7.15 (m, 2H), 7.04-6.97 (m, 2H), 3.83 (t, J=3.6 Hz, 1H), 2.65-2.54 (m, 2H), 2.41 (d, J=13.8 Hz, 2H), 2.01 (s, 3H), 1.95 (dd, J=14.3, 3.3 Hz, 2H), 1.50 (t, J=13.6 Hz, 2H).

Example 10

5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-1H-indazole Step A: 5-(4-(2-((2,6-difluorobenzyl)oxy)-1,1,1,3,3,3-hexafluoropropan-2-yl)phenyl)-5-((4-fluorophenyl)sulfonyl)-2-oxocyclohexanecarbaldehyde

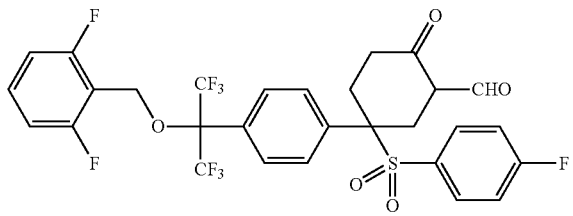 [SMILES: O=CC1CC(c2ccc(C(OCc3c(F)cccc3F)(C(F)(F)F)C(F)(F)F)cc2)(S(=O)(=O)c2ccc(F)cc2)CCC1=O]

Under inert atmosphere in a 25 mL round bottomed flask, to a solution of 4-(4-(2-((2,6-difluorobenzyl)oxy)-1,1,1,3,3,3-hexafluoropropan-2-yl)phenyl)-4-((4-fluorophenyl)sulfonyl)cyclohexanone (100 mg, 0.160 mmol, from Example 3) in dry tetrahydrofuran (5 mL) was added potassium tert-butoxide (44.9 mg, 0.40 mmol,) and ethyl formate (35.6 mg, 0.480 mmol). The mixture was stirred at room temperature for 2 h, quenched with water (50 mL) and extracted with ethyl acetate (3×50 mL). The combined organic layer was dried (sodium sulfate), filtered and concentrated under reduced pressure to give 5-(4-(2-((2,6-difluorobenzyl)oxy)-1,1,1,3,3,3-hexafluoropropan-2-yl)phenyl)-5-((4-fluorophenyl)sulfonyl)-2-oxocyclohexanecarbaldehyde (75 mg, 71.8% yield) as white solids. LC/MS (M−1): 651.0; LC retention time: 2.320 min (analytical HPLC Method H); 1H NMR (400 MHz, DMSO-d6): δ ppm 8.64 (s, 1H), 7.59 (d, J=8.2 Hz, 2H), 7.39-7.34 (m, 3H), 7.32-7.23 (m, 2H), 6.99-6.93 (m, 4H), 4.71 (s, 2H), 3.42 (d, J=15.2 Hz, 1H), 3.14 (d, J=14.8 Hz, 1H), 2.84-2.80 (m, 1H), 2.66-2.57 (m, 2H), 2.30-2.25 (m, 1H), 1.27-1.22 (m, 1H); 19F NMR (376 MHz): −70.20, −102.27, −114.42.

Step B: 5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-1H-indazole

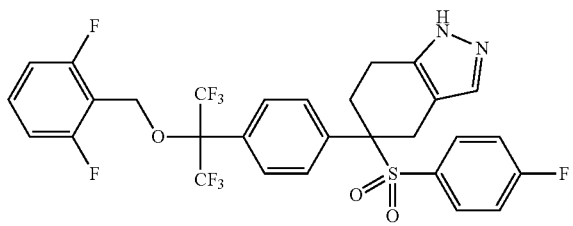 [SMILES: O=S(=O)(c1ccc(F)cc1)C1(c2ccc(C(OCc3c(F)cccc3F)(C(F)(F)F)C(F)(F)F)cc2)CCc2[nH]ncc2C1]

To a solution of 5-(4-(2-((2,6-difluorobenzyl)oxy)-1,1,1,3,3,3-hexafluoropropan-2-yl)phenyl)-5-((4-fluorophenyl)sulfonyl)-2-oxocyclohexanecarbaldehyde (75 mg, 0.115 mmol) in glacial acetic acid (3 mL) was added hydrazine (0.115 ml, 0.115 mmol,). The mixture was stirred at 115° C. for 1 h and concentrated. The yellow oil was neutralized by slow addition of saturated sodium bicarbonate (50 mL). The aqueous portion was extracted with ethyl acetate (3×50 mL). The combined organic layer was washed with water (50 mL) and saturated brine (50 mL), dried (sodium sulfate), filtered and concentrated under reduced pressure to give crude product as off white gummy solid. The crude product was purified by Preparative HPLC to yield white solids of 5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazole (30 mg, 40% yield). LC/MS (M+1): 649.2; LC retention time: 2.38 min (analytical HPLC Method H); 1H NMR (400 MHz, DMSO-d6): δ 12.35 (br-s, 1H), 7.62-7.45 (m, 10H), 7.36-7.18 (m, 2H), 4.61 (s, 2H), 3.59-3.55 (m, 1H), 3.29 (d, J=18.8 Hz, 1H), 3.01 (d, J=8.8 Hz 1H), 2.85 (dd, J=16.7, 4.8 Hz, 1H), 2.51-2.49 (m, 1H), 2.48-2.38 (m, 1H); 19F NMR (376 MHz): −69.77, −104.20, −115.03.

Example 11

6-(4-(2-((2,6-difluorobenzyl)oxy)-1,1,1,3,3,3-hexafluoropropan-2-yl)phenyl)-6-((4-fluorophenyl)sulfonyl)-4,5,6,7-tetrahydrobenzo[d]thiazol-2-amine Step A: 2-bromo-4-(4-(2-((2,6-difluorobenzyl)oxy)-1,1,1,3,3,3-hexafluoropropan-2-yl)phenyl)-4-((4-fluorophenyl)sulfonyl)cyclohexanone

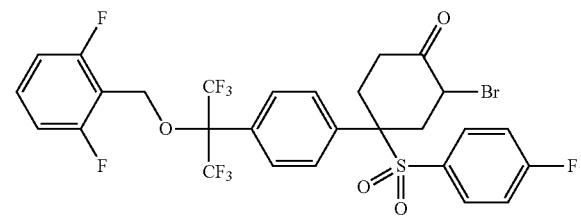 [SMILES: O=C1CCC(c2ccc(C(OCc3c(F)cccc3F)(C(F)(F)F)C(F)(F)F)cc2)(S(=O)(=O)c2ccc(F)cc2)CC1Br]

In a 25 mL dry round bottomed flask, a solution of 4-(4-(2-((2,6-difluorobenzyl)oxy)-1,1,1,3,3,3-hexafluoropropan-2-yl)phenyl)-4-((4-fluorophenyl)sulfonyl)cyclohexanone (200 mg, 0.320 mmol) in dry tetrahydrofuran (3.0 mL) was cooled to 0° C. under inert atmosphere. To that was added phenyltrimethylammonium tribromide (144 mg, 0.384 mmol). The reaction mixture was allowed to reach room temperature with constant stirring for another 30 min. The reaction mixture was quenched with water (10 mL) and extracted with ethyl acetate (3×15 mL). The combined organic phase was subsequently washed with water (2×10 mL), brine (10 mL), dried (sodium sulphate), filtered and concentrated under reduced pressure to give crude 2-bromo-4-(4-(2-((2,6-difluorobenzyl)oxy)-1,1,1,3,3,3-hexafluoropropan-2-yl)phenyl)-4-((4-fluorophenyl)sulfonyl)cyclohexanone as yellowish solid (200 mg). LC/MS (M+18): 720.0.

Step B: 6-(4-(2-((2,6-difluorobenzyl)oxy)-1,1,1,3,3,3-hexafluoropropan-2-yl)phenyl)-6-((4-fluorophenyl)sulfonyl)-4,5,6,7-tetrahydrobenzo[d]thiazol-2-amine

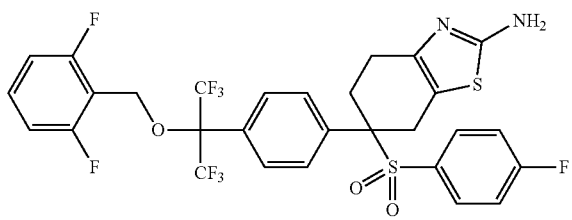 [SMILES: Nc1nc2c(s1)CC(c1ccc(C(OCc3c(F)cccc3F)(C(F)(F)F)C(F)(F)F)cc1)(S(=O)(=O)c1ccc(F)cc1)CC2]

To a solution of crude 2-bromo-4-(4-(2-((2,6-difluoro benzyl)oxy)-1,1,1,3,3,3-hexafluoropropan-2-yl)phenyl)-4-((4-fluorophenyl)sulfonyl)cyclohexanone from Step A (29 mg) in ethanol (4.0 mL) at room temperature under inert atmosphere was added triethylamine (8.62 µl, 0.062 mmol) followed by thiourea (6.28 mg, 0.082 mmol). The reaction mixture was heated to 50° C. and stirred at that temperature for 12 h. The reaction mixture was quenched with water (10 mL) and extracted with dichloromethane (3×10 mL). The combined organic phase was subsequently washed with water (10 mL) and brine (10 mL), dried (sodium sulphate), filtered and concentrated under reduced pressure. The crude material was purified through Prep-HPLC to yield 6-(4-(2-((2,6-difluoro benzyl)oxy)-1,1,1,3,3,3-hexafluoropropan-2-yl)phenyl)-6-((4-fluorophen-yl)sulfonyl)-4,5,6,7-tetrahydrobenzo[d]thiazol-2-amine (8.0 mg, 28% yield) as cream color solid. LC/MS (M+1): 681.0; LC retention time: 11.05 min (analytical HPLC Method D); 1H NMR (400 MHz, DMSO-d6): δ ppm 7.56-7.54 (d, J=8.4 Hz, 2H), 7.40-7.34 (m, 3H), 7.27-7.26 (m, 1H), 7.26-7.24 (m, 1H), 6.97-6.92 (m, 4H), 4.70-4.66 (m, 4H), 3.67 (dt, J=14.4, 1.6 Hz, 1H), 3.32 (d, J=14.8 Hz, 1H), 2.97-2.92 (m, 1H), 2.82-2.76 (m, 1H), 2.70-2.63 (m, 1H), 2.36-2.28 (m, 1H).

The Examples in TABLE 1 below were prepared in the same manner as outlined in the examples above, substituting the appropriate amine, alcohol and ketone intermediates.

| Example number | Structure | MS observed (M + 1) | HPLC ret. time (min.) | HPLC method |
|---|---|---|---|---|
| 12 | 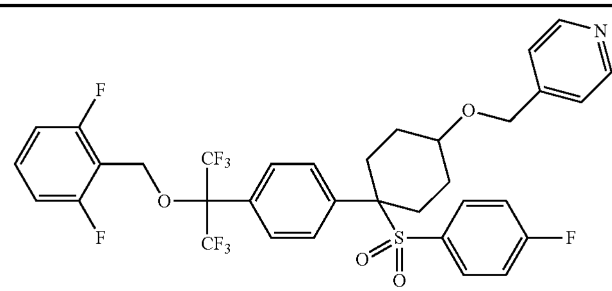 | 718.2 | 2.449 | G |
| 13 | 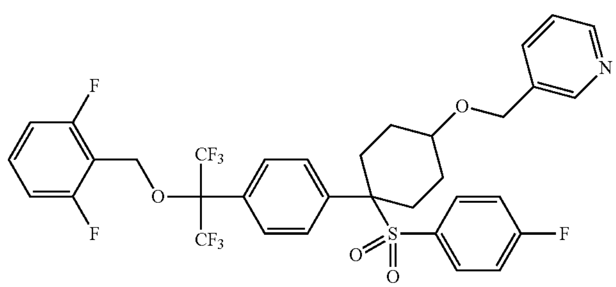 [SMILES: O=S(=O)(c1ccc(F)cc1)C1(c2ccc(C(OCc3c(F)cccc3F)(C(F)(F)F)C(F)(F)F)cc2)CCC(OCc2cccnc2)CC1] | 718.2 | 2.439 | G |
| 14 | 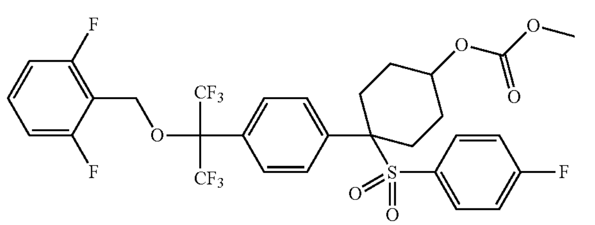 [SMILES: COC(=O)OC1CCC(c2ccc(C(OCc3c(F)cccc3F)(C(F)(F)F)C(F)(F)F)cc2)(S(=O)(=O)c2ccc(F)cc2)CC1] | 702.0 (M + 18) | 2.549 | G |
| 15 | 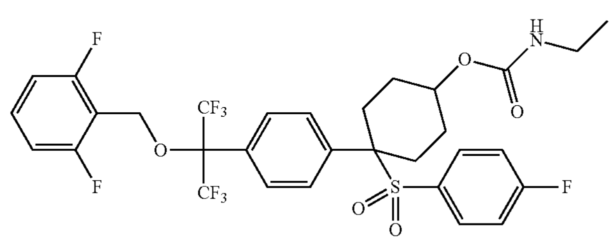 [SMILES: CCNC(=O)OC1CCC(c2ccc(C(OCc3c(F)cccc3F)(C(F)(F)F)C(F)(F)F)cc2)(S(=O)(=O)c2ccc(F)cc2)CC1] | 715.2 (M + 18) | 2.464 | G |

-continued

| Example number | Structure | MS observed (M + 1) | HPLC ret. time (min.) | HPLC method |
|---|---|---|---|---|
| 16 | 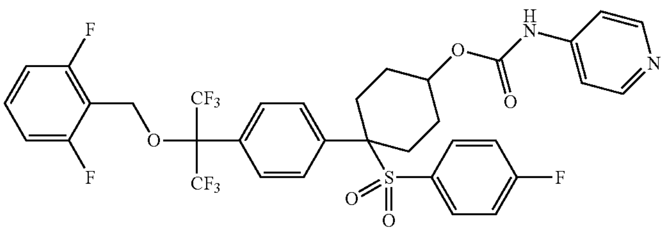 [SMILES: O=C(Nc1ccncc1)OC1CCC(c2ccc(C(OCc3c(F)cccc3F)(C(F)(F)F)C(F)(F)F)cc2)(S(=O)(=O)c2ccc(F)cc2)CC1] | 747.2 | 2.341 | G |
| 17 | 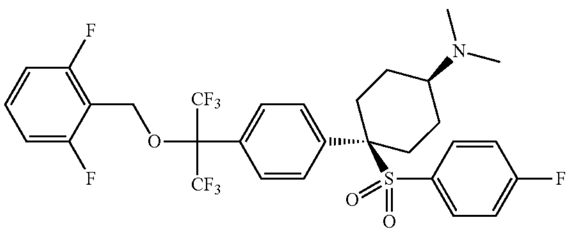 [SMILES: CN(C)[C@H]1CC[C@@](c2ccc(C(OCc3c(F)cccc3F)(C(F)(F)F)C(F)(F)F)cc2)(S(=O)(=O)c2ccc(F)cc2)CC1] | 654.2 | 2.13 | B |
| 18 | 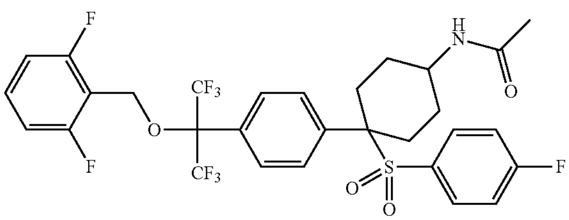 [SMILES: CC(=O)NC1CCC(c2ccc(C(OCc3c(F)cccc3F)(C(F)(F)F)C(F)(F)F)cc2)(S(=O)(=O)c2ccc(F)cc2)CC1] | 668.0 | 2.194 | G |
| 19 | 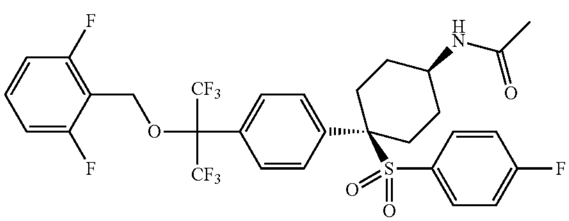 [SMILES: CC(=O)N[C@H]1CC[C@@](c2ccc(C(OCc3c(F)cccc3F)(C(F)(F)F)C(F)(F)F)cc2)(S(=O)(=O)c2ccc(F)cc2)CC1] | 668.3 | 2.20 | B |
| 20 | 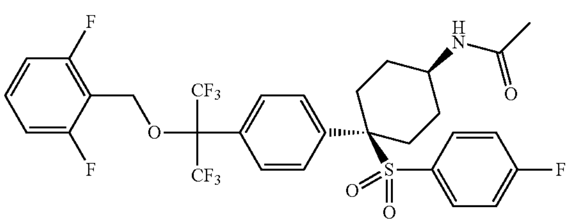 [SMILES: CC(=O)N[C@H]1CC[C@@](c2ccc(C(OCc3c(F)cccc3F)(C(F)(F)F)C(F)(F)F)cc2)(S(=O)(=O)c2ccc(F)cc2)CC1] | 668.3 | 2.23 | B |
| 21 | 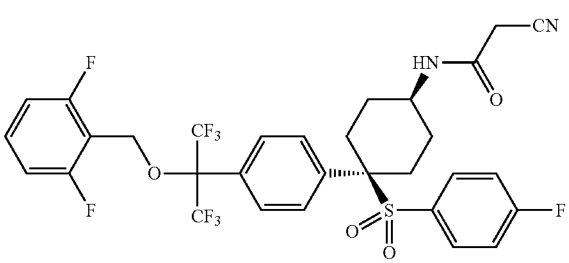 [SMILES: N#CCC(=O)N[C@H]1CC[C@@](c2ccc(C(OCc3c(F)cccc3F)(C(F)(F)F)C(F)(F)F)cc2)(S(=O)(=O)c2ccc(F)cc2)CC1] | 710.0 (M + 18) | 2.130 | G |

-continued

| Example number | Structure | MS observed (M + 1) | HPLC ret. time (min.) | HPLC method |
|---|---|---|---|---|
| 22 | 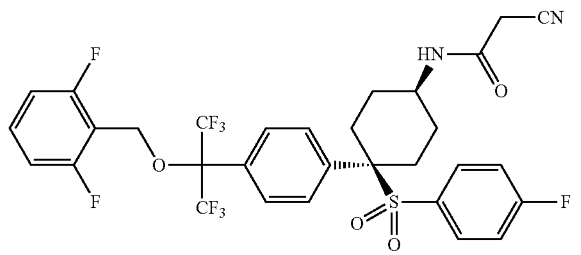 [SMILES: N#CCC(=O)N[C@H]1CC[C@@](c2ccc(C(OCc3c(F)cccc3F)(C(F)(F)F)C(F)(F)F)cc2)(S(=O)(=O)c2ccc(F)cc2)CC1] | 710.0 (M + 18) | 2.191 | G |
| 23 | 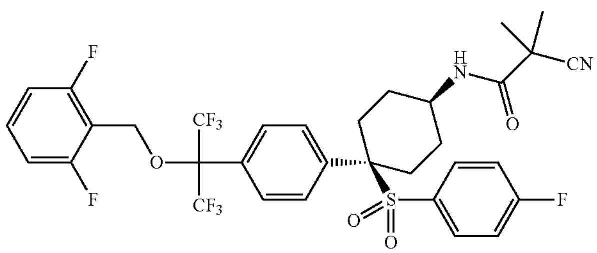 [SMILES: CC(C)(C#N)C(=O)N[C@H]1CC[C@@](c2ccc(C(OCc3c(F)cccc3F)(C(F)(F)F)C(F)(F)F)cc2)(S(=O)(=O)c2ccc(F)cc2)CC1] | 738.3 (M + 18) | 2.34 | B |
| 24 | 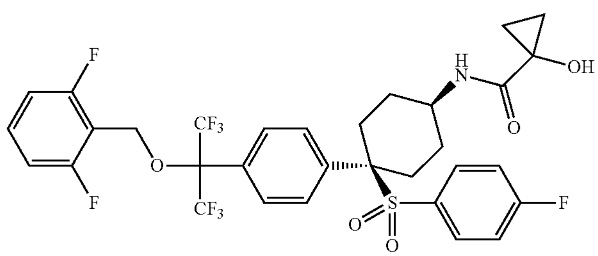 [SMILES: O=C(N[C@H]1CC[C@@](c2ccc(C(OCc3c(F)cccc3F)(C(F)(F)F)C(F)(F)F)cc2)(S(=O)(=O)c2ccc(F)cc2)CC1)C1(O)CC1] | 710.4 | 2.27 | B |
| 25 | 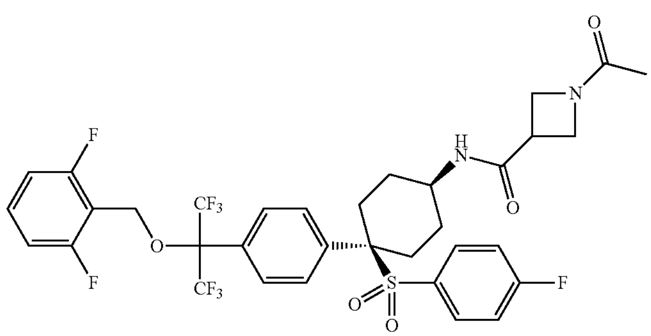 [SMILES: CC(=O)N1CC(C(=O)N[C@H]2CC[C@@](c3ccc(C(OCc4c(F)cccc4F)(C(F)(F)F)C(F)(F)F)cc3)(S(=O)(=O)c3ccc(F)cc3)CC2)C1] | 750.8 | 11.32 | D |
| 26 | 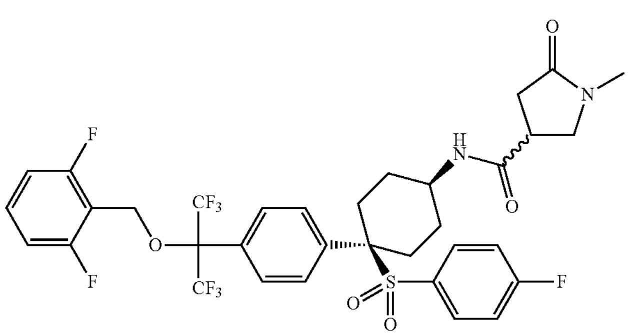 [SMILES: CN1CC(C(=O)N[C@H]2CC[C@@](c3ccc(C(OCc4c(F)cccc4F)(C(F)(F)F)C(F)(F)F)cc3)(S(=O)(=O)c3ccc(F)cc3)CC2)CC1=O] | 751.4 | 2.18 | B |

-continued
| Example number | Structure | MS observed (M + 1) | HPLC ret. time (min.) | HPLC method |
|---|---|---|---|---|
| 27 | 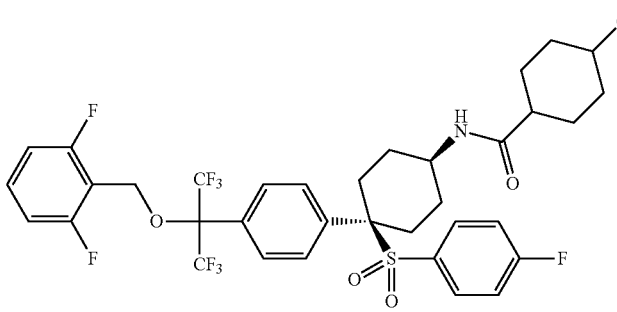 (diastereomer 1) | 752.3 | 2.19 | B |
| 28 | 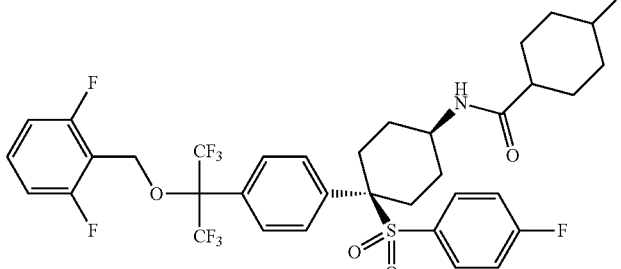 (diastereomer 2) | 752.3 | 2.17 | B |
| 29 | 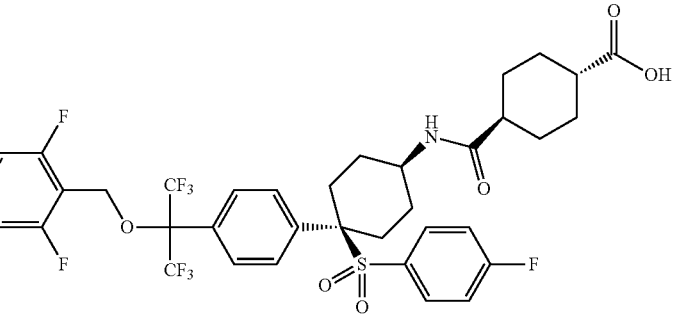 | 780.3 | 1.90 | B |
| 30 | 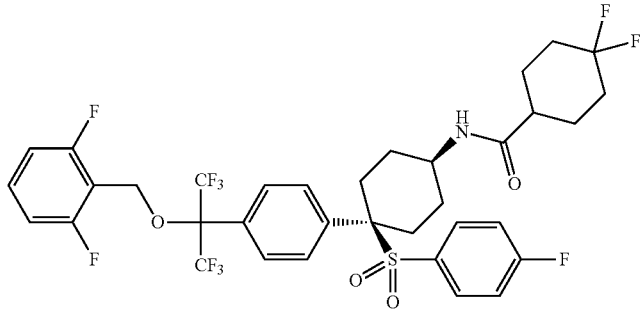 [SMILES: O=C(N[C@H]1CC[C@@](c2ccc(C(OCc3c(F)cccc3F)(C(F)(F)F)C(F)(F)F)cc2)(S(=O)(=O)c2ccc(F)cc2)CC1)C1CCC(F)(F)CC1] | 772.5 | 2.48 | B |

| Example number | Structure | MS observed (M + 1) | HPLC ret. time (min.) | HPLC method |
|---|---|---|---|---|
| 31 | 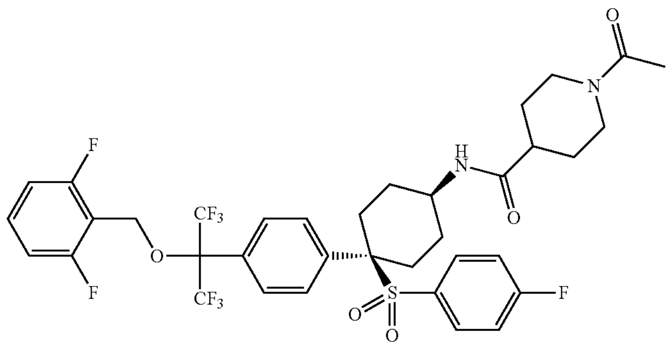 [SMILES: CC(=O)N1CCC(C(=O)N[C@H]2CC[C@@](c3ccc(C(OCc4c(F)cccc4F)(C(F)(F)F)C(F)(F)F)cc3)(S(=O)(=O)c3ccc(F)cc3)CC2)CC1] | 779.5 | 2.14 | B |
| 32 | 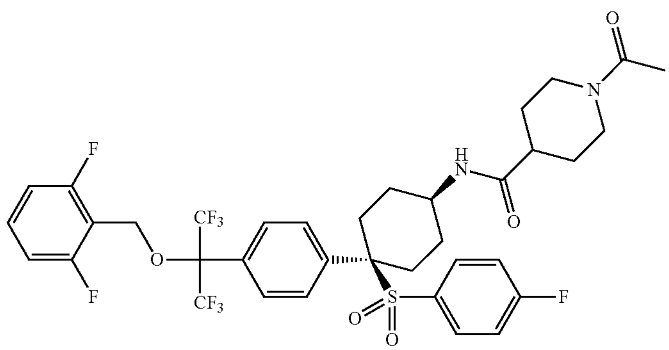 [SMILES: CC(=O)N1CCC(C(=O)N[C@H]2CC[C@@](c3ccc(C(OCc4c(F)cccc4F)(C(F)(F)F)C(F)(F)F)cc3)(S(=O)(=O)c3ccc(F)cc3)CC2)CC1] | 779.4 | 2.20 | B |
| 33 | 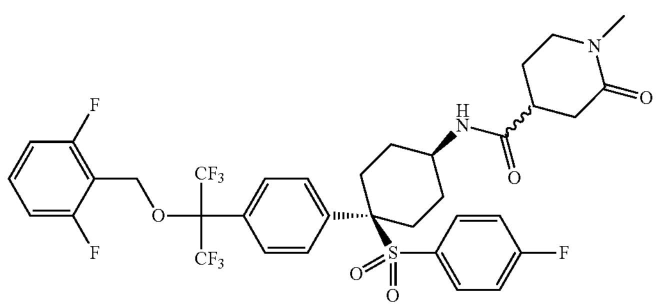 [SMILES: CN1CCC(C(=O)N[C@H]2CC[C@@](c3ccc(C(OCc4c(F)cccc4F)(C(F)(F)F)C(F)(F)F)cc3)(S(=O)(=O)c3ccc(F)cc3)CC2)CC1=O] | 765.5 | 2.18 | B |
| 34 | 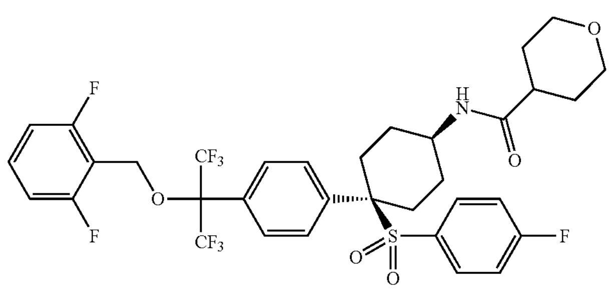 [SMILES: O=C(N[C@H]1CC[C@@](c2ccc(C(OCc3c(F)cccc3F)(C(F)(F)F)C(F)(F)F)cc2)(S(=O)(=O)c2ccc(F)cc2)CC1)C1CCOCC1] | 738.1 | 2.209 | G |
| 35 | 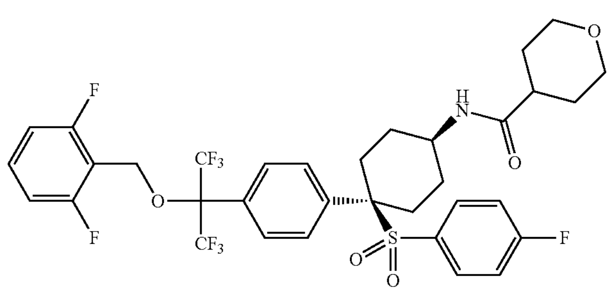 | 738.2 | 2.252 | G |

-continued
| Example number | Structure | MS observed (M + 1) | HPLC ret. time (min.) | HPLC method |
|---|---|---|---|---|
| 36 | 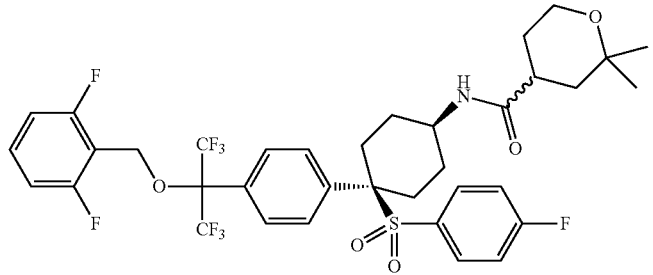 [SMILES: CC1(C)CC(C(=O)N[C@H]2CC[C@@](c3ccc(C(OCc4c(F)cccc4F)(C(F)(F)F)C(F)(F)F)cc3)(S(=O)(=O)c3ccc(F)cc3)CC2)CCO1] | 766.5 | 2.39 | B |
| 37 | 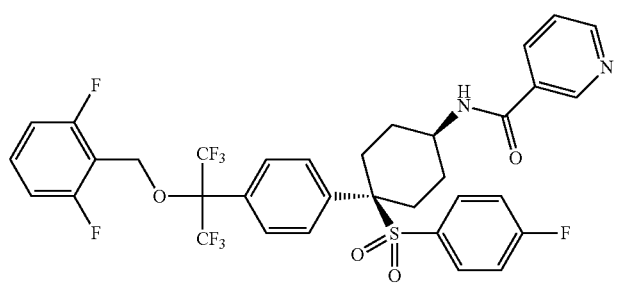 [SMILES: O=C(N[C@H]1CC[C@@](c2ccc(C(OCc3c(F)cccc3F)(C(F)(F)F)C(F)(F)F)cc2)(S(=O)(=O)c2ccc(F)cc2)CC1)c1cccnc1] | 731.0 | 2.256 | G |
| 38 | 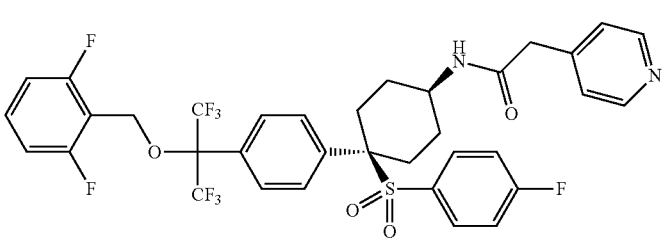 [SMILES: O=C(Cc1ccncc1)N[C@H]1CC[C@@](c2ccc(C(OCc3c(F)cccc3F)(C(F)(F)F)C(F)(F)F)cc2)(S(=O)(=O)c2ccc(F)cc2)CC1] | 745.2 | 2.134 | G |
| 39 | 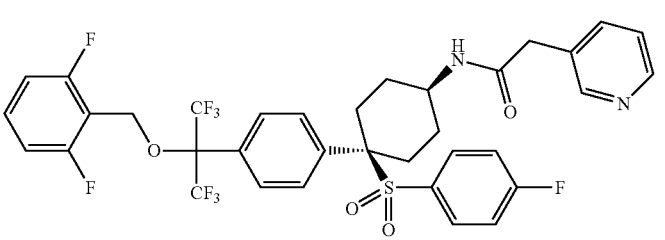 [SMILES: O=C(Cc1cccnc1)N[C@H]1CC[C@@](c2ccc(C(OCc3c(F)cccc3F)(C(F)(F)F)C(F)(F)F)cc2)(S(=O)(=O)c2ccc(F)cc2)CC1] | 745.2 | 2.203 | G |
| 40 | 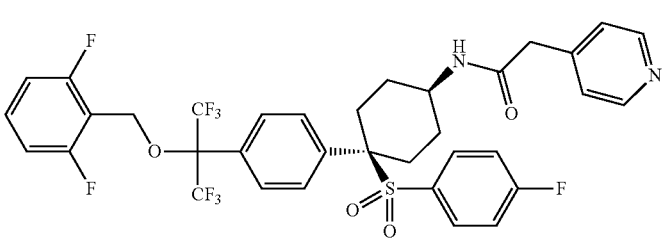 [SMILES: O=C(Cc1ccncc1)N[C@H]1CC[C@@](c2ccc(C(OCc3c(F)cccc3F)(C(F)(F)F)C(F)(F)F)cc2)(S(=O)(=O)c2ccc(F)cc2)CC1] | 745.2 | 2.190 | G |

| Example number | Structure | MS observed (M + 1) | HPLC ret. time (min.) | HPLC method |
|---|---|---|---|---|
| 41 | 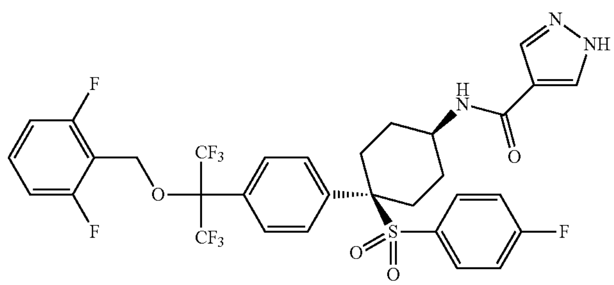 [SMILES: O=C(N[C@H]1CC[C@@](c2ccc(C(OCc3c(F)cccc3F)(C(F)(F)F)C(F)(F)F)cc2)(S(=O)(=O)c2ccc(F)cc2)CC1)c1cn[nH]c1] | 720.2 | 2.13 | C |
| 42 | 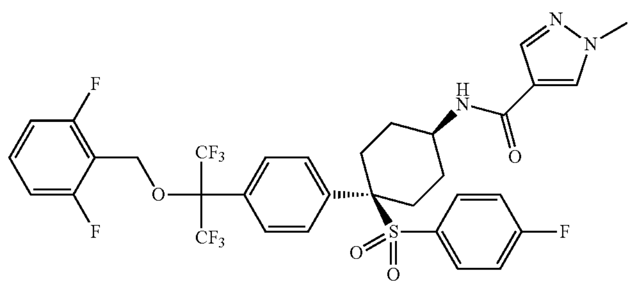 [SMILES: Cn1cc(C(=O)N[C@H]2CC[C@@](c3ccc(C(OCc4c(F)cccc4F)(C(F)(F)F)C(F)(F)F)cc3)(S(=O)(=O)c3ccc(F)cc3)CC2)cn1] | 734.4 | 2.25 | C |
| 43 | 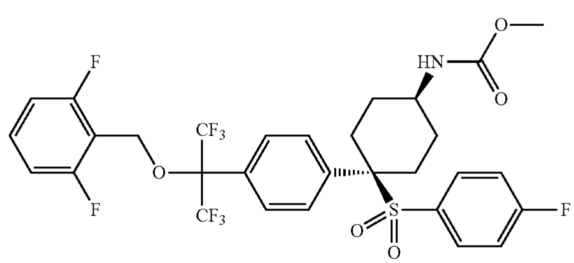 [SMILES: COC(=O)N[C@H]1CC[C@@](c2ccc(C(OCc3c(F)cccc3F)(C(F)(F)F)C(F)(F)F)cc2)(S(=O)(=O)c2ccc(F)cc2)CC1] | 701.0 (M + 18) | 2.261 | G |
| 44 | 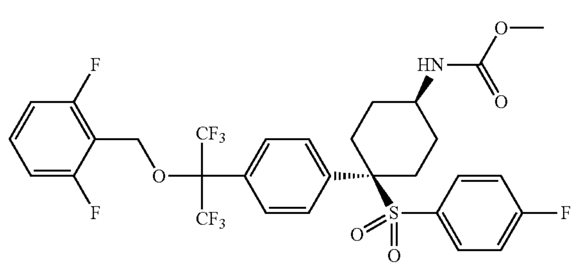 [SMILES: COC(=O)N[C@H]1CC[C@@](c2ccc(C(OCc3c(F)cccc3F)(C(F)(F)F)C(F)(F)F)cc2)(S(=O)(=O)c2ccc(F)cc2)CC1] | 701.0 (M + 18) | 2.295 | G |
| 45 | 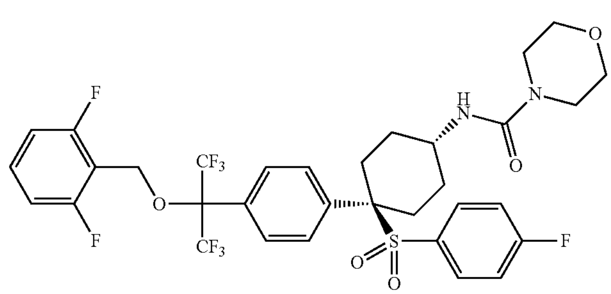 [SMILES: O=C(N[C@H]1CC[C@](c2ccc(C(OCc3c(F)cccc3F)(C(F)(F)F)C(F)(F)F)cc2)(S(=O)(=O)c2ccc(F)cc2)CC1)N1CCOCC1] | 739.0 | 2.115 | G |

-continued

| Example number | Structure | MS observed (M + 1) | HPLC ret. time (min.) | HPLC method |
|---|---|---|---|---|
| 46 | 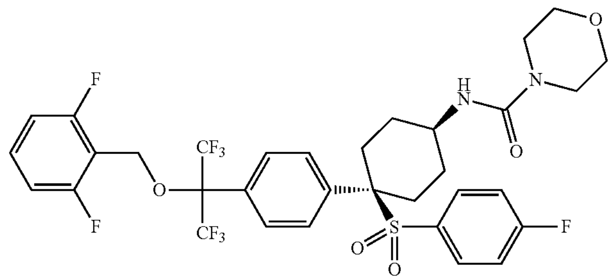 [SMILES: O=C(N[C@H]1CC[C@@](c2ccc(C(OCc3c(F)cccc3F)(C(F)(F)F)C(F)(F)F)cc2)(S(=O)(=O)c2ccc(F)cc2)CC1)N1CCOCC1] | 739.1 | 2.147 | G |
| 47 | 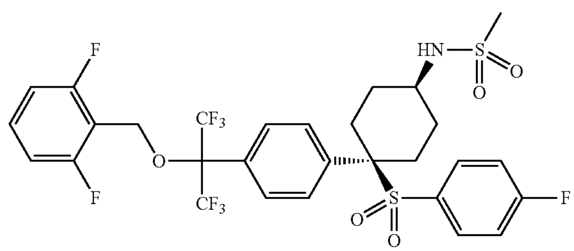 [SMILES: CS(=O)(=O)N[C@H]1CC[C@@](c2ccc(C(OCc3c(F)cccc3F)(C(F)(F)F)C(F)(F)F)cc2)(S(=O)(=O)c2ccc(F)cc2)CC1] | 721.0 (M + 18) | 2.168 | G |
| 48 | 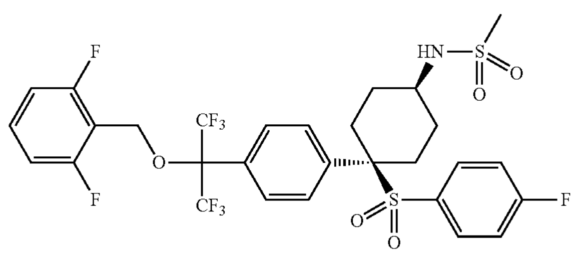 [SMILES: CS(=O)(=O)N[C@H]1CC[C@@](c2ccc(C(OCc3c(F)cccc3F)(C(F)(F)F)C(F)(F)F)cc2)(S(=O)(=O)c2ccc(F)cc2)CC1] | 721.0 (M + 18) | 2.208 | G |
| 49 | 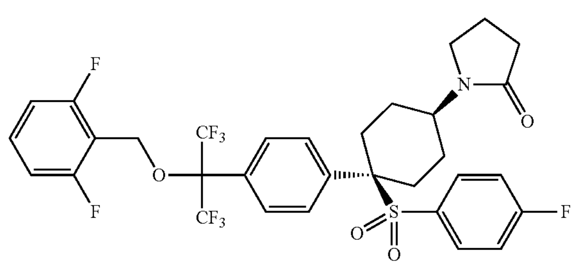 [SMILES: O=C1CCCN1[C@H]1CC[C@@](c2ccc(C(OCc3c(F)cccc3F)(C(F)(F)F)C(F)(F)F)cc2)(S(=O)(=O)c2ccc(F)cc2)CC1] | 694.2 | 2.24 | B |
| 50 | 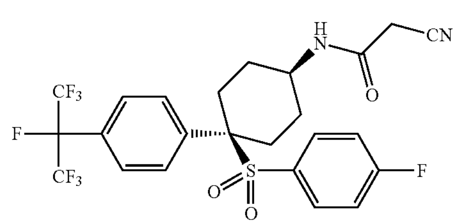 | 586.2 (M + 18) | 2.01 | B |

-continued

| Example number | Structure | MS observed (M + 1) | HPLC ret. time (min.) | HPLC method |
|---|---|---|---|---|
| 51 | 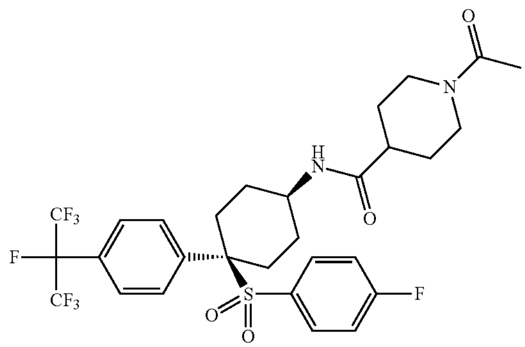 [SMILES: CC(=O)N1CCC(C(=O)N[C@H]2CC[C@@](c3ccc(C(F)(C(F)(F)F)C(F)(F)F)cc3)(S(=O)(=O)c3ccc(F)cc3)CC2)CC1] | 655.3 | 1.94 | B |
| 52 | 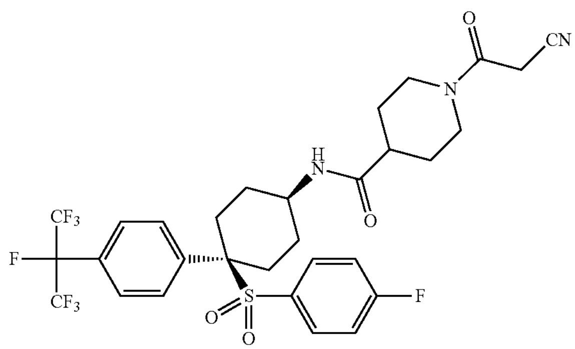 [SMILES: N#CCC(=O)N1CCC(C(=O)N[C@H]2CC[C@@](c3ccc(C(F)(C(F)(F)F)C(F)(F)F)cc3)(S(=O)(=O)c3ccc(F)cc3)CC2)CC1] | 697.3 (M + 18) | 1.96 | B |
| 53 | 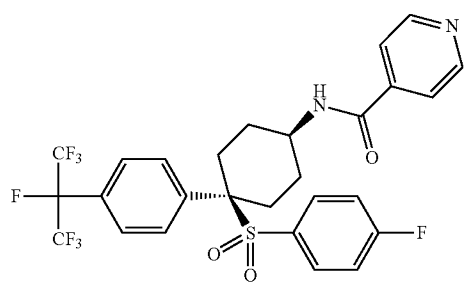 [SMILES: O=C(N[C@H]1CC[C@@](c2ccc(C(F)(C(F)(F)F)C(F)(F)F)cc2)(S(=O)(=O)c2ccc(F)cc2)CC1)c1ccncc1] | 607.2 | 2.04 | B |
| 54 | 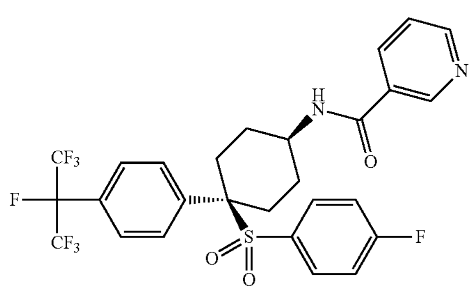 | 607.2 | 2.01 | B |
| 55 | 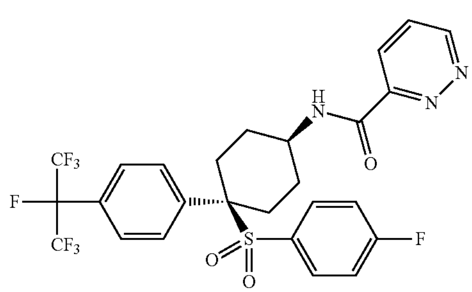 [SMILES: O=C(N[C@H]1CC[C@@](c2ccc(C(F)(C(F)(F)F)C(F)(F)F)cc2)(S(=O)(=O)c2ccc(F)cc2)CC1)c1cccnn1] | 608.1 | 2.05 | B |

-continued

| Example number | Structure | MS observed (M + 1) | HPLC ret. time (min.) | HPLC method |
|---|---|---|---|---|
| 56 | 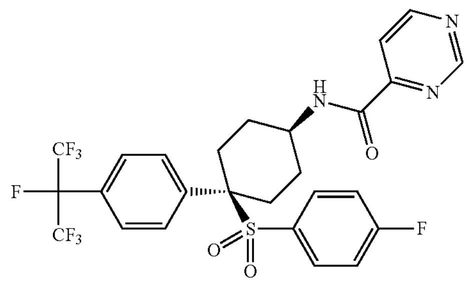 [SMILES: O=C(N[C@H]1CC[C@@](c2ccc(C(F)(C(F)(F)F)C(F)(F)F)cc2)(S(=O)(=O)c2ccc(F)cc2)CC1)c1ccncn1] | 608.2 | 2.08 | B |
| 57 | 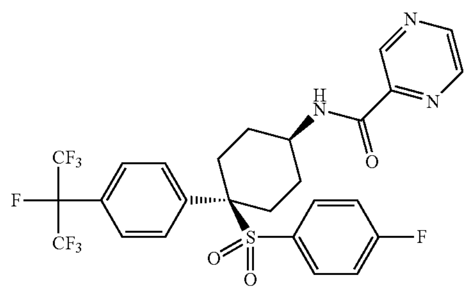 [SMILES: O=C(N[C@H]1CC[C@@](c2ccc(C(F)(C(F)(F)F)C(F)(F)F)cc2)(S(=O)(=O)c2ccc(F)cc2)CC1)c1cnccn1] | 608.2 | 2.09 | B |
| 58 | 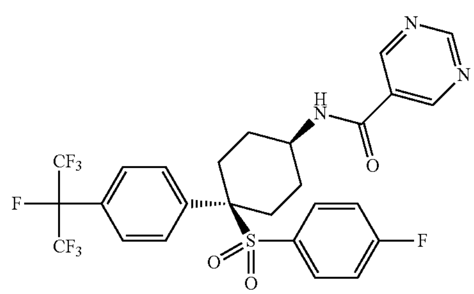 [SMILES: O=C(N[C@H]1CC[C@@](c2ccc(C(F)(C(F)(F)F)C(F)(F)F)cc2)(S(=O)(=O)c2ccc(F)cc2)CC1)c1cncnc1] | 608.1 | 1.97 | B |
| 59 | 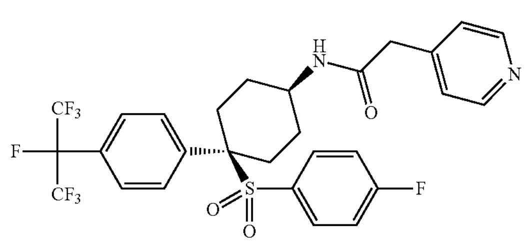 [SMILES: O=C(Cc1ccncc1)N[C@H]1CC[C@@](c2ccc(C(F)(C(F)(F)F)C(F)(F)F)cc2)(S(=O)(=O)c2ccc(F)cc2)CC1] | 621.2 | 1.96 | B |
| 60 | 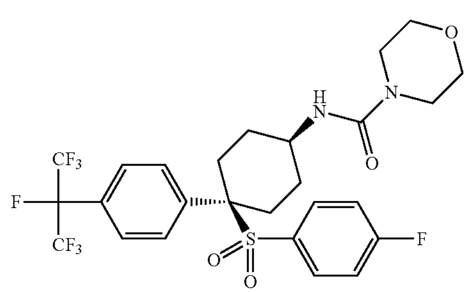 [SMILES: O=C(N[C@H]1CC[C@@](c2ccc(C(F)(C(F)(F)F)C(F)(F)F)cc2)(S(=O)(=O)c2ccc(F)cc2)CC1)N1CCOCC1] | 615.2 | 1.97 | B |

-continued

| Example number | Structure | MS observed (M + 1) | HPLC ret. time (min.) | HPLC method |
|---|---|---|---|---|
| 61 | 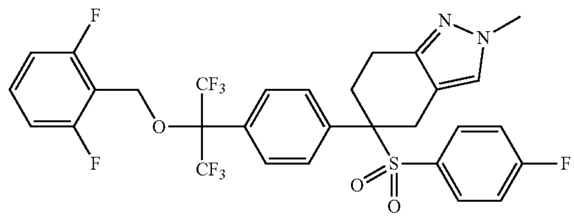 | 663.0 | 13.59 | D |
| 62 | 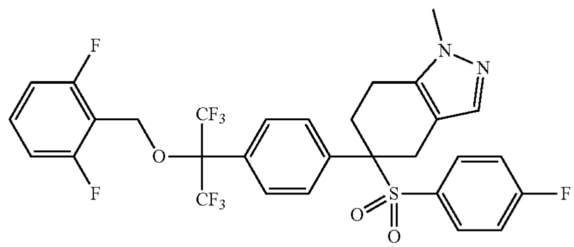 [SMILES: Cn1ncc2c1CCC(c1ccc(C(OCc3c(F)cccc3F)(C(F)(F)F)C(F)(F)F)cc1)(S(=O)(=O)c1ccc(F)cc1)C2] | 663.0 | 13.67 | D |
| 63 | 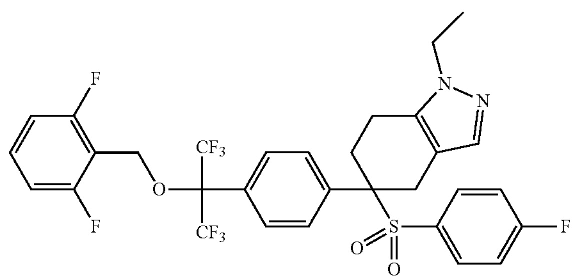 [SMILES: CCn1ncc2c1CCC(c1ccc(C(OCc3c(F)cccc3F)(C(F)(F)F)C(F)(F)F)cc1)(S(=O)(=O)c1ccc(F)cc1)C2] | 677.2 | 14.29 | D |
| 64 | 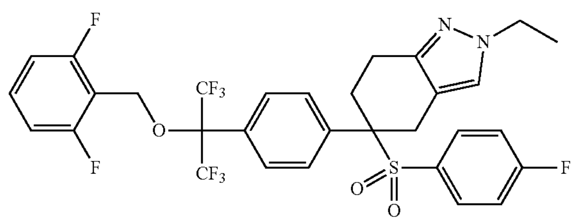 [SMILES: CCn1cc2c(n1)CCC(c1ccc(C(OCc3c(F)cccc3F)(C(F)(F)F)C(F)(F)F)cc1)(S(=O)(=O)c1ccc(F)cc1)C2] | 677.2 | 14.25 | D |
| 65 | 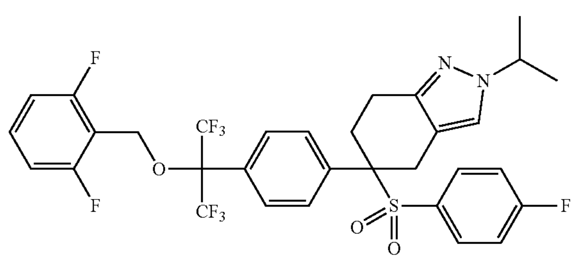 [SMILES: CC(C)n1cc2c(n1)CCC(c1ccc(C(OCc3c(F)cccc3F)(C(F)(F)F)C(F)(F)F)cc1)(S(=O)(=O)c1ccc(F)cc1)C2] | 691.0 | 15.53 | D |
| 66 | 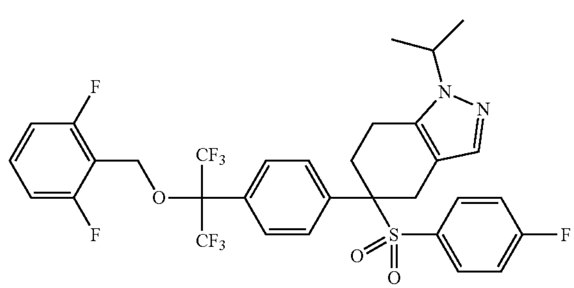 [SMILES: CC(C)n1ncc2c1CCC(c1ccc(C(OCc3c(F)cccc3F)(C(F)(F)F)C(F)(F)F)cc1)(S(=O)(=O)c1ccc(F)cc1)C2] | 691.2 | 15.17 | D |

-continued

| Example number | Structure | MS observed (M + 1) | HPLC ret. time (min.) | HPLC method |
|---|---|---|---|---|
| 67 | 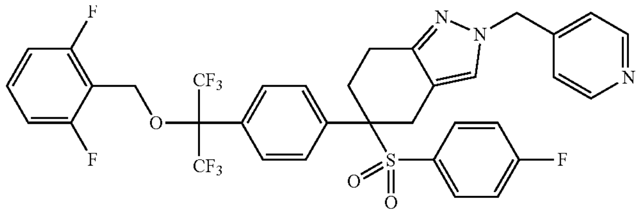 [SMILES: O=S(=O)(c1ccc(F)cc1)C1(c2ccc(C(OCc3c(F)cccc3F)(C(F)(F)F)C(F)(F)F)cc2)CCc2nn(Cc3ccncc3)cc2C1] | 740.0 | 18.56 | D |
| 68 | 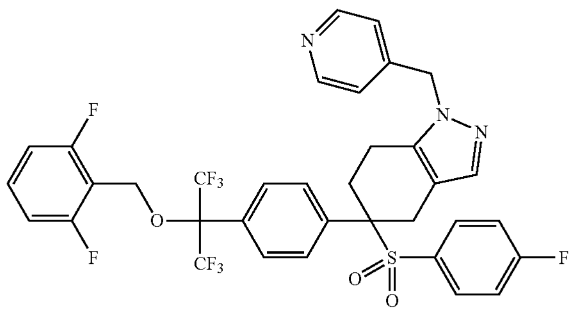 [SMILES: O=S(=O)(c1ccc(F)cc1)C1(c2ccc(C(OCc3c(F)cccc3F)(C(F)(F)F)C(F)(F)F)cc2)CCc2c(cnn2Cc2ccncc2)C1] | 740.0 | 18.73 | D |
| 69 | enantiomer 2 | 733.0 | 13.91 | D |
| 70 | enantiomer 1 | 733.0 | 13.92 | D |
| 71 | 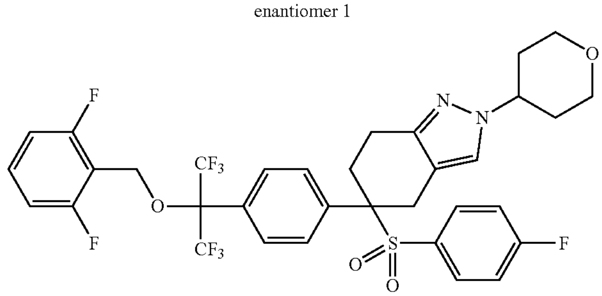 | 733.0 | 13.88 | D |

Example 72

N-(6-(4-(2-((2,6-difluorobenzyl)oxy)-1,1,1,3,3,3-hexafluoropropan-2-yl)phenyl)-6-((4-fluorophenyl)sulfonyl)-4,5,6,7-tetrahydrobenzo[d]thiazol-2-yl)acetamide

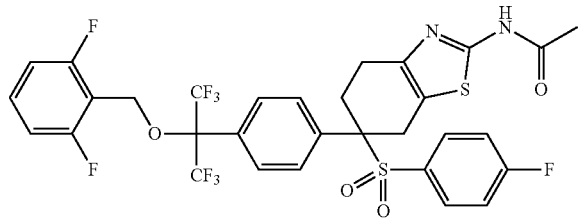

To a solution of 6-(4-(2-((2,6-difluorobenzyl)oxy)-1,1,1,3,3,3-hexafluoropropan-2-yl) phenyl)-6-((4-fluorophenyl)sulfonyl)-4,5,6,7-tetrahydrobenzo[d]thiazol-2-amine (3) (40 mg, 0.059 mmol, Example 11) in DCM (6.0 mL) was added pyridine (4.75 µl, 0.059 mmol) followed by Acetic anhydride (5.55 µl, 0.059 mmol). It was stirred at room temperature for 2 h. After completion of the reaction, it was dried under reduced pressure to remove DCM. Resulting gummy residue was directly purified by preparative HPLC to get N-(6-(4-(2-((2,6-difluorobenzyl)oxy)-1,1,1,3,3,3-hexafluoro propan-2-yl)phenyl)-6-((4-fluorophenyl)sulfonyl)-4,5,6,7-tetrahydrobenzo[d]thiazol-2-yl)acetamide (4.0 mg, 0.009 mmol, 10% yield) as white solid. LC/MS (M+1): 723.0; LC retention time: 22.07 min (analytical HPLC Method D); 1H NMR (400 MHz, DMSO-d6): δ ppm 7.56-7.54 (d, J=8.4 Hz, 2H), 7.39-7.34 (m, 3H), 7.29-7.26 (m, 2H), 6.99-6.93 (m, 4H), 4.68 (s, 2H), 3.74 (d, J=15.6 Hz, 1H), 3.47 (d, J=16.8 Hz, 1H), 3.06-2.88 (m, 2H), 2.75-2.67 (m, 1H), 2.46-2.39 (m, 1H), 2.21 (s, 3H).

Examples 73 and 74

5-(4-(2-((2,6-difluorobenzyl)oxy)-1,1,1,3,3,3-hexafluoropropan-2-yl)phenyl)-5-((4-fluorophenyl)sulfonyl)-2-(pyridin-4-yl)-4,5,6,7-tetrahydro-2H-indazole and 5-(4-(2-((2,6-difluorobenzyl)oxy)-1,1,1,3,3,3-hexafluoropropan-2-yl)phenyl)-5-((4-fluorophenyl)sulfonyl)-1-(pyridin-4-yl)-4,5,6,7-tetrahydro-1H-indazole

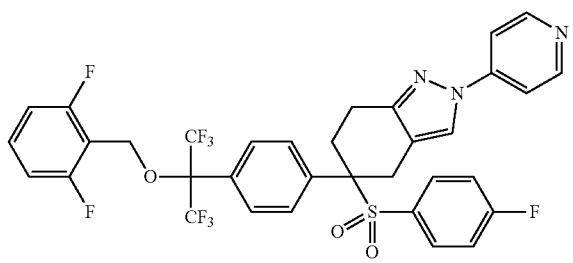 [SMILES: O=S(=O)(c1ccc(F)cc1)C1(c2ccc(C(OCc3c(F)cccc3F)(C(F)(F)F)C(F)(F)F)cc2)CCc2nn(C3CCOCC3)cc2C1]

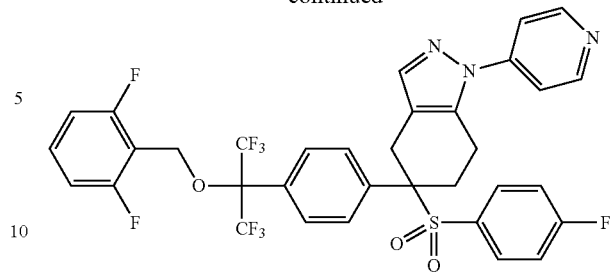

In to a 25 ml of round-bottomed flask 5-(4-(2-((2,6-difluorobenzyl)oxy)-1,1,1,3,3,3-hexafluoro propan-2-yl)phenyl)-5-((4-fluorophenyl)sulfonyl)-2-oxocyclohexanecarbaldehyde (1) (85 mg, 0.130 mmol) and AcOH (4 mL) was taken. 4-hydrazinylpyridine-hydrochloride (18.9 mg, 0.130 mmol) was added to the mixture at room temperature and then it was heated to 115° C. and stirred for 1 h. Reaction mass was concentrated as such to get crude yellow oil, this was diluted with 10 mL bicarbonate solution. The aqueous portion was extracted with DCM (3×10 mL). Combined organic layer was dried over anhydrous sodium-sulphate, filtered and concentrated to produce crude product (82 mg) as gummy oil. The regio-isomers were separated by preparative HPLC to yield 5-(4-(2-((2,6-difluorobenzyl)oxy)-1, 1,1,3,3,3-hexafluoropropan-2-yl)phenyl)-5-((4-fluorophenyl)sulfonyl)-2-(pyridin-4-yl)-4,5,6,7-tetrahydro-2H-indazole (Example 73, 28 mg, 0.039 mmol, 29% yield) and 5-(4-(2-((2,6-difluorobenzyl)oxy)-1,1,1,3,3,3-hexafluoropropan-2-yl)phenyl)-5-((4-fluorophenyl)sulfonyl)-1-(pyridin-4-yl)-4,5,6,7-tetrahydro-1H-indazole (Example 74, 16 mg, 0.022 mmol, 17% yield).

Analytical Data of Example 73: LC/MS (M+1): 726.0; LC retention time: 18.24 min (analytical HPLC Method D); 1H NMR (400 MHz, CDCl3): δ ppm 8.58 (d, J=6.4 Hz, 2H), 7.84 (s, 1H), 7.56-7.38 (m, 4H), 7.47-7.20 (m, 5H), 7.00-6.90 (m, 4H), 4.66 (s, 2H), 3.64 (d, J=16.0 Hz, 1H), 3.53 (d, J=16.0 Hz, 1H), 3.10-3.05 (m, 2H), 2.75-2.65 (m, 1H), 2.60-2.53 (m, 1H).

Analytical Data of Example 74: LC/MS (M+1): 726.0; LC retention time: 18.36 min (analytical HPLC Method D); 1H NMR (400 MHz, CDCl3): δ ppm 8.58 (s, 2H), 7.64-7.51 (m, 3H), 7.49-7.22 (m, 7H), 7.05-6.87 (m, 4H), 4.70 (s, 2H), 3.64 (d, J=15.6 Hz, 1H), 3.38 (d, J=15.6 Hz, 1H), 3.10 (d, J=6.4 Hz, 2H), 2.69 (d, J=6.0 Hz, 2H).

Examples 75 and 76

1-(4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)piperidin-1-yl)ethanone, and 1-(4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-1H-indazol-1-yl)piperidin-1-yl)ethanone

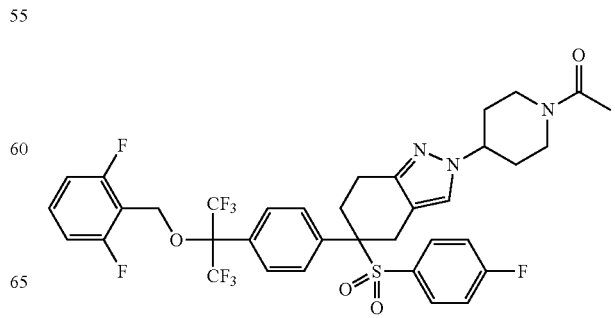

-continued

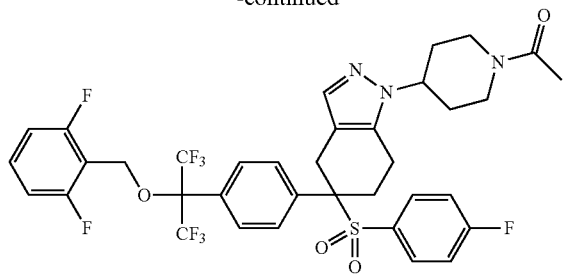

In a 25 ml round-bottomed flask, 5-(4-(2-((2,6-difluorobenzyl)oxy)-1,1,1,3,3,3-hexafluoropropan-2-yl)phenyl)-5-((4-fluorophenyl)sulfonyl)-2-oxocyclohexanecarbaldehyde (1) (170 mg, 0.261 mmol) was taken in AcOH (4 mL). To this mixture 1-(4-hydrazinylpiperidin-1-yl)ethanone hydrochloride (76 mg, 0.391 mmol) was added and heated to 115° C. for 1 hr with constant stirring. The yellow oil crude residue obtained upon evaporation of volatiles from the reaction mixture. Crude residue was then diluted with 10 mL saturated sodium bicarbonate solution. Aqueous layer was extracted with DCM (3×15 mL) and combined organic layer was dried over anhydrous sodium sulphate, filtered and concentrated to produce the crude product as a mix of regioisomers (180 mg Crude). The regioisomers were separated by preparative HPLC purification to yield 1-(4-(5-(4-(2-((2,6-difluorobenzyl)oxy)-1,1,1,3,3,3-hexafluoro-propan-2-yl)phenyl)-5-((4-fluorophenyl)sulfonyl)-4,5,6,7-tetrahydro-2H-indazol-2-yl)piperidin-1-yl)ethanone (Example 75, 8.0 mg, 10.34 μmol, 3.97% yield) and 1-(4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-1H-indazol-1-yl) piperidin-1-yl)ethanone (Example 76, 56 mg, 0.072 mmol, 27.8% yield).

Analytical Data of Example 75: LC/MS (M+1): 774.2; LC retention time: 11.88 min (analytical HPLC Method D); 1H NMR (400 MHz, CDCl$_3$): δ ppm 7.55-7.48 (m, 2H), 7.44-7.32 (m, 3H), 7.30-7.21 (m, 2H), 7.19 (s, 1H), 6.99-6.91 (m, 4H), 4.71 (m, 1H), 4.67 (s, 2H), 4.24-4.10 (m, 1H), 3.92-3.82 (m, 1H), 3.55 (d, J=15.6 Hz, 1H), 3.38 (d, J=15.6 Hz, 1H), 3.20-3.10 (m, 1H), 3.08-2.88 (m, 2H), 2.72-2.55 (m, 2H), 2.50-2.35 (m, 1H), 2.20-2.00 (m, 5H), 1.90-1.73 (m, 2H).

Analytical Data of Example 76: LC/MS (M+1): 774.2; LC retention time: 12.09 min (analytical HPLC Method D); 1H NMR (400 MHz, CDCl$_3$): δ ppm 7.52 (d, J=8.4 Hz, 2H), 7.40-7.34 (m, 3H), 7.33-7.24 (m, 3H), 7.03-6.90 (m, 4H), 4.68 (d, J=6.0 Hz, 2H), 4.59 (d, J=13.6 Hz, 1H), 3.99-3.78 (m, 2H), 3.53 (d, J=14.8 Hz, 1H), 3.27 (d, J=15.2 Hz, 1H), 3.12-3.02 (m, 2H), 2.86 (dd, J=16.0, 4.8 Hz, 1H), 2.70-2.52 (m, 2H), 2.37-2.23 (m, 1H), 2.13-1.72 (m, 6H), 1.70-1.50 (m, 1H).

Example 77

4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)benzoic acid Step A: Mixture of 4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)benzoic acid and 4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-1H-indazol-1-yl)benzoic acid

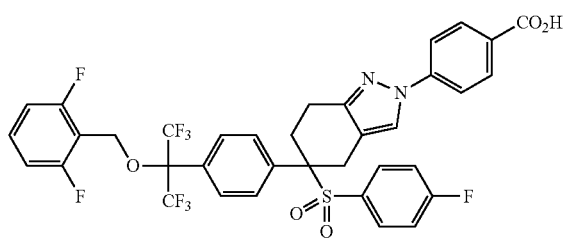 [SMILES: O=C(O)c1ccc(-n2cc3c(n2)CCC(c2ccc(C(OCc4c(F)cccc4F)(C(F)(F)F)C(F)(F)F)cc2)(S(=O)(=O)c2ccc(F)cc2)C3)cc1]

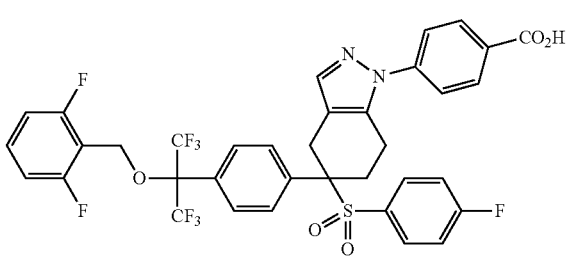

In a 10 ml of round-bottomed flask 5-(4-(2-((2,6-difluorobenzyl)oxy)-1,1,1,3,3,3-hexafluoro-pro-pan-2-yl)phenyl)-5-((4-fluorophenyl)sulfonyl)-2-oxocyclohexanecarbaldehyde (65 mg, 0.100 mmol) in AcOH (4 mL) was taken. To this, 4-hydrazinylbenzoic acid (22.73 mg, 0.149 mmol) was added and further stirred for 1 h at 115° C. Upon completion of reaction, it was concentrated to get yellow oil. This crude product thus obtained was diluted with 50 ml of saturated aqueous bicarbonate solution and was extracted with DCM (3×50 mL). The combined organic layer was dried over anhydrous sodium sulphate, filtered and concentrated to getting crude product (85 mg as a mixture of regioisomers) and the crude material was as such taken to the next step.

Step B: methyl 4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)benzoate and methyl 4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-1H-indazol-1-yl)benzoate

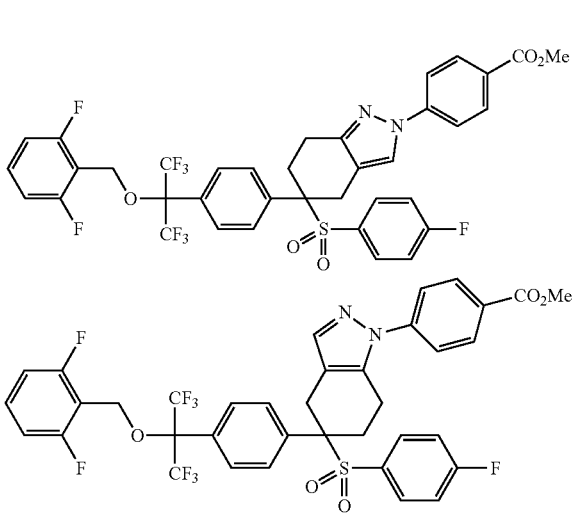

From previous step, the crude 4-(5-(4-(2-((2,6-difluorobenzyl)oxy)-1,1,1,3,3,3-hexafluoro-propan-2-yl)phenyl)-5-((4-fluoro-phenyl)sulfonyl)-4,5,6,7-tetrahydro-2H-indazol-2-yl)benzoic acid (85 mg, 0.111 mmol) and p-TsOH (31.6 mg, 0.166 mmol) was dissolved in 20 mL of methanol. This mixture was heated to 65° C. for 1 h. After completion of reaction, volatiles were removed under vacuum to get the brown oil. It was diluted with 50 mL bicarbonate solution and extracted with DCM (3×20 mL). The combined organic layer was dried over anhydrous sodium sulphate, filtered and concentrated to get crude product. By prep purification the two regioisomers were separated to provide methyl 4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)benzoate (21 mg, 0.027 mmol, 24% yield) and methyl 4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-1H-indazol-1-yl)benzoate (57 mg, 0.073 mmol, 65% yield).

Analytical data of methyl 4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)benzoate: LC/MS (M+1): 783.2; LC retention time: 21.86 min (analytical HPLC Method D); 1H NMR (400 MHz, CDCl$_3$): δ ppm 8.06 (d, J=8.8 Hz, 2H), 7.81 (s, 1H), 7.64 (d, J=8.8 Hz, 2H), 7.54 (d, J=8.4 Hz, 2H), 7.40 (d, J=8.2 Hz, 2H), 7.35-7.20 (m, 3H), 7.02-6.83 (m, 4H), 4.66 (s, 2H), 3.90 (s, 3H), 3.65 (d, J=15.6, Hz, 1H), 3.53 (d, J=15.6 Hz, 1H), 3.12-3.00 (m, 2H), 2.75-2.45 (m, 2H).

Analytical data of methyl 4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-1H-indazol-1-yl)benzoate: LC/MS (M+1): 783.2; LC retention time: 17.07 min (analytical HPLC Method D); 1H NMR (400 MHz, CDCl$_3$): δ ppm 8.05 (d, J=4.8 Hz, 2H), 7.61-7.52 (m, 3H), 7.47 (d, J=8.8 Hz, 4H), 7.39-7.22 (m, 3H), 7.00-6.89 (m, 4H), 4.71 (dd, J=13.2, 10.0 Hz 2H), 3.90 (s, 3H), 3.63 (d, J=16.8 Hz, 1H), 3.39 (d, J=16.8 Hz, 1H), 3.10-2.95 (m, 2H), 2.75-2.61 (m, 2H).

Step C: 4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)benzoic acid

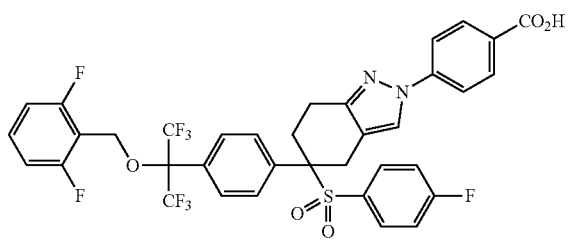

In a 25 mL round-bottomed flask, methyl 4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)benzoate (15 mg, 0.019 mmol) was dissolved in tetrahydrofuran (3 mL) and LITHIUM HYDROXIDE (3.06 mg, 0.128 mmol) was added in reaction and stirred at room temperature for 12 h. After complete consumption of SM, reaction mixture was concentrated in rota-vap to remove most of the THF to obtain oily crude product. The crude oil was then diluted with 5 mL water, extracted with DCM (3×10 mL). Combined organic layer was dried with anhydrous sodium sulphate, filtered and concentrated to generate the gummy crude product, which was later purified by preparative HPLC to getting desired product as 4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)benzoic acid (4.5 mg, 5.85 μmol, 30.5% yield) as white solids. LC/MS (M+1): 769.2; LC retention time: 19.70 min (analytical HPLC Method D); 1H NMR (400 MHz, d6-DMSO): δ ppm 12.92 (br-s, 1H), 8.38 (s, 1H), 7.96 (d, J=8.8 Hz, 2H), 7.79 (d, J=9.2 Hz, 2H), 7.61-7.47 (m, 5H), 7.39-7.29 (m, 4H), 7.19 (t, J=8.0 Hz, 2H), 4.61 (s, 2H), 3.69 (d, J=16 Hz, 1H), 3.41 (d, J=15.6 Hz, 1H), 3.16-2.89 (m, 2H), 2.39-2.28 (m, 2H).

Example 78

2-(5-(4-(2-((2,6-difluorobenzyloxy)oxy)-1,1,1,3,3,3-hexafluoropropan-2-yl)phenyl)-5-((4-fluorophenyl)sulfonyl)-4,5,6,7-tetrahydro-2H-indazol-2-yl)acetic acid Step A: ethyl 2-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)acetate, and enatiomers 1 and 2 of ethyl 2-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-1H-indazol-1-yl)acetate

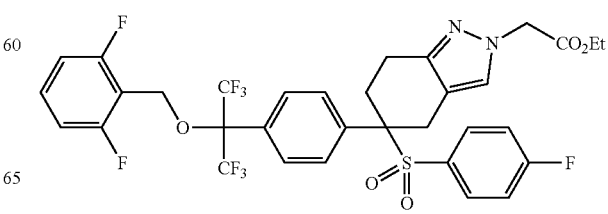

-continued

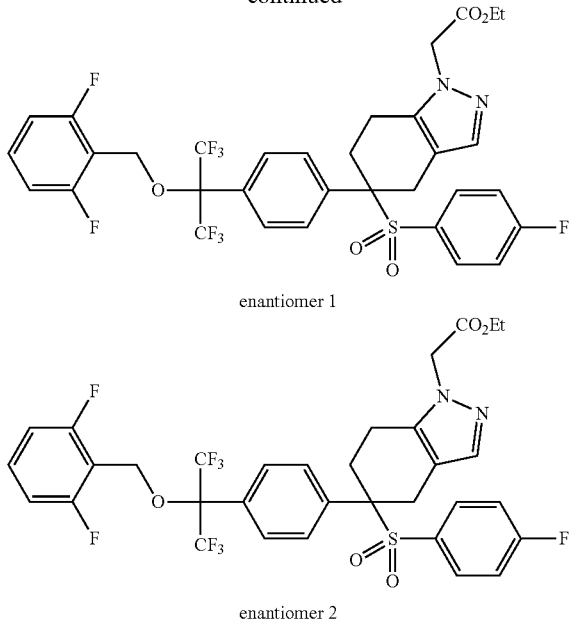

enantiomer 1 enantiomer 2

In a 25 ml round-bottomed flask 5-(4-(2-((2,6-difluorobenzyl)oxy)-1,1,1,3,3,3-hexafluoropropan-2-yl)phenyl)-5-((4-fluorophenyl)sulfonyl)-2-oxocyclohexanecarbaldehyde (80 mg, 0.123 mmol) was dissolved in AcOH (4 mL). Ethyl 2-hydrazinylacetate hydrochloride (28.4 mg, 0.184 mmol) was added and stirred for 1 h at 115° C. Reaction mass was concentrated as such to getting crude yellow oil. Crude oil was diluted with 50 ml bicarbonate solution. Aq layer was extracted with DCM (3×50 ml). The combined organic layer was dried with anhydrous sodium sulphate, filtered and concentrated to give a crude mixture (85 mg). The crude compound was purified by SFC method to produce ethyl 2-(5-(4-(2-((2,6-difluorobenzyl)oxy)-1,1,1,3,3,3-hexafluoropropan-2-yl)phenyl)-5-((4-fluorophenyl) sulfonyl)-4,5,6,7-tetrahydro-2H-indazol-2-yl)acetate (30 mg, 0.041 mmol, 33% yield), enantiomer 1 of ethyl 2-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-1H-indazol-1-yl)acetate (16 mg, 0.022 mmol, 17% yield) and enantiomer 2 of ethyl 2-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-1H-indazol-1-yl)acetate (20 mg, 0.027 mmol, 22% yield).

Analytical data of ethyl 2-(5-(4-(2-((2,6-difluorobenzyl)oxy)-1,1,1,3,3,3-hexafluoropropan-2-yl)phenyl)-5-((4-fluorophenyl) sulfonyl)-4,5,6,7-tetrahydro-2H-indazol-2-yl)acetate: 1H NMR (400 MHz, CDCl$_3$): δ ppm 7.52 (d, J=7.2 Hz, 2H), 7.45-7.20 (m, 6H), 7.00-6.89 (m, 4H), 4.86-4.63 (m, 4H), 4.17 (q, J=7.2 Hz, 2H), 3.58 (d, J=15.6 Hz, 1H), 3.43 (d, J=15.6 Hz, 1H), 3.10-2.90 (m, 2H), 2.71-2.59 (m, 1H), 2.49-2.40 (m, 1H), 1.22 (t, J=7.2 Hz, 3H).

Analytical data of enantiomer 1 of ethyl 2-(5-(4-(2-((2,6-difluorobenzyl)oxy)-1,1,1,3,3,3-hexafluoropropan-2-yl) phenyl)-5-((4-fluorophenyl)sulfonyl)-4,5,6,7-tetrahydro-1H-indazol-1-yl)acetate: 1H NMR (400 MHz, CDCl$_3$): δ ppm 7.53 (d, J=7.2 Hz, 2H), 7.45-7.22 (m, 6H), 7.00-6.87 (m, 4H), 4.75-4.50 (m, 4H), 4.03 (q, J=7.2 Hz, 2H), 3.60-3.50 (m, 1H), 3.31 (d, J=15.6 Hz, 1H), 3.13-2.98 (m, 2H), 2.85-2.61 (m, 1H), 2.35-2.20 (m, 1H), 1.07 (t, J=7.2 Hz, 3H).

Step B: 2-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)acetic acid

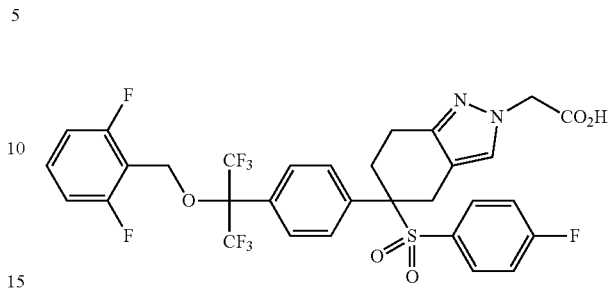

In a 25 ml round-bottomed flask ethyl 2-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl) acetate (30 mg, 0.041 mmol) was dissolved in THF (2 mL) and Water (0.5 mL). LiOH (2.445 mg, 0.102 mmol) was added to the mixture and stirred for 12 h at room temperature. THF was evaporated from the reaction mixture & residual aqueous part was diluted with 10 mL 1.5 N HCl solution. Total aq. part was extracted with 3×15 mL ethyl acetate. Combined organic layer was dried over sodium sulphate & on evaporation it produces crude product (28 mg). The crude was purified by Prep HPLC to have pure 2-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)acetic acid (7.32 mg, 10.36 μmol, 25% yield) as white solids. LC/MS (M+1): 707.0; LC retention time: 18.07 min (analytical HPLC Method D); 1H NMR (400 MHz, DMSO-d6): δ ppm 12.60 (br-s, 1H), 7.60-7.45 (m, 6H), 7.39-7.15 (m, 6H), 4.80-4.62 (m, 4H), 3.65-3.60 (m, 1H), 3.30-3.26 (m, 1H), 3.02 (d, J=9.2 Hz, 1H), 2.82 (dd, J=16.4, 9.2 Hz, 1H), 2.40-2.18 (m, 2H).

Example 79

2-(5-(4-(2-((2,6-difluorobenzyl)oxy)-1,1,1,3,3,3-hexafluoropropan-2-yl)phenyl)-5-((4-fluorophenyl) sulfonyl)-4,5,6,7-tetrahydro-1H-indazol-1-yl)acetic acid, enantiomer 1

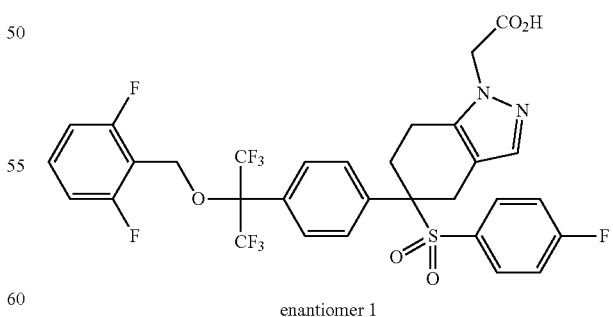

enantiomer 1

In a 25 ml round-bottomed flask enantiomer 1 of ethyl 2-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-1H-indazol-1-yl) acetate (14 mg, 0.019 mmol) was dissolved in THF (2 mL) and Water (0.5 mL). LiOH (1.141 mg, 0.048 mmol) was added to the mixture and stirred for 12 h at room temperature. THF was evaporated from the reaction mixture & residual aqueous part was diluted with 10 mL 1.5N HCl solution. Total aq. part was extracted with 3×15 mL EtOAc. Combined organic layer was dried over sodium sulphate & on evaporation it produces crude product (13 mg). The crude was purified by Preparative HPLC to have pure 2-(5-(4-(2-((2,6-difluorobenzyl)oxy)-1,1,1,3,3,3-hexafluoropropan-2-yl)phenyl)-5-((4-fluorophenyl) sulfonyl)-4,5,6,7-tetrahydro-1H-indazol-1-yl)acetic acid (4.89 mg, 6.92 μmol, 36% yield) as white solids. LC/MS (M+1): 707.2; LC retention time: 18.07 min (analytical HPLC Method D); 1H NMR (400 MHz, DMSO-d6): δ ppm 12.80 (br-s, 1H), 7.60-7.53 (m, 5H), 7.48-7.16 (m, 7H), 4.65-4.60 (m, 4H), 3.56-3.51 (m, 1H), 3.30-3.26 (m, 1H), 3.07-3.03 (m, 1H), 2.84-2.77 (m, 1H), 2.47-2.12 (m, 2H).

Example 80

3-(5-(4-(2-((2,6-difluorobenzyl)oxy)-1,1,1,3,3,3-hexafluoropropan-2-yl)phenyl)-5-((4-fluorophenyl) sulfonyl)-4,5,6,7-tetrahydro-2H-indazol-2-yl)propanoic acid Step A: ethyl 3-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)propanoate and ethyl 3-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-1H-indazol-1-yl)propanoate

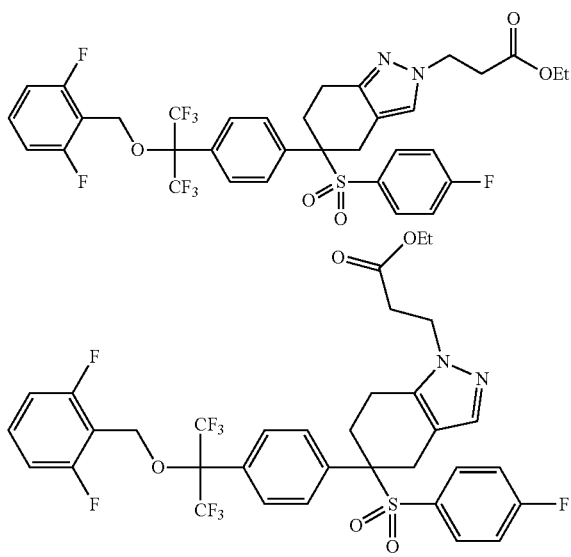

In a 25 mL flask, under nitrogen atmosphere, to a solution of 5-(4-(2-((2,6-difluoro benzyl)oxy)-1,1,1,3,3,3-hexafluoropropan-2-yl)phenyl)-5-((4-fluorophenyl)sulfonyl)-4,5,6,7-tetra-hydro-2H-indazole (250 mg, 0.385 mmol) in DMF (2 mL) was added ethyl 3-bromopropanoate (84 mg, 0.463 mmol) and stirred for 3 h at 115° C. The reaction mixture was diluted with 15 mL water and was then extracted with EtOAc (3×15 mL). Combined organic layer was dried over anhydrous sodium sulphate, filtered and concentrated to get crude product. It was purified by preparative HPLC to get desired product as a mixture of two isomers (120 mg). Further separation by chiral SFC yielded ethyl 3-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)propanoate (peak 1, 21 mg, 0.028 mmol, 7% yield) and ethyl 3-(5-(4-(2-((2,6-difluorobenzyl)oxy)-1,1,1,3,3,3-hexafluoropropan-2-yl)phenyl)-5-((4-fluoro phenyl)sulfonyl)-4,5,6,7-tetrahydro-1H-indazol-1-yl)propanoate (peak 2, 20 mg, 0.027 mmol, 7% yield).

Analytical data of 3-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)propanoate: 1H NMR (400 MHz, CDCl₃): δ ppm 7.51 (d, J=8.4 Hz, 2H), 7.45-7.20 (m, 6H), 7.00-6.88 (m, 4H), 4.67 (s, 2H), 4.33-4.20 (m, 2H), 4.08 (q, J=7.2 Hz, 2H), 3.53 (d, J=13.0 Hz, 1H), 3.37 (d, J=12.8 Hz, 1H), 3.05-2.85 (m, 2H), 2.82-2.71 (m, 2H), 2.67-2.51 (m, 1H), 2.50-2.32 (m, 1H), 1.17 (t, J=7.2 Hz, 2H).

Analytical data of ethyl 3-(5-(4-(2-((2,6-difluorobenzyl)oxy)-1,1,1,3,3,3-hexafluoropropan-2-yl)phenyl)-5-((4-fluoro phenyl)sulfonyl)-4,5,6,7-tetrahydro-1H-indazol-1-yl)propanoate: 1H NMR (400 MHz, CDCl₃): δ ppm 7.51 (d, J=8.4 Hz, 2H), 7.41-7.22 (m, 6H), 7.00-6.90 (m, 4H), 4.68 (s, 2H), 4.15-4.00 (m, 2H), 3.95 (q, J=7.0 Hz, 2H), 3.52 (d, J=15.2 Hz, 1H), 3.29 (d, J=14.8 Hz, 1H), 3.10-2.90 (m, 3H), 2.85-2.60 (m, 3H), 2.40-2.25 (m, 1H), 1.11 (t, J=7.0 Hz, 2H).

Step B: 3-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl) propanoic acid

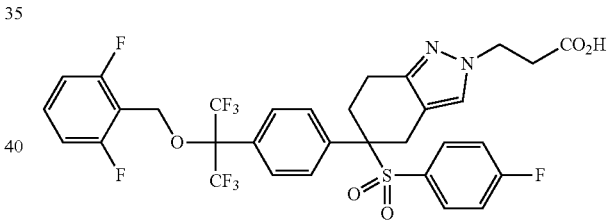

Ethyl-3-(5-(4-(2-((2,6-difluorobenzyl)oxy)-1,1,1,3,3,3-hexafluoropropan-2-yl)phenyl)-5-((4-fluoro-phenyl)sulfonyl)-4,5,6,7-tetrahydro-2H-indazol-2-yl)propanoate (20 mg, 0.027 mmol) was dissolved in Tetrahydrofuran (3 mL) and LiOH (1.280 mg, 0.053 mmol) was added. The mixture was stirred for 12 h at room temperature. Volatiles were removed under vacuum, and residue was treated with 10 ml water solution. Aqueous portion was acidified to pH=6.0 by 1.5 N HCl solution and treated with EtOAc (3×20 mL). Combined organic layer was dried over anhydrous sodium sulphate, filtered and concentrated to generate crude product (22 mg). It was then purified by preparative HPLC to generate pure 3-(5-(4-(2-((2,6-difluorobenzyl)oxy)-1,1,1,3,3,3-hexafluoropropan-2-yl)phenyl)-5-((4-fluorophenyl) sulfonyl)-4,5,6,7-tetrahydro-2H-indazol-2-yl)propanoic acid (7.0 mg, 9.71 μmol, 36% yield). LC/MS (M+1): 721.0; LC retention time: 17.78 min (analytical HPLC Method D); 1H NMR (400 MHz, CD₃OD): δ ppm 7.55-7.46 (m, 6H), 7.43-7.39 (m, 2H), 7.17-7.05 (m, 4H), 4.70 (s, 2H), 4.26 (br-s, 2H), 3.59 (d, J=14.8 Hz, 1H), 3.48 (d, J=14.6 Hz, 1H), 3.18-3.09 (m, 1H), 2.98-2.70 (m, 3H), 2.67-2.50 (m, 1H), 2.48-2.25 (m, 1H).

Example 81

3-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-1H-indazol-1-yl)propanoic acid

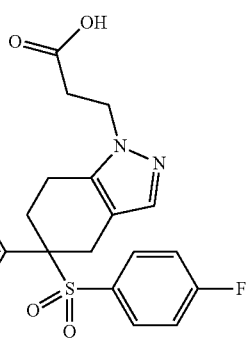

Following conditions similar to Example 80, 3-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-1H-indazol-1-yl)propanoic acid was synthesized. LC/MS (M+1): 721.0; LC retention time: 17.87 min (analytical HPLC Method D); 1H NMR (400 MHz, CD$_3$OD): δ ppm 7.63-7.37 (m, 8H), 7.20-7.00 (m, 4H), 4.70 (s, 2H), 4.20-4.00 (m, 2H), 3.57 (d, J=15.6 Hz, 1H), 3.45 (d, J=14.8 Hz, 1H), 3.22-3.01 (m, 2H), 2.80-2.51 (m, 3H), 2.49-2.30 (m, 1H).

Example 82

1-(4-(4-(4-(2-((2,6-difluorobenzyl)oxy)-1,1,1,3,3,3-hexafluoropropan-2-yl)phenyl)-4-((4-fluorophenyl)sulfonyl)cyclohexyl)piperazin-1-yl)ethanone, Diastereomer 1

Step A: 1-benzyl-4-(4-(4-(2-((2,6-difluorobenzyl)oxy)-1,1,1,3,3,3-hexafluoropropan-2-yl)phenyl)-4-((4-fluorophenyl)sulfonyl)cyclohexyl)piperazine, Diastereomer 1

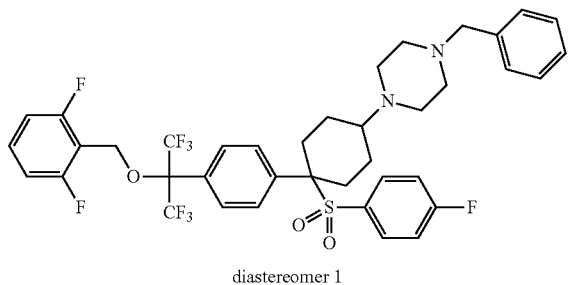 [SMILES: O=S(=O)(c1ccc(F)cc1)C1(c2ccc(C(OCc3c(F)cccc3F)(C(F)(F)F)C(F)(F)F)cc2)CCC(N2CCN(Cc3ccccc3)CC2)CC1]

diastereomer 1

To a stirred solution of 4-(4-(2-((2,6-difluorobenzyl)oxy)-1,1,1,3,3,3-hexafluoropropan-2-yl)phenyl)-4-((4-fluorophenyl)sulfonyl)cyclohexanamine diastereomer 1 (200 mg, 0.320 mmol) in acetonitrile (10 mL) was added N-benzyl-2-chloro-N-(2-chloroethyl)ethanamine (74.2 mg, 0.320 mmol) followed by DIPEA (0.168 mL, 0.959 mmol), stirred the resulting pale yellow color solution at 50° C. for overnight. After completion, volatiles were evaporated under reduced pressure and the residue was dissolved in dichloromethane (25 mL), washed with water (20 mL), saturated brine solution (20 mL). The layers were separated and the organic layer was dried over anhydrous Na2SO4, filtered and concentrated to afford crude product. The crude product was purified by ISCO comb-flash chromatogram (eluted with 5% methanol in chloroform) to generate 1-benzyl-4-(4-(4-(2-((2,6-difluorobenzyl)oxy)-1,1,1,3,3,3-hexafluoropropan-2-yl)phenyl)-4-((4-fluorophenyl) sulfonyl)cyclohexyl) piperazine diastereomer 1 (10 mg, 0.012 mmol, 4% yield) as white solid. LC/MS (M+1): 785.2; LC retention time: 10.16 min (analytical HPLC Method D); 1H NMR (400 MHz, DMSO-d6): δ ppm 7.65-7.45 (m, 5H), 7.32-7.12 (m, 11H), 4.66 (s, 2H), 3.35 (s, 2H), 2.74-2.58 (m, 3H), 2.39-2.17 (m, 8H), 2.17-2.01 (m, 2H), 1.92 (d, J=13.5 Hz, 2H), 1.05-0.77 (m, 2H).

Step B: 1-(4-(4-(2-((2,6-difluorobenzyl)oxy)-1,1,1,3,3,3-hexafluoropropan-2-yl)phenyl)-4-((4-fluorophenyl)sulfonyl)cyclohexyl)piperazine, Diastereomer 1

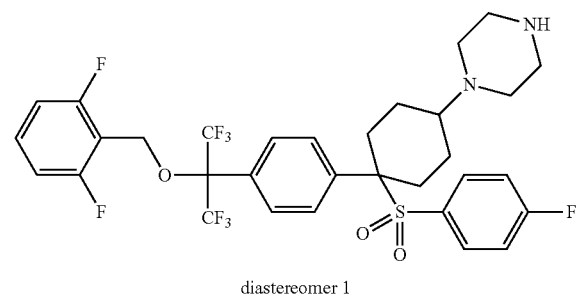 [SMILES: O=S(=O)(c1ccc(F)cc1)C1(c2ccc(C(OCc3c(F)cccc3F)(C(F)(F)F)C(F)(F)F)cc2)CCC(N2CCNCC2)CC1]

diastereomer 1

To a solution of 1-benzyl-4-(4-(4-(2-((2,6-difluorobenzyl)oxy)-1,1,1,3,3,3-hexafluoro propan-2-yl)phenyl)-4-((4-fluorophenyl)sulfonyl)cyclohexyl)piperazine diastereomer 1 (20 mg, 0.025 mmol) in Acetic Acid (4 mL) was added Pd/C (0.027 mg, 0.255 μmol). De-gasified the solution by applying vacuum and back filled with nitrogen for two times. The mixture was then stirred under hydrogen gas (using balloon) for 2 h. After the completion, the mixture was filtered and washed with acetic acid (2×10 mL). Clear filtrate was concentrated under vacuum to get transparent gummy solid. The gummy material was dissolved in Acetonitrile (1 mL), added 1 N HCl & stirred for 5 min. This mixture was directly lyophilized to produce white solids of 1-(4-(4-(2-((2,6-difluorobenzyl)oxy)-1,1,1,3,3,3-hexafluoropropan-2-yl) phenyl)-4-((4-fluorophenyl)sulfonyl) cyclohexyl)piperazine.HCl diastereomer 1 (18 mg, 0.025 mmol, 97% yield). LC/MS (M+1): 695.2.

Step C: 1-(4-(4-(4-(2-((2,6-difluorobenzyl)oxy)-1,1,1,3,3,3-hexafluoropropan-2-yl)phenyl)-4-((4-fluorophenyl)sulfonyl)cyclohexyl)piperazin-1-yl)ethanone, Diastereomer 1

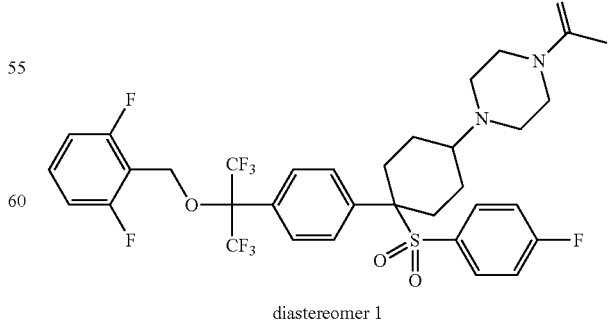

diastereomer 1

To a suspension of 1-(4-(4-(2-((2,6-difluorobenzyl)oxy)-1,1,1,3,3,3-hexafluoropropan-2-yl)phenyl)-4-((4-fluorophenyl)sulfonyl)cyclohexyl)piperazine.HCl diastereomer 1 (20 mg, 0.029 mmol) in DCM (5 mL) was added Et3N (4.01 µl, 0.029 mmol) followed by Ac2O (2.72 µl, 0.029 mmol) and stirred the resulting pale yellow color solution at room temperature for 2 h. The resulting reaction mixture was subjected to prep-HPLC for purification to afford 1-(4-(4-(4-(2-((2,6-difluorobenzyl)oxy)-1,1,1,3,3,3-hexafluoropropan-2-yl)phenyl)-4-((4-fluorophenyl)sulfonyl) cyclohexyl)piperazin-1-yl)ethanone diastereomer 1 (10 mg, 0.014 mmol, 47.1% yield) as white solid. LC/MS (M+1): 737.2; LC retention time: 9.47 min (analytical HPLC Method D); 1H NMR (400 MHz, DMSO-d6): δ ppm 7.58-7.49 (m, 5H), 7.25-7.20 (m, 6H), 4.66 (s, 2H), 3.32-3.28 (br-s, 4H), 2.71-2.67 (m, 2H), 2.38-2.27 (m, 5H), 2.17-2.11 (m, 2H), 1.92 (d, J=13.5 Hz, 2H), 1.89 (s, 3H), 1.05-0.77 (m, 2H).

Example 83

1-(4-(4-(4-(2-((2,6-difluorobenzyl)oxy)-1,1,1,3,3,3-hexafluoropropan-2-yl)phenyl)-4-((4-fluorophenyl)sulfonyl)cyclohexyl)piperazin-1-yl)ethanone, Diastereomer 2

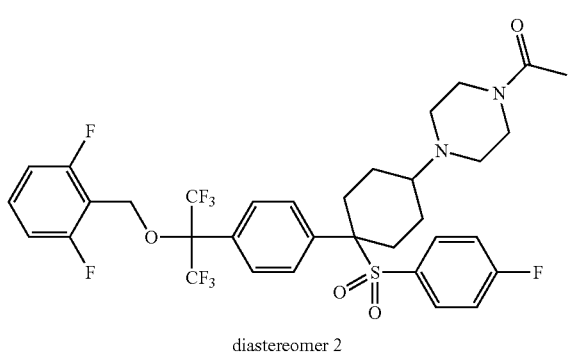 [SMILES: CC(=O)N1CCN(C2CCC(c3ccc(C(OCc4c(F)cccc4F)(C(F)(F)F)C(F)(F)F)cc3)(S(=O)(=O)c3ccc(F)cc3)CC2)CC1]

diastereomer 2

Following conditions similar to Example 82, 1-(4-(4-(4-(2-((2,6-difluorobenzyl)oxy)-1,1,1,3,3,3-hexafluoropropan-2-yl)phenyl)-4-((4-fluorophenyl)sulfonyl)cyclohexyl)piperazin-1-yl)ethanone diastereomer 2 was synthesized. LC/MS (M+1): 737.0; LC retention time: 9.60 min (analytical HPLC Method D); 1H NMR (400 MHz, DMSO-d6): δ ppm 7.65-7.55 (m, 5H), 7.30-7.20 (m, 6H), 4.65 (s, 2H), 3.52-3.45 (m, 1H), 3.45-3.41 (m, 2H), 3.20-3.03 (br-s, 3H), 2.60-2.56 (m, 1H), 2.50-2.41 (m, 4H), 2.34-2.32 (m, 1H), 2.28-2.25 (m, 2H), 2.17-1.99 (m, 4H), 1.14 (s, 2H).

Example 84

1-(4-(4-(2-((2,6-difluorobenzyl)oxy)-1,1,1,3,3,3-hexafluoropropan-2-yl)phenyl)-4-((4-fluorophenyl)sulfonyl)cyclohexyl)-4-methylpiperazine, Diastereomer 2

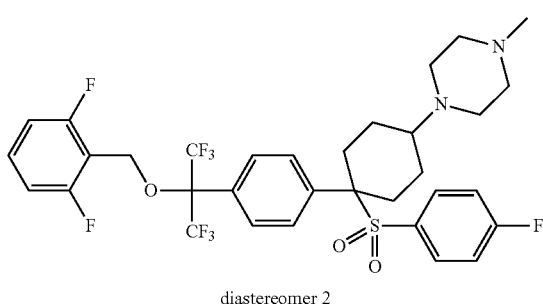 [SMILES: CN1CCN(C2CCC(c3ccc(C(OCc4c(F)cccc4F)(C(F)(F)F)C(F)(F)F)cc3)(S(=O)(=O)c3ccc(F)cc3)CC2)CC1]

diastereomer 2

1-(4-(4-(2-((2,6-difluorobenzyl)oxy)-1,1,1,3,3,3-hexafluoropropan-2-yl)phenyl)-4-((4-fluorophenyl)sulfonyl)cyclohexyl)piperazine diastereomer 2 was reacted with paraformaldehyde and sodium borohydride in trifluoroethanol to provide 1-(4-(4-(2-((2,6-difluorobenzyl)oxy)-1,1,1,3,3,3-hexafluoropropan-2-yl)phenyl)-4-((4-fluorophenyl) sulfonyl) cyclohexyl)-4-methylpiperazine diastereomer 2. LC/MS (M+1): 709.2; LC retention time: 9.15 min (analytical HPLC Method D); 1H NMR (400 MHz, CD3OD): δ ppm 7.71-7.60 (m, 2H), 7.60-7.47 (m, 3H), 7.44-7.36 (m, 2H), 7.20-7.05 (m, 4H), 4.78-4.73 (m, 2H), 2.84-2.73 (m, 3H), 2.37-2.26 (m, 5H), 2.23-2.11 (m, 4H), 1.93-1.90 (m, 3H), 1.52-1.40 (m, 3H), 1.39-1.23 (m, 2H).

Example 85

4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-1H-indazol-1-yl)benzoic acid

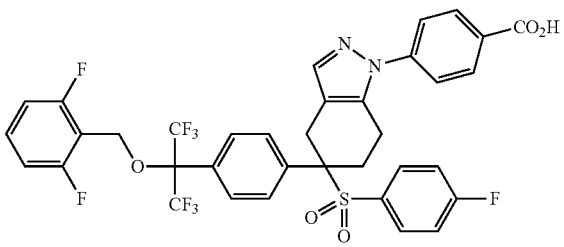 [SMILES: O=C(O)c1ccc(-n2ncc3c2CCC(c2ccc(C(OCc4c(F)cccc4F)(C(F)(F)F)C(F)(F)F)cc2)(S(=O)(=O)c2ccc(F)cc2)C3)cc1]

Following conditions similar to Step C of Example 77, methyl 4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-1H-indazol-1-yl)benzoate was converted to 4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-1H-indazol-1-yl)benzoic acid (31 mg, 0.04 mmol, 63% yield). LC/MS (M+1): 769.2; LC retention time: 19.56 min (analytical HPLC Method D); 1H NMR (400 MHz, CDCl3): δ ppm 8.12-8.10 (m, 2H), 7.50-7.43 (t, 3H), 7.39-7.32 (m, 4H), 7.31-7.28 (m, 3H), 7.00-6.86 (m, 4H), 4.70 (dd, J=12.4, 10.0 Hz, 2H), 3.63 (d, J=16.0 Hz, 1H), 3.39 (d, J=15.6 Hz, 1H), 3.14-2.99 (m, 2H), 2.71-2.62 (m, 2H).

Example 86

4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)cyclohexanecarboxylic acid, Diastereomer 1

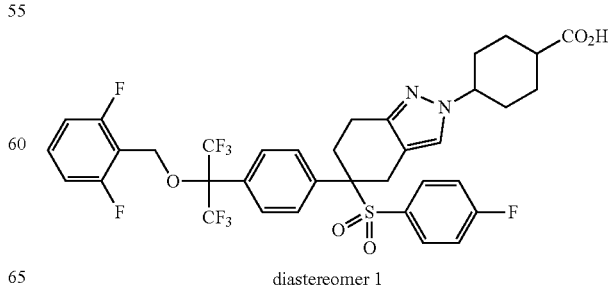

diastereomer 1

Step A: ethyl 4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)cyclohexanecarboxylate, Diastereomers 1, 2 and 3

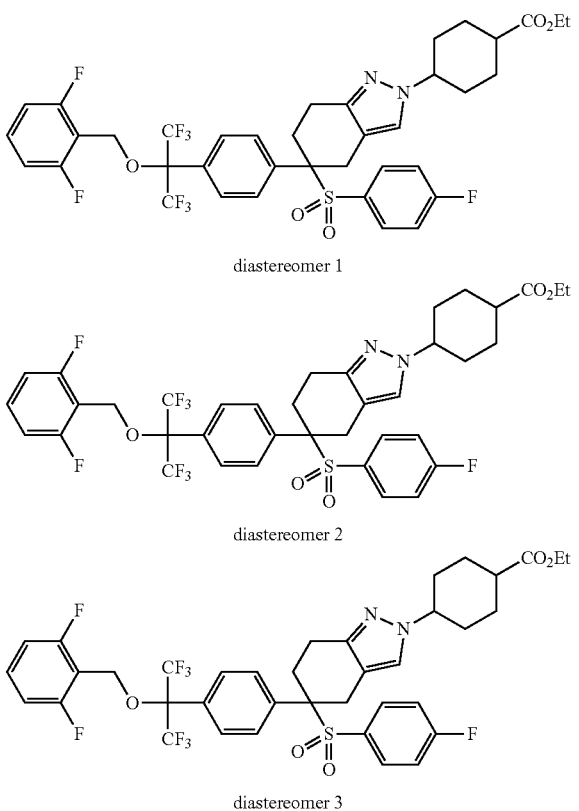

To a stirred solution of 5-(4-(2-((2,6-difluorobenzyl)oxy)-1,1,1,3,3,3-hexafluoropropan-2-yl)phenyl)-5-((4-fluorophenyl)sulfonyl)-2-oxocyclohexanecarbaldehyde (1 g, 1.533 mmol) in acetic acid (25 mL) was added ethyl 4-hydrazinylcyclohexanecarboxylate (0.714 g, 3.83 mmol) at room temperature and stirred at 115° C. for 4 hours. After completion of the reaction, reaction mixture was concentrated under high vacuum (to remove excess of AcOH) and then reaction mixture was quenched with 10% sodium bicarbonate solution (50 mL). The aqueous mixture was extracted with ethyl acetate (2×70 mL). Combined ethyl acetate layer was washed with brine solution (100 mL), dried over anhydrous sodium sulphate and concentrated to get 2.0 g of light yellow gummy liquid of crude product. The crude compound was purified by column chromatography using combiflash (40 μm Red-Sep column was used and eluted with 30% ethyl acetate in hexane) to get desired product (0.650 μm, 0.833 mmol, 54% yield) as mixture of diastereomers. The mixture was purified by SFC to generate diastereomer 1 (170 mg, 0.217 mmol, 14% yield) and mixture A (150 mg, 0.191 mmol, 12% yield). Mixture A was further purified in SFC to generate diastereomer 2 (peak 1, 25 mg) and diastereomer 3 (peak 2, 40 mg).

Analytical diastereomer 1: LC/MS (M+1): 803.3; 1H NMR (400 MHz, CDCl₃): δ ppm 7.51 (d, J=8.60 Hz, 2H), 7.42-7.32 (m, 3H), 7.31-7.24 (m, 2H), 7.22-7.14 (m, 1H), 7.02-6.88 (m, 4H), 4.67 (s, 2H), 4.12 (q, J=7.13 Hz, 2H), 3.97-3.92 (m, 1H), 3.59-3.50 (m, 1H), 3.39 (d, J=15.4 Hz, 1H), 3.06-2.83 (m, 2H), 2.67-2.62 (m, 1H), 2.50-2.36 (m, 1H), 2.33-2.28 (m, 1H), 2.21-1.99 (m, 4H), 1.78-1.46 (m, 4H), 1.25 (t, J=7.20 Hz, 3H).

Analytical diastereomer 2: LC/MS (M+1): 803.2; 1H NMR (400 MHz, CDCl₃): δ ppm 7.58-7.48 (m, 2H), 7.43-7.31 (m, 3H), 4.30-7.19 (m, 3H), 7.00-6.88 (m, 4H), 4.67 (s, 2H), 4.14 (q, J=7.20 Hz, 2H), 4.06-3.92 (m, 1H), 3.55 (d, J=15.4 Hz, 1H), 3.41 (d, J=15.4 Hz, 1H), 3.09-2.83 (m, 2H), 2.71-2.51 (m, 1H), 2.50-2.35 (m, 1H), 2.35-2.15 (m, 1H), 2.05-1.75 (m, 4H), 1.73-1.43 (m, 4H), 1.23 (t, J=7.20 Hz, 3H).

Analytical diastereomer 3: LC/MS (M+1): 803.3; 1H NMR (400 MHz, CDCl₃): δ ppm 7.51 (d, J=8.41 Hz, 2H), 7.43-7.34 (m, 3H), 7.34 (d, J=1.95 Hz, 1H), 7.30-7.24 (m, 1H), 7.19 (s, 1H), 7.02-6.82 (m, 4H), 4.67 (s, 2H), 4.12 (q, J=7.40 Hz, 2H), 4.00-3.88 (m, 1H), 3.53 (d, J=15.0 Hz, 1H), 3.40 (d, J=15.6 Hz, 1H), 3.09-2.87 (m, 2H), 2.65-2.61 (m, 1H), 2.50-2.35 (m, 1H), 2.32-2.26 (m, 1H), 2.21-2.00 (m, 4H), 1.78-1.44 (m, 4H), 1.24 (t, J=7.20 Hz, 3H).

Step B: 4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)cyclohexanecarboxylic acid, Diastereomer 1

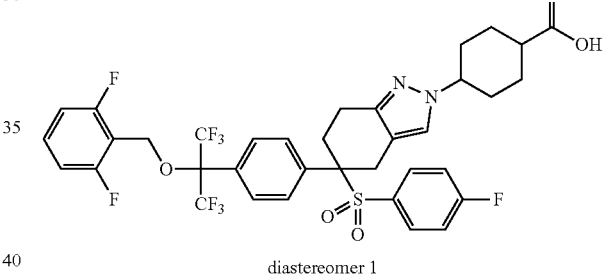

diastereomer 1

At room temperature, a solution of LiOH.H2O (24.31 mg, 0.579 mmol) in H2O (3 mL) was added to a ethanolic (3 mL) solution of ethyl 4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)cyclohexanecarboxylate diastereomer 1 (155 mg, 0.193 mmol) and stirred for 6 hours. After completion of the reaction, excess ethanol was removed under high vacuum to generate crude residue. The residue thus obtained was dissolved in 20 mL water and washed with diethyl ether (2×10 mL). Remaining aqueous layer was neutralized with citric acid (pH~6-7, monitored by pH paper) and extracted with DCM (3×30 mL). Combined DCM layer was washed with brine solution, dried over sodium sulphate and concentrated to get crude (200 mg) desired acid. The crude product was purified by preparative HPLC to get white solids of 4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)cyclohexanecarboxylic acid diastereomer 1 (85 mg, 0.109 mmol, 56.3% yield). LC/MS (M+1): 775.2; LC retention time: 18.79 min (analytical HPLC Method D); 1H NMR (400 MHz, DMSO-d6): δ ppm 12.12 (br-s, 1H), 7.64-7.44 (m, 6H), 7.40-7.13 (m, 6H), 4.61 (s, 2H), 4.00-3.88 (m, 1H), 3.58 (d, J=15.3 Hz, 1H), 3.31-3.25 (m, 1H), 3.00 (d, J=10.3 Hz, 1H), 2.81-2.79 (m, 1H), 2.71-2.60 (m, 1H), 2.43-2.25 (m, 2H), 1.96-1.85 (m, 4H) 1.68-1.51 (m, 2H) 1.50-1.35 (m, 2H).

Example 87

4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)cyclohexanecarboxylic acid, Diastereomer 2

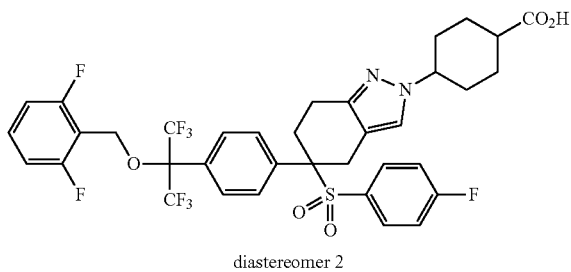 [SMILES: O=C(O)C1CCC(n2cc3c(n2)CCC(c2ccc(C(OCc4c(F)cccc4F)(C(F)(F)F)C(F)(F)F)cc2)(S(=O)(=O)c2ccc(F)cc2)C3)CC1]

diastereomer 2

Following conditions described in Step B of Example 86, ethyl 4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)cyclohexanecarboxylate, diastereomer 2 (25 mg, 0.031 mmol) was converted to 4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)cyclohexanecarboxylic acid, diastereomer 2 (12 mg, 15.3 μmol, 49% yield). LC/MS (M+1): 775.0; 1H NMR (400 MHz, DMSO-d6): δ ppm 12.00 (br-s, 1H), 7.64-7.44 (m, 6H), 7.39-7.14 (m, 6H), 4.62 (s, 2H), 3.97-3.83 (m, 1H), 3.58 (d, J=16.6 Hz, 1H), 3.35-3.21 (m, 1H), 3.10-2.97 (m, 1H), 2.81 (dd, J=16.0, 4.5 Hz, 1H), 2.48-2.20 (m, 3H), 2.08-1.90 (m, 2H), 1.89-1.70 (m, 4H), 1.57-1.40 (m, 2H).

Example 88

4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)cyclohexanecarboxylic acid, Diastereomer 3

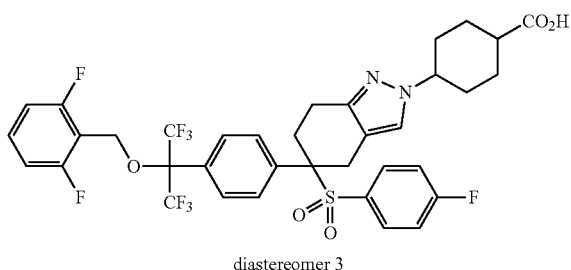 [SMILES: O=C(O)C1CCC(n2cc3c(n2)CCC(c2ccc(C(OCc4c(F)cccc4F)(C(F)(F)F)C(F)(F)F)cc2)(S(=O)(=O)c2ccc(F)cc2)C3)CC1]

diastereomer 3

Following conditions described in Step B of Example 86, ethyl 4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)cyclohexanecarboxylate, diastereomer 3 (40 mg, 0.050 mmol) was converted to 4-(5-(4-(2-((2,6-difluorobenzyl)oxy)-1,1,1,3,3,3-hexafluoropropan-2-yl)phenyl)-5-((4-fluorophenyl)sulfonyl)-4,5,6,7-tetrahydro-2H-indazol-2-yl)cyclohexanecarboxylic acid, diastereomer 3 (25 mg, 0.032 mmol, 64% yield). LC/MS (M+1): 775.2; LC retention time: 18.79 min (analytical HPLC Method D); 1H NMR (400 MHz, DMSO-d6): δ ppm 12.12 (br-s, 1H), 7.65-7.44 (m, 6H), 7.41-7.30 (m, 4H), 7.29-7.17 (m, 2H), 4.61 (s, 2H), 4.00-3.86 (m, 1H), 3.58 (d, J=15.4 Hz, 1H), 3.31-3.25 (m, 1H), 3.00 (d, J=10.6 Hz, 1H), 2.83-2.80 (m, 1H), 2.70-2.61 (m, 1H), 2.43-2.25 (m, 2H), 1.97-1.83 (m, 4H) 1.70-1.50 (m, 2H) 1.50-1.35 (m, 2H).

Examples 89 and 90

4-(4-(2-(benzyloxy)-1,1,1,3,3,3-hexafluoropropan-2-yl)phenyl)-4-((4-fluorophenyl)sulfonyl)cyclohexanecarbonitrile, Diastereomers 1 and 2

Step A: 2-(4-(bromomethyl)phenyl)-1,1,1,3,3,3-hexafluoropropan-2-ol

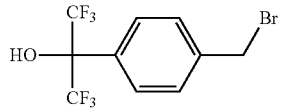

N-Bromosuccinimide (13.79 g, 77 mmol) and 2,2'-azobis(2-methylpropionitrile) (0.025 g, 0.155 mmol) were added to a solution of 1,1,1,3,3,3-hexafluoro-2-(p-tolyl)propan-2-ol (20.00 g, 77 mmol) in carbon tetrachloride (80 mL). The resulting suspension was heated to reflux under nitrogen for 4 h, cooled to room temperature and filtered through a celite pad. The filter cake was rinsed with ether and the filtrate was concentrated under reduced pressure. The residue was treated with ether (100 mL) and hexanes (50 mL), stirred for 15 min and filtered. The filtrate was concentrated under reduced pressure and dried under vacuum to give crude product as tan liquid (27.07 g). 1H NMR analysis showed a 69:15:16 molar ratio of the desired 2-(4-(bromomethyl)phenyl)-1,1,1,3,3,3-hexafluoropropan-2-ol, unreacted 1,1,1,3,3,3-hexafluoro-2-(p-tolyl)propan-2-ol and 2-(4-(dibromomethyl)phenyl)-1,1,1,3,3,3-hexafluoropropan-2-ol. The mixture was used without further purification, assuming ~70% purity of the desired 2-(4-(bromomethyl)phenyl)-1,1,1,3,3,3-hexafluoropropan-2-ol.

Step B: 1,1,1,3,3,3-hexafluoro-2-(4-((phenylsulfonyl)methyl)phenyl)propan-2-ol

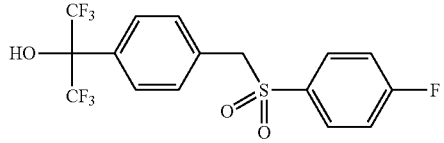 [SMILES: O=S(=O)(Cc1ccc(C(O)(C(F)(F)F)C(F)(F)F)cc1)c1ccc(F)cc1]

Sodium 4-fluorobenzenesulfinate (12.62 g, 69.3 mmol) was added in small portions to a stirred solution of 2-(4-(bromomethyl)phenyl)-1,1,1,3,3,3-hexafluoropropan-2-ol (20.00 g, ~70% pure from Step A) in N,N-dimethylformamide (80 mL). The mixture warmed up slightly during the addition. After 6 h at ambient temperature, the mixture was diluted with ethyl acetate (1 L), washed with water (3×200 mL), brine (100 mL), dried (magnesium sulfate), filtered and concentrated under reduced pressure. The residue was dissolved in dichloromethane (40 mL), triturated with hexanes (400 mL), stirred for 30 min and filtered. The filter cake was washed with hexanes (100 mL) and dried under vacuum to give 1,1,1,3,3,3-hexafluoro-2-(4-((phenylsulfonyl)methyl)phenyl)propan-2-ol as white solid (14.84 g, 82% yield). LC/MS (M+23): 439.2; 1H NMR (400 MHz, CDCl$_3$) δ ppm 7.64 (d, J=8.1 Hz, 2H), 7.62-7.54 (m, 2H), 7.20 (d, J=8.6 Hz, 2H), 7.15-7.06 (m, 2H), 4.34 (s, 2H), 3.59 (s, 1H).

Step C: 1-(2-(benzyloxy)-1,1,1,3,3,3-hexafluoropropan-2-yl)-4-(((4-fluorophenyl)sulfonyl)methyl)benzene

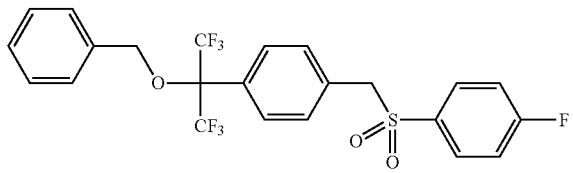 [SMILES: O=S(=O)(Cc1ccc(C(OCc2ccccc2)(C(F)(F)F)C(F)(F)F)cc1)c1ccc(F)cc1]

A mixture of 1,1,1,3,3,3-hexafluoro-2-(4-(((4-fluorophenyl)sulfonyl)methyl)phenyl)propan-2-ol (14.84 g, 35.6 mmol), benzyl bromide (6.71 g, 39.2 mmol) and potassium carbonate (14.78 g, 107 mmol) in N,N-dimethylformamide (150 mL) was stirred under nitrogen for 16 h at room temperature. The mixture was quenched with saturated ammonium chloride (100 mL), diluted with ethyl acetate (800 mL), washed with water (2×200 mL), brine (50 mL), dried (magnesium sulfate), filtered and concentrated under reduced pressure. The residue was dissolved in toluene (40 mL), triturated with hexanes (500 mL), stirred for 30 min and filtered. The filter cake was washed with hexanes (100 mL) and dried under vacuum to give first batch of 1-(2-(benzyloxy)-1,1,1,3,3,3-hexafluoropropan-2-yl)-4-(((4-fluorophenyl)sulfonyl)methyl)benzene as yellow solid (14.239 g). The filtrate was concentrated. Silica gel chromatography, eluting with 5-30% ethyl acetate in hexanes, gave the second batch of the desired product as white solid (1.480 g). The combined yield of the product is 87%. LC/MS (M+18): 524.3; LC retention time: 4.486 min (analytical HPLC Method A); 1H NMR (400 MHz, CDCl$_3$) δ ppm 7.67-7.60 (m, 2H), 7.56 (d, J=8.1 Hz, 2H), 7.45-7.31 (m, 5H), 7.23 (d, J=8.6 Hz, 2H), 7.11 (t, J=8.6 Hz, 2H), 4.62 (s, 2H), 4.34 (s, 2H).

Step D: tert-butyl 5-(4-(2-(benzyloxy)-1,1,1,3,3,3-hexafluoropropan-2-yl)phenyl)-5-((4-fluorophenyl)sulfonyl)-2-oxocyclohexanecarboxylate

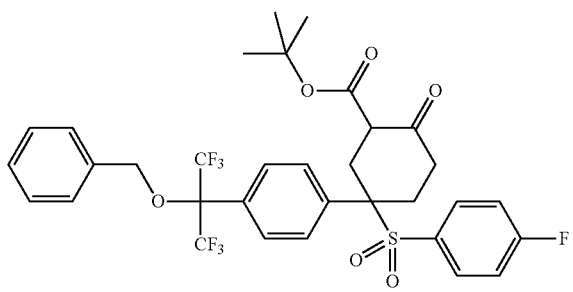 [SMILES: CC(C)(C)OC(=O)C1CC(c2ccc(C(OCc3ccccc3)(C(F)(F)F)C(F)(F)F)cc2)(S(=O)(=O)c2ccc(F)cc2)CCC1=O]

In a 500 mL dry round bottomed flask, to a solution of 1-(2-(benzyloxy)-1,1,1,3,3,3-hexafluoropropan-2-yl)-4-(((4-fluorophenyl)sulfonyl)methyl)benzene (5 g, 9.87 mmol) in THF (125 mL) under nitrogen atmosphere was added potassium tert-butoxide (3.32 g, 29.6 mmol) followed by tert-butyl acrylate (3.15 mL, 21.72 mmol). The reaction mixture was stirred at room temperature (25° C.) for 3 h. After completion of the reaction, it was quenched with saturated NH4Cl solution (150 mL) and extracted with ethyl acetate (2×100 mL), the combined organic layer was washed with brine solution (100 mL), dried over anhydrous sodium sulphate and concentrated to get brown colored oil (crude weight 6.8 g). The crude was purified by combi-flash chromatogram (40 g red-sep silica column, eluted with 10-15% ethyl acetate in hexane). The fractions were collected and concentrated under reduced pressure to obtain tert-butyl 5-(4-(2-(benzyloxy)-1,1,1,3,3,3-hexafluoropropan-2-yl)phenyl)-5-((4-fluorophenyl)sulfonyl)-2-oxocyclohexanecarboxylate (5 g, 4.50 mmol, 45% yield) as pale yellow solid. LC/MS (M+18): 706.2.

Step E: 4-(4-(2-(benzyloxy)-1,1,1,3,3,3-hexafluoropropan-2-yl)phenyl)-4-((4-fluorophenyl)sulfonyl)cyclohexanone

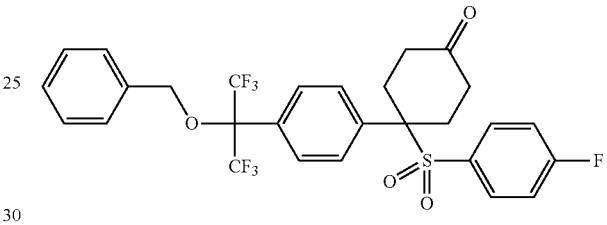

To a solution of tert-butyl 5-(4-(2-(benzyloxy)-1,1,1,3,3,3-hexafluoropropan-2-yl)phenyl)-5-((4-fluorophenyl)sulfonyl)-2-oxocyclohexanecarboxylate (5 g, 5.08 mmol) in 1,2-dichloroethane (100 mL) was added TFA (4.70 mL, 61.0 mmol). The reaction mixture was stirred at 70° C. for overnight. After completion of reaction, reaction mixture was concentrated under reduced pressure. The residue thus obtained was purified by combi-flash chromatogram (24 μm Red-Sep column, eluted with 20-24% ethyl acetate in pet ether) to yield 4-(4-(2-(benzyloxy)-1,1,1,3,3,3-hexafluoropropan-2-yl)phenyl)-4-((4-fluorophenyl)sulfonyl)cyclohexanone (2.5 g, 4.25 mmol, 84% yield) as a off white solid. LC/MS (M+18): 606.3; LC retention time: 20.15 min (analytical HPLC Method D); 1H NMR (400 MHz, CDCl$_3$): δ ppm 7.63 (d, J=8.47 Hz, 2H), 7.46-7.32 (m, 7H), 7.30-7.18 (m, 2H), 7.03-6.90 (m, 2H), 4.68 (s, 2H), 2.93-2.81 (m, 2H), 2.74 (td, J=13.7, 4.39 Hz, 2H), 2.61-2.49 (m, 2H) 2.31-2.15 (m, 2H).

Step F: 4-(4-(2-(benzyloxy)-1,1,1,3,3,3-hexafluoropropan-2-yl)phenyl)-4-((4-fluorophenyl)sulfonyl)cyclohexanecarbonitrile, Diastereomers 1 and 2

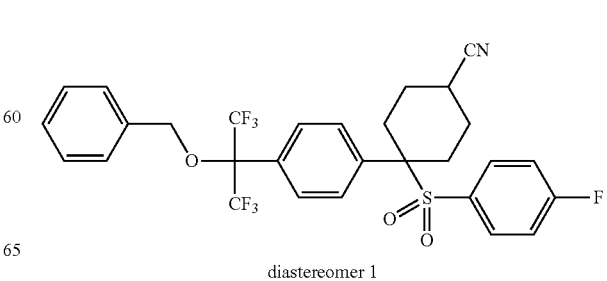

diastereomer 1

-continued

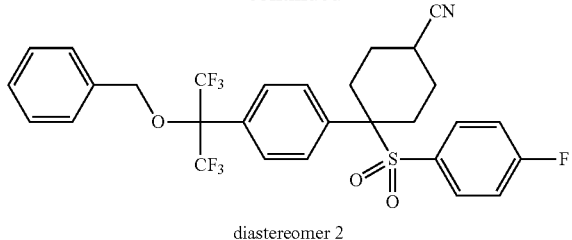

diastereomer 2

To a solution of TOSMIC (66.3 mg, 0.340 mmol) in DME (2.5 ml) at −60° C., was added potassium t-butoxide (95 mg, 0.850 mmol) and stirred for 10 min. 4-(4-(2-(benzyloxy)-1,1,1,3,3,3-hexafluoropropan-2-yl)phenyl)-4-((4-fluorophenyl)sulfonyl)cyclohexanone (100 mg, 0.170 mmol) was added to the above reaction mixture and stirring was continued at same temperature for another 30 min. It was then allowed to warm to room temperature. Methanol (2 mL) was added to the mixture and it was heated to 60° C. with continuous stirring for 20 minutes. The reaction mixture was quenched by pouring the entire mixture into a saturated citric acid solution (15 mL). Resulting solution was extracted with ethyl acetate (2×15 mL), combined organic layers was washed with brine solution, dried over anhydrous Na2SO4, filtered and concentrated to dryness to afford crude product (167 mg). The crude was purified by reverse phase preparative HPLC and later the diastereomers were separated by SFC to afford diastereomer 1 (peak 1, 5 mg, 7.36 µmol, 4% yield) as white solid and diastereomer 2 (peak 2, 7 mg, 10.30 µmol, 6% yield) as white solid.

Analytical data of diastereomer 1: LC/MS (M+18): 629.2; LC retention time: 21.06 min (analytical HPLC Method D); 1H NMR (400 MHz, DMSO-d6): δ ppm 7.61 (d, J=8.03 Hz, 2H), 7.53-7.35 (m, 7H), 7.25-7.17 (m, 2H), 6.94-6.83 (m, 2H), 4.66 (s, 2H), 3.78 (s, 3H), 3.02 (br-s, 1H), 2.73 (d, J=14.5 Hz, 2H), 2.55 (td, J=13.8, 3.5 Hz, 2H), 2.05 (d, J=12.5 Hz, 2H), 1.67-1.48 (m, 2H).

Analytical data of diastereomer 2: LC/MS (M+18): 629.2; LC retention time: 20.76 min (analytical HPLC Method D); 1H NMR (400 MHz, DMSO-d6): δ ppm 7.63 (d, J=8.53 Hz, 2H), 7.50-7.33 (m, 7H), 7.20-7.11 (m, 2H), 6.90-6.78 (m, 2H), 4.67 (s, 2H), 3.77 (s, 3H), 2.96-2.69 (m, 3H), 2.39-2.08 (m, 4H), 1.59-1.37 (m, 2H).

Example 91

1-benzyl-4-(4-(4-(2-((2,6-difluorobenzyl)oxy)-1,1,1,3,3,3-hexafluoropropan-2-yl)phenyl)-4-((4-fluorophenyl)sulfonyl)cyclohexyl)piperazine, Diastereomer 2

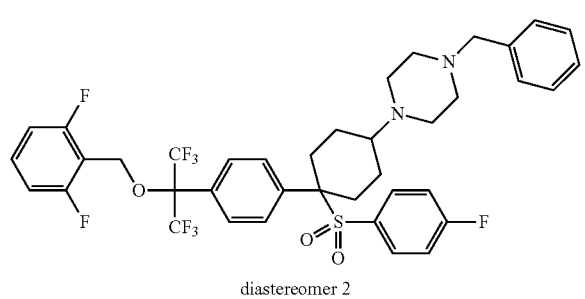 [SMILES: O=S(=O)(c1ccc(F)cc1)C1(c2ccc(C(OCc3c(F)cccc3F)(C(F)(F)F)C(F)(F)F)cc2)CCC(N2CCN(Cc3ccccc3)CC2)CC1]

diastereomer 2

Following conditions described for Step A of Example 82, 4-(4-(2-((2,6-difluorobenzyl)oxy)-1,1,1,3,3,3-hexafluoropropan-2-yl)phenyl)-4-((4-fluorophenyl)sulfonyl)cyclohexanamine diastereomer 2 was converted to 1-benzyl-4-(4-(4-(2-((2,6-difluorobenzyl)oxy)-1,1,1,3,3,3-hexafluoropropan-2-yl)phenyl)-4-((4-fluorophenyl)sulfonyl)cyclohexyl) piperazine diastereomer 2. LC/MS (M+1): 785.2; LC retention time: 17.10 min (analytical HPLC Method D); 1H NMR (400 MHz, CDCl3): δ ppm 7.58-7.50 (m, 2H), 7.48-7.40 (m, 6H), 7.40-7.32 (m, 1H), 7.32-7.28 (m, 1H), 7.15 (dd, J=8.7, 5.0 Hz, 2H), 7.01-6.82 (m, 4H), 4.68 (s, 2H), 4.11 (s, 2H), 3.47-3.34 (m, 7H), 3.08 (d, J=13.5 Hz, 3H), 2.52 (d, J=10.7 Hz, 2H), 2.14-1.92 (m, 5H).

Example 92

4-((4-fluorophenyl)sulfonyl)-4-(4-(1,1,1,3,3,3-hexafluoro-2-hydroxypropan-2-yl)phenyl)cyclohexanecarboxylic acid, Diastereomer 1

Step A: 4-(4-(2-(benzyloxy)-1,1,1,3,3,3-hexafluoropropan-2-yl)phenyl)-4-((4-fluorophenyl)sulfonyl) cyclohexanecarbonitrile

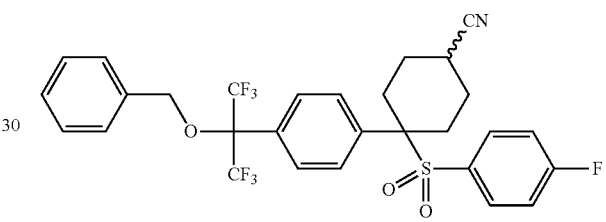

To a solution of TOSMIC (83 mg, 0.425 mmol) in DME (5.0 ml) at −60° C. under inert atmosphere, was added Potassium t-butoxide (95 mg, 0.850 mmol) and was stirred the resulting reaction mixture for 10 min. 4-(4-(2-(benzyloxy)-1,1,1,3,3,3-hexafluoropropan-2-yl)phenyl)-4-((4-fluorophenyl)sulfonyl)cyclohexanone (125 mg, 0.212 mmol) was then added to the above reaction mixture and stirred at −60° C. for another 30 min. Allowed to warm to room temperature. After completion, the reaction mixture was quenched by pouring the entire mixture into a saturated citric acid solution (15 mL). Resulting solution was extracted with ethyl acetate (2×15 mL), combined organic layers was washed with brine solution, dried over anhydrous Na2SO4, filtered and concentrated to dryness to afford crude product (215 mg). The crude was purified by reverse phase preparative HPLC and isolated the desired product as a mixture of two diastereomers.

Step B: 4-(4-(2-(benzyloxy)-1,1,1,3,3,3-hexafluoropropan-2-yl)phenyl)-4-((4-fluorophenyl)sulfonyl) cyclohexanecarboxylic acid

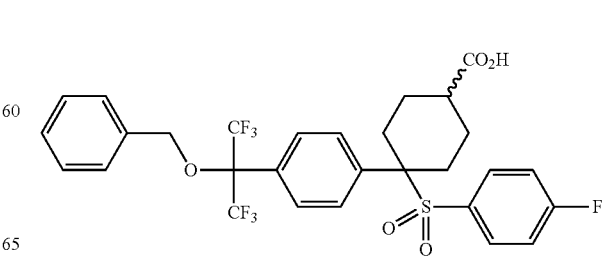

Concentrated HCl (1.0 mL) was added slowly to a solution of 4-(4-(2-(benzyloxy)-1, 1, 1, 3, 3, 3-hexafluoropropan-2-yl) phenyl)-4-((4-Fluorophenyl)sulfonyl)cyclohexanecarbonitrile (400 mg, 0.667 mmol) in dioxane (10 mL). The resulting suspension was heated to 100° C. under sealed tube conditions for 12 h. After completion of the reaction, all volatiles were removed under reduced pressure, dried under vacuum to afford 4-(4-(2-(benzyloxy)-1,1,1,3,3,3-hexafluoropropan-2-yl)phenyl)-4-((4-fluorophenyl)sulfonyl)cyclohexanecarboxylic acid (450 mg, 0.291 mmol, 43% yield) as gummy liquid. LC/MS (M+18): 636.1.

Step C: 4-((4-fluorophenyl)sulfonyl)-4-(4-(1,1,1,3,3,3-hexafluoro-2-hydroxypropan-2-yl)phenyl)cyclohexanecarboxylic acid, Diastereomer 1

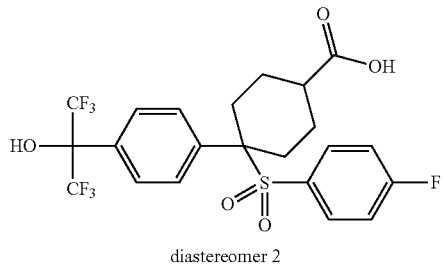 [SMILES: O=C(O)C1CCC(c2ccc(C(O)(C(F)(F)F)C(F)(F)F)cc2)(S(=O)(=O)c2ccc(F)cc2)CC1]

diastereomer 2

To a solution of 4-(4-(2-(benzyloxy)-1,1,1,3,3,3-hexafluoropropan-2-yl)phenyl)-4-((4-fluorophenyl)sulfonyl)cyclohexanecarboxylic acid (400 mg, 0.647 mmol) in acetic acid (10 mL) was added Pd/C (68.8 mg, 64.7 µmol) and stirred under atmospheric pressure using hydrogen bladder for 2 h. After completion, the reaction mixture was filtered through celite pad, washed with acetic acid (2×10 mL). Combined clear filtrate was concentrated to dryness to afford crude gummy product as mixture of diastereomers. Diastereomers were separated by reverse phase preparative HPLC to give 4-((4-fluorophenyl)sulfonyl)-4-(4-(1,1,1,3,3,3-hexafluoro-2-hydroxypropan-2-yl)phenyl)cyclohexanecarboxylic acid diastereomer 1 (peak 1, 200 mg, 0.378 mmol, 25% yield) and 4-((4-fluorophenyl)sulfonyl)-4-(4-(1,1,1,3,3,3-hexafluoro-2-hydroxypropan-2-yl)phenyl)cyclohexanecarboxylic acid diastereomer 2 (peak 2, 202 mg, 0.382 mmol, 25% yield).

Analytical data of 4-((4-fluorophenyl)sulfonyl)-4-(4-(1,1,1,3,3,3-hexafluoro-2-hydroxypropan-2-yl)phenyl)cyclohexanecarboxylic acid diastereomer 1: LC/MS (M+18): 546.2; LC retention time: 9.67 min (analytical HPLC Method D); $^1$H NMR (400 MHz, DMSO-$d_6$): δ ppm 8.82 (s, 1H), 7.63-7.60 (m, 2H), 7.44-7.41 (m, 2H), 7.25-7.21 (m, 4H), 2.49-2.44 (m, 3H), 2.20-2.14 (m, 2H), 2.08-2.05 (m, 2H), 1.13-1.23 (m, 2H).

Analytical data of 4-((4-fluorophenyl)sulfonyl)-4-(4-(1,1,1,3,3,3-hexafluoro-2-hydroxypropan-2-yl)phenyl)cyclohexanecarboxylic acid diastereomer 2: LC/MS (M+18): 546.2; LC retention time: 9.54 min (analytical HPLC Method D); $^1$H NMR (400 MHz, DMSO-$d_6$): δ ppm 9.18 (s, 1H), 7.68-7.66 (m, 2H), 7.48-7.46 (m, 2H), 7.29-7.27 (m, 4H), 2.73-2.72 (m, 2H), 2.39-2.36 (m, 1H), 2.17-2.10 (m, 2H), 1.97-1.94 (m, 2H), 1.18-1.15 (m, 2H).

Example 93 rac-tert-butyl ((2R,4R)-4-((4-fluorophenyl)sulfonyl)-4-(4-(1,1,1,3,3,3-hexafluoro-2-hydroxypropan-2-yl)phenyl)-2-methylcyclohexyl)carbamate, Diastereomer 2

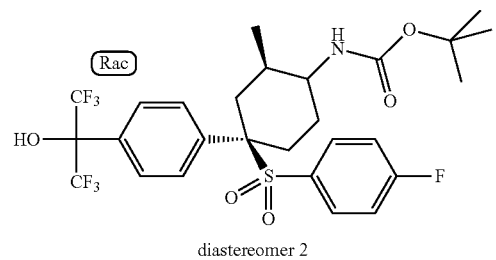 [SMILES: C[C@@H]1C[C@](c2ccc(C(O)(C(F)(F)F)C(F)(F)F)cc2)(S(=O)(=O)c2ccc(F)cc2)CCC1NC(=O)OC(C)(C)C]

diastereomer 2

Step A: rac-(2R,4R)-4-(4-(2-(benzyloxy)-1,1,1,3,3,3-hexafluoropropan-2-yl)phenyl)-4-((4-fluorophenyl)sulfonyl)-2-methylcyclohexanone

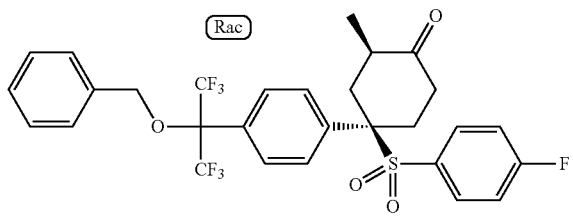 [SMILES: C[C@@H]1C[C@](c2ccc(C(OCc3ccccc3)(C(F)(F)F)C(F)(F)F)cc2)(S(=O)(=O)c2ccc(F)cc2)CCC1=O]

A solution of 4-(4-(2-(benzyloxy)-1,1,1,3,3,3-hexafluoropropan-2-yl)phenyl)-4-((4-fluorophenyl)sulfonyl)cyclohexanone (2.5 g, 4.25 mmol) in THF (75 mL) was cooled to −78° C. under inert atmosphere. To that was added LHMDS [1M in toluene] (6.37 mL, 6.37 mmol) drop wise and stirred the resulting pale yellow color solution at the same temperature for 30 minutes. Temperature was then gradually allowed to reach −33° C. Methyl iodide (0.531 mL, 8.50 mmol) was added to the above reaction mixture and stirred at −33° C. for another 1 h. The reaction mixture was warmed to room temperature; stirring was continued for another 18 h. The reaction was quenched with saturated NH4Cl solution (50 mL), extracted with ethyl acetate (3×50 mL), combined organic layer was washed with brine solution, dried over anhydrous Na2SO4, filtered and concentrated to dryness to afford the crude product. The crude product was purified by ISCO comb-flash chromatogram (120 µm red-sep silica column was used and eluted with 30% ethyl acetate in pet-ether) to afford rac-(2R,4R)-4-(4-(2-(benzyloxy)-1,1,1,3,3,3-hexafluoropropan-2-yl)phenyl)-4-((4-fluorophenyl)sulfonyl)-2-methylcyclohexanone (800 mg, 1.328 mmol, 31% yield) as white solid. LC/MS (M+18): 620.2; 1H NMR (400 MHz, CDCl$_3$): δ ppm 7.65 (d, J=8.31 Hz, 2H), 7.54-7.34 (m, 8H), 7.31-7.20 (m, 2H), 7.07-6.90 (m, 1H), 4.71 (s, 2H), 2.98-2.81 (m, 2H), 2.73 (td, J=13.9, 4.5 Hz, 1H) 2.60-2.38 (m, 2H), 2.36-2.20 (m, 2H) 1.18-1.06 (m, 3H).

Step B: rac-(2R,4R)-4-(4-(2-(benzyloxy)-1,1,1,3,3,3-hexafluoropropan-2-yl)phenyl)-4-((4-fluorophenyl)sulfonyl)-2-methylcyclohexanone oxime

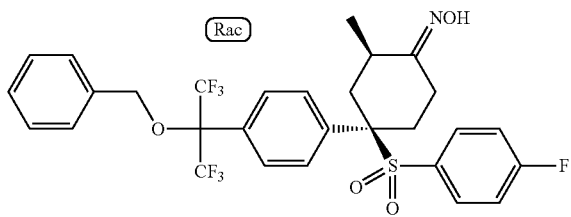

To a solution of rac-(2R,4R)-4-(4-(2-(benzyloxy)-1,1,1,3,3,3-hexafluoropropan-2-yl)phenyl)-4-((4-fluorophenyl)sulfonyl)-2-methylcyclohexanone (800 mg, 1.328 mmol) in ethanol (20 mL) was added hydroxylamine hydrochloride (185 mg, 2.66 mmol); the resulting colorless solution was), stirred at room temperature for 16 h. Volatiles were removed under reduced pressure followed by drying to dryness under high-vacuum to afford rac-(2R,4R)-4-(4-(2-(benzyloxy)-1,1,1,3,3,3-hexafluoropropan-2-yl)phenyl)-4-((4-fluorophenyl)sulfonyl)-2-methylcyclohexanone oxime (800 mg, 1.295 mmol, 98% yield) as pale yellow solid. LC/MS (M+1): 618.2.

Step C: rac-(2R,4R)-4-(4-(2-(benzyloxy)-1,1,1,3,3,3-hexafluoropropan-2-yl)phenyl)-4-((4-fluorophenyl)sulfonyl)-2-methylcyclohexanamine, Diastereomers 1 and 2

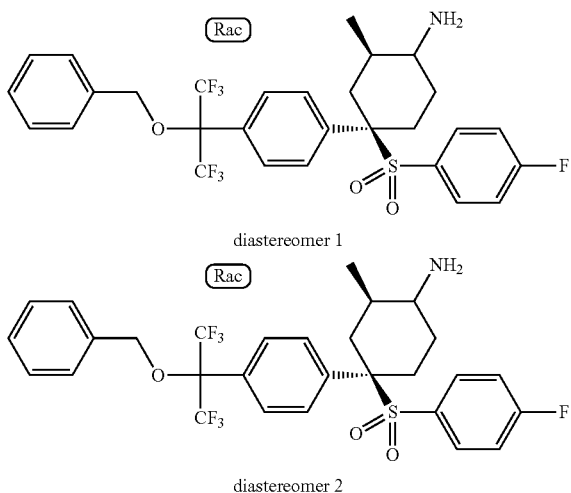

diastereomer 1 diastereomer 2

To a stirred solution of rac-(2R,4R)-4-(4-(2-(benzyloxy)-1,1,1,3,3,3-hexafluoropropan-2-yl)phenyl)-4-((4-fluorophenyl)sulfonyl)-2-methylcyclohexanone oxime (1.0 g, 1.619 mmol) in 4 M methanolic solution of ammonia (50 mL) was added Raney Nickel [1 g] and stirred under hydrogen atmosphere (Bladder) for 4 h. After complete consumption of starting material, it was filtered through celite pad, washed with methanol, combined clear filtrate was concentrated under reduced pressure to get mixture of diastereomers as white solid (1.0 g). The diastereomer mixture was separated by SFC to afford rac-(2R,4R)-4-(4-(2-(benzyloxy)-1,1,1,3,3,3-hexafluoropropan-2-yl)phenyl)-4-((4-fluorophenyl)sulfonyl)-2-methylcyclohexanamine diastereomer 1 (peak 1, 400 mg, 0.663 mmol, 41% yield) and rac-(2R,4R)-4-(4-(2-(benzyloxy)-1,1,1,3,3,3-hexafluoropropan-2-yl)phenyl)-4-((4-fluorophenyl)sulfonyl)-2-methylcyclohexanamine diastereomer 2 (peak 2, 120 mg, 0.200 mmol, 12% yield).

Analytical data of diastereomer 1: LC/MS (M+1): 604.2; LC retention time: 9.54 min (analytical HPLC Method D); 1H NMR (400 MHz, DMSO-d6): δ ppm 7.57-7.46 (m, 4H), 7.46-7.35 (m, 5H), 7.26-7.18 (m, 4H), 4.63 (s, 2H), 2.67-2.65 (m, 1H), 2.32-2.24 (m, 1H), 2.15-2.13 (m, 1H), 1.88 (s, 2H) 1.85-1.74 (m, 2H), 0.98 (s, 4H), 0.91 (d, J=13.5 Hz, 1H).

Analytical data of diastereomer 2: LC/MS (M+1): 604.2; LC retention time: 9.54 min (analytical HPLC Method D); 1H NMR (400 MHz, DMSO-d6): δ ppm 7.57-7.47 (m, 4H), 7.46-7.36 (m, 5H), 7.27-7.19 (m, 4H), 4.62 (s, 2H), 2.78 (br-s, 1H), 2.62-2.52 (m, 2H), 2.37-2.29 (m, 1H), 1.88 (s, 3H), 1.65 (d, J=16.5 Hz, 1H), 1.33-1.18 (m, 2H), 0.88 (d, J=7.03 Hz, 3H).

Step D: rac-2-(4-((1R,3R)-4-amino-1-((4-fluorophenyl)sulfonyl)-3-methylcyclohexyl)phenyl)-1,1,1,3,3,3-hexafluoropropan-2-ol, Diastereomer 1

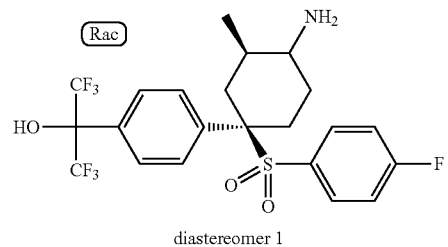 [SMILES: C[C@@H]1C[C@](c2ccc(C(O)(C(F)(F)F)C(F)(F)F)cc2)(S(=O)(=O)c2ccc(F)cc2)CCC1N]

diastereomer 1

To a solution of rac-(2R,4R)-4-(4-(2-(benzyloxy)-1,1,1,3,3,3-hexafluoropropan-2-yl)phenyl)-4-((4-fluorophenyl)sulfonyl)-2-methylcyclohexanamine diastereomer 1 (350 mg, 0.580 mmol) in Acetic Acid (25 mL) was added Pd/C (61.7 mg, 0.580 mmol). The reaction mixture was stirred at room temperature under hydrogen pressure (Bladder pressure) for 2 h. After completion, it was filtered through celite pad, washed with acetic acid (2×20 mL). Combined filtrate was concentrated to dryness to afford white gummy solid. The gummy material thus obtained was dissolved in Acetonitrile [10 mL], added 1N HCl solution [10 mL] and lyophilized to afford rac-2-(4-((1R,3R)-4-amino-1-((4-fluorophenyl)sulfonyl)-3-methylcyclohexyl)phenyl)phenyl)-1,1,1,3,3,3-hexafluoropropan-2-ol hydrochloride, diastereomer 1 (350 mg, 0.636 mmol, 97% yield) as white solid. LC/MS (M+1): 514.2.

Step E: rac-2-(4-((1R,3R)-4-amino-1-((4-fluorophenyl)sulfonyl)-3-methylcyclohexyl)phenyl)-1,1,1,3,3,3-hexafluoropropan-2-ol, Diastereomer 2

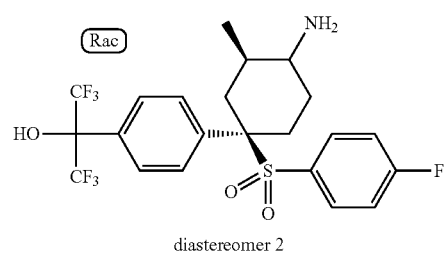 [SMILES: C[C@@H]1C[C@](c2ccc(C(O)(C(F)(F)F)C(F)(F)F)cc2)(S(=O)(=O)c2ccc(F)cc2)CCC1N]

diastereomer 2

Following conditions described in Step D, rac-(2R,4R)-4-(4-(2-(benzyloxy)-1,1,1,3,3,3-hexafluoropropan-2-yl)phenyl)-4-((4-fluorophenyl)sulfonyl)-2-methylcyclohexanamine diastereomer 2 was concerted to rac-2-(4-((1R,3R)-4-amino-1-((4-fluorophenyl)sulfonyl)-3-methylcyclohexyl)phenyl)-1,1,1,3,3,3-hexafluoropropan-2-ol hydrochloride, diastereomer 2. LC/MS (M+1): 514.2.

Step F: rac-tert-butyl ((2R,4R)-4-((4-fluorophenyl)sulfonyl)-4-(4-(1,1,1,3,3,3-hexafluoro-2-hydroxypropan-2-yl)phenyl)-2-methylcyclohexyl)carbamate, Diastereomer 1

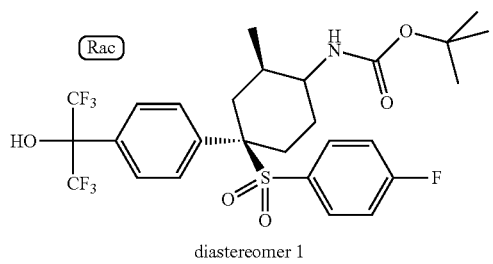 [SMILES: C[C@@H]1C[C@](c2ccc(C(O)(C(F)(F)F)C(F)(F)F)cc2)(S(=O)(=O)c2ccc(F)cc2)CCC1NC(=O)OC(C)(C)C]

diastereomer 1 rac-2-(4-((1R,3R)-4-amino-1-((4-fluorophenyl)sulfonyl)-3-methylcyclohexyl)phenyl)-1,1,1,3,3,3-hexafluoropropan-2-ol hydrochloride, diastereomer 1 (315 mg, 0.573 mmol) in dichloromethane (5 mL) was added Et₃N (0.240 mL, 1.718 mmol) followed by Boc2O (0.160 mL, 0.687 mmol) and the resulting color less clear solution was stirred at room temperature for 12 h. After completion of the reaction, it was dried under reduced pressure to remove dichloromethane and unreacted triethylamine to afford 430 mg light brown colored gummy crude product. It was purified by ISCO comb-flash chromatogram (using 40 µm Red-sep silica column and eluted with 20% ethyl acetate in pet-ether) to generate rac-tert-butyl ((2R,4R)-4-((4-fluorophenyl)sulfonyl)-4-(4-(1,1,1,3,3,3-hexafluoro-2-hydroxypropan-2-yl)phenyl)-2-methylcyclohexyl)carbamate, diastereomer 1 (300 mg, 0.489 mmol, 85% yield) as white solid. LC/MS (M−1): 612.2; LC retention time: 18.95 min (analytical HPLC Method D); 1H NMR (400 MHz, DMSO-d6): δ ppm 8.77 (s, 1H), 7.66-7.56 (m, 2H), 7.49-7.36 (m, 2H), 7.21 (d, J=7.03 Hz, 4H), 6.64-6.53 (m, 1H), 3.06-2.91 (m, 1H), 2.67-2.55 (m, 2H), 2.07 (s, 2H), 1.89-1.71 (m, 2H), 1.31 (s, 9H), 1.11-0.97 (m, 1H), 0.95-0.81 (m, 3H).

Step G: rac-tert-butyl ((2R,4R)-4-((4-fluorophenyl)sulfonyl)-4-(4-(1,1,1,3,3,3-hexafluoro-2-hydroxypropan-2-yl)phenyl)-2-methylcyclohexylcarbamate, Diastereomer 2

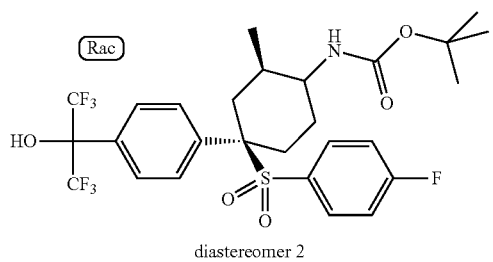 [SMILES: C[C@@H]1C[C@](c2ccc(C(O)(C(F)(F)F)C(F)(F)F)cc2)(S(=O)(=O)c2ccc(F)cc2)CCC1NC(=O)OC(C)(C)C]

diastereomer 2

Following conditions described in Step F, rac-2-(4-((1R,3R)-4-amino-1-((4-fluorophenyl)sulfonyl)-3-methylcyclohexyl)phenyl)-1,1,1,3,3,3-hexafluoropropan-2-ol hydrochloride, diastereomer 2 was concerted to rac-tert-butyl ((2R,4R)-4-((4-fluorophenyl)sulfonyl)-4-(4-(1,1,1,3,3,3-hexafluoro-2-hydroxypropan-2-yl)phenyl)-2-methylcyclohexyl)carbamate, diastereomer 2. LC/MS (M−1): 612.2; LC retention time: 18.90 min (analytical HPLC Method D); 1H NMR (400 MHz, DMSO-d6): δ ppm 8.74 (s, 1H), 7.56 (d, J=8.4 Hz, 2H), 7.42-7.30 (m, 2H), 7.25-7.00 (m, 5H), 3.51-3.40 (m, 1H), 2.40-2.25 (m, 4H), 2.17 (d, J=12.8 Hz, 1H), 1.17 (d, J=12.8 Hz, 1H), 1.43-1.37 (m, 1H), 1.40 (s, 9H), 0.90 (m, 3H).

Example 94

N-(4-((4-fluorophenyl)sulfonyl)-4-(4-(1,1,1,3,3,3-hexafluoro-2-hydroxypropan-2-yl)phenyl)-1-methylcyclohexyl)nicotinamide Step A: (S)-N-(4-(4-(2-(benzyloxy)-1,1,1,3,3,3-hexafluoropropan-2-yl)phenyl)-4-((4-fluorophenyl)sulfonyl)cyclohexylidene)-2-methylpropane-2-sulfinamide

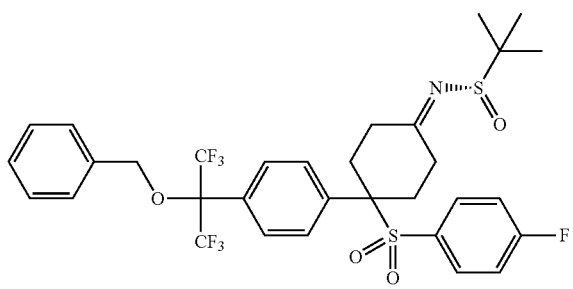 [SMILES: CC(C)(C)[S@](=O)N=C1CCC(c2ccc(C(OCc3ccccc3)(C(F)(F)F)C(F)(F)F)cc2)(S(=O)(=O)c2ccc(F)cc2)CC1]

To a stirred solution of 4-(4-(2-(benzyloxy)-1,1,1,3,3,3-hexafluoropropan-2-yl)phenyl)-4-((4-fluorophenyl)sulfonyl)cyclohexanone (1.4 g, 2.379 mmol) in THF (50 mL) was added Ti(OEt)4 (1.507 mL, 7.14 mmol) under nitrogen atmosphere, After 5 minutes (S)-(−)-2-methyl-2-propanesulfinamide (0.346 g, 2.85 mmol) was added to the above reaction mixture and stirred for 5 h at room temperature. The reaction mixture was poured into an equal volume (50 mL) of aqueous saturated sodium bicarbonate solution with rapid stirring and immediately filtered through filter paper. The filter cake was washed with ethyl acetate (2×50 mL). The layers in the filtrate were separated and the aqueous layer was extracted with ethyl acetate (2×100 mL). Combined organic layer was washed with aqueous saturated sodium bicarbonate solution (200 mL), dried over magnesium sulfate, filtered and concentrated to get (S)-N-(4-(4-(2-(benzyloxy)-1,1,1,3,3,3-hexafluoropropan-2-yl)phenyl)-4-((4-fluorophenyl)sulfonyl)cyclohexylidene)-2-methylpropane-2-sulfinamide (1.5 g). This material was taken forward without any purification at this stage. LC/MS (M+1): 692.2.

Step B: (S)-N-(4-(4-(2-(benzyloxy)-1,1,1,3,3,3-hexafluoropropan-2-yl)phenyl)-4-((4-fluorophenyl)sulfonyl)-1-methylcyclohexyl)-2-methylpropane-2-sulfinamide

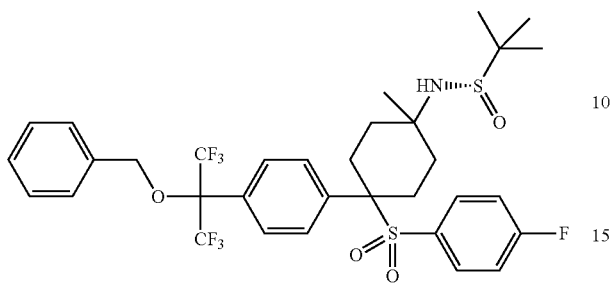

A solution of (S)-N-(4-(4-(2-(benzyloxy)-1,1,1,3,3,3-hexafluoropropan-2-yl)phenyl)-4-((4-fluorophenyl)sulfonyl)cyclohexylidene)-2-methylpropane-2-sulfinamide (1.3 g, 1.88 mmol) in diethyl ether (25 mL) was cooled to −78° C. under inert atmosphere. To that was added methylmagnesium bromide (3 molar solution in diethyl ether) (1.879 mL, 5.64 mmol) and allowed to reach room temperature gradually with constant stirring for 6 h. Reaction mixture was quenched with precooled (in ice bath) saturated NH4Cl solution, extracted with EtOAc (2×50 mL). Combined organic layer was washed with brine solution, dried over sodium sulphate and concentrated to get crude (S)-N-(4-(4-(2-(benzyloxy)-1,1,1,3,3,3-hexafluoropropan-2-yl)phenyl)-4-((4-fluorophenyl)sulfonyl)-1-methylcyclohexyl)-2-methyl propane-2-sulfinamide (1.123 g). This material was taken forward without any purification at this stage. LC/MS (M+1): 708.2.

Step C: 4-(4-(2-(benzyloxy)-1,1,1,3,3,3-hexafluoropropan-2-yl)phenyl)-4-((4-fluorophenyl)sulfonyl)-1-methylcyclohexanamine

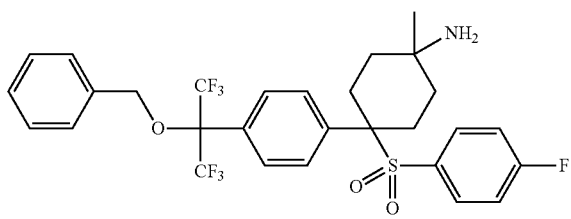 [SMILES: CC1(N)CCC(c2ccc(C(OCc3ccccc3)(C(F)(F)F)C(F)(F)F)cc2)(S(=O)(=O)c2ccc(F)cc2)CC1]

To a stirred solution of previously obtained crude (S)-N-(4-(4-(2-(benzyloxy)-1,1,1,3,3,3-hexafluoropropan-2-yl)phenyl)-4-((4-fluorophenyl)sulfonyl)-1-methylcyclohexyl)-2-methyl propane-2-sulfinamide (1.123 g, 1.587 mmol, ~78% pure) in 1,4-Dioxane (15 mL) was added HCl solution in 1,4-dioxane (0.793 mL, 3.17 mmol) at 10° C. and allowed to reach room temperature and stirred at room temperature for overnight. After completion of the reaction, reaction mixture was quenched with 10% Na2CO3 solution, extracted with EtOAc (2×50 mL). The combined organic layer was washed with brine solution, dried over sodium sulphate and concentrated under vacuum to get crude product (1.0 g) as light yellowish gummy liquid. The crude material was purified by preparative HPLC to get 4-(4-(2-(benzyloxy)-1,1,1,3,3,3-hexafluoropropan-2-yl)phenyl)-4-((4-fluorophenyl)sulfonyl)-1-methylcyclohexanamine hydrochloride (0.85 g, 1.301 mmol, 82% yield). LC/MS (M+1): 604.2; 1H NMR (400 MHz, CDCl3): δ ppm 7.56 (d, J=8.22 Hz, 2H), 7.45-7.31 (m, 7H), 7.20 (dd, J=8.6, 5.2 Hz, 2H), 6.94 (t, J=8.5 Hz, 2H), 4.70 (s, 2H), 2.77-2.57 (m, 2H), 2.46-2.24 (m, 2H), 1.58 (d, J=13.6 Hz, 2H), 1.37-1.17 (m, 2H), 1.04 (s, 3H).

Step D: 2-(4-(4-amino-1-((4-fluorophenyl)sulfonyl)-4-methylcyclohexyl)phenyl)-1,1,1,3,3,3-hexafluoropropan-2-ol

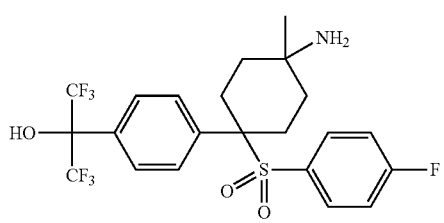 [SMILES: CC1(N)CCC(c2ccc(C(O)(C(F)(F)F)C(F)(F)F)cc2)(S(=O)(=O)c2ccc(F)cc2)CC1]

To a stirred solution of 4-(4-(2-(benzyloxy)-1,1,1,3,3,3-hexafluoropropan-2-yl)phenyl)-4-((4-fluorophenyl)sulfonyl)-1-methylcyclohexanamine (320 mg, 0.530 mmol) in Acetic Acid (15 mL) was added Pd/C (65 mg, 0.061 mmol) at room temperature and stirred H2-balloon pressure for 4 h. After completion of the reaction, it was filtered through celite pad to remove Pd/C, the celite pad was washed two times with 15 mL AcOH. Clear filtrate was then concentrated under high vacuum to get product residue. The residue was dissolved in acetonitrile (4 mL) and to that was added 1N HCl (5 mL), stirred at RT for 15 minutes and concentrated under high vacuum to generate white solids of 2-(4-(4-amino-1-((4-fluorophenyl)sulfonyl)-4-methylcyclohexyl)phenyl)-1,1,1,3,3,3-hexafluoropropan-2-ol hydrochloride (250 mg, 0.436 mmol, 82% yield). LC/MS (M+1): 514.2; LC retention time: 7.73 min (analytical HPLC Method D); 1H NMR (400 MHz, DMSO-d6): δ ppm 8.80 (s, 1H), 8.15 (br-s, 2H), 7.57 (d, J=8.3 Hz, 2H), 7.37 (d, J=8.7 Hz, 2H), 7.26-7.05 (m, 4H), 2.50-2.36 (m, 4H), 1.96 (d, J=14.3 Hz, 2H), 1.30 (t, J=12.1 Hz, 2H), 1.07 (s, 3H).

Step E: N-(4-((4-fluorophenyl)sulfonyl)-4-(4-(1,1,1,3,3,3-hexafluoro-2-hydroxypropan-2-yl)phenyl)-1-methylcyclohexyl)nicotinamide

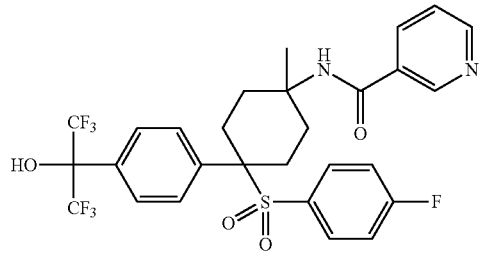 [SMILES: CC1(NC(=O)c2cccnc2)CCC(c2ccc(C(O)(C(F)(F)F)C(F)(F)F)cc2)(S(=O)(=O)c2ccc(F)cc2)CC1]

BOP (14.48 mg, 0.033 mmol) and DIEA (0.019 mL, 0.109 mmol) were added to a mixture of 2-(4-((1s,4s)-4-amino-1-((4-fluorophenyl)sulfonyl)-4-methylcyclohexyl)phenyl)-1,1,1,3,3,3-hexafluoropropan-2-ol, HCl (12 mg, 0.022 mmol) and nicotinic acid (4.03 mg, 0.033 mmol) in DMF (0.5 mL). After stirring for 1 h at rt, the reaction was complete. The mixture was diluted with DMF (1 mL), and submitted for purification. The crude material was purified via preparative LC/MS with the following conditions: Column: Waters XBridge C18, 19×200 mm, 5-µm particles; Mobile Phase A:

5:95 acetonitrile:water with 10-mM ammonium acetate; Mobile Phase B: 95:5 acetonitrile:water with 10-mM ammonium acetate; Gradient: 20-90% B over 12 minutes, then a 3-minute hold at 100% B; Flow: 20 mL/min. Fractions containing the desired product were combined and dried via centrifugal evaporation to give the desired product (9.9 mg, 72% yield). LC/MS (M+1): 514.2; LC retention time: 1.81 min (analytical HPLC Method B); 1H NMR (500 MHz, 1:1 mixture of $CDCl_3$-$CD_3OD$) δ ppm 8.96 (d, J=1.7 Hz, 1H), 8.69 (dd, J=4.9, 1.5 Hz, 1H), 8.18 (dt, J=8.0, 1.9 Hz, 1H), 7.72 (d, J=8.4 Hz, 2H), 7.54 (dd, J=7.9, 5.0 Hz, 1H), 7.42 (d, J=8.9 Hz, 2H), 7.28-7.20 (m, 2H), 7.02 (t, J=8.6 Hz, 2H), 2.64-2.46 (m, 6H), 1.32 (s, 3H), 1.29-1.16 (m, 2H).

Example 95

N-(4-((4-fluorophenyl)sulfonyl)-1-methyl-4-(4-(perfluoropropan-2-yl)phenyl)cyclohexyl)-2-(pyridin-4-yl)acetamide Step A: tert-butyl (4-((4-fluorophenyl)sulfonyl)-4-(4-(1,1,1,3,3,3-hexafluoro-2-hydroxypropan-2-yl)phenyl)-1-methylcyclohexyl)carbamate

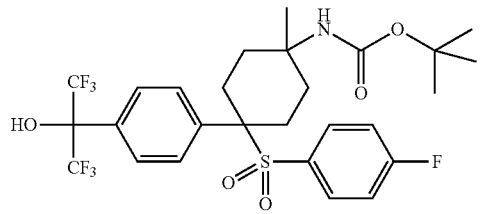 [SMILES: CC1(NC(=O)OC(C)(C)C)CCC(c2ccc(C(O)(C(F)(F)F)C(F)(F)F)cc2)(S(=O)(=O)c2ccc(F)cc2)CC1]

DIEA (0.286 mL, 1.637 mmol) was added to a mixture of 2-(4-(4-amino-1-((4-fluorophenyl)sulfonyl)-4-methylcyclohexyl)phenyl)-1,1,1,3,3,3-hexafluoropropan-2-ol, HCl (225 mg, 0.409 mmol) and BOC2O (179 mg, 0.818 mmol) in CH2Cl2 (4 mL) and THF (4 mL). The resulting solution was stirred at rt for 22 h, diluted with EtOAc (80 mL), washed with water (2×10 mL), brine (10 mL), dried (MgSO4) and concentrated. Silica gel chromatography, eluting with 10-30% EtOAc in hexanes, gave the desired product as white solid (240.6 mg, 96% yield). LC/MS (M−56+1): 558.0; LC retention time: 4.333 min (analytical HPLC Method A); 1H NMR (400 MHz, 1:1 mixture of $CDCl_3$-$CD_3OD$) δ ppm 7.68 (d, J=8.6 Hz, 2H), 7.33 (d, J=8.8 Hz, 2H), 7.20 (dd, J=8.7, 5.2 Hz, 2H), 6.99 (t, J=8.6 Hz, 2H), 5.63 (br. s., 1H), 2.58-2.36 (m, 4H), 2.30-2.16 (m, 2H), 1.48 (s, 9H), 1.21-1.07 (m, 5H).

Step B: tert-butyl (4-((4-fluorophenyl)sulfonyl)-1-methyl-4-(4-(perfluoropropan-2-yl)phenyl)cyclohexyl)carbamate

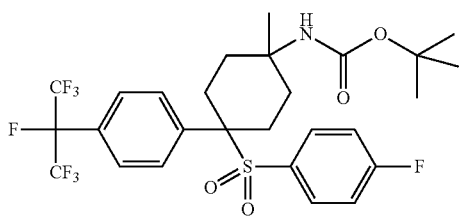 [SMILES: CC1(NC(=O)OC(C)(C)C)CCC(c2ccc(C(F)(C(F)(F)F)C(F)(F)F)cc2)(S(=O)(=O)c2ccc(F)cc2)CC1]

A mixture of tert-butyl (4-((4-fluorophenyl)sulfonyl)-4-(4-(1,1,1,3,3,3-hexafluoro-2-hydroxypropan-2-yl)phenyl)-1-methylcyclohexyl)carbamate (240 mg, 0.391 mmol) and DAST (0.310 mL, 2.347 mmol) in 1,2-dichloroethane (4 mL) in a sealed vial was stirred at 55° C. for 15 h. The mixture was cooled to 0° C., quenched with MeOH (1 mL), diluted with EtOAc (40 mL), washed with water (2×8 mL), brine (8 mL), dried (MgSO4) and concentrated. Silica gel chromatography, eluting with 10-40% EtOAc in hexanes, gave the desired product (195 mg, 81% yield). LC/MS (M−56+1): 560.1; LC retention time: 4.615 min (analytical HPLC Method A); 1H NMR (400 MHz, CDCl3) δ ppm 7.53 (d, J=8.4 Hz, 2H), 7.36 (d, J=8.6 Hz, 2H), 7.22-7.14 (m, 2H), 6.99-6.89 (m, 2H), 4.38 (s, 1H), 2.59-2.47 (m, 2H), 2.44-2.33 (m, 2H), 2.21 (d, J=13.7 Hz, 2H), 1.47 (s, 9H), 1.22-1.07 (m, 5H).

Step C: 4-((4-fluorophenyl)sulfonyl)-1-methyl-4-(4-(perfluoropropan-2-yl)phenyl)cyclohexanamine

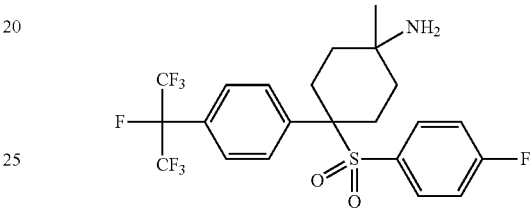

A mixture of tert-butyl (4-((4-fluorophenyl)sulfonyl)-1-methyl-4-(4-(perfluoropropan-2-yl)phenyl)cyclohexyl)carbamate (195 mg) in $CH_2Cl_2$ (3 mL) and 4 N HCl in dioxane (3 mL) was stirred at rt for 18 h. The mixture was concentrated and dried under vacuum to give 4-((4-fluorophenyl)sulfonyl)-1-methyl-4-(4-(perfluoropropan-2-yl)phenyl)cyclohexanamine hydrochloride (173 mg, 99% yield). LC/MS (M+1): 516.1; LC retention time: 3.798 min (analytical HPLC Method A); $^1$H NMR (400 MHz, $CD_3OD$) δ ppm 7.60 (d, J=8.4 Hz, 2H), 7.50 (d, J=8.7 Hz, 2H), 7.28-7.20 (m, 2H), 7.14-7.03 (m, 2H), 2.73-2.53 (m, 4H), 2.07 (d, J=15.2 Hz, 2H), 1.63-1.47 (m, 2H), 1.22 (s, 3H).

Step D: N-(4-((4-fluorophenyl)sulfonyl)-1-methyl-4-(4-(perfluoropropan-2-yl)phenyl)cyclohexyl)-2-(pyridin-4-yl)acetamide

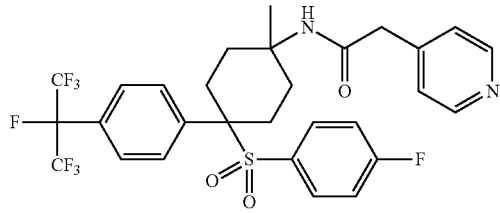 [SMILES: CC1(NC(=O)Cc2ccncc2)CCC(c2ccc(C(F)(C(F)(F)F)C(F)(F)F)cc2)(S(=O)(=O)c2ccc(F)cc2)CC1]

HATU (10.33 mg, 0.027 mmol) and DIEA (0.016 mL, 0.091 mmol) were added to a stirred mixture of 4-((4-fluorophenyl)sulfonyl)-1-methyl-4-(4-(perfluoropropan-2-yl)phenyl)cyclohexanamine hydrochloride (10 mg, 0.018 mmol) and 4-pyridylacetic acid hydrochloride (6.29 mg, 0.036 mmol) in DMF (0.5 mL). After stirring for 1 h at rt, the crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-90% B over 10 minutes, then a 5-minute hold at 100% B; Flow: 20 mL/min. Fractions containing the desired product were combined and dried via centrifugal evaporation to give the title compound (8.5 mg, 72% yield). LC/MS (M+1): 635.2; LC retention time: 2.27 min (analytical HPLC Method B); 1H NMR (500 MHz, 1:1 mixture of CDCl$_3$-CD$_3$OD) δ ppm 8.60-8.46 (m, 2H), 7.57 (d, J=8.5 Hz, 2H), 7.48-7.39 (m, 4H), 7.21-7.12 (m, 2H), 7.01 (t, J=8.5 Hz, 2H), 3.61 (s, 2H), 2.55-2.33 (m, 6H), 1.21 (s, 3H), 1.17-1.05 (m, 2H).

Example 96

2-((1s,4s)-4-((4-fluorophenyl)sulfonyl)-4-(4-(perfluoropropan-2-yl)phenyl)cyclohexyl)-1H-pyrrolo[3,4-c]pyridine-1,3(2H)-dione

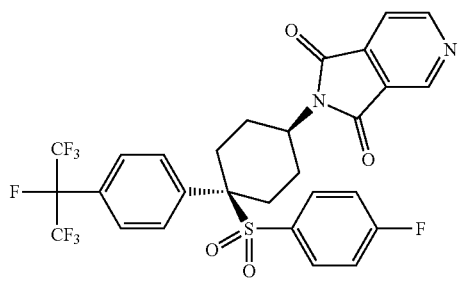 [SMILES: O=C1c2ccncc2C(=O)N1[C@H]1CC[C@@](c2ccc(C(F)(C(F)(F)F)C(F)(F)F)cc2)(S(=O)(=O)c2ccc(F)cc2)CC1]

A mixture of (1s,4s)-4-((4-fluorophenyl)sulfonyl)-4-(4-(perfluoropropan-2-yl)phenyl)cyclohexanamine hydrochloride (15 mg, 0.028 mmol, from Step E of Example 9) and furo[3,4-c]pyridine-1,3-dione (6.24 mg, 0.042 mmol) in HOAc (0.5 mL) in a sealed vial was stirred at 90° C. for 30 h. LCMS analysis showed that the reaction was near completion. The mixture was concentrated and purified via preparative LC/MS with the following conditions: Column: Waters XBridge C18, 19×200 mm, 5-m particles; Mobile Phase A: 5:95 acetonitrile:water with 10-mM ammonium acetate; Mobile Phase B: 95:5 acetonitrile:water with 10-mM ammonium acetate; Gradient: 35-100% B over 20 minutes, then a 5-minute hold at 100% B; Flow: 20 mL/min. Fractions containing the desired product were combined and dried via centrifugal evaporation to give the title compound (9.7 mg, 55% yield). LC/MS (M+1): 633.1; LC retention time: 2.39 min (analytical HPLC Method B).

The examples in TABLE 2 below were prepared from 2-(4-((1s,4s)-4-amino-1-(4-fluorophenylsulfonyl)cyclohexyl)phenyl)-1,1,1,3,3,3-hexafluoropropan-2-ol (intermediate 2) or 2-(4-((1r,4r)-4-amino-1-(4-fluorophenylsulfonyl)cyclohexyl)phenyl)-1,1,1,3,3,3-hexafluoropropan-2-ol (intermediate 1) or (1r,4r)-4-(4-fluorophenylsulfonyl)-4-(4-(perfluoropropan-2-yl)phenyl)cyclohexanamine or (1s,4s)-4-(4-fluorophenylsulfonyl)-4-(4-(perfluoropropan-2-yl)phenyl) cyclohexanamine (from Steps D and E of Example 9) in the same manner as outlined in the Step C of Example 7 above, substituting the appropriate acid and sulfonyl chloride.

TABLE 2

| Example number | Structure | MS observed (M + 1) | HPLC ret. time (min.) | HPLC method |
|---|---|---|---|---|
| 97 | 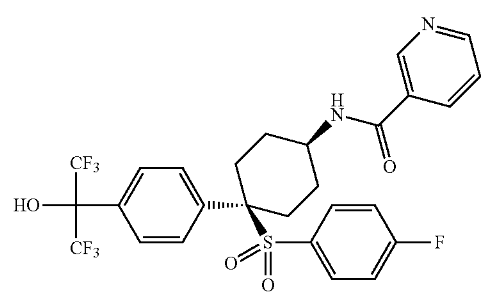 [SMILES: O=C(N[C@H]1CC[C@@](c2ccc(C(O)(C(F)(F)F)C(F)(F)F)cc2)(S(=O)(=O)c2ccc(F)cc2)CC1)c1cccnc1] | 605.3 | 1.81 | B |
| 98 | 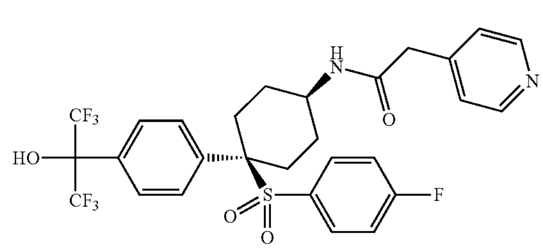 [SMILES: O=C(Cc1ccncc1)N[C@H]1CC[C@@](c2ccc(C(O)(C(F)(F)F)C(F)(F)F)cc2)(S(=O)(=O)c2ccc(F)cc2)CC1] | 619.2 | 1.77 | B |
| 99 | 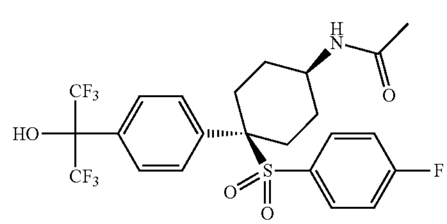 [SMILES: CC(=O)N[C@H]1CC[C@@](c2ccc(C(O)(C(F)(F)F)C(F)(F)F)cc2)(S(=O)(=O)c2ccc(F)cc2)CC1] | 542.2 | 1.74 | B |

TABLE 2-continued

| Example number | Structure | MS observed (M + 1) | HPLC ret. time (min.) | HPLC method |
|---|---|---|---|---|
| 100 | 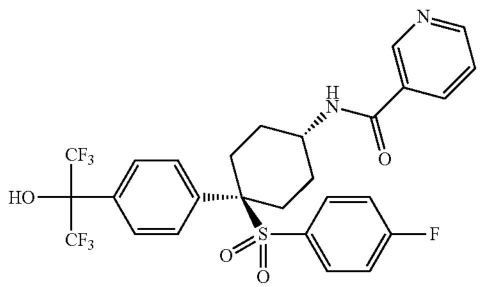 [SMILES: O=C(N[C@H]1CC[C@](c2ccc(C(O)(C(F)(F)F)C(F)(F)F)cc2)(S(=O)(=O)c2ccc(F)cc2)CC1)c1cccnc1] | 605.3 | 1.77 | B |
| 101 | 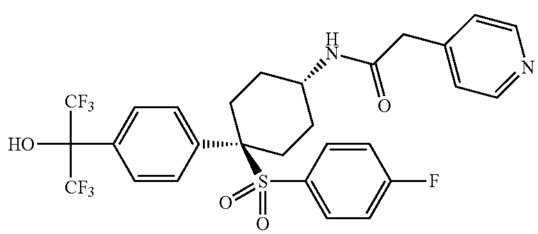 [SMILES: O=C(Cc1ccncc1)N[C@H]1CC[C@](c2ccc(C(O)(C(F)(F)F)C(F)(F)F)cc2)(S(=O)(=O)c2ccc(F)cc2)CC1] | 619.2 | 1.74 | B |
| 102 | diastereomer 2 | 621.2 | 2.03 | B |
| 103 | 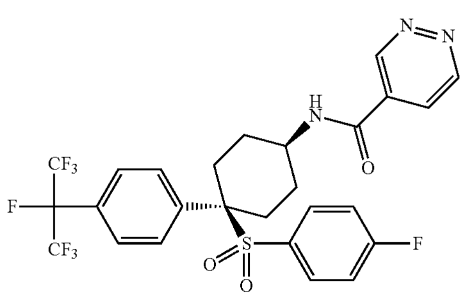 [SMILES: O=C(N[C@H]1CC[C@@](c2ccc(C(F)(C(F)(F)F)C(F)(F)F)cc2)(S(=O)(=O)c2ccc(F)cc2)CC1)c1ccnnc1] | 608.3 | 2.05 | B |
| 104 | 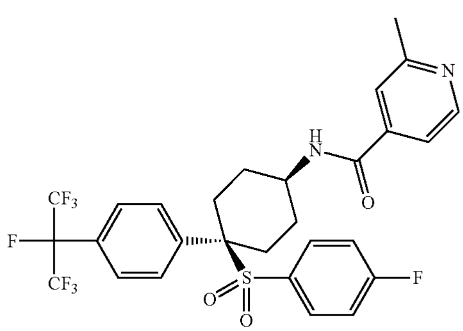 [SMILES: Cc1cc(C(=O)N[C@H]2CC[C@@](c3ccc(C(F)(C(F)(F)F)C(F)(F)F)cc3)(S(=O)(=O)c3ccc(F)cc3)CC2)ccn1] | 621.3 | 2.20 | B |

TABLE 2-continued

| Example number | Structure | MS observed (M + 1) | HPLC ret. time (min.) | HPLC method |
|---|---|---|---|---|
| 105 | 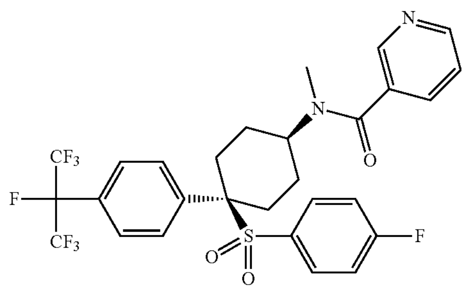 [SMILES: CN(C(=O)c1cccnc1)[C@H]1CC[C@@](c2ccc(C(F)(C(F)(F)F)C(F)(F)F)cc2)(S(=O)(=O)c2ccc(F)cc2)CC1] | 621.3 | 2.22 | B |
| 106 | 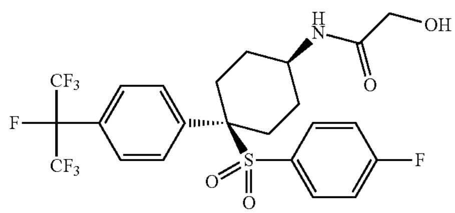 | 560.3 | 2.03 | B |
| 107 | 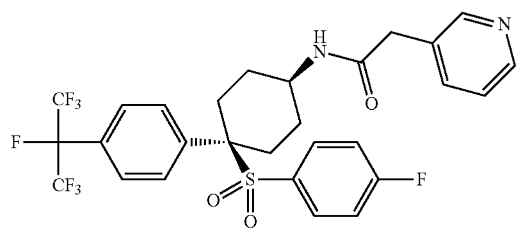 [SMILES: O=C(Cc1cccnc1)N[C@H]1CC[C@@](c2ccc(C(F)(C(F)(F)F)C(F)(F)F)cc2)(S(=O)(=O)c2ccc(F)cc2)CC1] | 621.2 | 1.97 | B |
| 108 | diastereomer 1 | 621.2 | 2.09 | B |
| 109 | 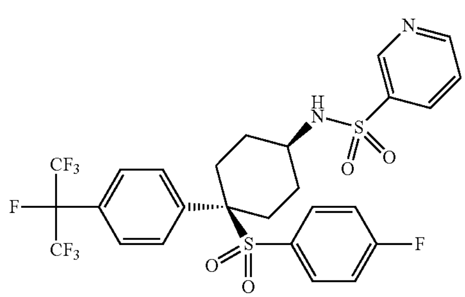 [SMILES: O=S(=O)(N[C@H]1CC[C@@](c2ccc(C(F)(C(F)(F)F)C(F)(F)F)cc2)(S(=O)(=O)c2ccc(F)cc2)CC1)c1cccnc1] | 643.0 | 2.25 | B |
| 110 | 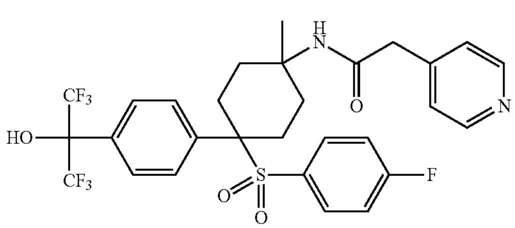 [SMILES: CC1(NC(=O)Cc2ccncc2)CCC(c2ccc(C(O)(C(F)(F)F)C(F)(F)F)cc2)(S(=O)(=O)c2ccc(F)cc2)CC1] | 633.2 | 1.69 | B |

TABLE 2-continued

| Example number | Structure | MS observed (M + 1) | HPLC ret. time (min.) | HPLC method |
|---|---|---|---|---|
| 111 | 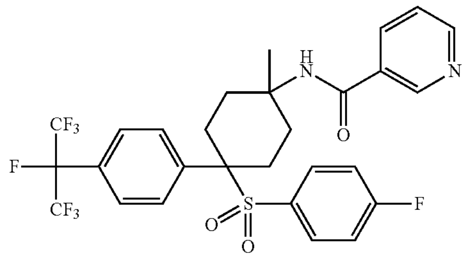 [SMILES: CC1(NC(=O)c2cccnc2)CCC(c2ccc(C(F)(C(F)(F)F)C(F)(F)F)cc2)(S(=O)(=O)c2ccc(F)cc2)CC1] | 635.1 | 2.27 | B |

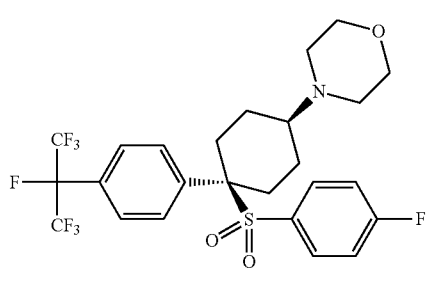 [SMILES: O=S(=O)(c1ccc(F)cc1)[C@]1(c2ccc(C(F)(C(F)(F)F)C(F)(F)F)cc2)CC[C@H](N2CCOCC2)CC1]

Example 112

4-((1s,4s)-4-(4-fluorophenylsulfonyl)-4-(4-(perfluoropropan-2-yl)phenyl)cyclohexyl)morpholine

Example 113

4-((1s,4s)-4-((4-fluorophenyl)sulfonyl)-4-(4-(perfluoropropan-2-yl)phenyl)cyclohexyl)thiomorpholine 1,1-dioxide

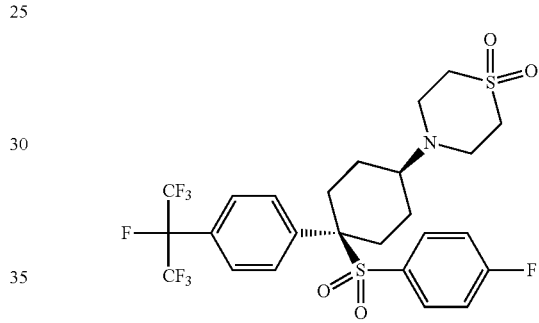

A DMF (0.5 mL) solution of (1s,4s)-4-((4-fluorophenyl)sulfonyl)-4-(4-(perfluoropropan-2-yl)phenyl)cyclohexanamine HCl salt (17 mg, 0.032 mmol from intermediate D), 1-iodo-2-(2-iodoethoxy)ethane (30.9 mg, 0.095 mmol) and potassium carbonate (53 mg, 0.383 mmol) was stirred at room temperature for 23 h. The crude was diluted with MeOH (1.5 mL) and filtered, the filtrate was acidified with 4 M HCl in dioxane (50 uL) and filtered again. The solution was purified via preparative LC/MS with the following conditions: Column: Waters XBridge C18, 19×200 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 20 minutes, then a 5-minute hold at 100% B; Flow: 20 mL/min. Fractions containing the desired product were combined and dried via centrifugal evaporation to give 4-((1s,4s)-4-(4-fluorophenylsulfonyl)-4-(4-(perfluoropropan-2-yl)phenyl)cyclohexyl)morpholine (9 mg, 48%). LC/MS (M+1): 572.2; LC retention time: 2.429 min (analytical HPLC Method B); 1H NMR (500 MHz, 1:1 mixture of CDCl$_3$-CD$_3$OD) δ ppm 7.57-7.52 (m, 2H), 7.51-7.45 (m, 2H), 7.30-7.24 (m, 2H), 7.03 (t, J=8.6 Hz, 2H), 3.76-3.69 (m, 4H), 2.79-2.71 (m, 2H), 2.51 (br. s., 4H), 2.28-2.19 (m, 2H), 2.18-2.08 (m, 3H), 1.40 (t, J=12.6 Hz, 2H).

Cesium carbonate (31.8 mg, 0.098 mmol) was added to a DMF (0.5 mL) solution of (1s,4s)-4-((4-fluorophenyl)sulfonyl)-4-(4-(perfluoropropan-2-yl)phenyl)cyclohexanamine HCl salt (10.5 mg, 0.020 mmol from intermediate D) and 1-chloro-2-((2-chloroethyl)sulfonyl)ethane (6 mg, 0.031 mmol). The mixture was heated at 60° C. for 3.5 h. Additional 1-chloro-2-((2-chloroethyl)sulfonyl)ethane (6 mg) was added. The mixture was stirred at 60° C. for 1.5 h then at ambient temperature for 16 h. The crude was diluted with MeOH (1.5 mL) and filtered. The solution was purified via preparative HPLC with the following conditions: Column: Phenomenex Luna C18, 21×100 mm, 5-μm particles; Mobile Phase A: 5:95 acetonitrile:water with 0.05% TFA; Mobile Phase B: 95:5 acetonitrile:water with 0.05% TFA; Gradient: 0-100% B over 8 minutes, then a 7-minute hold at 100% B; Flow: 20 mL/min. The product was further purified via preparative LC/MS with the following conditions: Column: Waters XBridge C18, 19×200 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-100% B over 15 minutes, then a 5-minute hold at 100% B; Flow: 20 mL/min. Fractions containing the desired product were combined and dried via centrifugal evaporation to give 4-((1s,4s)-4-((4-fluorophenyl)sulfonyl)-4-(4-(perfluoropropan-2-yl)phenyl)cyclohexyl)thiomorpholine 1,1-dioxide (3.6 mg, 30% yield). LC/MS (M+1): 620.0; LC retention time: 2.242 min (analytical HPLC Method B); 1H NMR (400 MHz, 1:1 mixture of CDCl$_3$-CD$_3$OD) δ ppm 7.51 (d, J=8.4 Hz, 2H), 7.40 (d, J=8.6 Hz, 2H), 7.22-7.15 (m, 2H), 6.97 (t, J=8.6 Hz, 2H), 3.28-3.21 (m, 4H), 3.20-3.13 (m, 4H), 2.94-2.83 (m, 2H), 2.78-2.68 (m, 1H), 2.32-2.11 (m, 4H), 1.71-1.60 (m, 2H).

Example 114

4-(1-((1s,4s)-4-(4-fluorophenylsulfonyl)-4-(4-(perfluoropropan-2-yl)phenyl)cyclohexyl)-1 H-1,2,3-triazol-4-yl)pyridine Step A: 1-((1s,4s)-4-azido-1-(4-(perfluoropropan-2-yl)phenyl)cyclohexylsulfonyl)-4-fluorobenzene

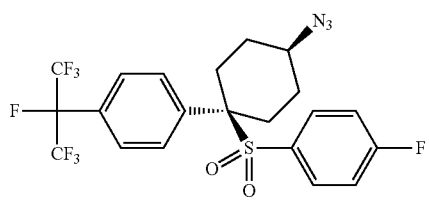 [SMILES: [N-]=[N+]=N[C@H]1CC[C@@](c2ccc(C(F)(C(F)(F)F)C(F)(F)F)cc2)(S(=O)(=O)c2ccc(F)cc2)CC1]

A MeOH (1 mL)-water (0.5 mL) solution of (1s,4s)-4-((4-fluorophenyl)sulfonyl)-4-(4-(perfluoropropan-2-yl)phenyl)cyclohexanamine HCl salt (50 mg, 0.10 mmol from intermediate D), potassium carbonate (20.67 mg, 0.15 mmol) and copper(II) sulfate (1.592 mg, 9.97 μmol) was stirred at room temperature. In a separate vial, colorless triflic anhydride (0.034 mL, 0.2 mmol) was added to a stirred CH$_2$Cl$_2$ (2 mL)-water (1 mL) bi-phase solution of sodium azide (64.8 mg, 1 mmol) at 0° C. After 1 h, the prepared triflic azide solution was added to the amine solution. The mixture was stirred at room temperature for 68 h. Silica gel chromatography, eluting with 0-50% ethyl acetate in hexanes, gave 1-((1s,4s)-4-azido-1-(4-(perfluoropropan-2-yl)phenyl)cyclohexylsulfonyl)-4-fluorobenzene (39.8 mg, 76%) as white solid. LC/MS (M+18): 545.4; 1H NMR (400 MHz, CDCl$_3$) δ ppm 7.55 (d, J=8.4 Hz, 2H), 7.38 (d, J=8.6 Hz, 2H), 7.26-7.18 (m, 2H), 7.01-6.92 (m, 2H), 3.78 (t, J=3.0 Hz, 1H), 2.64 (td, J=13.7, 3.4 Hz, 2H), 2.41 (d, J=12.7 Hz, 2H), 1.95 (d, J=14.1 Hz, 2H), 1.54-1.41 (m, 2H).

Step B: 4-(1-((1s,4s)-4-(4-fluorophenylsulfonyl)-4-(4-(perfluoropropan-2-yl)phenyl)cyclohexyl)-1H-1,2,3-triazol-4-yl)pyridine

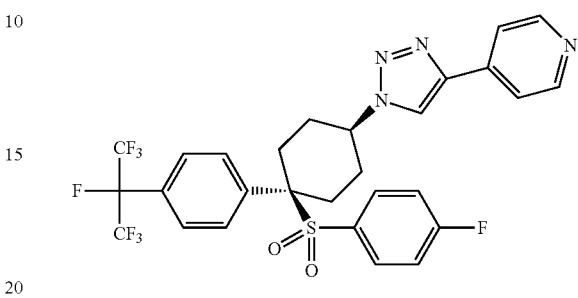

A THF (0.5 mL) solution of 1-((1s,4s)-4-azido-1-((4-fluorophenyl) sulfonyl)cyclohexyl)-4-(perfluoropropan-2-yl)benzene (18 mg, 0.034 mmol), 4-ethynylpyridine HCl salt (10 mg, 0.072 mmol), sodium ascorbate (3.72 mg, 0.019 mmol), 1M NaOH (0.072 mL, 0.072 mmol) and copper(II) sulfate (1.5 mg, 9.40 μmol) was heated at 90° C. for 19 h in a safety sealed vial. Additional 4-ethynylpyridine HCl salt (12.5 mg), copper(II) sulfate (5.8 mg), sodium ascorbate (31.6 mg), 1M NaOH (121 uL) and THF (0.5 mL) were added. The mixture was heated at 90° C. for additional 3.5 h. Silica gel chromatography, eluting with 0-100% ethyl acetate in hexanes, gave 4-(1-((1s,4s)-4-(4-fluorophenylsulfonyl)-4-(4-(perfluoropropan-2-yl)phenyl)cyclohexyl)-1H-1,2,3-triazol-4-yl)pyridine (15.2 mg, 67%) as yellow solid. LC/MS (M+1): 631.4; LC retention time: 0.92 min (analytical HPLC Method I); 1H NMR (400 MHz, CDCl$_3$) δ ppm 8.73-8.68 (m, 2H), 8.07 (s, 1H), 7.80-7.75 (m, 2H), 7.58 (d, J=8.6 Hz, 2H), 7.42 (d, J=8.6 Hz, 2H), 7.25-7.17 (m, 2H), 7.00-6.92 (m, 2H), 4.72-4.64 (m, 1H), 2.91 (ddd, J=14.1, 10.1, 3.5 Hz, 2H), 2.82-2.70 (m, 2H), 2.49-2.37 (m, 2H), 2.19-2.06 (m, 2H).

The examples in TABLE 3 below were prepared in the same manner as outlined in the Example 114 above, substituting the appropriate acetylene.

TABLE 3

| Example number | Structure | MS observed (M + 1) | HPLC ret. time (min.) | HPLC method |
|---|---|---|---|---|
| 115 | 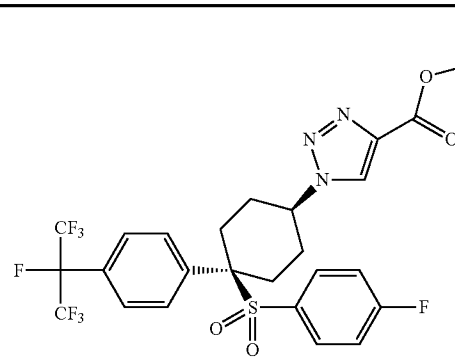 | 626.1 | 1.08 | I |

TABLE 3-continued

| Example number | Structure | MS observed (M + 1) | HPLC ret. time (min.) | HPLC method |
|---|---|---|---|---|
| 116 | 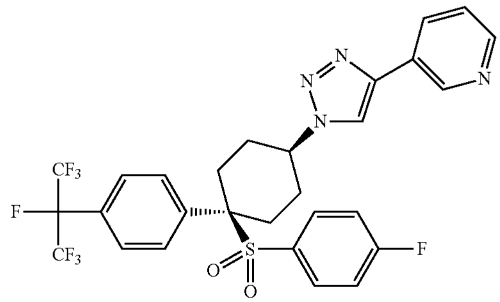 [SMILES: O=S(=O)(c1ccc(F)cc1)[C@]1(c2ccc(C(F)(C(F)(F)F)C(F)(F)F)cc2)CC[C@H](n2cc(-c3cccnc3)nn2)CC1] | 631.1 | 0.93 | I |
| 117 | 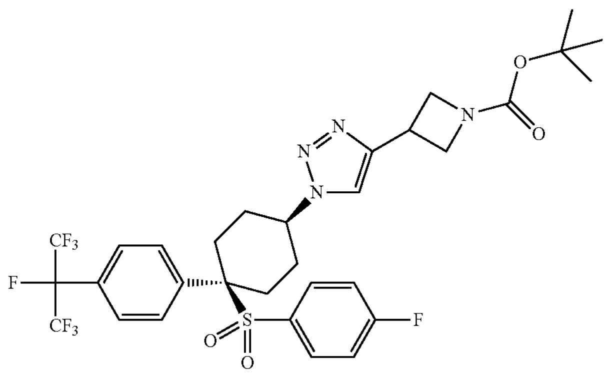 [SMILES: CC(C)(C)OC(=O)N1CC(c2cn([C@H]3CC[C@@](c4ccc(C(F)(C(F)(F)F)C(F)(F)F)cc4)(S(=O)(=O)c4ccc(F)cc4)CC3)nn2)C1] | 709.6 | 1.12 | I |

Example 118

1-((1s,4s)-4-(4-fluorophenylsulfonyl)-4-(4-(perfluoropropan-2-yl)phenyl)cyclohexyl)-1H-1,2,3-triazole-4-carboxylic acid

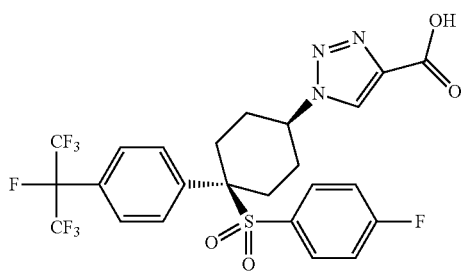 [SMILES: O=C(O)c1cn([C@H]2CC[C@@](c3ccc(C(F)(C(F)(F)F)C(F)(F)F)cc3)(S(=O)(=O)c3ccc(F)cc3)CC2)nn1]

A THF (0.184 mL) solution of ethyl 1-((1s,4s)-4-((4-fluorophenyl)sulfonyl)-4-(4-(perfluoropropan-2-yl)phenyl)cyclohexyl)-1H-1,2,3-triazole-4-carboxylate (10 mg, 0.016 mmol from Example 115) and 1M NaOH (0.184 mL, 0.184 mmol) was stirred at room temperature for 2 h. The organic solvent was evaporated. The residue was triturated with 1M HCl (1 mL) and filtered to give 1-((1s,4s)-4-(4-fluorophenylsulfonyl)-4-(4-(perfluoropropan-2-yl)phenyl)cyclohexyl)-1H-1,2,3-triazole-4-carboxylic acid (8.4 mg, 84%) as white solid. LC/MS (M+1): 598.0; LC retention time: 1.01 min (analytical HPLC Method I); 1H NMR (400 MHz, CDCl$_3$) δ ppm 8.34 (s, 1H), 7.58 (d, J=8.6 Hz, 2H), 7.41 (d, J=8.4 Hz, 2H), 7.21 (dd, J=8.9, 5.0 Hz, 2H), 6.97 (t, J=8.5 Hz, 2H), 4.67 (br. s., 1H), 2.90-2.69 (m, 4H), 2.49-2.36 (m, 2H), 2.18-2.07 (m, 2H).

Example 119

(1-((1s,4s)-4-(4-fluorophenylsulfonyl)-4-(4-(perfluoropropan-2-yl)phenyl)cyclohexyl)-1 H-1,2,3-triazol-4-yl)(morpholino)methanone

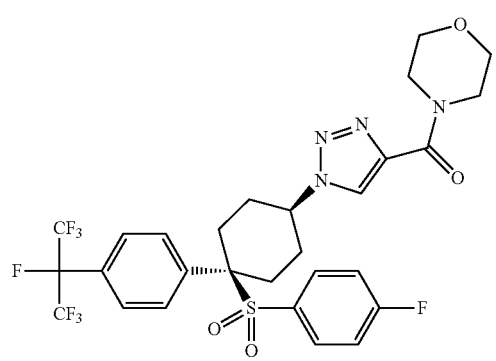 [SMILES: O=C(c1cn([C@H]2CC[C@@](c3ccc(C(F)(C(F)(F)F)C(F)(F)F)cc3)(S(=O)(=O)c3ccc(F)cc3)CC2)nn1)N1CCOCC1]

Hunig's base (10.08 μL, 0.058 mmol) was added to an acetonitrile (0.5 mL) solution of 1-((1s,4s)-4-((4-fluorophenyl)sulfonyl)-4-(4-(perfluoropropan-2-yl)phenyl)cyclohexyl)-1H-1,2,3-triazole-4-carboxylic acid (6.9 mg, 0.012 mmol from Example 118), morpholine (5 mg, 0.057 mmol) and BOP (8 mg, 0.018 mmol). The mixture was stirred at room temperature for 1 h. The solution was diluted with MeOH (1.5 mL) and purified via preparative LC/MS with the following conditions: Column: Waters XBridge C18, 19×200 mm, 5-μm particles; Guard Column: Waters XBridge C18, 19×10 mm, 5-μm particles; Mobile Phase A: 5:95 acetonitrile:water with 10-mM ammonium acetate;

Mobile Phase B: 95:5 acetonitrile:water with 10-mM ammonium acetate; Gradient: 25-90% B over 15 minutes, then a 5-minute hold at 100% B; Flow: 20 mL/min. Fractions containing the desired product were combined and dried via centrifugal evaporation to give (1-((1s,4s)-4-(4-fluorophenylsulfonyl)-4-(4-(perfluoropropan-2-yl)phenyl)cyclohexyl)-1H-1,2,3-triazol-4-yl)(morpholino)methanone (5.4 mg, 69%). LC/MS (M+1): 667.0; LC retention time: 2.114 min (analytical HPLC Method B); 1H NMR (500 MHz, 1:1 mixture of CDCl₃-CD₃OD) δ ppm 8.36 (s, 1H), 7.59-7.57 (m, 2H), 7.48 (d, J=8.7 Hz, 2H), 7.22 (dd, J=8.8, 5.1 Hz, 2H), 7.01 (t, J=8.5 Hz, 2H), 4.64-4.61 (m, 1H), 4.28 (br. s., 3H), 3.79 (br. s., 5H), 2.78-2.60 (m, 4H), 2.51 (d, J=14.2 Hz, 2H), 2.05-1.94 (m, 2H).

Example 120

1-((1s,4s)-4-(4-fluorophenylsulfonyl)-4-(4-(perfluoropropan-2-yl)phenyl)cyclohexyl)-N-(pyridin-3-yl)-1H-1,2,3-triazole-4-carboxamide

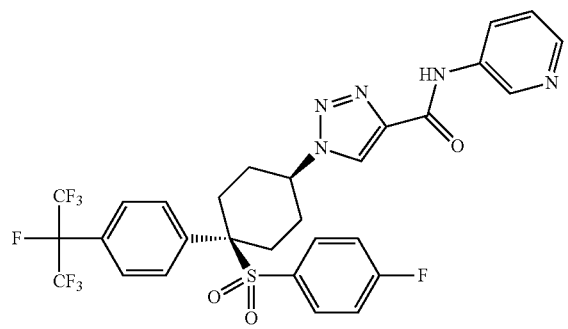 [SMILES: O=C(Nc1cccnc1)c1cn([C@H]2CC[C@@](c3ccc(C(F)(C(F)(F)F)C(F)(F)F)cc3)(S(=O)(=O)c3ccc(F)cc3)CC2)nn1]

Similar to the synthesis of Example 119, the title compound was prepared from Example 118. LC/MS (M+1): 674.0; LC retention time: 2.140 min (analytical HPLC Method B); 1H NMR (500 MHz, 1:1 mixture of CDCl₃-CD₃OD) δ ppm 9.04 (br. s., 1H), 8.55 (s, 1H), 8.39-8.32 (m, 2H), 7.61-7.59 (m, 2H), 7.56-7.46 (m, 3H), 7.27-7.18 (m, 2H), 7.01 (t, J=8.5 Hz, 2H), 2.78-2.65 (m, 4H), 2.52 (d, J=14.3 Hz, 2H), 2.09-1.95 (m, 2H).

Example 121

1-(3-(1-((1s,4s)-4-(4-fluorophenylsulfonyl)-4-(4-(perfluoropropan-2-yl)phenyl)cyclohexyl)-1H-1,2,3-triazol-4-yl)azetidin-1-yl)ethanone Step A: 4-(azetidin-3-yl)-1-((1s,4s)-4-(4-fluorophenylsulfonyl)-4-(4-(perfluoropropan-2-yl)phenyl)cyclohexyl)-1H-1,2,3-triazole

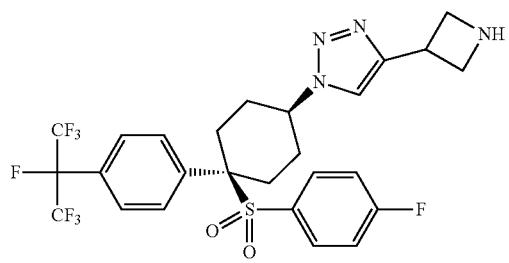 [SMILES: O=S(=O)(c1ccc(F)cc1)[C@]1(c2ccc(C(F)(C(F)(F)F)C(F)(F)F)cc2)CC[C@H](n2cc(C3CNC3)nn2)CC1]

4M HCl in dioxane (150 µL, 0.60 mmol) was added to a CH₂Cl₂ (150 µL) solution of tert-butyl 3-(1-((1s,4s)-4-((4-fluorophenyl)sulfonyl)-4-(4-(perfluoropropan-2-yl)phenyl)cyclohexyl)-1H-1,2,3-triazol-4-yl)azetidine-1-carboxylate (15.4 mg, 0.022 mmol from Example 117). The mixture was stirred at room temperature for 1 h. The solvent was evaporated to give crude 4-(azetidin-3-yl)-1-((1s,4s)-4-(4-fluorophenylsulfonyl)-4-(4-(perfluoropropan-2-yl)phenyl)cyclohexyl)-1H-1,2,3-triazole HCl salt (14.4 mg) as white solid. LC/MS (M+1): 609.1.

Step B: 1-(3-(1-((1s,4s)-4-(4-fluorophenylsulfonyl)-4-(4-(perfluoropropan-2-yl)phenyl)cyclohexyl)-1H-1,2,3-triazol-4-yl)azetidin-1-yl)ethanone

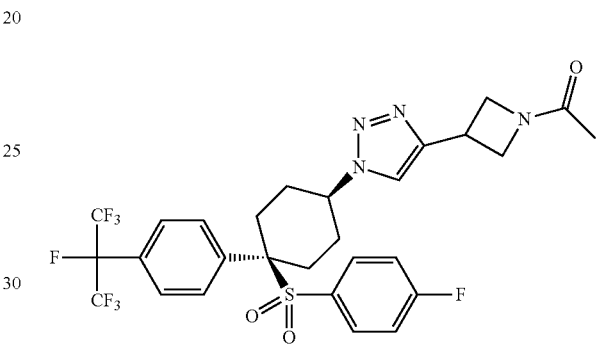

Acetic anhydride (1.2 µL, 0.013 mmol) was added to a CH₂Cl₂ (0.3 mL) solution of 4-(azetidin-3-yl)-1-((1s,4s)-4-((4-fluorophenyl)sulfonyl)-4-(4-(perfluoropropan-2-yl)phenyl)cyclohexyl)-1H-1,2,3-triazole HCl salt (7 mg, 10.85 µmol) and Hunig's base (9.48 µL, 0.054 mmol). The mixture was stirred at room temperature for 30 minute. The solvent was evaporated. The residue was dissolved in MeOH (2 mL) and the solution was purified via preparative LC/MS with the following conditions: Column: Waters XBridge C18, 19×200 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-85% B over 15 minutes, then a 5-minute hold at 100% B; Flow: 20 mL/min. Fractions containing the desired product were combined and dried via centrifugal evaporation to give 1-(3-(1-((1s,4s)-4-(4-fluorophenylsulfonyl)-4-(4-(perfluoropropan-2-yl)phenyl)cyclohexyl)-1H-1,2,3-triazol-4-yl)azetidin-1-yl)ethanone (3.7 mg, 51%). LC/MS (M+1): 651.1; LC retention time: 2.013 min (analytical HPLC Method B); 1H NMR (500 MHz, 1:1 mixture of CDCl₃-CD₃OD) δ ppm 7.91 (s, 1H), 7.58-7.56 (m, 2H), 7.47 (d, J=8.5 Hz, 2H), 7.25-7.19 (m, 2H), 7.00 (t, J=8.5 Hz, 2H), 4.62-4.53 (m, 2H), 4.44-4.35 (m, 2H), 4.12 (dd, J=9.7, 6.5 Hz, 1H), 4.06-3.97 (m, 1H), 2.77-2.57 (m, 4H), 2.48 (d, J=14.2 Hz, 2H), 1.98 (td, J=10.9, 4.0 Hz, 2H), 1.92 (s, 3H).

Example 122 rac-N-((2R,4R)-4-(4-fluorophenylsulfonyl)-2-methyl-4-(4-(perfluoropropan-2-yl)phenyl)cyclohexyl)nicotinamide Step A: rac-tert-butyl (2R,4R)-4-(4-fluorophenylsulfonyl)-2-methyl-4-(4-(perfluoropropan-2-yl)phenyl)cyclohexylcarbamate

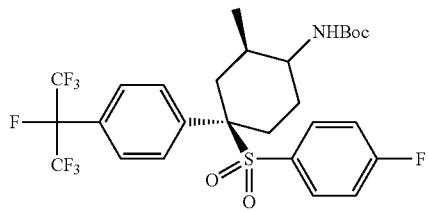 [SMILES: C[C@@H]1C[C@](c2ccc(C(F)(C(F)(F)F)C(F)(F)F)cc2)(S(=O)(=O)c2ccc(F)cc2)CCC1NC(=O)OC(C)(C)C]

To a ClCH$_2$CH$_2$Cl (2 mL) suspension of isomer 2 of tert-butyl ((2R,4R)-4-((4-fluorophenyl)sulfonyl)-4-(4-(1,1,1,3,3,3-hexafluoro-2-hydroxypropan-2-yl)phenyl)-2-methylcyclohexyl)carbamate (86 mg, 0.14 mmol) was added (diethylamino)sulfur trifluoride (0.056 mL, 0.42 mmol). The mixture was heated at 60° C. for 18 h in a safety sealed vial. The crude was slowly added to a cooled MeOH (2 mL) solution at 0° C. The resulting solution was concentrated. Silica gel chromatography, eluting with 0-100% ethyl acetate in hexanes, gave rac-tert-butyl (2R,4R)-4-(4-fluorophenylsulfonyl)-2-methyl-4-(4-(perfluoropropan-2-yl)phenyl)cyclohexylcarbamate (44.7 mg, 52%) as off-white solid. 1H NMR (400 MHz, CDCl$_3$) δ ppm 7.53 (d, J=8.4 Hz, 2H), 7.34 (d, J=8.4 Hz, 2H), 7.17-7.11 (m, 2H), 6.98-6.89 (m, 2H), 4.86 (d, J=8.8 Hz, 1H), 3.75 (d, J=6.1 Hz, 1H), 2.43-2.27 (m, 3H), 2.11 (t, J=13.7 Hz, 1H), 1.95 (dd, J=14.2, 2.8 Hz, 1H), 1.48 (s, 10H), 0.99 (d, J=6.8 Hz, 3H).

Step B: rac-(2R,4R)-4-(4-fluorophenylsulfonyl)-2-methyl-4-(4-(perfluoropropan-2-yl)phenyl)cyclohexanamine

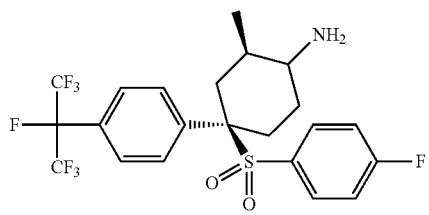 [SMILES: C[C@@H]1C[C@](c2ccc(C(F)(C(F)(F)F)C(F)(F)F)cc2)(S(=O)(=O)c2ccc(F)cc2)CCC1N]

4M HCl in dioxane (0.5 mL, 2.0 mmol) was added to a CH$_2$Cl$_2$ (0.5 mL) solution of rac-tert-butyl (2R,4R)-4-(4-fluorophenylsulfonyl)-2-methyl-4-(4-(perfluoropropan-2-yl)phenyl)cyclohexylcarbamate (44.7 mg). The mixture was stirred at room temperature for 2.5 h. The solvent was evaporated to give rac-(2R,4R)-4-(4-fluorophenylsulfonyl)-2-methyl-4-(4-(perfluoropropan-2-yl)phenyl)cyclohexanamine HCl salt (42 mg) as white solid. LC/MS (M+1): 516.3; 1H NMR (400 MHz, CDCl$_3$) δ ppm 7.56-7.54 (m, 2H), 7.37 (d, J=7.7 Hz, 2H), 7.21-7.13 (m, 2H), 7.05-6.95 (m, 2H), 3.25 (br. s., 1H), 2.63-2.53 (m, 1H), 2.49-2.24 (m, 3H), 2.07 (dd, J=15.3, 2.8 Hz, 1H), 1.85-1.72 (m, 1H), 1.71-1.58 (m, 1H), 1.10 (d, J=7.0 Hz, 3H).

Step C: rac-N-((2R,4R)-4-(4-fluorophenylsulfonyl)-2-methyl-4-(4-(perfluoropropan-2-yl)phenyl)cyclohexyl)nicotinamide

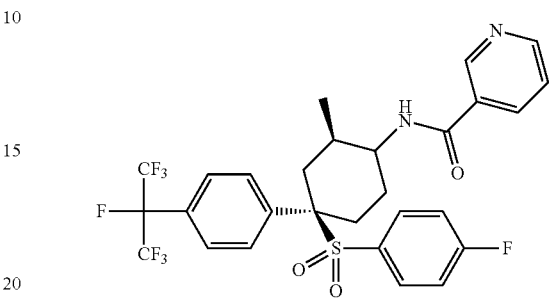

Similar to the synthesis of Example 119, the title compound was prepared by coupling rac-(2R,4R)-4-(4-fluorophenylsulfonyl)-2-methyl-4-(4-(perfluoropropan-2-yl)phenyl)cyclohexanamine HCl salt with nicotinic acid. LC/MS (M+1): 621.2; LC retention time: 2.13 min (analytical HPLC Method B); 1H NMR (400 MHz, 1:1 mixture of CDCl$_3$-CD$_3$OD) δ ppm 8.98 (d, J=1.8 Hz, 1H), 8.68 (dd, J=4.9, 1.6 Hz, 1H), 8.21 (dt, J=8.0, 1.9 Hz, 1H), 7.55-7.49 (m, 3H), 7.40 (d, J=8.0 Hz, 2H), 7.20-7.13 (m, 2H), 7.02-6.95 (m, 2H), 4.24 (d, J=3.0 Hz, 1H), 2.51-2.44 (m, 2H), 2.40 (d, J=9.0 Hz, 2H), 2.07-1.98 (m, 1H), 1.75 (br. s., 1H), 1.62-1.48 (m, 1H), 1.04 (d, J=6.8 Hz, 3H).

Example 123

N-((2R,4R)-4-(4-fluorophenylsulfonyl)-2-methyl-4-(4-(perfluoropropan-2-yl)phenyl)cyclohexyl)-2-(pyridin-4-yl)acetamide

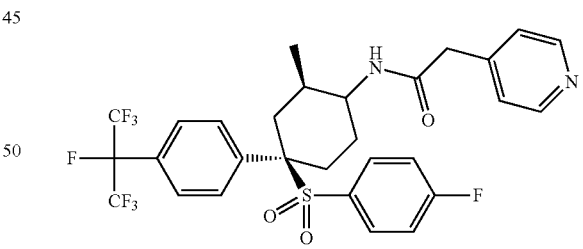

Similar to the synthesis of Example 119, the title compound was prepared by coupling rac-(2R,4R)-4-(4-fluorophenylsulfonyl)-2-methyl-4-(4-(perfluoropropan-2-yl)phenyl)cyclohexanamine HCl salt (from the Step B of Example 122) with 2-(pyridin-4-yl)acetic acid. LC/MS (M+1): 635.2; LC retention time: 2.08 min (analytical HPLC Method B); 1H NMR (400 MHz, 1:1 mixture of CDCl$_3$-CD$_3$OD) δ ppm 8.50-8.41 (m, 2H), 7.53 (d, J=8.3 Hz, 2H), 7.41-7.33 (m, 4H), 7.18-7.11 (m, 2H), 7.02-6.93 (m, 2H), 3.96 (d, J=2.8 Hz, 1H), 3.68 (s, 2H), 2.46-2.23 (m, 4H), 1.87 (dd, J=14.3, 2.5 Hz, 1H), 1.69-1.57 (m, 1H), 1.49-1.36 (m, 1H), 0.92 (d, J=6.8 Hz, 3H).

Example 124

4-(4-fluorophenylsulfonyl)-4-(4-(perfluoropropan-2-yl)phenyl)-N-(pyridin-3-yl)cyclohexanecarboxamide, Diastereomer 1

Step A: methyl 4-(4-fluorophenylsulfonyl)-4-(4-(1,1,1,3,3,3-hexafluoro-2-hydroxypropan-2-yl)phenyl)cyclohexanecarboxylate, Diastereomer 1

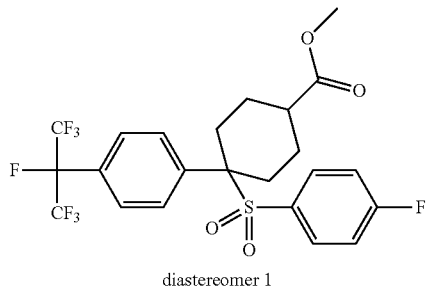 [SMILES: COC(=O)C1CCC(c2ccc(C(F)(C(F)(F)F)C(F)(F)F)cc2)(S(=O)(=O)c2ccc(F)cc2)CC1]

diastereomer 1

Thionyl chloride (0.079 mL, 1.079 mmol) was added dropwise to a stirred MeOH (2 mL) solution of isomer 1 of 4-((4-fluorophenyl)sulfonyl)-4-(4-(1,1,1,3,3,3-hexafluoro-2-hydroxypropan-2-yl)phenyl)cyclohexanecarboxylic acid (190 mg, 0.360 mmol, from Step C of Example 92). The mixture was heated at 65° C. for 1 h in a sealed safety vial. The solvent was evaporated to give methyl 4-(4-fluorophenylsulfonyl)-4-(4-(1,1,1,3,3,3-hexafluoro-2-hydroxypropan-2-yl)phenyl)cyclohexanecarboxylate and it was used in the next step without further purification (assuming 0.360 mmol). LC/MS (M+18): 560.3.

Step B: methyl 4-(4-fluorophenylsulfonyl)-4-(4-(perfluoropropan-2-yl)phenyl)cyclohexanecarboxylate, Diastereomer 1

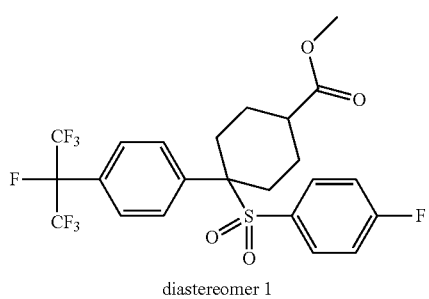 [SMILES: COC(=O)C1CCC(c2ccc(C(F)(C(F)(F)F)C(F)(F)F)cc2)(S(=O)(=O)c2ccc(F)cc2)CC1]

diastereomer 1

To the CH$_2$Cl$_2$ (2 mL) suspension of methyl 4-(4-fluorophenylsulfonyl)-4-(4-(1,1,1,3,3,3-hexafluoro-2-hydroxypropan-2-yl)phenyl)cyclohexanecarboxylate (assuming 0.360 mmol) was added (diethylamino)sulfur trifluoride (0.143 mL, 1.079 mmol). The mixture was heated at 60° C. for 3.5 h in a sealed safety vial. After cooled to ambient temperature, the crude was slowly added to a MeOH (2 mL) solution at 0° C. The resulting solution was concentrated. Silica gel chromatography, eluting with 0-100% ethyl acetate in hexanes, gave methyl 4-(4-fluorophenylsulfonyl)-4-(4-(perfluoropropan-2-yl)phenyl)cyclohexanecarboxylate, diastereomer 1 (164.5 mg, 84%) as white solid. LC/MS (M+18): 562.3; 1H NMR (400 MHz, CDCl$_3$) δ ppm 7.54 (d, J=8.4 Hz, 2H), 7.37 (d, J=8.6 Hz, 2H), 7.23-7.16 (m, 2H), 6.98-6.91 (m, 2H), 3.76 (s, 3H), 2.59-2.39 (m, 5H), 2.29 (dd, J=14.3, 2.6 Hz, 2H), 1.55-1.41 (m, 2H).

Step C: 4-(4-fluorophenylsulfonyl)-4-(4-(perfluoropropan-2-yl)phenyl)cyclohexanecarboxylic acid, Diastereomer 1

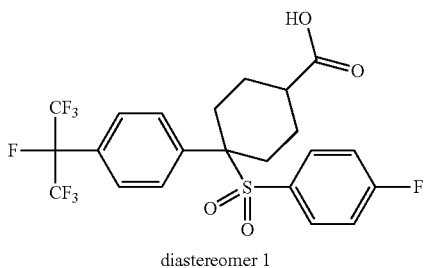 [SMILES: O=C(O)C1CCC(c2ccc(C(F)(C(F)(F)F)C(F)(F)F)cc2)(S(=O)(=O)c2ccc(F)cc2)CC1]

diastereomer 1

To a THF (1 mL) solution of methyl 4-(4-fluorophenylsulfonyl)-4-(4-(perfluoropropan-2-yl)phenyl)cyclohexanecarboxylate diastereomer 1 (164.5 mg, 0.302 mmol) was added 1M NaOH (0.5 mL, 0.500 mmol). The mixture was stirred at room temperature for 17 h. The organic solvent was evaporated. 1M HCl (0.5 mL) was added. The resulting suspension was filtered. The solid was washed with water (2 mL) and dried in vacuum to give 4-(4-fluorophenylsulfonyl)-4-(4-(perfluoropropan-2-yl)phenyl)cyclohexanecarboxylic acid diastereomer 1 (132 mg, 82%) as white solid. LC/MS (M+18): 548.2; 1H NMR (400 MHz, CDCl$_3$) δ ppm 7.55 (d, J=8.6 Hz, 2H), 7.39 (d, J=8.6 Hz, 2H), 7.25-7.19 (m, 2H), 6.96 (t, J=8.6 Hz, 2H), 2.67-2.42 (m, 6H), 2.32 (d, J=14.4 Hz, 1H), 1.59-1.47 (m, 2H).

Step D: 4-(4-fluorophenylsulfonyl)-4-(4-(perfluoropropan-2-yl)phenyl)-N-(pyridin-3-yl)cyclohexanecarboxamide, Diastereomer 1

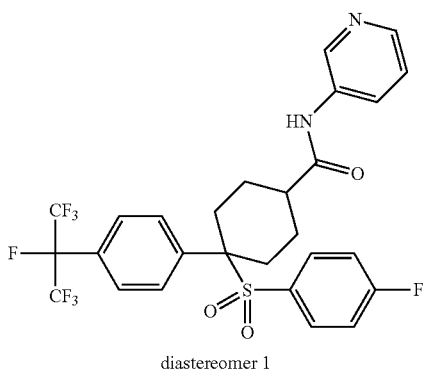 [SMILES: O=C(Nc1cccnc1)C1CCC(c2ccc(C(F)(C(F)(F)F)C(F)(F)F)cc2)(S(=O)(=O)c2ccc(F)cc2)CC1]

diastereomer 1

Similar to the synthesis of Example 119, the title compound was prepared by coupling 4-(4-fluorophenylsulfonyl)-4-(4-(perfluoropropan-2-yl)phenyl)cyclohexanecarboxylic acid with pyridin-3-amine. LC/MS (M+1): 607.1; LC retention time: 2.10 min (analytical HPLC Method B); 1H NMR (400 MHz, 1:1 mixture of CDCl$_3$-CD$_3$OD) δ ppm 8.63 (d, J=2.0 Hz, 1H), 8.22 (dd, J=4.8, 1.5 Hz, 1H), 8.18-8.12 (m, 1H), 7.58-7.53 (m, 2H), 7.44 (d, J=8.8 Hz, 2H), 7.33 (dd, J=8.7, 5.1 Hz, 1H), 7.28-7.21 (m, 2H), 7.00

(t, J=8.5 Hz, 2H), 2.88-2.76 (m, 2H), 2.57 (d, J=3.5 Hz, 1H), 2.43 (d, J=13.8 Hz, 2H), 2.28-2.18 (m, 2H), 1.69-1.56 (m, 2H).
The examples in TABLE 4 below were prepared in the same manner as outlined in the Example 124 above, substituting the appropriate amine.
TABLE 4
| Example number | Structure | MS observed (M + 1) | HPLC ret. time (min.) | HPLC method |
|---|---|---|---|---|
| 125 | 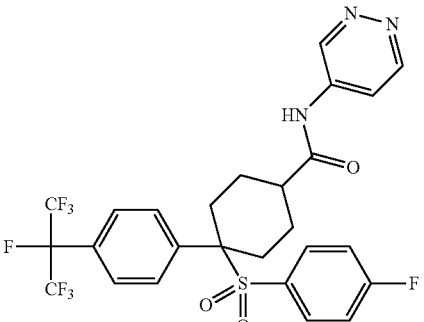 diastereomer 1 | 608.0 | 2.112 | B |
| 126 | 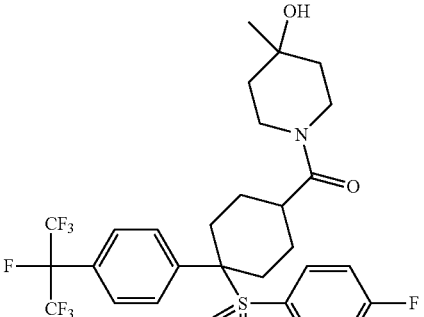 diastereomer 1 | 628.1 | 2.196 | B |
| 127 | 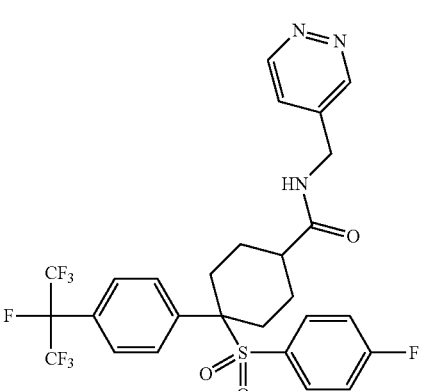 diastereomer 1 | 622.3 | 1.93 | B |

TABLE 4-continued
| Example number | Structure | MS observed (M + 1) | HPLC ret. time (min.) | HPLC method |
|---|---|---|---|---|
| 128 | 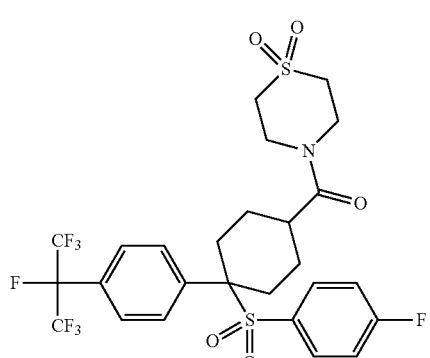 diastereomer 1 | 648.3 | 2.13 | B |
| 129 | 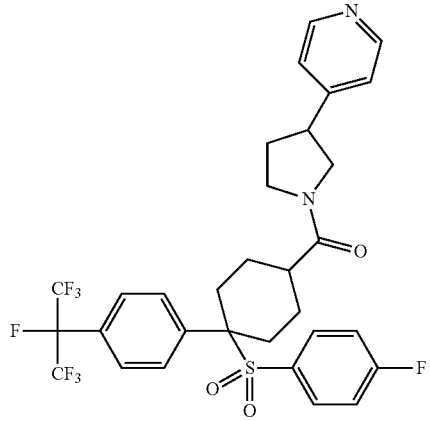 diastereomer 1 | 661.0 | 2.20 | B |
| 130 | 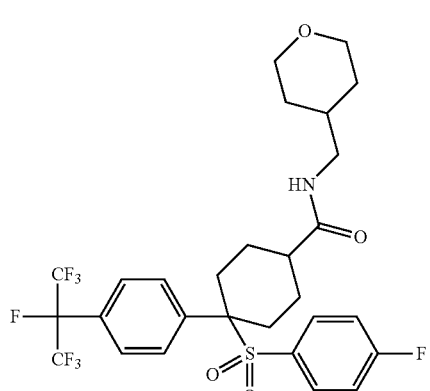 diastereomer 1 | 628.0 | 2.15 | B |

TABLE 4-continued
| Example number | Structure | MS observed (M + 1) | HPLC ret. time (min.) | HPLC method |
|---|---|---|---|---|
| 131 | 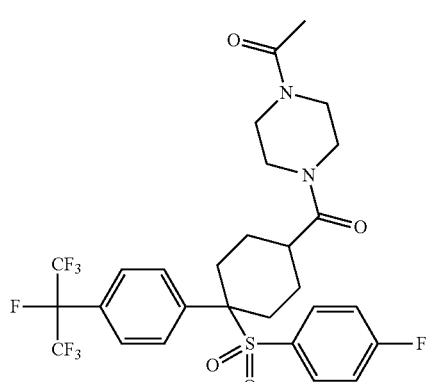 diastereomer 1 | 641.0 | 2.05 | B |
| 132 | 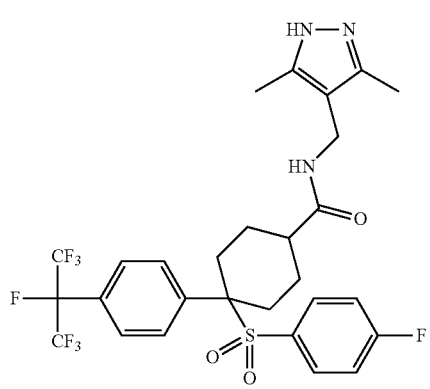 diastereomer 1 | 638.0 | 2.03 | B |
| 133 | 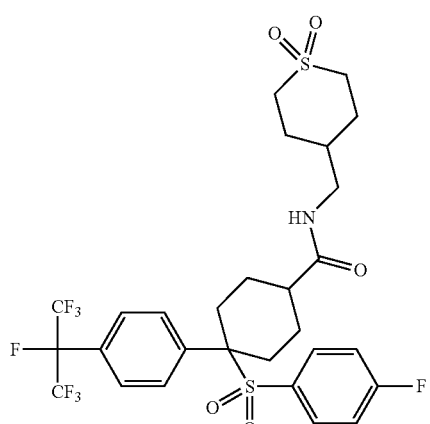 diastereomer 1 | 676.1 | 2.03 | B |

TABLE 4-continued

| Example number | Structure | MS observed (M + 1) | HPLC ret. time (min.) | HPLC method |
|---|---|---|---|---|
| 134 | 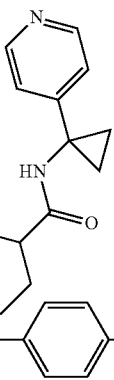 diastereomer 1 | 647.1 | 2.10 | B |
| 135 | 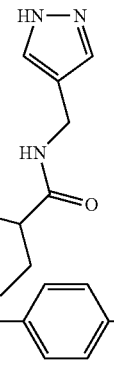 diastereomer 1 | 610.2 | 1.98 | B |
| 136 | 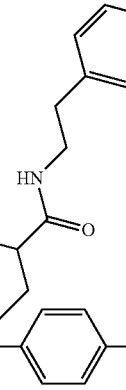 diastereomer 1 | 635.2 | 2.05 | B |

General RORγ SPA Binding Assay

The binding of potential ligands to RORγ is measured by competition with [$^3$H]25-hydroxycholesterol (Perkin Elmer NET674250UC) using a scintillation proximity assay (SPA) binding assay. The ligand binding domain of human RORγ (A262-S507) with an N-terminal His tag is expressed in *E. coli* and purified using nickel affinity chromatography. 15 ug/well RORγ (A262-S507) is incubated with test compound at varying concentrations in 3-fold serial dilution, with final concentrations ranging from 16.6 μM to 0.28 nM for 10 min at room temperature in PBS buffer (Invitrogen #14190-144) containing 0.5% fatty acid free BSA (Gemini Bio-Products, Cat. #700-107P) and 0.1% Glycerol (Sigma Cat# G5516). 10 nM of [$^3$H] 25-hydroxycholesterol is then added, and the reaction is incubated for 10 min. 10 mg/mL of Copper-His Tag-PVT beads (Perkin Elmer cat # RPNQ0095) are added, and the mixture is incubated for 60 min. The reaction is read on a TopCount Microplate scintillation plate reader (Perkin Elmer). The competition data of the test compound over a range of concentrations was plotted as percentage inhibition of radioligand specifically bound in the absence of test compound (percent of total signal). After correcting for non-specific binding, $IC_{50}$ values were determined. The $IC_{50}$ value is defined as the concentration of test compound needed to reduce [$^3$H] 25-hydroxycholesterol specific binding by 50% and is calculated using the four parameter logistic equation to fit the normalized data.

$IC_{50}$ values of some of the compounds of the invention in the RORγ binding assay are provided below.

| Example # | RORγ Binding $IC_{50}$, uM |
|---|---|
| 1 | 0.08 |
| 2 | 0.61 |
| 3 | 0.18 |
| 4 | 0.129 |
| 5 | 0.066 |
| 6 | 0.405 |
| 7 | 0.112 |
| 8 | 0.089 |
| 9 | 0.121 |
| 10 | 0.237 |
| 11 | 3.394 |
| 12 | 0.040 |
| 13 | 1.201 |
| 14 | 0.280 |
| 15 | 3.680 |
| 16 | 0.398 |
| 17 | 0.130 |
| 18 | 0.024 |
| 19 | 1.015 |
| 20 | 0.089 |
| 21 | 2.596 |
| 22 | 0.020 |
| 23 | 0.053 |
| 24 | 0.075 |
| 25 | 0.091 |
| 26 | 0.085 |
| 27 | 0.121 |
| 28 | 0.106 |
| 29 | 0.110 |
| 30 | 0.073 |
| 31 | 1.702 |
| 32 | 0.111 |
| 33 | 0.039 |
| 34 | 2.458 |
| 35 | 0.033 |
| 36 | 0.029 |
| 37 | 0.037 |
| 38 | 0.762 |
| 39 | 0.024 |
| 40 | 0.048 |
| 41 | 0.434 |
| 42 | 0.131 |
| 43 | 1.061 |
| 44 | 0.055 |
| 45 | 1.966 |
| 46 | 0.045 |
| 47 | 0.375 |
| 48 | 0.034 |
| 49 | 0.113 |
| 50 | 0.080 |
| 51 | 0.102 |
| 52 | 0.120 |
| 53 | 0.062 |
| 54 | 0.081 |
| 55 | 0.177 |
| 56 | 0.176 |
| 57 | 0.119 |
| 58 | 0.079 |
| 59 | 0.046 |
| 60 | 0.028 |
| 61 | 0.297 |
| 62 | 0.291 |
| 63 | 0.058 |
| 64 | 1.493 |
| 65 | 1.814 |
| 66 | 1.318 |
| 67 | 0.093 |
| 68 | 0.134 |
| 69 | 0.233 |
| 70 | 1.230 |
| 72 | 1.526 |
| 73 | 0.140 |
| 74 | 1.538 |
| 75 | 1.678 |
| 76 | 2.052 |
| 77 | 0.429 |
| 78 | 0.811 |
| 79 | 2.420 |
| 80 | 0.163 |
| 81 | 0.243 |
| 82 | 3.919 |
| 83 | 0.094 |
| 84 | 0.172 |
| 85 | 1.364 |
| 86 | 0.158 |
| 87 | 3.854 |
| 88 | 0.241 |
| 89 | 1.782 |
| 90 | 2.877 |
| 91 | 0.192 |
| 92 | 0.124 |
| 93 | 0.989 |
| 94 | 0.397 |
| 95 | 0.193 |
| 96 | 0.549 |
| 97 | 0.065 |
| 98 | 0.051 |
| 99 | 0.158 |
| 100 | 1.908 |
| 101 | 1.731 |
| 102 | 1.443 |
| 103 | 0.057 |
| 104 | 0.103 |
| 105 | 0.305 |
| 106 | 0.039 |
| 107 | 0.078 |
| 108 | 0.062 |
| 109 | 0.171 |
| 110 | 0.100 |
| 111 | 0.813 |
| 112 | 0.064 |
| 113 | 0.075 |
| 114 | 0.079 |
| 115 | 0.082 |
| 116 | 0.299 |
| 117 | 1.445 |
| 118 | 0.289 |
| 119 | 0.141 |
| 120 | 0.917 |
| 121 | 0.224 |
| 122 | 1.028 |
| 123 | 0.145 |
| 124 | 0.070 |
| 125 | 0.099 |
| 126 | 0.128 |
| 127 | 0.076 |
| 128 | 0.286 |
| 129 | 0.083 |
| 130 | 0.064 |
| 131 | 0.309 |
| 132 | 0.099 |
| 133 | 0.047 |
| 134 | 0.050 |
| 135 | 0.128 |
| 136 | 0.113 |

What is claimed is:

1. The compound having the following formula (I):

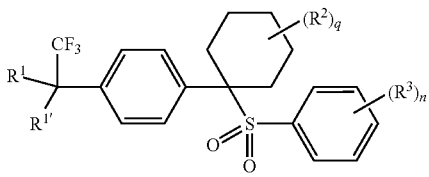

or a stereoisomer or pharmaceutically-acceptable salt thereof, wherein $R^1$ and $R^{1'}$ are, independently at each occurrence, hydrogen, halo, $CF_3$, $OCF_3$, CN, $NO_2$, —$(CH_2)_rOR^b$, —$(CH_2)_rS(O)_pR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^b S(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle substituted with 0-3 $R^a$, or —$(CH_2)_r$-5-7 membered heterocycle comprising carbon atoms and 1-4 heteroatoms selected from N, O, and $S(O)_p$ substituted with 0-3 $R^a$;

$R^2$ is independently at each occurrence, hydrogen, =O, —$(CH_2)_rOR^{2b}$, —$(CH_2)_rC(O)R^{2b}$, —$(CH_2)_rOC(O)OR^{2b}$, —$(CH_2)_rOC(O)NR^{11}R^{11}$, —$(CH_2)_rNR^{2b}C(O)R^{2c}$, —$(CH_2)_rNR^{2b}C(O)OR^{2c}$, —$(CH_2)_rNR^{2b}C(O)NR^{11}R^{11}$, —$(CH_2)_rNR^{11}R^{11}$—$NR^2S(O)_pR^c$, —$(CH_2)_rNR^{2b}S(O)_pNR^{11}R^{11}$, $C_{1-6}$ alkyl, —$(CH_2)_r$-3-10 membered carbocycle substituted with 0-3 R2a or —$(CH_2)_r$-4-10 membered heterocycle comprising carbon atoms, and 1-4 heteroatoms selected from N, O, and $S(O)_p$ substituted with 0-3 $R^{2a}$; or one $R^2$ together with an $R^2$ on an adjacent carbon combine to form a fused ring substituted with 0-3 $R^{2a}$, wherein the fused ring is selected from 3-10 membered carbocycle substituted with 0-3 $R^{2a}$, or 4-7 membered heterocycle comprising carbon atoms and 1-4 heteroatoms selected from N, O, and $S(O)_p$ substituted with 0-3 $R^{2a}$;

$R^{2a}$ is, independently at each occurrence, hydrogen, =O, halo, $OCF_3$, CN, $NO_2$, —$(CH_2)_rOR^b$, —$(CH_2)_rS(O)_pR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle substituted with 0-3 $R^a$, or —$(CH_2)_r$-5-7 membered heterocycle comprising carbon atoms and 1-4 heteroatoms selected from N, O, and $S(O)_p$ substituted with 0-3 $R^a$;

$R^{2b}$ is, independently at each occurrence, hydrogen, $CF_3$, —$(CH_2)rOR^b$, —$(CH_2)_rS(O)_pR^b$, —$(CH_2)_rC(O)R^{1d}$, —$(CH_2)_rC(O)OR^b$, —$(CH_2)rOC(O)R^b$, —$(CH_2)rNR^{11}R^{11}$, —$(CH_2)_rC(O)NR^{11}R^{11}$, —$(CH_2)rNR^bC(O)R^{1c}$, —$(CH_2)rNR^bC(O)OR^c$, —$(CH_2)rNR^bC(O)NR^{11}R^{11}$, —$(CH_2)rS(O)_2NR^{11}R^{11}$, —$(CH_2)rNR^bS(O)_2R^c$, $C_{1-6}$ alkyl substituted with 0-2 $R^a$, $C_{1-6}$ haloalkyl, —$(CH_2)_r$-3-14 membered carbocycle substituted with 0-3 $R^a$, or —$(CH_2)_r$-5-7 membered heterocycle comprising carbon atoms and 1-4 heteroatoms selected from N, O, and $S(O)_p$ substituted with 0-2 $R^a$;

$R^{2c}$ is, independently at each occurrence, hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or —$(CH_2)_r$-5-10 membered heterocycle comprising carbon atoms and 1-4 heteroatoms selected from N, O, and $S(O)_p$, substituted with 0-3 $R^a$;

$R^{2d}$ is, independently at each occurrence, hydrogen, $C_{1-6}$ alkyl substituted with 0-2 $R^d$, $C_{1-6}$ haloalkyl, $C(O)NR^{11}R^{11}$, $C_{3-6}$ cycloalkyl substituted with 0-2 $R^d$, or —$(CH_2)_r$-phenyl substituted with 0-2 $R^a$, a 5-10 membered heterocycle comprising carbon atoms and 1-4 heteroatoms selected from N, O, and S, substituted with 0-3 $R^a$;

$R^3$ is selected from hydrogen, halo, $N_3$, CN, —$(CH_2)_r$ $OR^{3b}$, —$(CH_2)_rNR^{11}R^{11}$, $C_{1-6}$ alkyl substituted with 0-3 $R^{3a}$, and $C_{3-10}$ cycloalkyl substituted with 0-3 $R^{3a}$; 4-10 membered heterocycle comprising carbon atoms and 1-4 heteroatoms selected from N, O, and $S(O)_p$, substituted with 0-3 $R^a$, or together with the carbon atoms to which they are attached, one $R^3$ combines with a second $R^3$ located on an adjacent atom to form a 5-7 membered carbocycle or a 5-7 membered heterocycle comprising carbon atoms and 1-4 heteroatom selected from N, O and S(O)p, each optionally substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CH_2)_r$ $OR^b$, —$(CH_2)_rS(O)_pR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CH_2)_r$-3-14 membered carbocycle substituted with 0-3 $R^a$, or a —$(CH_2)_r$-5-10 membered heterocycle comprising carbon atoms and 1-4 heteroatoms selected from N, O, and $S(O)_p$ substituted with 0-3 $R^a$;

$R^{3b}$ is, independently at each occurrence, hydrogen, $CF_3$, —$(CH_2)rOR^b$, —$(CH_2)_rS(O)_pR^b$, —$(CH_2)_rC(O)R^{1d}$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^{1c}$, —$(CH_2)_rNR^bC(O)OR^c$, —$(CH_2)_rNR^bC(O)NR^{11}R^{11}$, —$(CH_2)_rS(O)_2NR^{11}R^{11}$, —$(CH_2)rNR^bS(O)_2R^c$, $C_{1-6}$ alkyl substituted with 0-3 $R^a$, $C_{1-6}$ haloalkyl, —$(CH_2)_r$-3-14 membered carbocycle substituted with 0-3 $R^a$, or —$(CH_2)_r$-5-7 membered heterocycle comprising carbon atoms and 1-4 heteroatoms selected from N, O, and $S(O)_p$ substituted with 0-3 $R^a$;

$R^{11}$ is, independently at each occurrence, hydrogen, $C_{1-6}$ alkyl substituted with 0-3 $R^f$, $CF_3$, $C_{3-10}$ cycloalkyl substituted with 0-3 $R^f$, —$(CH)_r$-phenyl substituted with 0-3 $R^d$, or —$(CH_2)_r$-5-7 membered heterocycle comprising carbon atoms and 1-4 heteroatoms selected from N, O, and $S(O)_p$ substituted with 0-3 $R^d$;

or one $R^{11}$ and a second $R^{11}$, both attached to the same nitrogen atom, combine to form a heterocycle comprising carbon atoms and 1-4 heteroatoms selected from N, O, and $S(O)_p$ substituted with 0-3 $R^d$;

$R^a$ is, independently at each occurrence, hydrogen, =O, halo, $OCF_3$, $CF_3$, $CHF_2$, CN, $NO_2$, —$(CH_2)_rOR^b$, —$(CH_2)_rS(O)_pR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC$ (O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle, or —(CH$_2$)$_r$-5-7 membered heterocycle comprising carbon atoms and 1-4 heteroatoms selected from N, O, and S(O)$_p$ substituted with 0-3 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, —(CH$_2$)$_r$-5-7 membered heterocycle comprising carbon atoms and 1-4 heteroatoms selected from N, O, and S(O)$_p$ substituted with 0-3 R$^f$, or —(CH$_2$)$_r$-6-10 carbocycle substituted with 0-3 R$^d$;

R$^c$ is, independently at each occurrence, C$_{1-6}$ alkyl substituted with 0-3 R$^f$, —(CH$_2$)$_r$-C$_{3-6}$ cycloalkyl substituted with 0-3 R$^f$, or —(CH$_2$)$_r$-phenyl substituted with 0-3 R$^f$;

R$^d$ is, independently at each occurrence, hydrogen, =O, halo, OCF$_3$, CF$_3$, CN, NO$_2$, —OR$^e$, —(CH$_2$)$_r$C(O)R$^e$, —NR$^e$R$^e$, —NR$^e$C(O)OR$^e$, C(O)NR$^e$R$^e$, —NR$^e$C(O)R$^e$, CO$_2$R$^e$, —NR$^e$SO$_2$R$^e$, SO$_2$R$^e$, C$_{1-6}$ alkyl substituted with 0-3 R$^f$, C$_{3-6}$ cycloalkyl substituted with 0-3 R$^f$, —(CH$_2$)$_r$-phenyl substituted with 0-3 R$^f$ or —(CH$_2$)$_r$-5-7 membered heterocycle comprising carbon atoms and 1-4 heteroatoms selected from N, O, and S(O)$_p$ substituted with 0-3 R$^f$;

R$^e$ is, independently at each occurrence, selected from hydrogen, C(O)NR$^f$R$^f$, C$_{1-6}$ alkyl, C$_{3-6}$ cycloalkyl, or —(CH$_2$)$_r$-phenyl substituted with 0-3 R$^f$;

R$^f$ is, independently at each occurrence, =O, halo, CN, NH$_2$, NH(C$_{1-6}$ alkyl), N(C$_{1-6}$ alkyl)$_2$, SO$_2$(C$_{1-6}$ alkyl), CO$_2$H, CO$_2$(C$_{1-6}$ alkyl), OH, C$_{3-6}$ cycloalkyl, CF$_3$ or O(C$_{1-6}$ alkyl);

or R$^f$ is, independently at each occurrence, an optionally substituted —(CH$_2$)$_r$-5-10 membered heterocycle comprising carbon atoms and 1-4 heteroatoms selected from N, O, and S(O), phenyl or C$_{3-6}$ cycloalkyl, each group optionally substituted with halo, CN, CF$_3$, C$_{1-6}$ alkyl or O(C$_{1-6}$ alkyl);

q and n are independently selected from 0, 1, 2 and 3;
p is 0, 1, or 2; and
r is 0, 1, 2, 3, or 4.

2. A compound according to claim 1, or a stereoisomer or pharmaceutically-acceptable salt thereof, wherein R$^{1'}$ is CF$_3$.

3. A compound according to claim 1, or a stereoisomer or pharmaceutically-acceptable salt thereof, wherein
R$^1$ is halo, phenyl substituted with 0-3 R$^a$, or C$_{1-6}$ alkyl substituted with 0-3 R$^a$; and
R$^{1a}$ is, independently at each occurrence, hydrogen, CF$_3$, halo, C$_{1-6}$ alkyl substituted with 0-3 R$^a$, —(CH$_2$)$_r$OR$^b$, and —(CH$_2$)$_r$-phenyl substituted with 0-3 R$^f$.

4. A compound according to claim 1, or a stereoisomer or pharmaceutically-acceptable salt thereof, wherein:
R$^2$ is, independently at each occurrence, selected from hydrogen, =O, —(CH$_2$)$_r$OR$^{2b}$, —(CH$_2$)$_r$C(O)R$^{2b}$, —(CH$_2$)$_r$OC(O)OR$^{2b}$, —(CH$_2$)$_r$OC(O)NR$^{11}$R$^{11}$, —(CH$_2$)$_r$NR$^{2b}$C(O)R$^{2c}$, —(CH$_2$)$_r$NR$^{2b}$C(O)OR$^{2c}$, —(CH$_2$)$_r$NR$^{11}$R$^{11}$, —(CH$_2$)$_r$NR$^{2b}$C(O)NR$^{11}$R$^{11}$, —NR$^{2b}$S(O)$_p$R$^c$, C$_{1-6}$ alkyl, —(CH$_2$)$_r$-4-10 membered heterocycle comprising carbon atoms, and 1-4 heteroatoms selected from N, O, and S(O)$_p$ substituted with 0-3 R$^{2a}$; or one R$^2$ together with an R$^2$ on an adjacent carbon combine to form a fused ring substituted with 0-3 R$^{2a}$, wherein the fused ring is selected from a 4-7 membered heterocycle comprising carbon atoms and 1-4 heteroatoms selected from N, O, and S(O)$_p$ substituted with 0-3 R$^{2a}$;

R$^{2a}$ is hydrogen, NR$^{11}$R$^{11}$, or C$_{1-6}$ alkyl substituted with 0-3 R$^a$;

R$^{2b}$ is hydrogen, (CH$_2$)$_r$NR$^{11}$R$^{11}$, C$_{1-6}$ alkyl substituted with 0-3 R$^a$, C$_{3-6}$ cycloalkyl substituted with 0-3 R$^a$, or 5-7 membered heterocycle comprising carbon atoms and 1-4 heteroatoms selected from N, O, and S(O)$_p$ substituted with 0-3 R$^a$, or —(CH$_2$)$_r$-phenyl substituted with 0-3 R$^a$;

R$^{2c}$ is independently at each occurrence hydrogen, C$_{1-6}$ alkyl substituted with 0-3 R$^a$, C$_{2-6}$ alkenyl substituted with 0-3 R$^a$, C$_{3-6}$ cycloalkyl substituted with 0-3 R$^a$, C$_{6-10}$ aryl substituted with 0-3 R$^a$, or a 5-10 membered heterocycle comprising carbon atoms and 1-4 heteroatoms selected from N, O, and S, substituted with 0-3 R$^a$; and R$^{2d}$ is independently at each occurrence, hydrogen, C$_{1-6}$ alkyl substituted with 0-3 R$^d$, C$_{1-6}$ haloalkyl, C(O)NR$^{11}$R$^{11}$, C$_{3-6}$ cycloalkyl substituted with 0-2 R$^d$, —(CH$_2$)$_r$-phenyl substituted with 0-2 R$^a$, or a 5-10 membered heterocycle containing 1-4 heteroatoms selected from N, O, and S(O)$_p$, substituted with 0-3 R$^a$.

5. A compound according to claim 1, or a stereoisomer or pharmaceutically-acceptable salt thereof, wherein
R$^3$ is hydrogen, halo, N$_3$, CN, OR$^{3b}$, —NH$_2$, NH(C$_{1-6}$ alkyl), N(C$_{1-6}$ alkyl)$_2$, C$_{1-6}$ alkyl substituted with 0-3 R$^{3a}$ or C3-10 cycloalkyl substituted with 0-3 R$^{3a}$;

R$^{3a}$ is, independently at each occurrence, hydrogen, =O, halo, OCF$_3$, OCHF$_2$, CF$_3$, CHF$_2$, CN, NO$_2$, —(CH$_2$)$_r$OR$^b$, —(CH$_2$)rS(O)pRb, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CH$_2$)$_r$-3-14 membered carbocycle substituted with 0-3 R$^a$, a —(CH$_2$)$_r$-5-7 membered heteroaryl comprising carbon atoms and 1-4 heteroatoms selected from N, S or O substituted with 0-3 R$^a$, or a —(CH$_2$)$_r$-5-10 membered heterocycle comprising carbon atoms and 1-4 heteroatoms selected from N, O, and S(O)$_p$ substituted with 0-3 R$^a$; and R$^{3b}$ is, independently at each occurrence, hydrogen, C$_{1-6}$ alkyl substituted with 0-3 R$^a$ or phenyl substituted with 0-3 R$^a$.

6. A compound according to claim 1 having the following formula

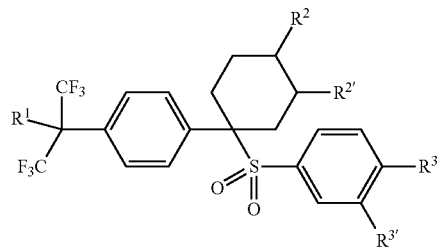

or a stereoisomer or pharmaceutically-acceptable salt thereof, wherein:
R$^1$ is hydrogen, CF$_3$, halo, C$_{1-6}$ alkyl substituted with 0-3 R$^a$, —(CH$_2$)$_r$OR$^b$, and —(CH$_2$)$_r$-phenyl substituted with 0-3 R$^a$;

R$^2$ and R$^{2'}$ are, independently at each occurrence, selected from hydrogen, =O, —(CH$_2$)$_r$OR$^{2b}$, —(CH$_2$)$_r$C(O)R$^{2b}$, —(CH$_2$)$_r$OC(O)OR$^{2b}$, —(CH$_2$)$_r$OC(O)NR$^{11}$R$^{11}$, —(CH$_2$)$_r$NR$^{2b}$C(O)R$^{2c}$, —(CH$_2$)$_r$NR$^{2b}$C(O)OR$^{2c}$, —(CH$_2$)$_r$NR$^{11}$R$^{11}$, —NR$^{2b}$S(O)$_p$R$^c$, —(CH$_2$)$_r$-5-7 membered heterocycle comprising carbon atoms, and 1-4 heteroatoms selected from N, O, and S(O)$_p$ substituted with 0-3 R$^2$a; or one R$^2$ together with an R$^2$ on an adjacent carbon combine to form a fused ring substituted with 0-3 R$^{2a}$, wherein the fused ring is selected from a 4-7 membered heterocycle comprising carbon atoms and 1-4 heteroatoms selected from N, O, and S(O)$_p$ substituted with 0-3 R$^{2a}$;

R$^{2a}$ is hydrogen, NR$^{11}$R$^{11}$, or C$_{1-6}$ alkyl substituted with 0-3 R$^a$;

R$^{2b}$ is hydrogen, C$_{1-6}$ alkyl substituted with 0-3 R$^a$, C$_{3-6}$ cycloalkyl substituted with 0-3 R$^a$, or 5-7 membered heterocycle comprising carbon atoms and 1-4 heteroatoms selected from N, O, and S(O)$_p$ substituted with 0-3 R$^a$, or —(CH$_2$)$_r$-phenyl substituted with 0-3 R$^a$;

R$^{2c}$ is independently at each occurrence hydrogen, C$_{1-6}$ alkyl substituted with 0-3 R$^a$, C$_{2-6}$ alkenyl substituted with 0-3 R$^a$, C$_{3-6}$ cycloalkyl substituted with 0-3 R$^a$, C$_{6-10}$ aryl substituted with 0-3 R$^a$, or a 5-10 membered heterocycle comprising carbon atoms and 1-4 heteroatoms selected from N, O, and S, substituted with 0-3 R$^a$;

R$^{2d}$ is, independently at each occurrence, hydrogen, C$_{1-6}$ alkyl substituted with 0-3 R$^d$ (Me) C$_{1-6}$ haloalkyl, C(O)NR$^{11}$R$^{11}$, C$_{3-6}$ cycloalkyl substituted with 0-2 R$^d$, or —(CH$_2$)$_r$-phenyl substituted with 0-2 R$^a$, a 5-10 membered heterocycle comprising carbon atoms and 1-4 heteroatoms selected from N, O, and S, substituted with 0-3 R$^a$;

R$^3$ and R$^{3'}$ are, independently, hydrogen, halo, N$_3$, CN, OR$^{3b}$, —NH$_2$, NH(C$_{1-6}$ alkyl), N(C$_{1-6}$ alkyl)$_2$, C$_{1-6}$ alkyl substituted with 0-3 R$^{3a}$ or C$_{3-10}$ cycloalkyl substituted with 0-3 R$^{3a}$;

R$^{3a}$ is, independently at each occurrence, hydrogen, =O, halo, OCF$_3$, OCHF$_2$, CF$_3$, CHF$_2$, CN, NO$_2$, —(CH$_2$)$_r$ OR$^b$, —(CH$_2$)rS(O)pRb, —(CH$_2$)$_r$C(O)R$^b$, —(CH$_2$)$_r$C (O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$ NR$^{11}$R$^{11}$, —NR$^b$S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CH$_2$)$_r$-3-14 membered carbocycle substituted with 0-3 R$^a$, or a —(CH$_2$)r-5-10 membered heterocycle comprising carbon atoms and 1-4 heteroatoms selected from N, O, and S(O)$_p$ substituted with 0-3 R$^a$;

R$^{3b}$ is, independently at each occurrence, hydrogen, C$_{1-6}$ alkyl substituted with 0-3 R$^a$ or phenyl substituted with 0-3 R$^a$;

R$^{11}$ is, independently at each occurrence, hydrogen, C$_{1-6}$ alkyl substituted with 0-3 R$^f$, CF$_3$, C$_{3-10}$ cycloalkyl substituted with 0-3 R$^f$, —(CH$_2$)$_r$-phenyl substituted with 0-3 R$^d$, or —(CH$_2$)$_r$-5-7 membered heterocycle comprising carbon atoms and 1-4 heteroatoms selected from N, O, and S(O)$_p$ substituted with 0-3 R$^d$;

R$^a$ is, independently at each occurrence, hydrogen, =O, halo, OCF$_3$, CF$_3$, CHF$_2$, CN, NO$_2$, —(CH$_2$)$_r$OR$^b$, —(CH$_2$)rS(O)pRb, —(CH$_2$)$_r$C(O)R$^b$, —(CH$_2$)$_r$C(O) OR$^b$, —(CH$_2$)$_r$OC(O)R$^b$, —(CH$_2$)$_r$NR$^{11}$R$^{11}$, —(CH$_2$)$_r$ C(O)NR$^{11}$R$^{11}$, —(CH$_2$)$_r$NR$^b$C(O)R$^c$, —(CH$_2$)$_r$NR$^b$C (O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^f$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle, or —(CH$_2$)$_r$-5-7 membered heterocycle comprising carbon atoms and 1-4 heteroatoms selected from N, O, and S(O)$_p$ substituted with 0-3 R$^f$;

R$^b$ is, independently at each occurrence, hydrogen, C$_{1-6}$ alkyl substituted with 0-3 R$^d$, C$_{1-6}$ haloalkyl, C$_{3-6}$ cycloalkyl substituted with 0-3 R$^d$, or —(CH$_2$)$_r$-5-7 membered heterocycle comprising carbon atoms and 1-4 heteroatoms selected from N, O, and S(O)$_p$ substituted with 0-3 R$^f$, or (CH$_2$)$_r$-6-10 carbocycle substituted with 0-3 R$^d$;

R$^c$ is, independently at each occurrence, C$_{1-6}$ alkyl substituted with 0-3 R$^f$, —(CH$_2$)$_r$-C$_{3-6}$ cycloalkyl substituted with 0-3 R$^f$, —(CH$_2$)$_r$-phenyl substituted with 0-3 R$^f$, or R$^d$ is, independently at each occurrence, hydrogen, =O, halo, OCF$_3$, CF$_3$, CN, NO$_2$, —(CH$_2$)$_r$C(O)R$^c$, —NR$^e$R$^e$, —NR$^e$C(O)OR$^c$, C(O)NR$^e$R$^e$, —NR$^e$C(O) R$^c$, CO$_2$R$^c$, —NR$^e$SO$_2$R$^c$, SO$_2$R$^c$, C$_{1-6}$ alkyl substituted with 0-3 R$^f$, C$_{3-6}$ cycloalkyl substituted with 0-3 R$^f$, —(CH$_2$)$_r$-phenyl substituted with 0-3 R$^f$ or —(CH$_2$)$_r$-5-7 membered heterocycle comprising carbon atoms and 1-4 heteroatoms selected from N, O, and S(O)$_p$ substituted with 0-3 R$^f$;

R$^e$is, independently at each occurrence, selected from hydrogen, C(O)NR$^f$R$^f$, C$_{1-6}$ alkyl, C$_{3-6}$ cycloalkyl, and —(CH$_2$)$_r$-phenyl substituted with 0-3 R$^f$;

R$^f$ is, independently at each occurrence, hydrogen, =O, halo, CN, NH$_2$, NH(C$_{1-6}$ alkyl), N(C$_{1-6}$ alkyl)$_2$, SO$_2$ (C$_{1-6}$ alkyl), CO$_2$H, CO$_2$(C$_{1-6}$ alkyl), OH, C$_{3-6}$ cycloalkyl, CF$_3$ or O(C$_{1-6}$ alkyl);

or R$^f$ is, independently at each occurrence, an optionally substituted —(CH$_2$)$_r$-5-10 membered heteroaryl comprising carbon atoms and 1-4 heteroatoms selected from N, O, and S(O), phenyl or C$_{3-6}$ cycloalkyl, each group optionally substituted with halo, CN, CF$_3$, C$_{1-6}$ alkyl or O(C$_{1-6}$ alkyl);

p is 0, 1, or 2; and r is 0, 1, 2, 3, or 4.

7. A compound according to claim 6, or a stereoisomer or pharmaceutically-acceptable salt thereof, wherein R$^1$ is 8. A compound according to claim 6, or a stereoisomer or pharmaceutically-acceptable salt thereof, wherein R$^{2'}$ is hydrogen.

9. A compound according to claim 6, or a stereoisomer or pharmaceutically-acceptable salt thereof, wherein is selected from:

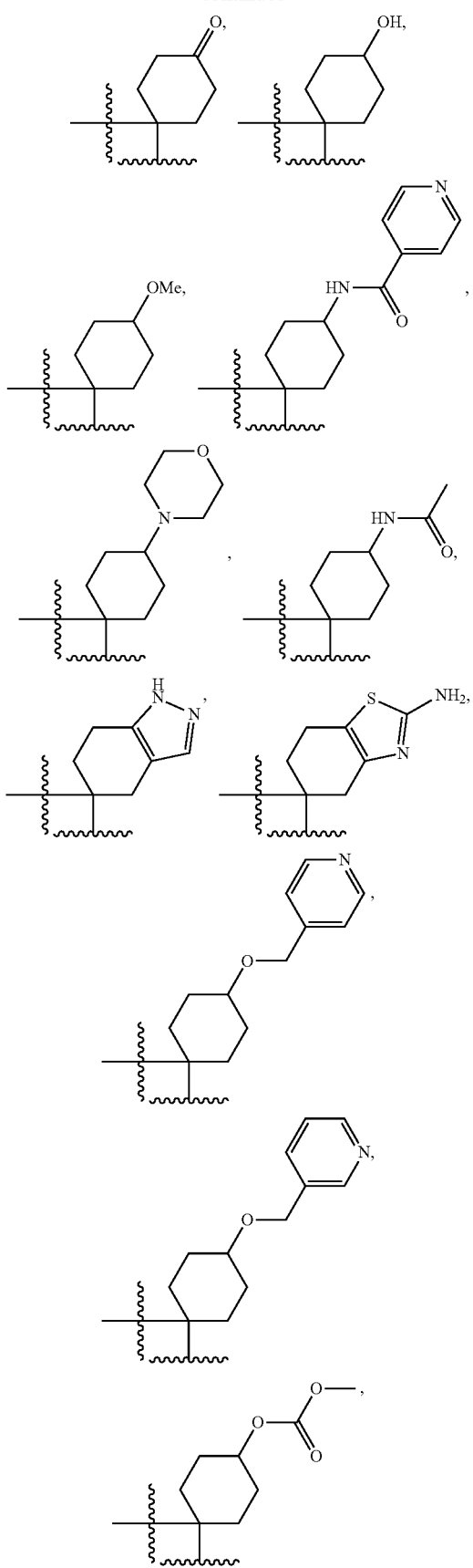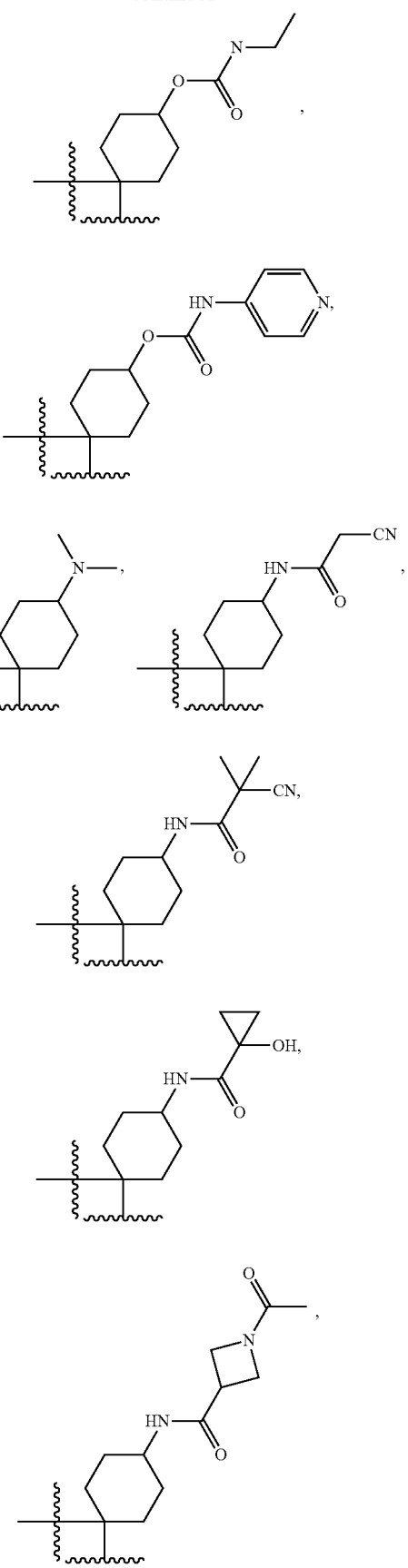

157
-continued
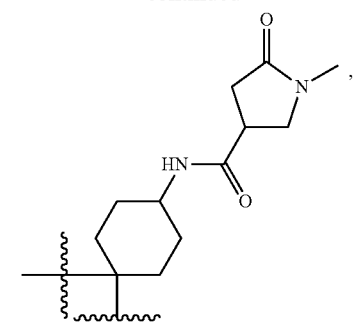
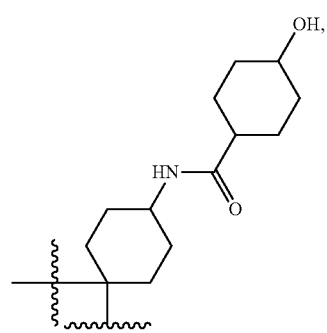
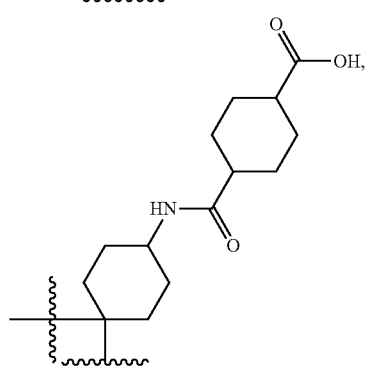
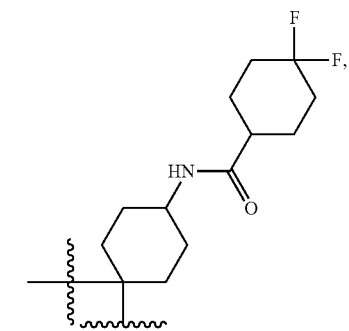
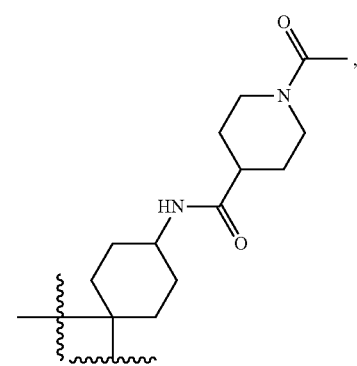
158
-continued
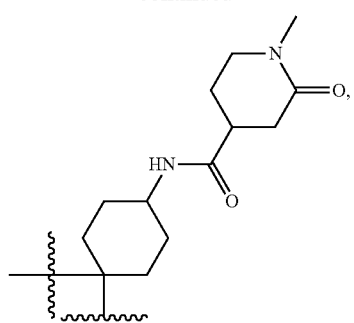
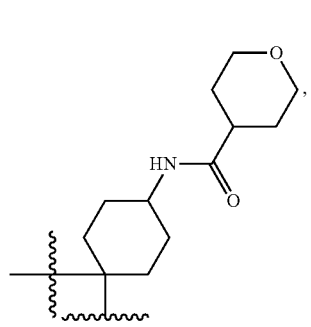
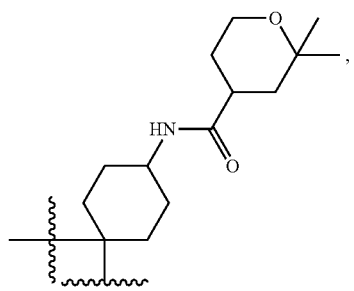
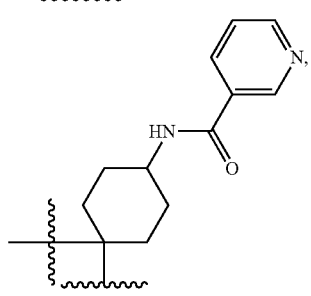
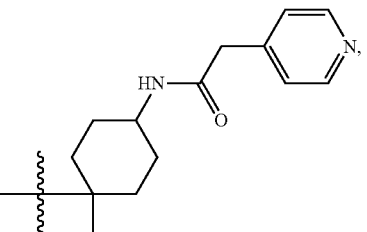
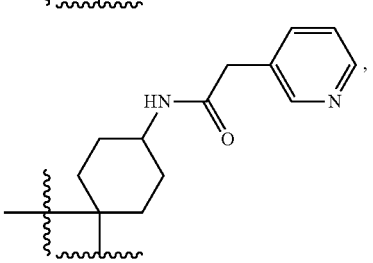

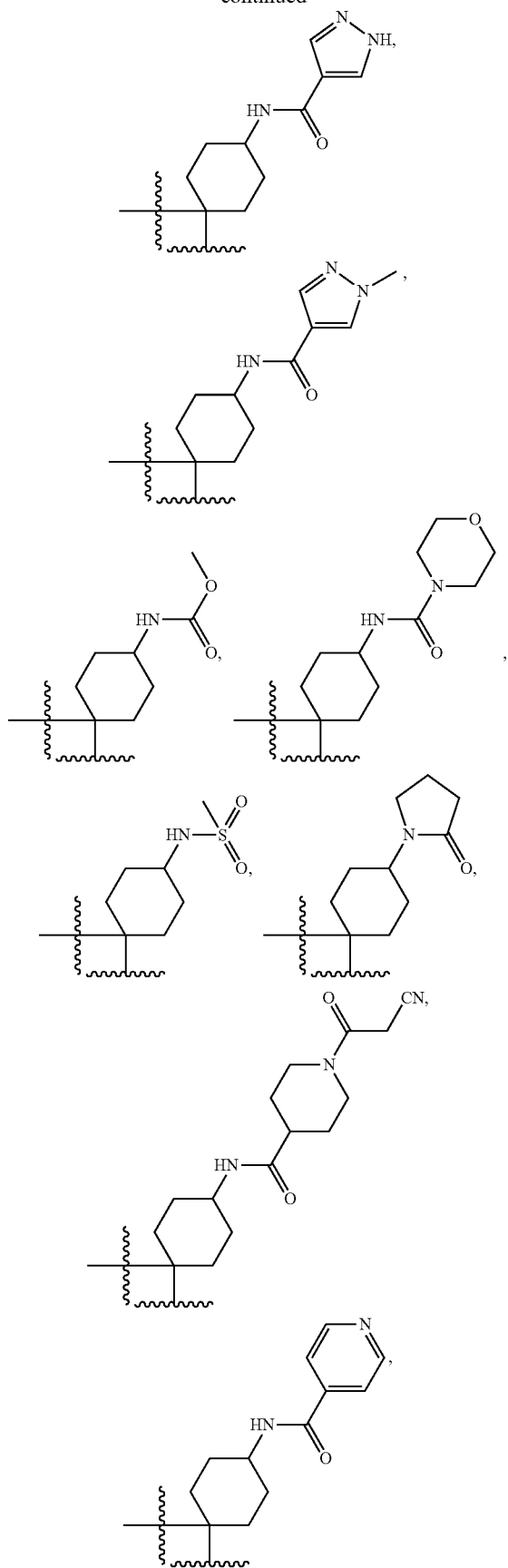
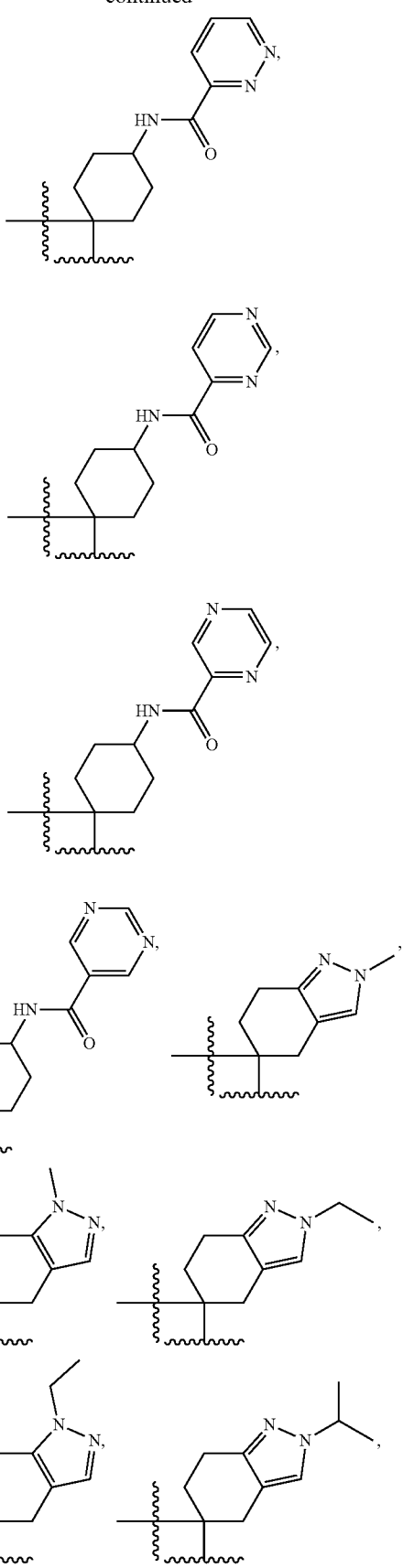

161
-continued
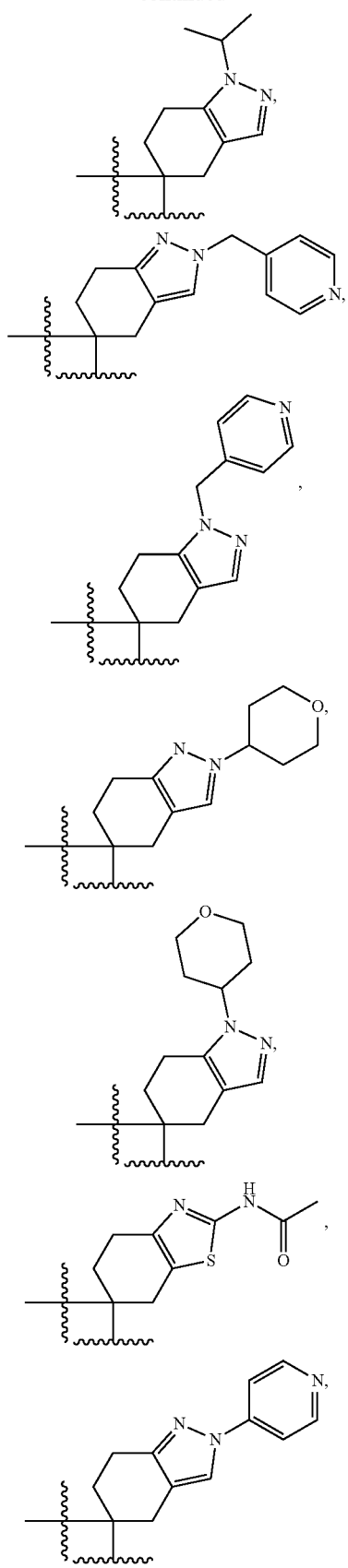
162
-continued
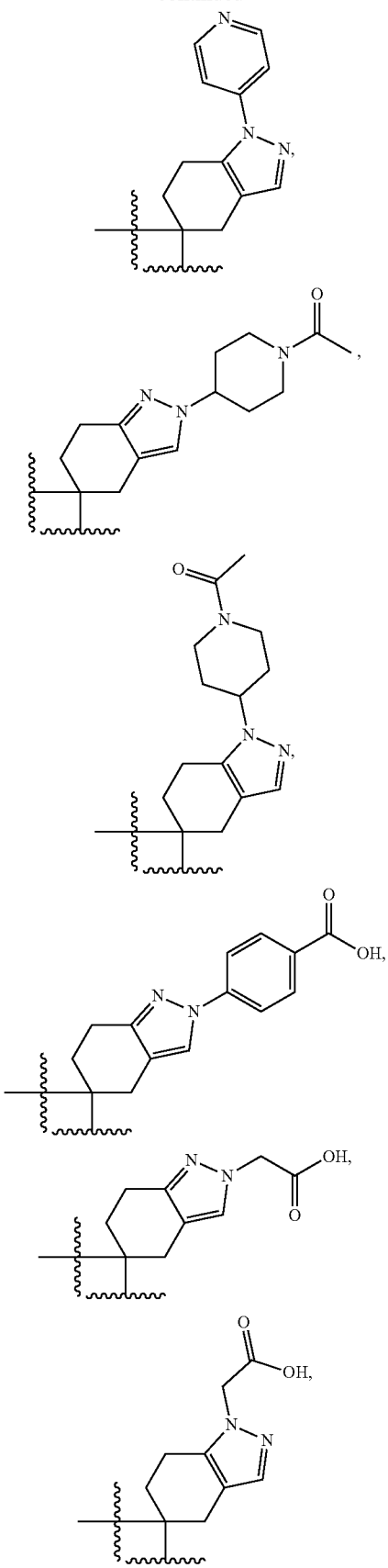

163
-continued
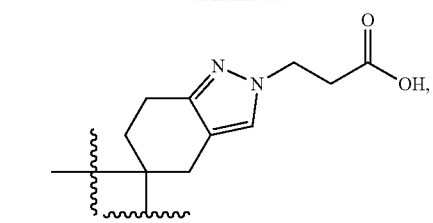
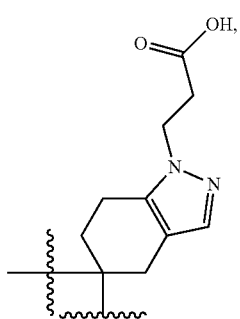
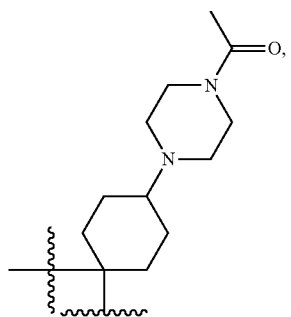
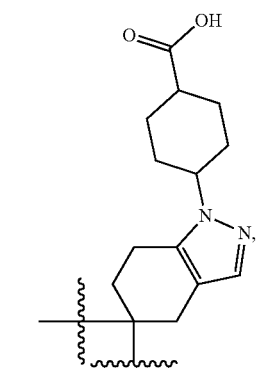
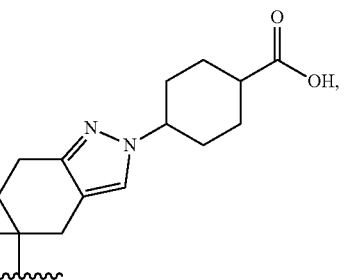
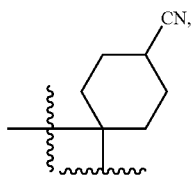
164
-continued
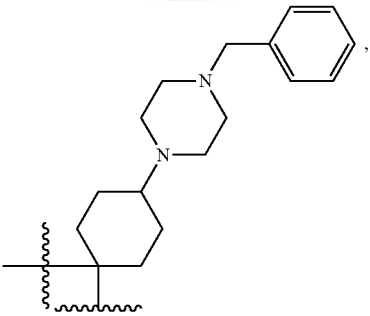
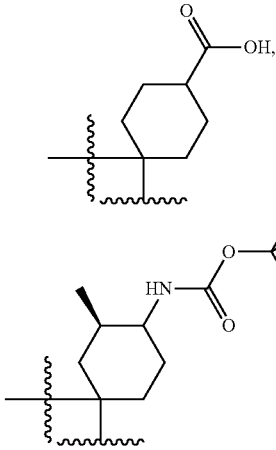
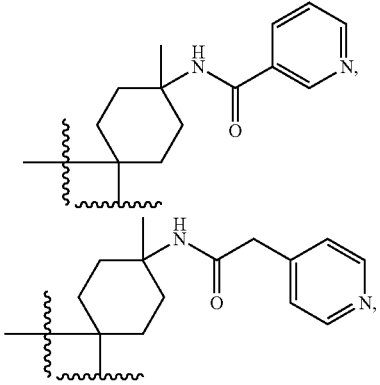
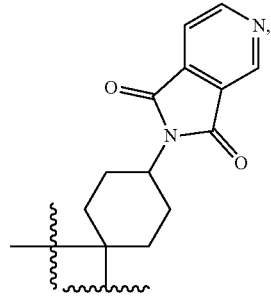
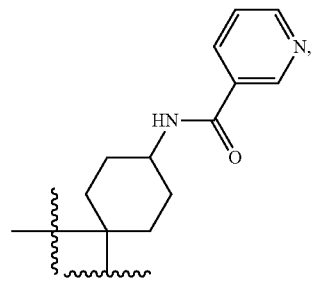

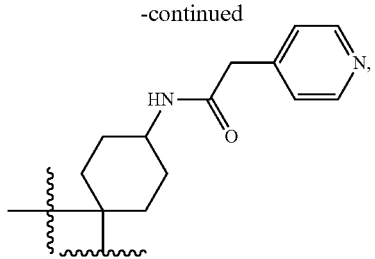
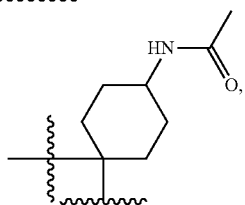
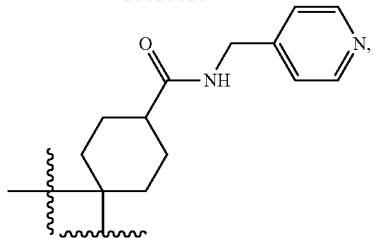
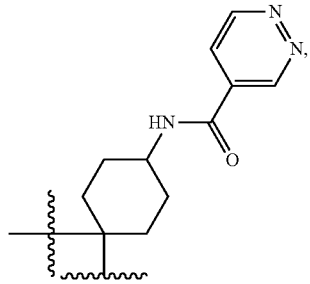
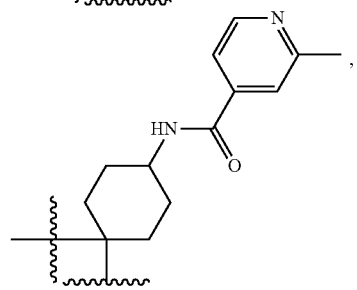
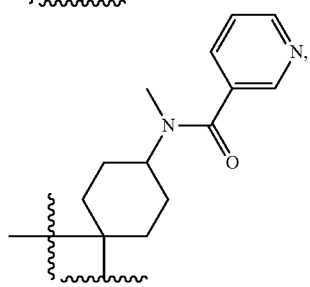
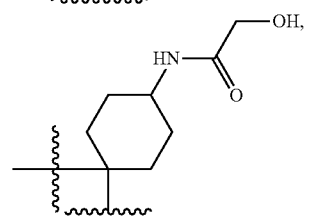
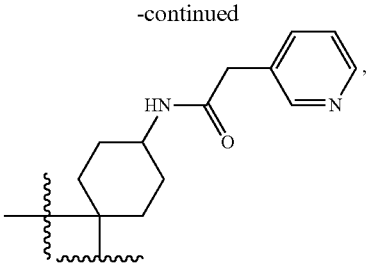
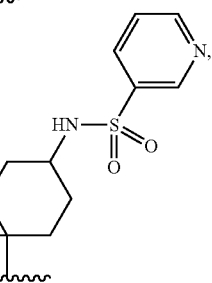
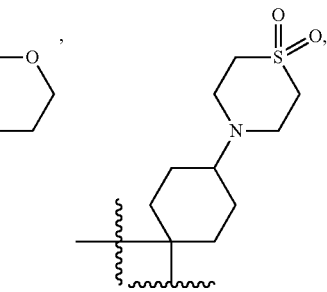
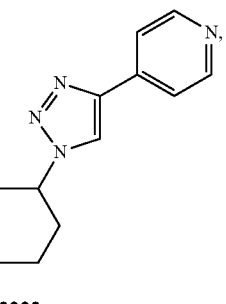
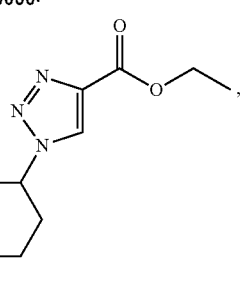
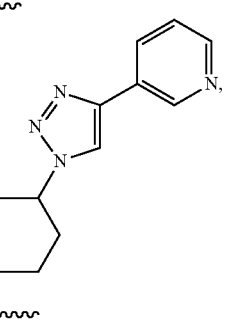

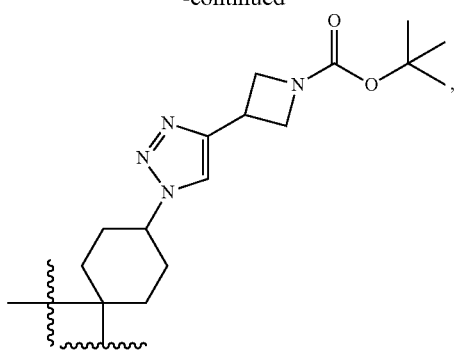
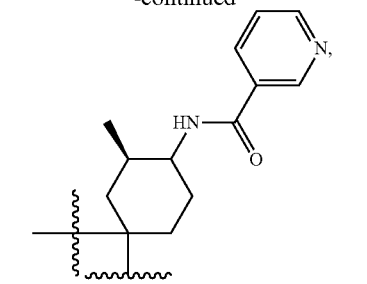
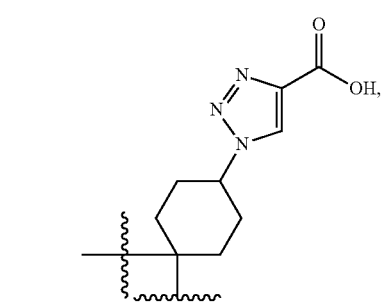
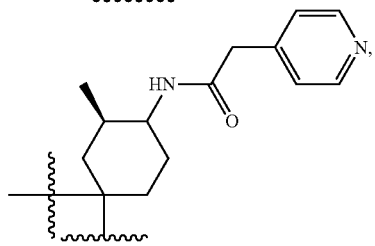
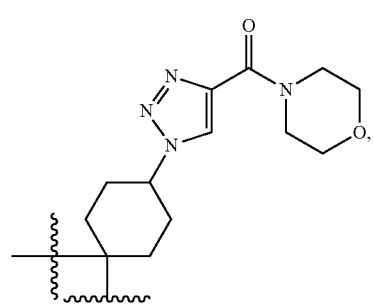
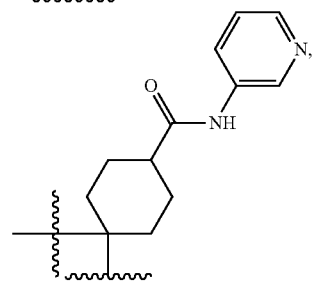
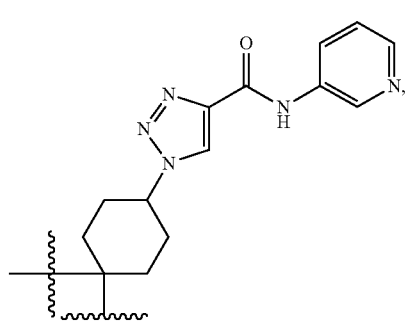
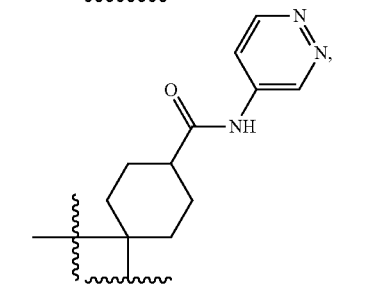
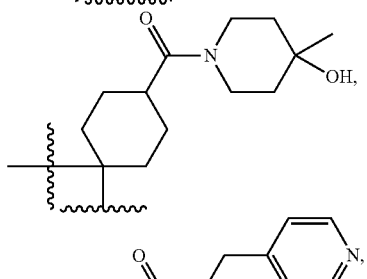
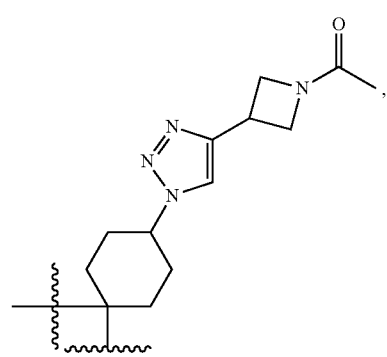
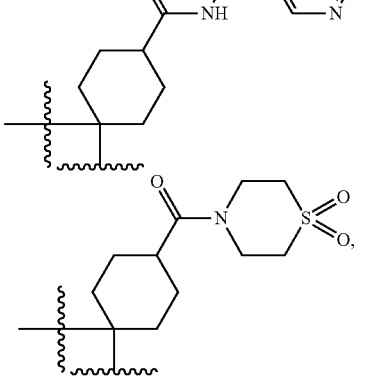

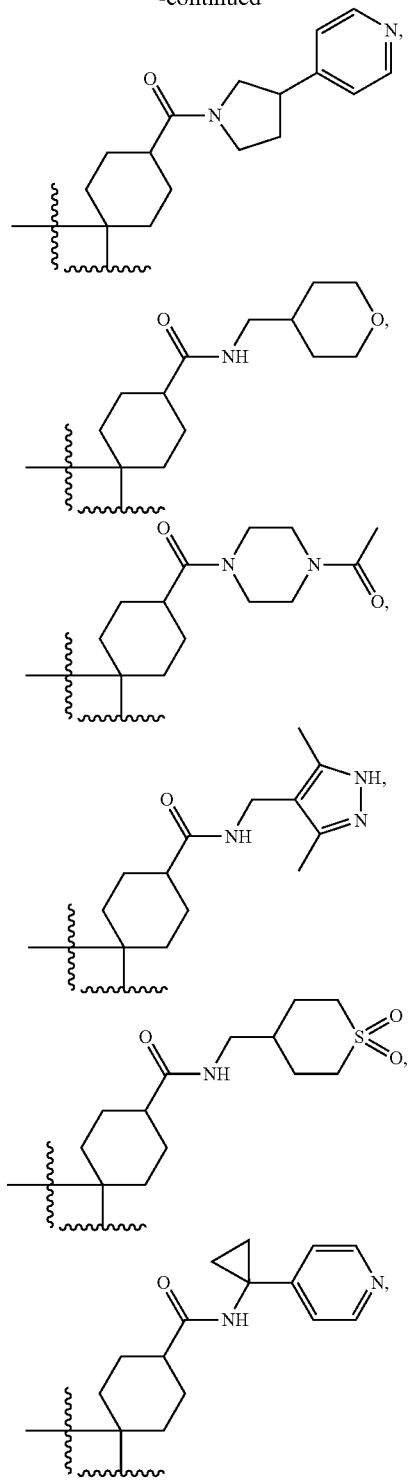

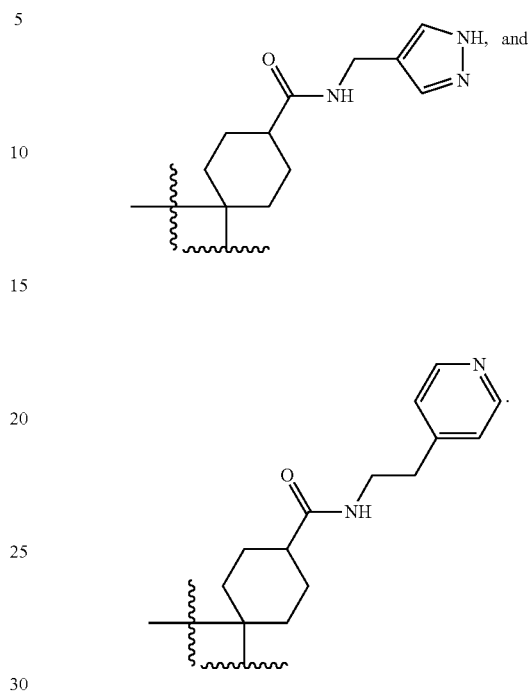

10. A compound according to claim 6, or a stereoisomer or pharmaceutically-acceptable salt thereof, wherein $R^3$ and $R^{3'}$ are, independently, hydrogen, halo, $N_3$, CN, —O(phenyl), —$NH_2$, NH($C_{1-6}$ alkyl), N($C_{1-6}$ alkyl)$_2$, $C_{1-6}$ alkyl or $C_{3-6}$ cycloalkyl.

11. A compound according to claim 6, or a stereoisomer or pharmaceutically-acceptable salt thereof, wherein $R^3$ is halo and $R^{3'}$ is hydrogen.

12. A pharmaceutical composition comprising one or more compounds according to claim 1 and a pharmaceutically acceptable carrier or diluent.

13. A method of treating a disease or disorder selected from an autoimmune disease or disorder, asthma, an allergic disease or disorder, a metabolic disease or disorder, and cancer in a subject, wherein the disease or disorder is selected from psoriasis, rheumatoid arthritis, inflammatory bowel disease, Crohn's disease, ulcerative colitis, psoriatic arthritis, ankylosing spondylitis and multiple sclerosis, said method comprising administering to the subject a therapeutically-effective amount of a compound according to claim 1.

* * * * *